(12) United States Patent
Raymond

(10) Patent No.: US 8,071,306 B2
(45) Date of Patent: Dec. 6, 2011

(54) METHODS FOR QUANTITATING SMALL RNA MOLECULES

(75) Inventor: Christopher K. Raymond, Seattle, WA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 112 days.

(21) Appl. No.: 11/779,759

(22) Filed: Jul. 18, 2007

(65) Prior Publication Data

US 2007/0292878 A1     Dec. 20, 2007

Related U.S. Application Data

(63) Continuation-in-part of application No. 10/579,029, filed as application No. PCT/US2006/002591 on Jan. 25, 2006.

(60) Provisional application No. 60/647,178, filed on Jan. 25, 2005.

(51) Int. Cl.
*C12Q 1/68* (2006.01)
*C12P 19/34* (2006.01)

(52) U.S. Cl. ............... 435/6.11; 435/6.16; 435/91.2

(58) Field of Classification Search .................. None
See application file for complete search history.

(56) References Cited

U.S. PATENT DOCUMENTS

2003/0186288 A1* 10/2003 Spivack et al. ............... 435/6

FOREIGN PATENT DOCUMENTS

| WO | 02/057479 A2 | 7/2002 |
|---|---|---|
| WO | 03/020739 A2 | 3/2003 |
| WO | 03/039523 A2 | 5/2003 |
| WO | 03/095467 A1 | 11/2003 |
| WO | 2005/098029 A2 | 10/2005 |
| WO | 2005/116250 A2 | 12/2005 |
| WO | 2006/033020 A2 | 3/2006 |
| WO | 2006/069584 A2 | 7/2006 |
| WO | 2006/081284 A2 | 8/2006 |

OTHER PUBLICATIONS

Lagos-Quintana et al. (Science, 2001, vol. 294, p. 853-858).*
Brownie et al. (Nucleic Acids Research, 1997, 25(16):3235-3241).*
Barad et al. (Genome Research, 2004, vol. 14, p. 2486-2494).*
Braasch et al. (Chemistry & Biology, 2001, p. 1-7).*
Crollius et al. (Nature Genetics, 2000, 25(2):235-238).*
Buck et al. (Biotechniques, 1999, 27:528-536).*
Lishanski et al. (Clinical Chemistry, 2000, 46:9, 1464-1470).*
Lau, N. C., et al., "An Abundant Class of Tiny RNAs With Probable Regulatory Roles in *Caenorhabditis elegans,*" Science 294(5543):858-862, Oct. 2001.

(Continued)

*Primary Examiner* — Stephanie K Mummert
(74) *Attorney, Agent, or Firm* — Christensen O'Connor Johnson Kindness PLLC

(57) ABSTRACT

In one aspect, the present invention provides methods for amplifying a microRNA molecule to produce DNA molecules. The methods each include the steps of: (a) using primer extension to make a DNA molecule that is complementary to a target microRNA molecule; and (b) using a universal forward primer and a reverse primer to amplify the DNA molecule to produce amplified DNA molecules. In some embodiments of the method, at least one of the forward primer and the reverse primer comprise at least one locked nucleic acid molecule.

6 Claims, 3 Drawing Sheets

OTHER PUBLICATIONS

Lau, N.C., et al., "An Abundant Class of Tiny RNAs With Probable Regulatory Roles in *Caenorhabditis elegans*," Supplementary Materials, Science 294(5543), Oct. 2001, 6 pages.

Raymond, C.K., et al., "Simple, Quantitative Primer-Extension PCR Assay for Direct Monitoring of MicroRNAs and Short-Interfering RNAs," RNA 11(11):1737-1744, Nov. 2005.

Chen, C., et al., "Real Time PCR: Advancing RNA Interference and MicroRNA Studies," Pharmaceutical Discovery Online, May 1, 2005, <http://www.appliedbiosystems.com/about/presskit/pdfs/pharma_discovery.html> [retrieved Sep. 7, 2006].

Grad, Y., et al., "Computational and Experimental Identification of *C. elegans* MicroRNAs," Molecular Cell 11:1253-1263, 2003.

Griffiths-Jones, S., "The MicroRNA Registry," Nucleic Acids Research 32 (Database issue):D109-D111, 2004.

Liu, C.G., et al., "An Oligonucleotide Microchip for Genome Wide MicroRNA Profiling in Human and Mouse Tissues," Proc. Nat'l Acad. Sci. USA 101(26):9740-9744, 2004.

Schmittgen, T.D., et al., "A High Throughput Method to Monitor the Expression of MicroRNA Precursors," Nucleic Acids Research 32(4):1-10, 2004.

Schoenike, B., et al., "Quantitative Sense-Specific Determination of Murine Coronavirus RNA by Reverse Transcription Polymerase Chain Reaction," Journal of Virological Methods 78:35-49, 1999.

* cited by examiner

SEQUENCE LISTING

```
<160> NUMBER OF SEQ ID NOS: 1043

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
catgatcagc tgggccaaga                                              20
```

```
<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
catgatcagc tgggccaaga aactatacaa cct                                   33

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
catgatcagc tgggccaaga tacatacttc t                                     31

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
catgatcagc tgggccaaga cacaaaccat tatg                                  34

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
catgatcagc tgggccaaga cgccaatatt tacgt                                 35

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
catgatcagc tgggccaaga tcaacatcag t                                     31

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
catgatcagc tgggccaaga ctgttcctgc tg                                    32

<210> SEQ ID NO 8
<211> LENGTH: 36
<212> TYPE: DNA
<213> ORGANISM: Artificial Sequence
<220> FEATURE:
<223> OTHER INFORMATION: Primer
```

-continued

<400> SEQUENCE: 8
catgatcagc tgggccaaga acaaacacca ttgtca    36

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
catgatcagc tgggccaaga tggcattcac cgcgtg    36

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
catgatcagc tgggccaaga tgagctacag tg    32

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
catgatcagc tgggccaaga aagggattcc tgggaa    36

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
catgatcagc tgggccaaga cccctatcac gat    33

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
catgatcagc tgggccaaga    20

<210> SEQ ID NO 14
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 14
tgaggtagta ggttg                                                    15

<210> SEQ ID NO 15
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(8)
<223> OTHER INFORMATION: Nucleotide at position 3 and/or 6 and/or 8 may
      be modified by 2'-O,4'-C-methylene-beta-D-ribofuranosyl moiety

<400> SEQUENCE: 15
tggaatgtaa agaagta                                                  17

<210> SEQ ID NO 16
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 16
tagcagcaca taatg                                                    15

<210> SEQ ID NO 17
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 17
tagcagcacg taaa                                                     14

<210> SEQ ID NO 18
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 18
tagcttatca gactgat                                                  17

<210> SEQ ID NO 19
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)

<223> OTHER INFORMATION: Nucleotide at position 4 may be modified by
     2'-O,4'-C-methylene-beta-D-ribofuranosyl moiety

<400> SEQUENCE: 19
tggctcagtt cagc                                                    14

<210> SEQ ID NO 20
<211> LENGTH: 13
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 3 and/or 6
     may be modified by 2'-O,4'-C-methylene-beta-D-ribofuranosyl moiety

<400> SEQUENCE: 20
tggagtgtga caa                                                     13

<210> SEQ ID NO 21
<211> LENGTH: 12
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
     modified by 2'-O,4'-C-methylene-beta-D-ribofuranosyl moiety

<400> SEQUENCE: 21
ttaaggcacg cg                                                      12

<210> SEQ ID NO 22
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(6)
<223> OTHER INFORMATION: Nucleotide at position 3 and/or 6 may be
     modified by 2'-O,4'-C-methylene-beta-D-ribofuranosyl moiety

<400> SEQUENCE: 22
tgagatgaag cactg                                                   15

<210> SEQ ID NO 23
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Nucleotide at position 3 may be modified by
     2'-O,4'-C-methylene-beta-D-ribofuranosyl moiety

<400> SEQUENCE: 23
gtccagtttt ccca                                                    14

<210> SEQ ID NO 24
<211> LENGTH: 16
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<222> LOCATION: (2)..(7)
<223> OTHER INFORMATION: Nucleotide at position 2 and/or 5 and/or 7 may
      be modified by 2'-O,4'-C-methylene-beta-D-ribofuranosyl moiety

<400> SEQUENCE: 24
ttaatgctaa tcgtga                                                    16

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
catgatcagc tgggccaaga gccaatattt ct                                  32

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
catgatcagc tgggccaaga gccaatattt c                                   31

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
catgatcagc tgggccaaga gccaatattt                                     30

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
catgatcagc tgggccaaga gccaatatt                                      29

<210> SEQ ID NO 29
<211> LENGTH: 28
<212> TYPE: DNA
<213> ORGANISM: Artificial Sequence
<220> FEATURE:
<223> OTHER INFORMATION: Primer

<400> SEQUENCE: 29
catgatcagc tgggccaaga gccaatat                                       28

<210> SEQ ID NO 30
<211> LENGTH: 27
<212> TYPE: DNA
<213> ORGANISM: Artificial Sequence
<220> FEATURE:
<223> OTHER INFORMATION: Primer
```

```
<400> SEQUENCE: 30
catgatcagc tgggccaaga gccaata                                      27

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
catgatcagc tgggccaaga gccaat                                       26

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
catgatcagc tgggccaaga gccaa                                        25

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
catgatcagc tgggccaaga gcca                                         24

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
catgatcagc tgggccaaga gcc                                          23

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
catgatcagc tgggccaaga gtctgtcaat tc                                32

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
catgatcagc tgggccaaga gtctgtcaat t                                 31

<210> SEQ ID NO 37
<211> LENGTH: 30
<212> TYPE: DNA
```

-continued

```
<213> ORGANISM: Artificial Sequence
<220> FEATURE:
<223> OTHER INFORMATION: Primer

<400> SEQUENCE: 37
catgatcagc tgggccaaga gtctgtcaat                                        30

<210> SEQ ID NO 38
<211> LENGTH: 29
<212> TYPE: DNA
<213> ORGANISM: Artificial Sequence
<220> FEATURE:
<223> OTHER INFORMATION: Primer

<400> SEQUENCE: 38
catgatcagc tgggccaaga gtctgtcaa                                         29

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
catgatcagc tgggccaaga gtctgtca                                          28

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
catgatcagc tgggccaaga gtctgtc                                           27

<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
catgatcagc tgggccaaga gtctgt                                            26

<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
catgatcagc tgggccaaga gtctg                                             25

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
catgatcagc tgggccaaga gtct                                              24
```

-continued

```
<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
catgatcagc tgggccaaga gtc                                              23

<210> SEQ ID NO 45
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 45
tagcagcaca gaaat                                                       15

<210> SEQ ID NO 46
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 3 and/or 5 may
      be modified by 2'-O,4'-C-methylene-beta-D-ribofuranosyl moiety

<400> SEQUENCE: 46
atgacctatg aattg                                                       15

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
catgatcagc tgggccaaga tacatacttc                                       30

<210> SEQ ID NO 48
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(8)
<223> OTHER INFORMATION: Nucleotide at position 2 and/or 3 and/or 6
      and/or 8 may be modified by 2'-O,4'-C-methylene-beta-D-
      ribofuranosyl moiety

<400> SEQUENCE: 48
tggaatgtaa agaagt                                                      16

<210> SEQ ID NO 49
<211> LENGTH: 30
<212> TYPE: DNA
```

```
<213> ORGANISM: Artificial Sequence
<220> FEATURE:
<223> OTHER INFORMATION: Primer

<400> SEQUENCE: 49
catgatcagc tgggccaaga caacaaaatc                              30

<210> SEQ ID NO 50
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 50
tggaagacta gtgatttt                                           18

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
catgatcagc tgggccaaga actttcggtt                              30

<210> SEQ ID NO 52
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(8)
<223> OTHER INFORMATION: Nucleotide at position 5 and/or 8 may be
      modified by 2'-O,4'-C-methylene-beta-D-ribofuranosyl moiety

<400> SEQUENCE: 52
taaagctaga taaccg                                             16

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
catgatcagc tgggccaaga cacaaattcg                              30

<210> SEQ ID NO 54
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 54
``` tacccctgtag atccg                                              15

<210> SEQ ID NO 55
<211> LENGTH: 31
<212> TYPE: DNA
<213> ORGANISM: Artificial Sequence
<220> FEATURE:
<223> OTHER INFORMATION: Primer

<400> SEQUENCE: 55
catgatcagc tgggccaaga acaaattcgg t                              31

<210> SEQ ID NO 56
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(9)
<223> OTHER INFORMATION: Nucleotide at position 3 and/or 6 and/or 9 may
      be modified by 2'-O,4'-C-methylene-beta-D-ribofuranosyl moiety

<400> SEQUENCE: 56 tacccctgtag aaccga                                              16

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
catgatcagc tgggccaaga cacaaaccat                                30

<210> SEQ ID NO 58
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 58
tagcagcaca taatg                                               15

<210> SEQ ID NO 59
<211> LENGTH: 29
<212> TYPE: DNA
<213> ORGANISM: Artificial Sequence
<220> FEATURE:
<223> OTHER INFORMATION: Primer

<400> SEQUENCE: 59
catgatcagc tgggccaaga tgtaaacca                                29

<210> SEQ ID NO 60
<211> LENGTH: 14
<212> TYPE: DNA
<213> ORGANISM: Artificial Sequence
<220> FEATURE:
<223> OTHER INFORMATION: Primer

```
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 60
tagcagcaca tcat                                                        14

<210> SEQ ID NO 61
<211> LENGTH: 29
<212> TYPE: DNA
<213> ORGANISM: Artificial Sequence
<220> FEATURE:
<223> OTHER INFORMATION: Primer

<400> SEQUENCE: 61
catgatcagc tgggccaaga cgccaatat                                        29

<210> SEQ ID NO 62
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 62
tagcagcacg taaa                                                        14

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
catgatcagc tgggccaaga acaagtgcct                                       30

<210> SEQ ID NO 64
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 64
actgcagtga aggc                                                        14

<210> SEQ ID NO 65
<211> LENGTH: 29
<212> TYPE: DNA
<213> ORGANISM: Artificial Sequence
<220> FEATURE:
<223> OTHER INFORMATION: Primer

<400> SEQUENCE: 65
catgatcagc tgggccaaga actacctgc                                        29
```

```
<210> SEQ ID NO 66
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 66
caaagtgctt acagtg                                                        16

<210> SEQ ID NO 67
<211> LENGTH: 29
<212> TYPE: DNA
<213> ORGANISM: Artificial Sequence
<220> FEATURE:
<223> OTHER INFORMATION: Primer

<400> SEQUENCE: 67
catgatcagc tgggccaaga tcagttttg                                          29

<210> SEQ ID NO 68
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 68
tgtgcaaatc tatgc                                                         15

<210> SEQ ID NO 69
<211> LENGTH: 30
<212> TYPE: DNA
<213> ORGANISM: Artificial Sequence
<220> FEATURE:
<223> OTHER INFORMATION: Primer

<400> SEQUENCE: 69
catgatcagc tgggccaaga tcagttttgc                                         30

<210> SEQ ID NO 70
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 70
tgtgcaaatc catg                                                          14

<210> SEQ ID NO 71
<211> LENGTH: 28
<212> TYPE: DNA
<213> ORGANISM: Artificial Sequence
```

```
<220> FEATURE:
<223> OTHER INFORMATION: Primer

<400> SEQUENCE: 71
catgatcagc tgggccaaga ctacctgc                                    28

<210> SEQ ID NO 72
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 72
taaagtgctt atagtgca                                               18

<210> SEQ ID NO 73
<211> LENGTH: 29
<212> TYPE: DNA
<213> ORGANISM: Artificial Sequence
<220> FEATURE:
<223> OTHER INFORMATION: Primer

<400> SEQUENCE: 73
catgatcagc tgggccaaga tcaacatca                                   29

<210> SEQ ID NO 74
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 74
tagcttatca gactgatg                                               18

<210> SEQ ID NO 75
<211> LENGTH: 30
<212> TYPE: DNA
<213> ORGANISM: Artificial Sequence
<220> FEATURE:
<223> OTHER INFORMATION: Primer

<400> SEQUENCE: 75
catgatcagc tgggccaaga ggaaatccct                                  30

<210> SEQ ID NO 76
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 76
```

```
atcacattgc cagg                                                    14

<210> SEQ ID NO 77
<211> LENGTH: 30
<212> TYPE: DNA
<213> ORGANISM: Artificial Sequence
<220> FEATURE:
<223> OTHER INFORMATION: Primer

<400> SEQUENCE: 77
catgatcagc tgggccaaga ggtaatccct                                   30

<210> SEQ ID NO 78
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 78
atcacattgc cagg                                                    14

<210> SEQ ID NO 79
<211> LENGTH: 30
<212> TYPE: DNA
<213> ORGANISM: Artificial Sequence
<220> FEATURE:
<223> OTHER INFORMATION: Primer

<400> SEQUENCE: 79
catgatcagc tgggccaaga tcagaccgag                                   30

<210> SEQ ID NO 80
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 80
cattgcactt gtctc                                                   15

<210> SEQ ID NO 81
<211> LENGTH: 29
<212> TYPE: DNA
<213> ORGANISM: Artificial Sequence
<220> FEATURE:
<223> OTHER INFORMATION: Primer

<400> SEQUENCE: 81
catgatcagc tgggccaaga gcctatcct                                    29

<210> SEQ ID NO 82
<211> LENGTH: 17
<212> TYPE: DNA
<213> ORGANISM: Artificial Sequence
<220> FEATURE:
<223> OTHER INFORMATION: Primer
<220> FEATURE:
```

```
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 82
ttcaagtaat ccaggat                                                    17

<210> SEQ ID NO 83
<211> LENGTH: 29
<212> TYPE: DNA
<213> ORGANISM: Artificial Sequence
<220> FEATURE:
<223> OTHER INFORMATION: Primer

<400> SEQUENCE: 83
catgatcagc tgggccaaga aacctatcc                                       29

<210> SEQ ID NO 84
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(8)
<223> OTHER INFORMATION: Nucleotide at position 3 and/or 5 and/or 8
      may be modified by 2'-O,4'-C-methylene-beta-D-ribofuranosyl moiety

<400> SEQUENCE: 84
ttcaagtaat tcaggat                                                    17

<210> SEQ ID NO 85
<211> LENGTH: 30
<212> TYPE: DNA
<213> ORGANISM: Artificial Sequence
<220> FEATURE:
<223> OTHER INFORMATION: Primer

<400> SEQUENCE: 85
catgatcagc tgggccaaga gcggaactta                                      30

<210> SEQ ID NO 86
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 86
ttcacagtgg ctaa                                                       14

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
catgatcagc tgggccaaga gcagaactta                                      30
```

```
<210> SEQ ID NO 88
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 88
ttcacagtgg ctaa                                                     14

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
catgatcagc tgggccaaga ctcaatagac                                     30

<210> SEQ ID NO 90
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 90
aaggagctca cagt                                                     14

<210> SEQ ID NO 91
<211> LENGTH: 28
<212> TYPE: DNA
<213> ORGANISM: Artificial Sequence
<220> FEATURE:
<223> OTHER INFORMATION: Primer

<400> SEQUENCE: 91
catgatcagc tgggccaaga aaccgatt                                       28

<210> SEQ ID NO 92
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 92
tagcaccatc tgaaat                                                   16

<210> SEQ ID NO 93
<211> LENGTH: 29
<212> TYPE: DNA
<213> ORGANISM: Artificial Sequence
<220> FEATURE:
```

```
<223> OTHER INFORMATION: Primer

<400> SEQUENCE: 93
catgatcagc tgggccaaga aacactgat                                    29

<210> SEQ ID NO 94
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 94
tagcaccatt tgaaatcag                                               19

<210> SEQ ID NO 95
<211> LENGTH: 30
<212> TYPE: DNA
<213> ORGANISM: Artificial Sequence
<220> FEATURE:
<223> OTHER INFORMATION: Primer

<400> SEQUENCE: 95
catgatcagc tgggccaaga cttccagtcg                                   30

<210> SEQ ID NO 96
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 96
tgtaaacatc ctcgac                                                  16

<210> SEQ ID NO 97
<211> LENGTH: 30
<212> TYPE: DNA
<213> ORGANISM: Artificial Sequence
<220> FEATURE:
<223> OTHER INFORMATION: Primer

<400> SEQUENCE: 97
catgatcagc tgggccaaga agctgagtgt                                   30

<210> SEQ ID NO 98
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 98
tgtaaacatc ctacact                                                 17
```

<210> SEQ ID NO 99
<211> LENGTH: 30
<212> TYPE: DNA
<213> ORGANISM: Artificial Sequence
<220> FEATURE:
<223> OTHER INFORMATION: Primer

<400> SEQUENCE: 99
catgatcagc tgggccaaga gctgagagtg                                    30

<210> SEQ ID NO 100
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 100
tgtaaacatc ctacact                                                  17

<210> SEQ ID NO 101
<211> LENGTH: 30
<212> TYPE: DNA
<213> ORGANISM: Artificial Sequence
<220> FEATURE:
<223> OTHER INFORMATION: Primer

<400> SEQUENCE: 101
catgatcagc tgggccaaga cttccagtcg                                    30

<210> SEQ ID NO 102
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: Nucleotide at position 2 and/or 7 may be
      modified by 2'-O,4'-C-methylene-beta-D-ribofuranosyl moiety

<400> SEQUENCE: 102
tgtaaacatc cccg                                                     14

<210> SEQ ID NO 103
<211> LENGTH: 29
<212> TYPE: DNA
<213> ORGANISM: Artificial Sequence
<220> FEATURE:
<223> OTHER INFORMATION: Primer

<400> SEQUENCE: 103
catgatcagc tgggccaaga gctgtaaac                                     29

<210> SEQ ID NO 104
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature

```
<222> LOCATION: (5)..(9)
<223> OTHER INFORMATION: Nucleotide at position 5 and/or 9 may be
      modified by 2'-O,4'-C-methylene-beta-D-ribofuranosyl moiety

<400> SEQUENCE: 104
ctttcagtcg gatgttt                                                    17

<210> SEQ ID NO 105
<211> LENGTH: 30
<212> TYPE: DNA
<213> ORGANISM: Artificial Sequence
<220> FEATURE:
<223> OTHER INFORMATION: Primer

<400> SEQUENCE: 105
catgatcagc tgggccaaga tccagtcaag                                      30

<210> SEQ ID NO 106
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 106
tgtaaacatc cttgac                                                     16

<210> SEQ ID NO 107
<211> LENGTH: 30
<212> TYPE: DNA
<213> ORGANISM: Artificial Sequence
<220> FEATURE:
<223> OTHER INFORMATION: Primer

<400> SEQUENCE: 107
catgatcagc tgggccaaga cagctatgcc                                      30

<210> SEQ ID NO 108
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 108
ggcaagatgc tggc                                                       14

<210> SEQ ID NO 109
<211> LENGTH: 30
<212> TYPE: DNA
<213> ORGANISM: Artificial Sequence
<220> FEATURE:
<223> OTHER INFORMATION: Primer

<400> SEQUENCE: 109
catgatcagc tgggccaaga gcaacttagt                                      30

<210> SEQ ID NO 110
```

```
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(8)
<223> OTHER INFORMATION: Nucleotide at position 6 and/or 8 may be
      modified by 2'-O,4'-C-methylene-beta-D-ribofuranosyl moiety

<400> SEQUENCE: 110
tattgcacat tactaag                                              17

<210> SEQ ID NO 111
<211> LENGTH: 29
<212> TYPE: DNA
<213> ORGANISM: Artificial Sequence
<220> FEATURE:
<223> OTHER INFORMATION: Primer

<400> SEQUENCE: 111
catgatcagc tgggccaaga caatgcaac                                 29

<210> SEQ ID NO 112
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 112
gtgcattgta gttgc                                                15

<210> SEQ ID NO 113
<211> LENGTH: 30
<212> TYPE: DNA
<213> ORGANISM: Artificial Sequence
<220> FEATURE:
<223> OTHER INFORMATION: Primer

<400> SEQUENCE: 113
catgatcagc tgggccaaga aacaaccagc                                30

<210> SEQ ID NO 114
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 114
tggcagtgtc ttag                                                 14

<210> SEQ ID NO 115
<211> LENGTH: 30
<212> TYPE: DNA
<213> ORGANISM: Artificial Sequence
<220> FEATURE:
<223> OTHER INFORMATION: Primer
```

```
<400> SEQUENCE: 115
catgatcagc tgggccaaga caatcagcta                                    30

<210> SEQ ID NO 116
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 116
taggcagtgt catt                                                     14

<210> SEQ ID NO 117
<211> LENGTH: 30
<212> TYPE: DNA
<213> ORGANISM: Artificial Sequence
<220> FEATURE:
<223> OTHER INFORMATION: Primer

<400> SEQUENCE: 117
catgatcagc tgggccaaga gcaatcagct                                    30

<210> SEQ ID NO 118
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 118
aggcagtgta gtta                                                     14

<210> SEQ ID NO 119
<211> LENGTH: 30
<212> TYPE: DNA
<213> ORGANISM: Artificial Sequence
<220> FEATURE:
<223> OTHER INFORMATION: Primer

<400> SEQUENCE: 119
catgatcagc tgggccaaga caggccggga                                    30

<210> SEQ ID NO 120
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 120
tattgcactt gtccc                                                    15
```

```
<210> SEQ ID NO 121
<211> LENGTH: 30
<212> TYPE: DNA
<213> ORGANISM: Artificial Sequence
<220> FEATURE:
<223> OTHER INFORMATION: Primer

<400> SEQUENCE: 121
catgatcagc tgggccaaga ctacctgcac                                          30

<210> SEQ ID NO 122
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 122
aaagtgctgt tcgt                                                           14

<210> SEQ ID NO 123
<211> LENGTH: 30
<212> TYPE: DNA
<213> ORGANISM: Artificial Sequence
<220> FEATURE:
<223> OTHER INFORMATION: Primer

<400> SEQUENCE: 123
catgatcagc tgggccaaga tgctcaataa                                          30

<210> SEQ ID NO 124
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 124
ttcaacgggt atttattga                                                      19

<210> SEQ ID NO 125
<211> LENGTH: 30
<212> TYPE: DNA
<213> ORGANISM: Artificial Sequence
<220> FEATURE:
<223> OTHER INFORMATION: Primer

<400> SEQUENCE: 125
catgatcagc tgggccaaga gcaaaaatgt                                          30

<210> SEQ ID NO 126
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
```

<223> OTHER INFORMATION: Nucleotide at position 2 and/or 4 may be
      modified by 2'-O,4'-C-methylene-beta-D-ribofuranosyl moiety

<400> SEQUENCE: 126
tttggcacta gcac                                                         14

<210> SEQ ID NO 127
<211> LENGTH: 30
<212> TYPE: DNA
<213> ORGANISM: Artificial Sequence
<220> FEATURE:
<223> OTHER INFORMATION: Primer

<400> SEQUENCE: 127
catgatcagc tgggccaaga aacaatacaa                                        30

<210> SEQ ID NO 128
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 128
tgaggtagta agttg                                                        15

<210> SEQ ID NO 129
<211> LENGTH: 30
<212> TYPE: DNA
<213> ORGANISM: Artificial Sequence
<220> FEATURE:
<223> OTHER INFORMATION: Primer

<400> SEQUENCE: 129
catgatcagc tgggccaaga cacaagatcg                                        30

<210> SEQ ID NO 130
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 130
aacccgtaga tccg                                                         14

<210> SEQ ID NO 131
<211> LENGTH: 30
<212> TYPE: DNA
<213> ORGANISM: Artificial Sequence
<220> FEATURE:
<223> OTHER INFORMATION: Primer

<400> SEQUENCE: 131
catgatcagc tgggccaaga cgcaaggtcg                                        30

<210> SEQ ID NO 132
<211> LENGTH: 14

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 132
cacccgtaga accg                                                       14

<210> SEQ ID NO 133
<211> LENGTH: 30
<212> TYPE: DNA
<213> ORGANISM: Artificial Sequence
<220> FEATURE:
<223> OTHER INFORMATION: Primer

<400> SEQUENCE: 133
catgatcagc tgggccaaga cacaagttcg                                      30

<210> SEQ ID NO 134
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 134
aacccgtaga tccg                                                       14

<210> SEQ ID NO 135
<211> LENGTH: 30
<212> TYPE: DNA
<213> ORGANISM: Artificial Sequence
<220> FEATURE:
<223> OTHER INFORMATION: Primer

<400> SEQUENCE: 135
catgatcagc tgggccaaga cttcagttat                                      30

<210> SEQ ID NO 136
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 136
tacagtactg tgataact                                                   18

<210> SEQ ID NO 137
<211> LENGTH: 30
<212> TYPE: DNA
<213> ORGANISM: Artificial Sequence
<220> FEATURE:
<223> OTHER INFORMATION: Primer
```

```
<400> SEQUENCE: 137
catgatcagc tgggccaaga tcatagccct                                          30

<210> SEQ ID NO 138
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 138
agcagcattg taca                                                           14

<210> SEQ ID NO 139
<211> LENGTH: 30
<212> TYPE: DNA
<213> ORGANISM: Artificial Sequence
<220> FEATURE:
<223> OTHER INFORMATION: Primer

<400> SEQUENCE: 139
catgatcagc tgggccaaga acaggagtct                                          30

<210> SEQ ID NO 140
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 140
tcaaatgctc agact                                                          15

<210> SEQ ID NO 141
<211> LENGTH: 30
<212> TYPE: DNA
<213> ORGANISM: Artificial Sequence
<220> FEATURE:
<223> OTHER INFORMATION: Primer

<400> SEQUENCE: 141
catgatcagc tgggccaaga gctacctgca                                          30

<210> SEQ ID NO 142
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 142
aaaagtgctt acagtg                                                         16
```

```
<210> SEQ ID NO 143
<211> LENGTH: 30
<212> TYPE: DNA
<213> ORGANISM: Artificial Sequence
<220> FEATURE:
<223> OTHER INFORMATION: Primer

<400> SEQUENCE: 143
catgatcagc tgggccaaga atctgcactg                                              30

<210> SEQ ID NO 144
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 144
taaagtgctg acagt                                                              15

<210> SEQ ID NO 145
<211> LENGTH: 28
<212> TYPE: DNA
<213> ORGANISM: Artificial Sequence
<220> FEATURE:
<223> OTHER INFORMATION: Primer

<400> SEQUENCE: 145
catgatcagc tgggccaaga tgatagcc                                                28

<210> SEQ ID NO 146
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 146
agcagcattg tacag                                                              15

<210> SEQ ID NO 147
<211> LENGTH: 30
<212> TYPE: DNA
<213> ORGANISM: Artificial Sequence
<220> FEATURE:
<223> OTHER INFORMATION: Primer

<400> SEQUENCE: 147
catgatcagc tgggccaaga acaaacacca                                              30

<210> SEQ ID NO 148
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
``` modified by 2'-O,4'-C-methylene-beta-D-ribofuranosyl moiety

<400> SEQUENCE: 148
tggagtgtga caat                                                        14

<210> SEQ ID NO 149
<211> LENGTH: 30
<212> TYPE: DNA
<213> ORGANISM: Artificial Sequence
<220> FEATURE:
<223> OTHER INFORMATION: Primer

<400> SEQUENCE: 149
catgatcagc tgggccaaga tggcattcac                                       30

<210> SEQ ID NO 150
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 150
ttaaggcacg cggt                                                        14

<210> SEQ ID NO 151
<211> LENGTH: 30
<212> TYPE: DNA
<213> ORGANISM: Artificial Sequence
<220> FEATURE:
<223> OTHER INFORMATION: Primer

<400> SEQUENCE: 151
catgatcagc tgggccaaga cacaggttaa                                       30

<210> SEQ ID NO 152
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 152
tccctgagac cctt                                                        14

<210> SEQ ID NO 153
<211> LENGTH: 30
<212> TYPE: DNA
<213> ORGANISM: Artificial Sequence
<220> FEATURE:
<223> OTHER INFORMATION: Primer

<400> SEQUENCE: 153
catgatcagc tgggccaaga tcacaagtta                                       30

<210> SEQ ID NO 154
<211> LENGTH: 14
<212> TYPE: DNA

```
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 154
tccctgagac ccta                                                     14

<210> SEQ ID NO 155
<211> LENGTH: 30
<212> TYPE: DNA
<213> ORGANISM: Artificial Sequence
<220> FEATURE:
<223> OTHER INFORMATION: Primer

<400> SEQUENCE: 155
catgatcagc tgggccaaga gcattattac                                    30

<210> SEQ ID NO 156
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 156
tcgtaccgtg agta                                                     14

<210> SEQ ID NO 157
<211> LENGTH: 28
<212> TYPE: DNA
<213> ORGANISM: Artificial Sequence
<220> FEATURE:
<223> OTHER INFORMATION: Primer

<400> SEQUENCE: 157
catgatcagc tgggccaaga cgcgtacc                                      28

<210> SEQ ID NO 158
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(9)
<223> OTHER INFORMATION: Nucleotide at position 2 and/or 5 and/or 9
      may be modified by 2'-O,4'-C-methylene-beta-D-ribofuranosyl moiety

<400> SEQUENCE: 158
cattattact tttggtacg                                                19

<210> SEQ ID NO 159
<211> LENGTH: 30
<212> TYPE: DNA
<213> ORGANISM: Artificial Sequence
<220> FEATURE:
<223> OTHER INFORMATION: Primer

<400> SEQUENCE: 159
```

```
catgatcagc tgggccaaga agccaagctc                                30
```

<210> SEQ ID NO 160
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 160

```
tcggatccgt ctga                                                 14
```

<210> SEQ ID NO 161
<211> LENGTH: 30
<212> TYPE: DNA
<213> ORGANISM: Artificial Sequence
<220> FEATURE:
<223> OTHER INFORMATION: Primer

<400> SEQUENCE: 161

```
catgatcagc tgggccaaga aaaagagacc                                30
```

<210> SEQ ID NO 162
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 162

```
tcacagtgaa ccgg                                                 14
```

<210> SEQ ID NO 163
<211> LENGTH: 30
<212> TYPE: DNA
<213> ORGANISM: Artificial Sequence
<220> FEATURE:
<223> OTHER INFORMATION: Primer

<400> SEQUENCE: 163

```
catgatcagc tgggccaaga gaaagagacc                                30
```

<210> SEQ ID NO 164
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 164

```
tcacagtgaa ccgg                                                 14
```

<210> SEQ ID NO 165

```
<211> LENGTH: 30
<212> TYPE: DNA
<213> ORGANISM: Artificial Sequence
<220> FEATURE:
<223> OTHER INFORMATION: Primer

<400> SEQUENCE: 165
catgatcagc tgggccaaga gcaagcccag                                     30

<210> SEQ ID NO 166
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(8)
<223> OTHER INFORMATION: Nucleotide at position 6 and/or 8 may be
      modified by 2'-O,4'-C-methylene-beta-D-ribofuranosyl moiety

<400> SEQUENCE: 166 cttttttgcgg tctg                                                     14

<210> SEQ ID NO 167
<211> LENGTH: 30
<212> TYPE: DNA
<213> ORGANISM: Artificial Sequence
<220> FEATURE:
<223> OTHER INFORMATION: Primer

<400> SEQUENCE: 167
catgatcagc tgggccaaga atgccctttt                                     30

<210> SEQ ID NO 168
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 168
cagtgcaatg ttaaaag                                                   17

<210> SEQ ID NO 169
<211> LENGTH: 30
<212> TYPE: DNA
<213> ORGANISM: Artificial Sequence
<220> FEATURE:
<223> OTHER INFORMATION: Primer

<400> SEQUENCE: 169
catgatcagc tgggccaaga atgccctttc                                     30

<210> SEQ ID NO 170
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety
```

```
<400> SEQUENCE: 170
cagtgcaatg atga                                                         14

<210> SEQ ID NO 171
<211> LENGTH: 30
<212> TYPE: DNA
<213> ORGANISM: Artificial Sequence
<220> FEATURE:
<223> OTHER INFORMATION: Primer

<400> SEQUENCE: 171
catgatcagc tgggccaaga cgaccatggc                                        30

<210> SEQ ID NO 172
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 172
taacagtcta cagcc                                                        15

<210> SEQ ID NO 173
<211> LENGTH: 30
<212> TYPE: DNA
<213> ORGANISM: Artificial Sequence
<220> FEATURE:
<223> OTHER INFORMATION: Primer

<400> SEQUENCE: 173
catgatcagc tgggccaaga acagctggtt                                        30

<210> SEQ ID NO 174
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 174
ttggtcccct tcaa                                                         14

<210> SEQ ID NO 175
<211> LENGTH: 30
<212> TYPE: DNA
<213> ORGANISM: Artificial Sequence
<220> FEATURE:
<223> OTHER INFORMATION: Primer

<400> SEQUENCE: 175
catgatcagc tgggccaaga tagctggttg                                        30

<210> SEQ ID NO 176
<211> LENGTH: 14
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 176
ttggtcccct tcaa                                                           14

<210> SEQ ID NO 177
<211> LENGTH: 30
<212> TYPE: DNA
<213> ORGANISM: Artificial Sequence
<220> FEATURE:
<223> OTHER INFORMATION: Primer

<400> SEQUENCE: 177
catgatcagc tgggccaaga ccctctggtc                                          30

<210> SEQ ID NO 178
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 178
tgtgactggt tgac                                                           14

<210> SEQ ID NO 179
<211> LENGTH: 30
<212> TYPE: DNA
<213> ORGANISM: Artificial Sequence
<220> FEATURE:
<223> OTHER INFORMATION: Primer

<400> SEQUENCE: 179
catgatcagc tgggccaaga tcacatagga                                          30

<210> SEQ ID NO 180
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 180
tatggctttt tattcct                                                        17

<210> SEQ ID NO 181
<211> LENGTH: 30
<212> TYPE: DNA
<213> ORGANISM: Artificial Sequence
<220> FEATURE:
<223> OTHER INFORMATION: Primer

<400> SEQUENCE: 181
```
catgatcagc tgggccaaga cacataggaa                                          30

<210> SEQ ID NO 182
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 182
tatggctttt cattcc                                                         16

<210> SEQ ID NO 183
<211> LENGTH: 30
<212> TYPE: DNA
<213> ORGANISM: Artificial Sequence
<220> FEATURE:
<223> OTHER INFORMATION: Primer

<400> SEQUENCE: 183
catgatcagc tgggccaaga tccatcatca                                          30

<210> SEQ ID NO 184
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 184
actccatttg ttttgatg                                                       18

<210> SEQ ID NO 185
<211> LENGTH: 30
<212> TYPE: DNA
<213> ORGANISM: Artificial Sequence
<220> FEATURE:
<223> OTHER INFORMATION: Primer

<400> SEQUENCE: 185
catgatcagc tgggccaaga ctacgcgtat                                          30

<210> SEQ ID NO 186
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 186
tattgcttaa gaatacgc                                                       18

<210> SEQ ID NO 187
<211> LENGTH: 29

```
<212> TYPE: DNA
<213> ORGANISM: Artificial Sequence
<220> FEATURE:
<223> OTHER INFORMATION: Primer

<400> SEQUENCE: 187
catgatcagc tgggccaaga cggcctgat                                     29

<210> SEQ ID NO 188
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 188
agctggtgtt gtga                                                     14

<210> SEQ ID NO 189
<211> LENGTH: 30
<212> TYPE: DNA
<213> ORGANISM: Artificial Sequence
<220> FEATURE:
<223> OTHER INFORMATION: Primer

<400> SEQUENCE: 189
catgatcagc tgggccaaga agacacgtgc                                    30

<210> SEQ ID NO 190
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 190
tctacagtgc acgt                                                     14

<210> SEQ ID NO 191
<211> LENGTH: 30
<212> TYPE: DNA
<213> ORGANISM: Artificial Sequence
<220> FEATURE:
<223> OTHER INFORMATION: Primer

<400> SEQUENCE: 191
catgatcagc tgggccaaga ctaccatagg                                    30

<210> SEQ ID NO 192
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety
```

```
<400> SEQUENCE: 192
agtggtttta ccct                                                    14

<210> SEQ ID NO 193
<211> LENGTH: 29
<212> TYPE: DNA
<213> ORGANISM: Artificial Sequence
<220> FEATURE:
<223> OTHER INFORMATION: Primer

<400> SEQUENCE: 193
catgatcagc tgggccaaga ccatcttta                                    29

<210> SEQ ID NO 194
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 194
taacactgtc tggtaa                                                  16

<210> SEQ ID NO 195
<211> LENGTH: 28
<212> TYPE: DNA
<213> ORGANISM: Artificial Sequence
<220> FEATURE:
<223> OTHER INFORMATION: Primer

<400> SEQUENCE: 195
catgatcagc tgggccaaga tccataaa                                     28

<210> SEQ ID NO 196
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 196
tgtagtgttt cctact                                                  16

<210> SEQ ID NO 197
<211> LENGTH: 28
<212> TYPE: DNA
<213> ORGANISM: Artificial Sequence
<220> FEATURE:
<223> OTHER INFORMATION: Primer

<400> SEQUENCE: 197
catgatcagc tgggccaaga tgagctac                                     28

<210> SEQ ID NO 198
<211> LENGTH: 15
<212> TYPE: DNA
<213> ORGANISM: Artificial Sequence
<220> FEATURE:
```

```
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 198
tgagatgaag cactg                                                      15

<210> SEQ ID NO 199
<211> LENGTH: 29
<212> TYPE: DNA
<213> ORGANISM: Artificial Sequence
<220> FEATURE:
<223> OTHER INFORMATION: Primer

<400> SEQUENCE: 199
catgatcagc tgggccaaga ctagtacat                                       29

<210> SEQ ID NO 200
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(9)
<223> OTHER INFORMATION: Nucleotide at position 3 and/or 5 and/or 9
      may be modified by 2'-O,4'-C-methylene-beta-D-ribofuranosyl moiety

<400> SEQUENCE: 200
tacagtatag atgatg                                                     16

<210> SEQ ID NO 201
<211> LENGTH: 29
<212> TYPE: DNA
<213> ORGANISM: Artificial Sequence
<220> FEATURE:
<223> OTHER INFORMATION: Primer

<400> SEQUENCE: 201
catgatcagc tgggccaaga aagggattc                                       29

<210> SEQ ID NO 202
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 202
gtccagtttt ccca                                                       14

<210> SEQ ID NO 203
<211> LENGTH: 28
<212> TYPE: DNA
<213> ORGANISM: Artificial Sequence
<220> FEATURE:
<223> OTHER INFORMATION: Primer

<400> SEQUENCE: 203
catgatcagc tgggccaaga aacccatg                                        28
```

```
<210> SEQ ID NO 204
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 204
tgagaactga attcca                                                     16

<210> SEQ ID NO 205
<211> LENGTH: 30
<212> TYPE: DNA
<213> ORGANISM: Artificial Sequence
<220> FEATURE:
<223> OTHER INFORMATION: Primer

<400> SEQUENCE: 205
catgatcagc tgggccaaga gcagaagcat                                      30

<210> SEQ ID NO 206
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 206
gtgtgtggaa atgc                                                       14

<210> SEQ ID NO 207
<211> LENGTH: 29
<212> TYPE: DNA
<213> ORGANISM: Artificial Sequence
<220> FEATURE:
<223> OTHER INFORMATION: Primer

<400> SEQUENCE: 207
catgatcagc tgggccaaga acaaagttc                                       29

<210> SEQ ID NO 208
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 208
tcagtgcact acagaact                                                   18

<210> SEQ ID NO 209
<211> LENGTH: 29
<212> TYPE: DNA
```

-continued

<213> ORGANISM: Artificial Sequence
<220> FEATURE:
<223> OTHER INFORMATION: Primer

<400> SEQUENCE: 209
catgatcagc tgggccaaga acaaagttc                                      29

<210> SEQ ID NO 210
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 210
tcagtgcatc acag                                                      14

<210> SEQ ID NO 211
<211> LENGTH: 29
<212> TYPE: DNA
<213> ORGANISM: Artificial Sequence
<220> FEATURE:
<223> OTHER INFORMATION: Primer

<400> SEQUENCE: 211
catgatcagc tgggccaaga ggagtgaag                                      29

<210> SEQ ID NO 212
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 212
tctggctccg tgtc                                                      14

<210> SEQ ID NO 213
<211> LENGTH: 28
<212> TYPE: DNA
<213> ORGANISM: Artificial Sequence
<220> FEATURE:
<223> OTHER INFORMATION: Primer

<400> SEQUENCE: 213
catgatcagc tgggccaaga cactggta                                       28

<210> SEQ ID NO 214
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 214
tctcccaacc cttg                                                14

<210> SEQ ID NO 215
<211> LENGTH: 29
<212> TYPE: DNA
<213> ORGANISM: Artificial Sequence
<220> FEATURE:
<223> OTHER INFORMATION: Primer

<400> SEQUENCE: 215
catgatcagc tgggccaaga cctcaagga                                29

<210> SEQ ID NO 216
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 216
actagactga agctc                                               15

<210> SEQ ID NO 217
<211> LENGTH: 29
<212> TYPE: DNA
<213> ORGANISM: Artificial Sequence
<220> FEATURE:
<223> OTHER INFORMATION: Primer

<400> SEQUENCE: 217
catgatcagc tgggccaaga cccaagttc                                29

<210> SEQ ID NO 218
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 218
tcagtgcatg acag                                                14

<210> SEQ ID NO 219
<211> LENGTH: 29
<212> TYPE: DNA
<213> ORGANISM: Artificial Sequence
<220> FEATURE:
<223> OTHER INFORMATION: Primer

<400> SEQUENCE: 219
catgatcagc tgggccaaga tcacttttg                                29

<210> SEQ ID NO 220
<211> LENGTH: 16
<212> TYPE: DNA
<213> ORGANISM: Artificial Sequence
<220> FEATURE:
<223> OTHER INFORMATION: Primer

```
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 220
ttgcatagtc acaaaa                                                        16

<210> SEQ ID NO 221
<211> LENGTH: 29
<212> TYPE: DNA
<213> ORGANISM: Artificial Sequence
<220> FEATURE:
<223> OTHER INFORMATION: Primer

<400> SEQUENCE: 221
catgatcagc tgggccaaga aataggtca                                          29

<210> SEQ ID NO 222
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(8)
<223> OTHER INFORMATION: Nucleotide at position 6 and/or 8 may be
      modified by 2'-O,4'-C-methylene-beta-D-ribofuranosyl moiety

<400> SEQUENCE: 222
aatcatacac ggttgac                                                       17

<210> SEQ ID NO 223
<211> LENGTH: 29
<212> TYPE: DNA
<213> ORGANISM: Artificial Sequence
<220> FEATURE:
<223> OTHER INFORMATION: Primer

<400> SEQUENCE: 223
catgatcagc tgggccaaga cgaaggcaa                                          29

<210> SEQ ID NO 224
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(8)
<223> OTHER INFORMATION: Nucleotide at position 3 and/or 8 may be
      modified by 2'-O,4'-C-methylene-beta-D-ribofuranosyl moiety

<400> SEQUENCE: 224
taggttatcc gtgtt                                                         15

<210> SEQ ID NO 225
<211> LENGTH: 28
<212> TYPE: DNA
<213> ORGANISM: Artificial Sequence
<220> FEATURE:
<223> OTHER INFORMATION: Primer

<400> SEQUENCE: 225
catgatcagc tgggccaaga ccccctatc                                          28
```

```
<210> SEQ ID NO 226
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 2 and/or 5 may be
      modified by 2'-O,4'-C-methylene-beta-D-ribofuranosyl moiety

<400> SEQUENCE: 226
ttaatgctaa tcgtgatagg                                              20

<210> SEQ ID NO 227
<211> LENGTH: 29
<212> TYPE: DNA
<213> ORGANISM: Artificial Sequence
<220> FEATURE:
<223> OTHER INFORMATION: Primer

<400> SEQUENCE: 227
catgatcagc tgggccaaga actcaccga                                    29

<210> SEQ ID NO 228
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 228
aacattcaac gctgtc                                                  16

<210> SEQ ID NO 229
<211> LENGTH: 29
<212> TYPE: DNA
<213> ORGANISM: Artificial Sequence
<220> FEATURE:
<223> OTHER INFORMATION: Primer

<400> SEQUENCE: 229
catgatcagc tgggccaaga actcaccga                                    29

<210> SEQ ID NO 230
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 230
aacattcaac ctgtcg                                                  16

<210> SEQ ID NO 231
<211> LENGTH: 30
<212> TYPE: DNA
<213> ORGANISM: Artificial Sequence
```

```
<220> FEATURE:
<223> OTHER INFORMATION: Primer

<400> SEQUENCE: 231
catgatcagc tgggccaaga tagttggcaa                                              30

<210> SEQ ID NO 232
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 232
tggttctaga cttgc                                                              15

<210> SEQ ID NO 233
<211> LENGTH: 29
<212> TYPE: DNA
<213> ORGANISM: Artificial Sequence
<220> FEATURE:
<223> OTHER INFORMATION: Primer

<400> SEQUENCE: 233
catgatcagc tgggccaaga tgtgagttc                                               29

<210> SEQ ID NO 234
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 234
tttggcaatg gtag                                                               14

<210> SEQ ID NO 235
<211> LENGTH: 29
<212> TYPE: DNA
<213> ORGANISM: Artificial Sequence
<220> FEATURE:
<223> OTHER INFORMATION: Primer

<400> SEQUENCE: 235
catgatcagc tgggccaaga cagtgaatt                                               29

<210> SEQ ID NO 236
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 236
```

-continued tatggcactg gtag                                                    14

<210> SEQ ID NO 237
<211> LENGTH: 29
<212> TYPE: DNA
<213> ORGANISM: Artificial Sequence
<220> FEATURE:
<223> OTHER INFORMATION: Primer

<400> SEQUENCE: 237
catgatcagc tgggccaaga acccttatc                                    29

<210> SEQ ID NO 238
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 238
tggacggaga actg                                                    14

<210> SEQ ID NO 239
<211> LENGTH: 29
<212> TYPE: DNA
<213> ORGANISM: Artificial Sequence
<220> FEATURE:
<223> OTHER INFORMATION: Primer

<400> SEQUENCE: 239
catgatcagc tgggccaaga aagcccaaa                                    29

<210> SEQ ID NO 240
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(10)
<223> OTHER INFORMATION: Nucleotide at position 3 and/or 5 and/or 10
      may be modified by 2'-O,4'-C-methylene-beta-D-ribofuranosyl moiety

<400> SEQUENCE: 240
caaagaattc tccttttgg                                               19

<210> SEQ ID NO 241
<211> LENGTH: 30
<212> TYPE: DNA
<213> ORGANISM: Artificial Sequence
<220> FEATURE:
<223> OTHER INFORMATION: Primer

<400> SEQUENCE: 241
catgatcagc tgggccaaga cggctgcaac                                   30

<210> SEQ ID NO 242
<211> LENGTH: 14
<212> TYPE: DNA
<213> ORGANISM: Artificial Sequence
<220> FEATURE:
<223> OTHER INFORMATION: Primer
<220> FEATURE:

```
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 242
tcgtgtcttg tgtt                                                         14

<210> SEQ ID NO 243
<211> LENGTH: 30
<212> TYPE: DNA
<213> ORGANISM: Artificial Sequence
<220> FEATURE:
<223> OTHER INFORMATION: Primer

<400> SEQUENCE: 243
catgatcagc tgggccaaga accctccacc                                        30

<210> SEQ ID NO 244
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 244
catcccttgc atgg                                                         14

<210> SEQ ID NO 245
<211> LENGTH: 29
<212> TYPE: DNA
<213> ORGANISM: Artificial Sequence
<220> FEATURE:
<223> OTHER INFORMATION: Primer

<400> SEQUENCE: 245
catgatcagc tgggccaaga actgatatc                                         29

<210> SEQ ID NO 246
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 246
gtgcctactg agct                                                         14

<210> SEQ ID NO 247
<211> LENGTH: 29
<212> TYPE: DNA
<213> ORGANISM: Artificial Sequence
<220> FEATURE:
<223> OTHER INFORMATION: Primer

<400> SEQUENCE: 247
catgatcagc tgggccaaga acctaatat                                         29
```

```
<210> SEQ ID NO 248
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 4 and/or 6
      may be modified by 2'-O,4'-C-methylene-beta-D-ribofuranosyl moiety

<400> SEQUENCE: 248
tgatatgttt gatatattag                                                 20

<210> SEQ ID NO 249
<211> LENGTH: 29
<212> TYPE: DNA
<213> ORGANISM: Artificial Sequence
<220> FEATURE:
<223> OTHER INFORMATION: Primer

<400> SEQUENCE: 249
catgatcagc tgggccaaga agctgctttt                                      29

<210> SEQ ID NO 250
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 250
caacggaatc ccaaaag                                                    17

<210> SEQ ID NO 251
<211> LENGTH: 29
<212> TYPE: DNA
<213> ORGANISM: Artificial Sequence
<220> FEATURE:
<223> OTHER INFORMATION: Primer

<400> SEQUENCE: 251
catgatcagc tgggccaaga ggctgtcaa                                       29

<210> SEQ ID NO 252
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 252
ctgacctatg aattgac                                                    17

<210> SEQ ID NO 253
<211> LENGTH: 29
<212> TYPE: DNA
<213> ORGANISM: Artificial Sequence
<220> FEATURE:
```

<223> OTHER INFORMATION: Primer

<400> SEQUENCE: 253
catgatcagc tgggccaaga ctgggactt                29

<210> SEQ ID NO 254
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 254
aactggccta caaag                15

<210> SEQ ID NO 255
<211> LENGTH: 28
<212> TYPE: DNA
<213> ORGANISM: Artificial Sequence
<220> FEATURE:
<223> OTHER INFORMATION: Primer

<400> SEQUENCE: 255
catgatcagc tgggccaaga tccacatg                28

<210> SEQ ID NO 256
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 256
tgtaacagca actcca                16

<210> SEQ ID NO 257
<211> LENGTH: 29
<212> TYPE: DNA
<213> ORGANISM: Artificial Sequence
<220> FEATURE:
<223> OTHER INFORMATION: Primer

<400> SEQUENCE: 257
catgatcagc tgggccaaga gccaatatt                29

<210> SEQ ID NO 258
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: Nucleotide at position 2 and/or 4 and/or 7 may
      be modified by 2'-O,4'-C-methylene-beta-D-ribofuranosyl moiety

<400> SEQUENCE: 258
tagcagcaca gaaata                16

<210> SEQ ID NO 259
<211> LENGTH: 30
<212> TYPE: DNA
<213> ORGANISM: Artificial Sequence
<220> FEATURE:
<223> OTHER INFORMATION: Primer

<400> SEQUENCE: 259
catgatcagc tgggccaaga ccaacaacag					30

<210> SEQ ID NO 260
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 260
taggtagttt cctgt					15

<210> SEQ ID NO 261
<211> LENGTH: 30
<212> TYPE: DNA
<213> ORGANISM: Artificial Sequence
<220> FEATURE:
<223> OTHER INFORMATION: Primer

<400> SEQUENCE: 261
catgatcagc tgggccaaga ccaacaacat					30

<210> SEQ ID NO 262
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 262
taggtagttt catgttg					17

<210> SEQ ID NO 263
<211> LENGTH: 29
<212> TYPE: DNA
<213> ORGANISM: Artificial Sequence
<220> FEATURE:
<223> OTHER INFORMATION: Primer

<400> SEQUENCE: 263
catgatcagc tgggccaaga gctgggtgg					29

<210> SEQ ID NO 264
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature

```
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 264
ttcaccacct tctc                                                        14

<210> SEQ ID NO 265
<211> LENGTH: 28
<212> TYPE: DNA
<213> ORGANISM: Artificial Sequence
<220> FEATURE:
<223> OTHER INFORMATION: Primer

<400> SEQUENCE: 265
catgatcagc tgggccaaga cctatctc                                         28

<210> SEQ ID NO 266
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 266
ggtccagagg ggag                                                        14

<210> SEQ ID NO 267
<211> LENGTH: 29
<212> TYPE: DNA
<213> ORGANISM: Artificial Sequence
<220> FEATURE:
<223> OTHER INFORMATION: Primer

<400> SEQUENCE: 267
catgatcagc tgggccaaga aaccaatgt                                        29

<210> SEQ ID NO 268
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 268
tacagtagtc tgcac                                                       15

<210> SEQ ID NO 269
<211> LENGTH: 29
<212> TYPE: DNA
<213> ORGANISM: Artificial Sequence
<220> FEATURE:
<223> OTHER INFORMATION: Primer

<400> SEQUENCE: 269
catgatcagc tgggccaaga gaacaggta                                        29

<210> SEQ ID NO 270
```

```
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 270
cccagtgttc agac                                                        14

<210> SEQ ID NO 271
<211> LENGTH: 30
<212> TYPE: DNA
<213> ORGANISM: Artificial Sequence
<220> FEATURE:
<223> OTHER INFORMATION: Primer

<400> SEQUENCE: 271
catgatcagc tgggccaaga gaacagatag                                       30

<210> SEQ ID NO 272
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 272
cccagtgttt agac                                                        14

<210> SEQ ID NO 273
<211> LENGTH: 29
<212> TYPE: DNA
<213> ORGANISM: Artificial Sequence
<220> FEATURE:
<223> OTHER INFORMATION: Primer

<400> SEQUENCE: 273
catgatcagc tgggccaaga acatcgtta                                        29

<210> SEQ ID NO 274
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 274
taacactgtc tggt                                                        14

<210> SEQ ID NO 275
<211> LENGTH: 29
<212> TYPE: DNA
<213> ORGANISM: Artificial Sequence
<220> FEATURE:
<223> OTHER INFORMATION: Primer
```

<400> SEQUENCE: 275
catgatcagc tgggccaaga gtcatcatt                                29

<210> SEQ ID NO 276
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(9)
<223> OTHER INFORMATION: Nucleotide at position 6 and/or 9 may be
      modified by 2'-O,4'-C-methylene-beta-D-ribofuranosyl moiety

<400> SEQUENCE: 276
taatactgcc tggtaat                                             17

<210> SEQ ID NO 277
<211> LENGTH: 30
<212> TYPE: DNA
<213> ORGANISM: Artificial Sequence
<220> FEATURE:
<223> OTHER INFORMATION: Primer

<400> SEQUENCE: 277
catgatcagc tgggccaaga ttttcccatg                               30

<210> SEQ ID NO 278
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(10)
<223> OTHER INFORMATION: Nucleotide at position 2 and/or 4 and/or 10
      may be modified by 2'-O,4'-C-methylene-beta-D-ribofuranosyl moiety

<400> SEQUENCE: 278
agaggtatag ggcat                                               15

<210> SEQ ID NO 279
<211> LENGTH: 29
<212> TYPE: DNA
<213> ORGANISM: Artificial Sequence
<220> FEATURE:
<223> OTHER INFORMATION: Primer

<400> SEQUENCE: 279
catgatcagc tgggccaaga ctagtggtc                                29

<210> SEQ ID NO 280
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 280
gtgaaatgtt taggacc                                             17

```
<210> SEQ ID NO 281
<211> LENGTH: 29
<212> TYPE: DNA
<213> ORGANISM: Artificial Sequence
<220> FEATURE:
<223> OTHER INFORMATION: Primer

<400> SEQUENCE: 281
catgatcagc tgggccaaga aggcatagg                                    29

<210> SEQ ID NO 282
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 282
ttccctttgt catcc                                                   15

<210> SEQ ID NO 283
<211> LENGTH: 30
<212> TYPE: DNA
<213> ORGANISM: Artificial Sequence
<220> FEATURE:
<223> OTHER INFORMATION: Primer

<400> SEQUENCE: 283
catgatcagc tgggccaaga cagactccgg                                   30

<210> SEQ ID NO 284
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 284
tccttcattc cacc                                                    14

<210> SEQ ID NO 285
<211> LENGTH: 27
<212> TYPE: DNA
<213> ORGANISM: Artificial Sequence
<220> FEATURE:
<223> OTHER INFORMATION: Primer

<400> SEQUENCE: 285
catgatcagc tgggccaaga ccacaca                                      27

<210> SEQ ID NO 286
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
```

```
<223> OTHER INFORMATION: Nucleotide at position 2 and/or 3 and/or 6 may
      be modified by 2'-O,4'-C-methylene-beta-D-ribofuranosyl moiety

<400> SEQUENCE: 286
tggaatgtaa ggaagtgt                                                   18

<210> SEQ ID NO 287
<211> LENGTH: 33
<212> TYPE: DNA
<213> ORGANISM: Artificial Sequence
<220> FEATURE:
<223> OTHER INFORMATION: Primer

<400> SEQUENCE: 287
catgatcagc tgggccaaga acaagctttt tgc                                  33

<210> SEQ ID NO 288
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(9)
<223> OTHER INFORMATION: Nucleotide at position 5 and/or 7 and/or 9 may
      be modified by 2'-O,4'-C-methylene-beta-D-ribofuranosyl moiety

<400> SEQUENCE: 288
ataagacgag caaaaag                                                    17

<210> SEQ ID NO 289
<211> LENGTH: 30
<212> TYPE: DNA
<213> ORGANISM: Artificial Sequence
<220> FEATURE:
<223> OTHER INFORMATION: Primer

<400> SEQUENCE: 289
catgatcagc tgggccaaga tcagccgctg                                      30

<210> SEQ ID NO 290
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 290
ctgtgcgtgt gaca                                                       14

<210> SEQ ID NO 291
<211> LENGTH: 29
<212> TYPE: DNA
<213> ORGANISM: Artificial Sequence
<220> FEATURE:
<223> OTHER INFORMATION: Primer

<400> SEQUENCE: 291
catgatcagc tgggccaaga aggcgaagg                                       29

<210> SEQ ID NO 292
<211> LENGTH: 15
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 292
ttccctttgt catcc                                                          15

<210> SEQ ID NO 293
<211> LENGTH: 29
<212> TYPE: DNA
<213> ORGANISM: Artificial Sequence
<220> FEATURE:
<223> OTHER INFORMATION: Primer

<400> SEQUENCE: 293
catgatcagc tgggccaaga ggccgtgac                                           29

<210> SEQ ID NO 294
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 294
taacagtctc cagtca                                                         16

<210> SEQ ID NO 295
<211> LENGTH: 30
<212> TYPE: DNA
<213> ORGANISM: Artificial Sequence
<220> FEATURE:
<223> OTHER INFORMATION: Primer

<400> SEQUENCE: 295
catgatcagc tgggccaaga ggtacaatca                                          30

<210> SEQ ID NO 296
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 296
accatcgacc gttg                                                           14

<210> SEQ ID NO 297
<211> LENGTH: 30
<212> TYPE: DNA
<213> ORGANISM: Artificial Sequence
<220> FEATURE:
<223> OTHER INFORMATION: Primer
```

```
<400> SEQUENCE: 297
catgatcagc tgggccaaga ctgcctgtct                                30

<210> SEQ ID NO 298
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 298
acagcaggca caga                                                 14

<210> SEQ ID NO 299
<211> LENGTH: 29
<212> TYPE: DNA
<213> ORGANISM: Artificial Sequence
<220> FEATURE:
<223> OTHER INFORMATION: Primer

<400> SEQUENCE: 299
catgatcagc tgggccaaga gtctgtcaa                                 29

<210> SEQ ID NO 300
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 300
atgacctatg aattgac                                              17

<210> SEQ ID NO 301
<211> LENGTH: 29
<212> TYPE: DNA
<213> ORGANISM: Artificial Sequence
<220> FEATURE:
<223> OTHER INFORMATION: Primer

<400> SEQUENCE: 301
catgatcagc tgggccaaga cacagttgc                                 29

<210> SEQ ID NO 302
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 302
taatctcagc tggca                                                15
```

-continued

```
<210> SEQ ID NO 303
<211> LENGTH: 29
<212> TYPE: DNA
<213> ORGANISM: Artificial Sequence
<220> FEATURE:
<223> OTHER INFORMATION: Primer

<400> SEQUENCE: 303
catgatcagc tgggccaaga atccaatca                                29

<210> SEQ ID NO 304
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 304
tactgcatca ggaactga                                            18

<210> SEQ ID NO 305
<211> LENGTH: 29
<212> TYPE: DNA
<213> ORGANISM: Artificial Sequence
<220> FEATURE:
<223> OTHER INFORMATION: Primer

<400> SEQUENCE: 305
catgatcagc tgggccaaga acatggtta                                29

<210> SEQ ID NO 306
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(9)
<223> OTHER INFORMATION: Nucleotide at position 4 and/or 9 may be
      modified by 2'-O,4'-C-methylene-beta-D-ribofuranosyl moiety

<400> SEQUENCE: 306
ttgtgcttga tctaac                                              16

<210> SEQ ID NO 307
<211> LENGTH: 30
<212> TYPE: DNA
<213> ORGANISM: Artificial Sequence
<220> FEATURE:
<223> OTHER INFORMATION: Primer

<400> SEQUENCE: 307
catgatcagc tgggccaaga aaagtgtcag                               30

<210> SEQ ID NO 308
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
``` modified by 2'-O,4'-C-methylene-beta-D-ribofuranosyl moiety

<400> SEQUENCE: 308
ccacaccgta tctg                                                           14

<210> SEQ ID NO 309
<211> LENGTH: 29
<212> TYPE: DNA
<213> ORGANISM: Artificial Sequence
<220> FEATURE:
<223> OTHER INFORMATION: Primer

<400> SEQUENCE: 309
catgatcagc tgggccaaga gaaacccag                                           29

<210> SEQ ID NO 310
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 310
agctacattg tctgc                                                          15

<210> SEQ ID NO 311
<211> LENGTH: 28
<212> TYPE: DNA
<213> ORGANISM: Artificial Sequence
<220> FEATURE:
<223> OTHER INFORMATION: Primer

<400> SEQUENCE: 311
catgatcagc tgggccaaga gagaccca                                            28

<210> SEQ ID NO 312
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 312
agctacatct ggct                                                           14

<210> SEQ ID NO 313
<211> LENGTH: 30
<212> TYPE: DNA
<213> ORGANISM: Artificial Sequence
<220> FEATURE:
<223> OTHER INFORMATION: Primer

<400> SEQUENCE: 313
catgatcagc tgggccaaga ggggtatttg                                          30

<210> SEQ ID NO 314
<211> LENGTH: 15
<212> TYPE: DNA

```
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 314
tgtcagtttg tcaaa                                                       15

<210> SEQ ID NO 315
<211> LENGTH: 28
<212> TYPE: DNA
<213> ORGANISM: Artificial Sequence
<220> FEATURE:
<223> OTHER INFORMATION: Primer

<400> SEQUENCE: 315
catgatcagc tgggccaaga taaacgga                                         28

<210> SEQ ID NO 316
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 316
caagtcacta gtggtt                                                      16

<210> SEQ ID NO 317
<211> LENGTH: 29
<212> TYPE: DNA
<213> ORGANISM: Artificial Sequence
<220> FEATURE:
<223> OTHER INFORMATION: Primer

<400> SEQUENCE: 317
catgatcagc tgggccaaga acaggattg                                        29

<210> SEQ ID NO 318
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 318
agggcccccc ctcaa                                                       15

<210> SEQ ID NO 319
<211> LENGTH: 29
<212> TYPE: DNA
<213> ORGANISM: Artificial Sequence
<220> FEATURE:
<223> OTHER INFORMATION: Primer

<400> SEQUENCE: 319
```

```
catgatcagc tgggccaaga atgtatgtg                                          29
```

<210> SEQ ID NO 320
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 320

```
tggtttaccg tccc                                                          14
```

<210> SEQ ID NO 321
<211> LENGTH: 30
<212> TYPE: DNA
<213> ORGANISM: Artificial Sequence
<220> FEATURE:
<223> OTHER INFORMATION: Primer

<400> SEQUENCE: 321

```
catgatcagc tgggccaaga gctttgacaa                                         30
```

<210> SEQ ID NO 322
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 322

```
cagtgcaata gtattgt                                                       17
```

<210> SEQ ID NO 323
<211> LENGTH: 30
<212> TYPE: DNA
<213> ORGANISM: Artificial Sequence
<220> FEATURE:
<223> OTHER INFORMATION: Primer

<400> SEQUENCE: 323

```
catgatcagc tgggccaaga aaagcaagta                                         30
```

<210> SEQ ID NO 324
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(7)
<223> OTHER INFORMATION: Nucleotide at position 5 and/or 7 may be
      modified by 2'-O,4'-C-methylene-beta-D-ribofuranosyl moiety

<400> SEQUENCE: 324

```
taaacgtgga tgtac                                                         15
```

<210> SEQ ID NO 325

```
<211> LENGTH: 30
<212> TYPE: DNA
<213> ORGANISM: Artificial Sequence
<220> FEATURE:
<223> OTHER INFORMATION: Primer

<400> SEQUENCE: 325
catgatcagc tgggccaaga tcaccaaaac                                              30

<210> SEQ ID NO 326
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 326
taagtgcttc catgt                                                              15

<210> SEQ ID NO 327
<211> LENGTH: 30
<212> TYPE: DNA
<213> ORGANISM: Artificial Sequence
<220> FEATURE:
<223> OTHER INFORMATION: Primer

<400> SEQUENCE: 327
catgatcagc tgggccaaga agaaagcact                                              30

<210> SEQ ID NO 328
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(8)
<223> OTHER INFORMATION: Nucleotide at position 2 and/or 8 may be
      modified by 2'-O,4'-C-methylene-beta-D-ribofuranosyl moiety

<400> SEQUENCE: 328
actttaacat ggaagtg                                                            17

<210> SEQ ID NO 329
<211> LENGTH: 30
<212> TYPE: DNA
<213> ORGANISM: Artificial Sequence
<220> FEATURE:
<223> OTHER INFORMATION: Primer

<400> SEQUENCE: 329
catgatcagc tgggccaaga ctactaaaac                                              30

<210> SEQ ID NO 330
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety
```

-continued

<400> SEQUENCE: 330
taagtgcttc catgt                                                        15

<210> SEQ ID NO 331
<211> LENGTH: 30
<212> TYPE: DNA
<213> ORGANISM: Artificial Sequence
<220> FEATURE:
<223> OTHER INFORMATION: Primer

<400> SEQUENCE: 331
catgatcagc tgggccaaga acactcaaac                                        30

<210> SEQ ID NO 332
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 332
taagtgcttc catgt                                                        15

<210> SEQ ID NO 333
<211> LENGTH: 29
<212> TYPE: DNA
<213> ORGANISM: Artificial Sequence
<220> FEATURE:
<223> OTHER INFORMATION: Primer

<400> SEQUENCE: 333
catgatcagc tgggccaaga cagcaggta                                         29

<210> SEQ ID NO 334
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(9)
<223> OTHER INFORMATION: Nucleotide at position 3 and/or 6 and/or 9 may
      be modified by 2'-O,4'-C-methylene-beta-D-ribofuranosyl moiety

<400> SEQUENCE: 334
tttaacatgg gggtacc                                                      17

<210> SEQ ID NO 335
<211> LENGTH: 29
<212> TYPE: DNA
<213> ORGANISM: Artificial Sequence
<220> FEATURE:
<223> OTHER INFORMATION: Primer

<400> SEQUENCE: 335
catgatcagc tgggccaaga ccactgaaa                                         29

<210> SEQ ID NO 336
<211> LENGTH: 19
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 336
taagtgcttc catgtttca                                              19

<210> SEQ ID NO 337
<211> LENGTH: 28
<212> TYPE: DNA
<213> ORGANISM: Artificial Sequence
<220> FEATURE:
<223> OTHER INFORMATION: Primer

<400> SEQUENCE: 337
catgatcagc tgggccaaga ttcgccct                                    28

<210> SEQ ID NO 338
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(8)
<223> OTHER INFORMATION: Nucleotide at position 5 and/or 8 may be
      modified by 2'-O,4'-C-methylene-beta-D-ribofuranosyl moiety

<400> SEQUENCE: 338
aaaagctggg ttgagagg                                               18

<210> SEQ ID NO 339
<211> LENGTH: 30
<212> TYPE: DNA
<213> ORGANISM: Artificial Sequence
<220> FEATURE:
<223> OTHER INFORMATION: Primer

<400> SEQUENCE: 339
catgatcagc tgggccaaga agaggtcgac                                  30

<210> SEQ ID NO 340
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 340
gcacattaca cggt                                                   14

<210> SEQ ID NO 341
<211> LENGTH: 30
<212> TYPE: DNA
<213> ORGANISM: Artificial Sequence
<220> FEATURE:
<223> OTHER INFORMATION: Primer

<400> SEQUENCE: 341
```

```
catgatcagc tgggccaaga ccagcagcac                                    30
```

<210> SEQ ID NO 342
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 342

```
ccactgcccc aggt                                                     14
```

<210> SEQ ID NO 343
<211> LENGTH: 30
<212> TYPE: DNA
<213> ORGANISM: Artificial Sequence
<220> FEATURE:
<223> OTHER INFORMATION: Primer

<400> SEQUENCE: 343

```
catgatcagc tgggccaaga acaccaatgc                                    30
```

<210> SEQ ID NO 344
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 344

```
cgcatcccct aggg                                                     14
```

<210> SEQ ID NO 345
<211> LENGTH: 30
<212> TYPE: DNA
<213> ORGANISM: Artificial Sequence
<220> FEATURE:
<223> OTHER INFORMATION: Primer

<400> SEQUENCE: 345

```
catgatcagc tgggccaaga acacttactg                                    30
```

<210> SEQ ID NO 346
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 346

```
cctagtaggt gtcc                                                     14
```

<210> SEQ ID NO 347
<211> LENGTH: 30

```
<212> TYPE: DNA
<213> ORGANISM: Artificial Sequence
<220> FEATURE:
<223> OTHER INFORMATION: Primer

<400> SEQUENCE: 347
catgatcagc tgggccaaga ctggaggaag                                              30

<210> SEQ ID NO 348
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 348
cctctgggcc cttc                                                               14

<210> SEQ ID NO 349
<211> LENGTH: 30
<212> TYPE: DNA
<213> ORGANISM: Artificial Sequence
<220> FEATURE:
<223> OTHER INFORMATION: Primer

<400> SEQUENCE: 349
catgatcagc tgggccaaga acggaagggc                                              30

<210> SEQ ID NO 350
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 350
ctggccctct ctgc                                                               14

<210> SEQ ID NO 351
<211> LENGTH: 30
<212> TYPE: DNA
<213> ORGANISM: Artificial Sequence
<220> FEATURE:
<223> OTHER INFORMATION: Primer

<400> SEQUENCE: 351
catgatcagc tgggccaaga tctctgcagg                                              30

<210> SEQ ID NO 352
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety
```

```
<400> SEQUENCE: 352
gcaaagcaca cggc                                                    14

<210> SEQ ID NO 353
<211> LENGTH: 30
<212> TYPE: DNA
<213> ORGANISM: Artificial Sequence
<220> FEATURE:
<223> OTHER INFORMATION: Primer

<400> SEQUENCE: 353
catgatcagc tgggccaaga ttctaggata                                   30

<210> SEQ ID NO 354
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 354 gccctgggc ctat                                                     14

<210> SEQ ID NO 355
<211> LENGTH: 30
<212> TYPE: DNA
<213> ORGANISM: Artificial Sequence
<220> FEATURE:
<223> OTHER INFORMATION: Primer

<400> SEQUENCE: 355
catgatcagc tgggccaaga aaaggcatca                                   30

<210> SEQ ID NO 356
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 356
tccagctcct atatg                                                   15

<210> SEQ ID NO 357
<211> LENGTH: 30
<212> TYPE: DNA
<213> ORGANISM: Artificial Sequence
<220> FEATURE:
<223> OTHER INFORMATION: Primer

<400> SEQUENCE: 357
catgatcagc tgggccaaga tcaacaaaat                                   30

<210> SEQ ID NO 358
<211> LENGTH: 17
<212> TYPE: DNA
<213> ORGANISM: Artificial Sequence
<220> FEATURE:
```

```
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 358
tccagcatca gtgattt                                                    17

<210> SEQ ID NO 359
<211> LENGTH: 29
<212> TYPE: DNA
<213> ORGANISM: Artificial Sequence
<220> FEATURE:
<223> OTHER INFORMATION: Primer

<400> SEQUENCE: 359
catgatcagc tgggccaaga tgagctcct                                       29

<210> SEQ ID NO 360
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 360
tccctgtcct ccagg                                                      15

<210> SEQ ID NO 361
<211> LENGTH: 30
<212> TYPE: DNA
<213> ORGANISM: Artificial Sequence
<220> FEATURE:
<223> OTHER INFORMATION: Primer

<400> SEQUENCE: 361
catgatcagc tgggccaaga ggctataaag                                      30

<210> SEQ ID NO 362
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 362
tccgtctcag ttac                                                       14

<210> SEQ ID NO 363
<211> LENGTH: 28
<212> TYPE: DNA
<213> ORGANISM: Artificial Sequence
<220> FEATURE:
<223> OTHER INFORMATION: Primer

<400> SEQUENCE: 363
catgatcagc tgggccaaga gacgggtg                                        28
```

<210> SEQ ID NO 364
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
    modified by 2'-O,4'-C-methylene-beta-D-ribofuranosyl moiety

<400> SEQUENCE: 364
tctcacacag aaatcg                                                  16

<210> SEQ ID NO 365
<211> LENGTH: 30
<212> TYPE: DNA
<213> ORGANISM: Artificial Sequence
<220> FEATURE:
<223> OTHER INFORMATION: Primer

<400> SEQUENCE: 365
catgatcagc tgggccaaga gccctggact                                   30

<210> SEQ ID NO 366
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
    modified by 2'-O,4'-C-methylene-beta-D-ribofuranosyl moiety

<400> SEQUENCE: 366
tgctgactcc tagt                                                    14

<210> SEQ ID NO 367
<211> LENGTH: 30
<212> TYPE: DNA
<213> ORGANISM: Artificial Sequence
<220> FEATURE:
<223> OTHER INFORMATION: Primer

<400> SEQUENCE: 367
catgatcagc tgggccaaga agaggcaggc                                   30

<210> SEQ ID NO 368
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
    modified by 2'-O,4'-C-methylene-beta-D-ribofuranosyl moiety

<400> SEQUENCE: 368
tgtctgcccg catg                                                    14

<210> SEQ ID NO 369
<211> LENGTH: 30
<212> TYPE: DNA

```
<213> ORGANISM: Artificial Sequence
<220> FEATURE:
<223> OTHER INFORMATION: Primer

<400> SEQUENCE: 369
catgatcagc tgggccaaga tacagatgga                                    30

<210> SEQ ID NO 370
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(9)
<223> OTHER INFORMATION: Nucleotide at position 4 and/or 6 and/or 9 may
      be modified by 2'-O,4'-C-methylene-beta-D-ribofuranosyl moiety

<400> SEQUENCE: 370
aattgcacgg tatcc                                                    15

<210> SEQ ID NO 371
<211> LENGTH: 30
<212> TYPE: DNA
<213> ORGANISM: Artificial Sequence
<220> FEATURE:
<223> OTHER INFORMATION: Primer

<400> SEQUENCE: 371
catgatcagc tgggccaaga tcaccattgc                                    30

<210> SEQ ID NO 372
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 372
aattgcactt tagcaat                                                  17

<210> SEQ ID NO 373
<211> LENGTH: 30
<212> TYPE: DNA
<213> ORGANISM: Artificial Sequence
<220> FEATURE:
<223> OTHER INFORMATION: Primer

<400> SEQUENCE: 373
catgatcagc tgggccaaga aaacgtggaa                                    30

<210> SEQ ID NO 374
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(8)
<223> OTHER INFORMATION: Nucleotide at position 2 and/or 8 may be
      modified by 2'-O,4'-C-methylene-beta-D-ribofuranosyl moiety

<400> SEQUENCE: 374
```

```
acatagagga aattccac                                          18

<210> SEQ ID NO 375
<211> LENGTH: 30
<212> TYPE: DNA
<213> ORGANISM: Artificial Sequence
<220> FEATURE:
<223> OTHER INFORMATION: Primer

<400> SEQUENCE: 375
catgatcagc tgggccaaga ccaggttcca                             30

<210> SEQ ID NO 376
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 376
gcctgctggg gtgg                                              14

<210> SEQ ID NO 377
<211> LENGTH: 30
<212> TYPE: DNA
<213> ORGANISM: Artificial Sequence
<220> FEATURE:
<223> OTHER INFORMATION: Primer

<400> SEQUENCE: 377
catgatcagc tgggccaaga acactcaaaa                             30

<210> SEQ ID NO 378
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 378
gtgccgccat cttt                                              14

<210> SEQ ID NO 379
<211> LENGTH: 30
<212> TYPE: DNA
<213> ORGANISM: Artificial Sequence
<220> FEATURE:
<223> OTHER INFORMATION: Primer

<400> SEQUENCE: 379
catgatcagc tgggccaaga acgctcaaat                             30

<210> SEQ ID NO 380
<211> LENGTH: 14
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 380
aaagtgctgc gaca                                                         14

<210> SEQ ID NO 381
<211> LENGTH: 30
<212> TYPE: DNA
<213> ORGANISM: Artificial Sequence
<220> FEATURE:
<223> OTHER INFORMATION: Primer

<400> SEQUENCE: 381
catgatcagc tgggccaaga ggaaagcgcc                                        30

<210> SEQ ID NO 382
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 382
actcaaaatg gggg                                                         14

<210> SEQ ID NO 383
<211> LENGTH: 30
<212> TYPE: DNA
<213> ORGANISM: Artificial Sequence
<220> FEATURE:
<223> OTHER INFORMATION: Primer

<400> SEQUENCE: 383
catgatcagc tgggccaaga acaccccaaa                                        30

<210> SEQ ID NO 384
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 384
gaagtgcttc gattttgg                                                     18

<210> SEQ ID NO 385
<211> LENGTH: 29
<212> TYPE: DNA
<213> ORGANISM: Artificial Sequence
<220> FEATURE:
<223> OTHER INFORMATION: Primer

<400> SEQUENCE: 385
catgatcagc tgggccaaga cacttatca                                         29
```

```
<210> SEQ ID NO 386
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(9)
<223> OTHER INFORMATION: Nucleotide at position 3 and/or 5 and/or 9 may
      be modified by 2'-O,4'-C-methylene-beta-D-ribofuranosyl moiety

<400> SEQUENCE: 386
ttataataca acctgataag                                              20

<210> SEQ ID NO 387
<211> LENGTH: 30
<212> TYPE: DNA
<213> ORGANISM: Artificial Sequence
<220> FEATURE:
<223> OTHER INFORMATION: Primer

<400> SEQUENCE: 387
catgatcagc tgggccaaga tcacgcgagc                                   30

<210> SEQ ID NO 388
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 388
tttgttcgtt cggc                                                    14

<210> SEQ ID NO 389
<211> LENGTH: 28
<212> TYPE: DNA
<213> ORGANISM: Artificial Sequence
<220> FEATURE:
<223> OTHER INFORMATION: Primer

<400> SEQUENCE: 389
catgatcagc tgggccaaga aacatgga                                     28

<210> SEQ ID NO 390
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(9)
<223> OTHER INFORMATION: Nucleotide at position 3 and/or 6 and/or 9 may
      be modified by 2'-O,4'-C-methylene-beta-D-ribofuranosyl moiety

<400> SEQUENCE: 390
atcatagagg aaaatcca                                                18

<210> SEQ ID NO 391
<211> LENGTH: 30
<212> TYPE: DNA
<213> ORGANISM: Artificial Sequence
```

<220> FEATURE:
<223> OTHER INFORMATION: Primer

<400> SEQUENCE: 391
catgatcagc tgggccaaga acacaggacc                                           30

<210> SEQ ID NO 392
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 392
ctcctgactc cagg                                                            14

<210> SEQ ID NO 393
<211> LENGTH: 27
<212> TYPE: DNA
<213> ORGANISM: Artificial Sequence
<220> FEATURE:
<223> OTHER INFORMATION: Primer

<400> SEQUENCE: 393
catgatcagc tgggccaaga tacgttc                                              27

<210> SEQ ID NO 394
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 394
tggtagacta tggaacg                                                         17

<210> SEQ ID NO 395
<211> LENGTH: 30
<212> TYPE: DNA
<213> ORGANISM: Artificial Sequence
<220> FEATURE:
<223> OTHER INFORMATION: Primer

<400> SEQUENCE: 395
catgatcagc tgggccaaga gcgcatgttc                                           30

<210> SEQ ID NO 396
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 396
tggttgacca taga                                                          14

<210> SEQ ID NO 397
<211> LENGTH: 30
<212> TYPE: DNA
<213> ORGANISM: Artificial Sequence
<220> FEATURE:
<223> OTHER INFORMATION: Primer

<400> SEQUENCE: 397
catgatcagc tgggccaaga aagatgtgga                                         30

<210> SEQ ID NO 398
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 398
tatgtaatat ggtccaca                                                      18

<210> SEQ ID NO 399
<211> LENGTH: 29
<212> TYPE: DNA
<213> ORGANISM: Artificial Sequence
<220> FEATURE:
<223> OTHER INFORMATION: Primer

<400> SEQUENCE: 399
catgatcagc tgggccaaga acagagagc                                          29

<210> SEQ ID NO 400
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(8)
<223> OTHER INFORMATION: Nucleotide at position 5 and/or 8 may be
      modified by 2'-O,4'-C-methylene-beta-D-ribofuranosyl moiety

<400> SEQUENCE: 400
tatacaaggg caagct                                                        16

<210> SEQ ID NO 401
<211> LENGTH: 30
<212> TYPE: DNA
<213> ORGANISM: Artificial Sequence
<220> FEATURE:
<223> OTHER INFORMATION: Primer

<400> SEQUENCE: 401
catgatcagc tgggccaaga cgaatccacc                                         30

<210> SEQ ID NO 402
<211> LENGTH: 15
<212> TYPE: DNA
<213> ORGANISM: Artificial Sequence
<220> FEATURE:
<223> OTHER INFORMATION: Primer
<220> FEATURE:

```
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 402
gaagttgttc gtggt                                                     15

<210> SEQ ID NO 403
<211> LENGTH: 30
<212> TYPE: DNA
<213> ORGANISM: Artificial Sequence
<220> FEATURE:
<223> OTHER INFORMATION: Primer

<400> SEQUENCE: 403
catgatcagc tgggccaaga agccacaatc                                     30

<210> SEQ ID NO 404
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 404
agatcagaag gtgattgt                                                  18

<210> SEQ ID NO 405
<211> LENGTH: 29
<212> TYPE: DNA
<213> ORGANISM: Artificial Sequence
<220> FEATURE:
<223> OTHER INFORMATION: Primer

<400> SEQUENCE: 405
catgatcagc tgggccaaga acaggccat                                      29

<210> SEQ ID NO 406
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(10)
<223> OTHER INFORMATION: Nucleotide at position 3 and/or 5 and/or 8
      and/or 10 may be modified by 2'-O,4'-C-methylene-beta-D-
      ribofuranosyl moiety

<400> SEQUENCE: 406
aatataacac agatggc                                                   17

<210> SEQ ID NO 407
<211> LENGTH: 30
<212> TYPE: DNA
<213> ORGANISM: Artificial Sequence
<220> FEATURE:
<223> OTHER INFORMATION: Primer

<400> SEQUENCE: 407
catgatcagc tgggccaaga acggctagtg                                     30
```

```
<210> SEQ ID NO 408
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 408
acttcacctg gtccacta                                                  18

<210> SEQ ID NO 409
<211> LENGTH: 30
<212> TYPE: DNA
<213> ORGANISM: Artificial Sequence
<220> FEATURE:
<223> OTHER INFORMATION: Primer

<400> SEQUENCE: 409
catgatcagc tgggccaaga ggccttctga                                     30

<210> SEQ ID NO 410
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 410
ctggacttag ggtc                                                      14

<210> SEQ ID NO 411
<211> LENGTH: 30
<212> TYPE: DNA
<213> ORGANISM: Artificial Sequence
<220> FEATURE:
<223> OTHER INFORMATION: Primer

<400> SEQUENCE: 411
catgatcagc tgggccaaga ggccttctga                                     30

<210> SEQ ID NO 412
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 412
ctggacttgg agtc                                                      14

<210> SEQ ID NO 413
<211> LENGTH: 30
<212> TYPE: DNA
<213> ORGANISM: Artificial Sequence
```

```
<220> FEATURE:
<223> OTHER INFORMATION: Primer

<400> SEQUENCE: 413
catgatcagc tgggccaaga ctgaggggcc                                              30

<210> SEQ ID NO 414
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 414
agctcggtct gagg                                                               14

<210> SEQ ID NO 415
<211> LENGTH: 30
<212> TYPE: DNA
<213> ORGANISM: Artificial Sequence
<220> FEATURE:
<223> OTHER INFORMATION: Primer

<400> SEQUENCE: 415
catgatcagc tgggccaaga ttcaaaacat                                              30

<210> SEQ ID NO 416
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 416
cagcagcaat tcatgtttt                                                          19

<210> SEQ ID NO 417
<211> LENGTH: 30
<212> TYPE: DNA
<213> ORGANISM: Artificial Sequence
<220> FEATURE:
<223> OTHER INFORMATION: Primer

<400> SEQUENCE: 417
catgatcagc tgggccaaga ggcggacacg                                              30

<210> SEQ ID NO 418
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 418
```
atcgggaatg tcgt                                                         14

<210> SEQ ID NO 419
<211> LENGTH: 31
<212> TYPE: DNA
<213> ORGANISM: Artificial Sequence
<220> FEATURE:
<223> OTHER INFORMATION: Primer

<400> SEQUENCE: 419
catgatcagc tgggccaaga acggttttac c                                      31

<210> SEQ ID NO 420
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(9)
<223> OTHER INFORMATION: Nucleotide at position 2 and/or 7 and/or 9 may
      be modified by 2'-O,4'-C-methylene-beta-D-ribofuranosyl moiety

<400> SEQUENCE: 420
taatactgtc tggtaaaa                                                     18

<210> SEQ ID NO 421
<211> LENGTH: 30
<212> TYPE: DNA
<213> ORGANISM: Artificial Sequence
<220> FEATURE:
<223> OTHER INFORMATION: Primer

<400> SEQUENCE: 421
catgatcagc tgggccaaga tgcatgacgg                                        30

<210> SEQ ID NO 422
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 422
tgtcttgcag gccg                                                         14

<210> SEQ ID NO 423
<211> LENGTH: 30
<212> TYPE: DNA
<213> ORGANISM: Artificial Sequence
<220> FEATURE:
<223> OTHER INFORMATION: Primer

<400> SEQUENCE: 423
catgatcagc tgggccaaga atgggacatc                                        30

<210> SEQ ID NO 424
<211> LENGTH: 16
<212> TYPE: DNA
<213> ORGANISM: Artificial Sequence
<220> FEATURE:
<223> OTHER INFORMATION: Primer
<220> FEATURE:

```
<221> NAME/KEY: misc_feature
<222> LOCATION: (4)..(8)
<223> OTHER INFORMATION: Nucleotide at position 4 and/or 8 may be
      modified by 2'-O,4'-C-methylene-beta-D-ribofuranosyl moiety

<400> SEQUENCE: 424
ttgcatatgt aggatg                                                    16

<210> SEQ ID NO 425
<211> LENGTH: 30
<212> TYPE: DNA
<213> ORGANISM: Artificial Sequence
<220> FEATURE:
<223> OTHER INFORMATION: Primer

<400> SEQUENCE: 425
catgatcagc tgggccaaga accagctaac                                     30

<210> SEQ ID NO 426
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 426
tggcagtgta ttgttagc                                                  18

<210> SEQ ID NO 427
<211> LENGTH: 30
<212> TYPE: DNA
<213> ORGANISM: Artificial Sequence
<220> FEATURE:
<223> OTHER INFORMATION: Primer

<400> SEQUENCE: 427
catgatcagc tgggccaaga tattaggaac                                     30

<210> SEQ ID NO 428
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(7)
<223> OTHER INFORMATION: Nucleotide at position 5 and/or 7 may be
      modified by 2'-O,4'-C-methylene-beta-D-ribofuranosyl moiety

<400> SEQUENCE: 428
tttttgcgat gtgtt                                                     15

<210> SEQ ID NO 429
<211> LENGTH: 30
<212> TYPE: DNA
<213> ORGANISM: Artificial Sequence
<220> FEATURE:
<223> OTHER INFORMATION: Primer

<400> SEQUENCE: 429
catgatcagc tgggccaaga aaactcagta                                     30
```

<210> SEQ ID NO 430
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(10)
<223> OTHER INFORMATION: Nucleotide at position 4 and/or 7 and/or 10
      may be modified by 2'-O,4'-C-methylene-beta-D-ribofuranosyl moiety

<400> SEQUENCE: 430
aaaccgttac cattactga                                                19

<210> SEQ ID NO 431
<211> LENGTH: 28
<212> TYPE: DNA
<213> ORGANISM: Artificial Sequence
<220> FEATURE:
<223> OTHER INFORMATION: Primer

<400> SEQUENCE: 431
catgatcagc tgggccaaga aactatac                                      28

<210> SEQ ID NO 432
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 432
tgaggtagta ggttg                                                    15

<210> SEQ ID NO 433
<211> LENGTH: 28
<212> TYPE: DNA
<213> ORGANISM: Artificial Sequence
<220> FEATURE:
<223> OTHER INFORMATION: Primer

<400> SEQUENCE: 433
catgatcagc tgggccaaga aaccacac                                      28

<210> SEQ ID NO 434
<211> LENGTH: 28
<212> TYPE: DNA
<213> ORGANISM: Artificial Sequence
<220> FEATURE:
<223> OTHER INFORMATION: Primer

<400> SEQUENCE: 434
catgatcagc tgggccaaga aaccatac                                      28

<210> SEQ ID NO 435
<211> LENGTH: 28
<212> TYPE: DNA
<213> ORGANISM: Artificial Sequence
<220> FEATURE:
<223> OTHER INFORMATION: Primer

<400> SEQUENCE: 435
catgatcagc tgggccaaga actatgca                                      28

```
<210> SEQ ID NO 436
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 436
agaggtagta ggttg                                                          15

<210> SEQ ID NO 437
<211> LENGTH: 28
<212> TYPE: DNA
<213> ORGANISM: Artificial Sequence
<220> FEATURE:
<223> OTHER INFORMATION: Primer

<400> SEQUENCE: 437
catgatcagc tgggccaaga actataca                                            28

<210> SEQ ID NO 438
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 438
tgaggtagga ggttg                                                          15

<210> SEQ ID NO 439
<211> LENGTH: 28
<212> TYPE: DNA
<213> ORGANISM: Artificial Sequence
<220> FEATURE:
<223> OTHER INFORMATION: Primer

<400> SEQUENCE: 439
catgatcagc tgggccaaga aactatac                                            28

<210> SEQ ID NO 440
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 440
tgaggtagta gattg                                                          15

<210> SEQ ID NO 441
<211> LENGTH: 28
<212> TYPE: DNA
```

<213> ORGANISM: Artificial Sequence
<220> FEATURE:
<223> OTHER INFORMATION: Primer

<400> SEQUENCE: 441
catgatcagc tgggccaaga actgtaca                                    28

<210> SEQ ID NO 442
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 442
tgaggtagta gtttg                                                  15

<210> SEQ ID NO 443
<211> LENGTH: 28
<212> TYPE: DNA
<213> ORGANISM: Artificial Sequence
<220> FEATURE:
<223> OTHER INFORMATION: Primer

<400> SEQUENCE: 443
catgatcagc tgggccaaga acagcaca                                    28

<210> SEQ ID NO 444
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 444
tgaggtagta gtttg                                                  15

<210> SEQ ID NO 445
<211> LENGTH: 30
<212> TYPE: DNA
<213> ORGANISM: Artificial Sequence
<220> FEATURE:
<223> OTHER INFORMATION: Primer

<400> SEQUENCE: 445
catgatcagc tgggccaaga acaaaagttg                                  30

<210> SEQ ID NO 446
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 446
atcacacaaa ggcaac                                                16

<210> SEQ ID NO 447
<211> LENGTH: 27
<212> TYPE: DNA
<213> ORGANISM: Artificial Sequence
<220> FEATURE:
<223> OTHER INFORMATION: Primer

<400> SEQUENCE: 447
catgatcagc tgggccaaga acgtgga                                    27

<210> SEQ ID NO 448
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(9)
<223> OTHER INFORMATION: Nucleotide at position 3, 6 and/or 9 may be
      modified by 2'-O,4'-C-methylene-beta-D-ribofuranosyl moiety
<220> FEATURE:
<221> NAME/KEY: misc_feature
<222> LOCATION: (3)..(9)
<223> OTHER INFORMATION: Nucleotide at position 3 and/or 6 and/or 9 may
      be modified by 2'-O,4'-C-methylene-beta-D-ribofuranosyl moiety

<400> SEQUENCE: 448
atcatagagg aaaatcc                                               17

<210> SEQ ID NO 449
<211> LENGTH: 30
<212> TYPE: DNA
<213> ORGANISM: Artificial Sequence
<220> FEATURE:
<223> OTHER INFORMATION: Primer

<400> SEQUENCE: 449
catgatcagc tgggccaaga acagttcttc                                 30

<210> SEQ ID NO 450
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 450
aagctgccag ttga                                                  14

<210> SEQ ID NO 451
<211> LENGTH: 29
<212> TYPE: DNA
<213> ORGANISM: Artificial Sequence
<220> FEATURE:
<223> OTHER INFORMATION: Primer

<400> SEQUENCE: 451
catgatcagc tgggccaaga ccatcatta                                  29

<210> SEQ ID NO 452

```
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 452
taatactgcc gggt                                                           14

<210> SEQ ID NO 453
<211> LENGTH: 30
<212> TYPE: DNA
<213> ORGANISM: Artificial Sequence
<220> FEATURE:
<223> OTHER INFORMATION: Primer

<400> SEQUENCE: 453
catgatcagc tgggccaaga ctgttcctgc                                          30

<210> SEQ ID NO 454
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 454
tggctcagtt cagc                                                           14

<210> SEQ ID NO 455
<211> LENGTH: 30
<212> TYPE: DNA
<213> ORGANISM: Artificial Sequence
<220> FEATURE:
<223> OTHER INFORMATION: Primer

<400> SEQUENCE: 455
catgatcagc tgggccaaga accgatttca                                          30

<210> SEQ ID NO 456
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 456
tagcaccatt tgaaat                                                         16

<210> SEQ ID NO 457
<211> LENGTH: 30
<212> TYPE: DNA
<213> ORGANISM: Artificial Sequence
<220> FEATURE:
<223> OTHER INFORMATION: Primer
```

-continued

<400> SEQUENCE: 457
catgatcagc tgggccaaga tatctgcact                                          30

<210> SEQ ID NO 458
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 458
taaggtgcat ctagt                                                          15

<210> SEQ ID NO 459
<211> LENGTH: 30
<212> TYPE: DNA
<213> ORGANISM: Artificial Sequence
<220> FEATURE:
<223> OTHER INFORMATION: Primer

<400> SEQUENCE: 459
catgatcagc tgggccaaga gaactgcctt                                          30

<210> SEQ ID NO 460
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 460
tggagagaaa ggca                                                           14

<210> SEQ ID NO 461
<211> LENGTH: 28
<212> TYPE: DNA
<213> ORGANISM: Artificial Sequence
<220> FEATURE:
<223> OTHER INFORMATION: Primer

<400> SEQUENCE: 461
catgatcagc tgggccaaga cccaccga                                            28

<210> SEQ ID NO 462
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 462
aacattcatt gctgtc                                                         16

<210> SEQ ID NO 463
<211> LENGTH: 30
<212> TYPE: DNA
<213> ORGANISM: Artificial Sequence
<220> FEATURE:
<223> OTHER INFORMATION: Primer

<400> SEQUENCE: 463
catgatcagc tgggccaaga acaagtgccc                                              30

<210> SEQ ID NO 464
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 464
actgcagtga gggc                                                               14

<210> SEQ ID NO 465
<211> LENGTH: 30
<212> TYPE: DNA
<213> ORGANISM: Artificial Sequence
<220> FEATURE:
<223> OTHER INFORMATION: Primer

<400> SEQUENCE: 465
catgatcagc tgggccaaga agccacagtc                                              30

<210> SEQ ID NO 466
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 466
agatcagaag gtgactgt                                                           18

<210> SEQ ID NO 467
<211> LENGTH: 28
<212> TYPE: DNA
<213> ORGANISM: Artificial Sequence
<220> FEATURE:
<223> OTHER INFORMATION: Primer

<400> SEQUENCE: 467
catgatcagc tgggccaaga acgtggat                                                28

<210> SEQ ID NO 468
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(9)

<223> OTHER INFORMATION: Nucleotide at position 2 and/or 9 may be
      modified by 2'-O,4'-C-methylene-beta-D-ribofuranosyl moiety

<400> SEQUENCE: 468
atcgtagagg aaaatccac                                                    19

<210> SEQ ID NO 469
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 469
atgacctatg atttgac                                                      17

<210> SEQ ID NO 470
<211> LENGTH: 29
<212> TYPE: DNA
<213> ORGANISM: Artificial Sequence
<220> FEATURE:
<223> OTHER INFORMATION: Primer

<400> SEQUENCE: 470
catgatcagc tgggccaaga tgtgaacaa                                          29

<210> SEQ ID NO 471
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(9)
<223> OTHER INFORMATION: Nucleotide at position 4 and/or 7 and/or 9 may
      be modified by 2'-O,4'-C-methylene-beta-D-ribofuranosyl moiety

<400> SEQUENCE: 471
attcctagaa attgttc                                                      17

<210> SEQ ID NO 472
<211> LENGTH: 29
<212> TYPE: DNA
<213> ORGANISM: Artificial Sequence
<220> FEATURE:
<223> OTHER INFORMATION: Primer

<400> SEQUENCE: 472
catgatcagc tgggccaaga tacctgcac                                          29

<210> SEQ ID NO 473
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 473
caaagtgcta acagtg 16

<210> SEQ ID NO 474
<211> LENGTH: 30
<212> TYPE: DNA
<213> ORGANISM: Artificial Sequence
<220> FEATURE:
<223> OTHER INFORMATION: Primer

<400> SEQUENCE: 474
catgatcagc tgggccaaga tccaaaacat 30

<210> SEQ ID NO 475
<211> LENGTH: 30
<212> TYPE: DNA
<213> ORGANISM: Artificial Sequence
<220> FEATURE:
<223> OTHER INFORMATION: Primer

<400> SEQUENCE: 475
catgatcagc tgggccaaga gaacaggtag 30

<210> SEQ ID NO 476
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
    modified by 2'-O,4'-C-methylene-beta-D-ribofuranosyl moiety

<400> SEQUENCE: 476
cctagtaggt gctc 14

<210> SEQ ID NO 477
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
    modified by 2'-O,4'-C-methylene-beta-D-ribofuranosyl moiety

<400> SEQUENCE: 477
actagactga ggctc 15

<210> SEQ ID NO 478
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
    modified by 2'-O,4'-C-methylene-beta-D-ribofuranosyl moiety

<400> SEQUENCE: 478
gcaaagcaca gggc 14

<210> SEQ ID NO 479
<211> LENGTH: 31

```
<212> TYPE: DNA
<213> ORGANISM: Artificial Sequence
<220> FEATURE:
<223> OTHER INFORMATION: Primer

<400> SEQUENCE: 479
catgatcagc tgggccaaga acggcattac c                                    31

<210> SEQ ID NO 480
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(9)
<223> OTHER INFORMATION: Nucleotide at position 2 and/or 7 and/or 9 may
      be modified by 2'-O,4'-C-methylene-beta-D-ribofuranosyl moiety

<400> SEQUENCE: 480
taatactgtc tggtaatg                                                   18

<210> SEQ ID NO 481
<211> LENGTH: 29
<212> TYPE: DNA
<213> ORGANISM: Artificial Sequence
<220> FEATURE:
<223> OTHER INFORMATION: Primer

<400> SEQUENCE: 481
catgatcagc tgggccaaga atccagtca                                       29

<210> SEQ ID NO 482
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 482
taggcagtgt aatt                                                       14

<210> SEQ ID NO 483
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 483
tatgtagtat ggtccaca                                                   18

<210> SEQ ID NO 484
<211> LENGTH: 30
<212> TYPE: DNA
<213> ORGANISM: Artificial Sequence
<220> FEATURE:
<223> OTHER INFORMATION: Primer
```

```
<400> SEQUENCE: 484
catgatcagc tgggccaaga gcactggact                                    30

<210> SEQ ID NO 485
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 485 tgctgaccc tagt                                                      14

<210> SEQ ID NO 486
<211> LENGTH: 29
<212> TYPE: DNA
<213> ORGANISM: Artificial Sequence
<220> FEATURE:
<223> OTHER INFORMATION: Primer

<400> SEQUENCE: 486
catgatcagc tgggccaaga aacaaaatc                                     29

<210> SEQ ID NO 487
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 487
tggaagactt gtgatttt                                                 18

<210> SEQ ID NO 488
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 488
tgtctgcccg agtg                                                     14

<210> SEQ ID NO 489
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety
```

-continued

```
<400> SEQUENCE: 489
ttaatgctaa ttgtgatagg                                              20

<210> SEQ ID NO 490
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 490
ttcagctcct atatg                                                   15

<210> SEQ ID NO 491
<211> LENGTH: 29
<212> TYPE: DNA
<213> ORGANISM: Artificial Sequence
<220> FEATURE:
<223> OTHER INFORMATION: Primer

<400> SEQUENCE: 491
catgatcagc tgggccaaga aggcaaagg                                    29

<210> SEQ ID NO 492
<211> LENGTH: 31
<212> TYPE: DNA
<213> ORGANISM: Artificial Sequence
<220> FEATURE:
<223> OTHER INFORMATION: Primer

<400> SEQUENCE: 492
catgatcagc tgggccaaga acacaaattc g                                 31

<210> SEQ ID NO 493
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: Nucleotide at position 2 and/or 4 and/or 7 may
      be modified by 2'-O,4'-C-methylene-beta-D-ribofuranosyl moiety

<400> SEQUENCE: 493
ccctgtagaa ccgaat                                                  16

<210> SEQ ID NO 494
<211> LENGTH: 15
<212> TYPE: DNA
<213> ORGANISM: Artificial Sequence
<220> FEATURE:
<223> OTHER INFORMATION: Primer

<400> SEQUENCE: 494
tcacagtgaa ccggt                                                   15

<210> SEQ ID NO 495
<211> LENGTH: 15
<212> TYPE: DNA
<213> ORGANISM: Artificial Sequence
<220> FEATURE:
```

-continued

<223> OTHER INFORMATION: Primer

<400> SEQUENCE: 495
agctggtgtt gtgaa                                                          15

<210> SEQ ID NO 496
<211> LENGTH: 16
<212> TYPE: DNA
<213> ORGANISM: Artificial Sequence
<220> FEATURE:
<223> OTHER INFORMATION: Primer

<400> SEQUENCE: 496
tgagatgaag cactgt                                                         16

<210> SEQ ID NO 497
<211> LENGTH: 16
<212> TYPE: DNA
<213> ORGANISM: Artificial Sequence
<220> FEATURE:
<223> OTHER INFORMATION: Primer

<400> SEQUENCE: 497
tctcccaacc cttgta                                                         16

<210> SEQ ID NO 498
<211> LENGTH: 15
<212> TYPE: DNA
<213> ORGANISM: Artificial Sequence
<220> FEATURE:
<223> OTHER INFORMATION: Primer

<400> SEQUENCE: 498
aacattcaac gctgt                                                          15

<210> SEQ ID NO 499
<211> LENGTH: 16
<212> TYPE: DNA
<213> ORGANISM: Artificial Sequence
<220> FEATURE:
<223> OTHER INFORMATION: Primer

<400> SEQUENCE: 499
tgtaacagca actcca                                                         16

<210> SEQ ID NO 500
<211> LENGTH: 30
<212> TYPE: DNA
<213> ORGANISM: Artificial Sequence
<220> FEATURE:
<223> OTHER INFORMATION: Synthetic

<400> SEQUENCE: 500
catgatcagc tgggccaaga aagaagtgca                                          30

<210> SEQ ID NO 501
<211> LENGTH: 29
<212> TYPE: DNA
<213> ORGANISM: Artificial Sequence
<220> FEATURE:
<223> OTHER INFORMATION: Synthetic

<400> SEQUENCE: 501
catgatcagc tgggccaaga aagaagtgc                                           29

<210> SEQ ID NO 502

```
<211> LENGTH: 28
<212> TYPE: DNA
<213> ORGANISM: Artificial Sequence
<220> FEATURE:
<223> OTHER INFORMATION: Synthetic

<400> SEQUENCE: 502
catgatcagc tgggccaaga aagaagtg                                          28

<210> SEQ ID NO 503
<211> LENGTH: 27
<212> TYPE: DNA
<213> ORGANISM: Artificial Sequence
<220> FEATURE:
<223> OTHER INFORMATION: Synthetic

<400> SEQUENCE: 503
catgatcagc tgggccaaga aagaagt                                           27

<210> SEQ ID NO 504
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(10)
<223> OTHER INFORMATION: Nucleotide at position 4 and/or 8 and/or 10
      may be modified by 2'-O,4'-C-methylene-beta-D-ribofuranosyl moiety

<400> SEQUENCE: 504
aaacaaacat ggtgcac                                                      17

<210> SEQ ID NO 505
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Nucleotide at position 4 and/or 5 and/or 8 may
      be modified by 2'-O,4'-C-methylene-beta-D-ribofuranosyl moiety

<400> SEQUENCE: 505
aaacaaacat ggtgc                                                        15

<210> SEQ ID NO 506
<211> LENGTH: 30
<212> TYPE: DNA
<213> ORGANISM: Artificial Sequence
<220> FEATURE:
<223> OTHER INFORMATION: Synthetic

<400> SEQUENCE: 506
catgatcagc tgggccaaga ggcacacaaa                                        30

<210> SEQ ID NO 507
<211> LENGTH: 29
<212> TYPE: DNA
<213> ORGANISM: Artificial Sequence
<220> FEATURE:
<223> OTHER INFORMATION: Synthetic

<400> SEQUENCE: 507
catgatcagc tgggccaaga ggcacacaa                                         29
```

<210> SEQ ID NO 508
<211> LENGTH: 28
<212> TYPE: DNA
<213> ORGANISM: Artificial Sequence
<220> FEATURE:
<223> OTHER INFORMATION: Synthetic

<400> SEQUENCE: 508
catgatcagc tgggccaaga ggcacaca                                28

<210> SEQ ID NO 509
<211> LENGTH: 27
<212> TYPE: DNA
<213> ORGANISM: Artificial Sequence
<220> FEATURE:
<223> OTHER INFORMATION: Synthetic

<400> SEQUENCE: 509
catgatcagc tgggccaaga ggcacac                                 27

<210> SEQ ID NO 510
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 510
aaagtgcttc cactttgt                                           18

<210> SEQ ID NO 511
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 511
aaagtgcttc cacttt                                             16

<210> SEQ ID NO 512
<211> LENGTH: 30
<212> TYPE: DNA
<213> ORGANISM: Artificial Sequence
<220> FEATURE:
<223> OTHER INFORMATION: Synthetic

<400> SEQUENCE: 512
catgatcagc tgggccaaga gacaaacaaa                              30

<210> SEQ ID NO 513
<211> LENGTH: 29
<212> TYPE: DNA
<213> ORGANISM: Artificial Sequence
<220> FEATURE:
<223> OTHER INFORMATION: Synthetic

<400> SEQUENCE: 513

```
catgatcagc tgggccaaga gacaaacaa                                        29
```

<210> SEQ ID NO 514
<211> LENGTH: 28
<212> TYPE: DNA
<213> ORGANISM: Artificial Sequence
<220> FEATURE:
<223> OTHER INFORMATION: Synthetic

<400> SEQUENCE: 514

```
catgatcagc tgggccaaga gacaaaca                                         28
```

<210> SEQ ID NO 515
<211> LENGTH: 27
<212> TYPE: DNA
<213> ORGANISM: Artificial Sequence
<220> FEATURE:
<223> OTHER INFORMATION: Synthetic

<400> SEQUENCE: 515

```
catgatcagc tgggccaaga gacaaac                                          27
```

<210> SEQ ID NO 516
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(10)
<223> OTHER INFORMATION: Nucleotide at position 3 and/or 5 and/or 7
      and/or 10 may be modified by 2'-O,4'-C-methylene-beta-D-
      ribofuranosyl moiety

<400> SEQUENCE: 516

```
aaagtgcatc cattttgt                                                    18
```

<210> SEQ ID NO 517
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 517

```
aaagtgcatc catttt                                                      16
```

<210> SEQ ID NO 518
<211> LENGTH: 30
<212> TYPE: DNA
<213> ORGANISM: Artificial Sequence
<220> FEATURE:
<223> OTHER INFORMATION: Synthetic

<400> SEQUENCE: 518

```
catgatcagc tgggccaaga gtaacactct                                       30
```

<210> SEQ ID NO 519
<211> LENGTH: 29
<212> TYPE: DNA
<213> ORGANISM: Artificial Sequence
<220> FEATURE:
<223> OTHER INFORMATION: Synthetic

```
<400> SEQUENCE: 519
catgatcagc tgggccaaga gtaacactc                                         29

<210> SEQ ID NO 520
<211> LENGTH: 28
<212> TYPE: DNA
<213> ORGANISM: Artificial Sequence
<220> FEATURE:
<223> OTHER INFORMATION: Synthetic

<400> SEQUENCE: 520
catgatcagc tgggccaaga gtaacact                                          28

<210> SEQ ID NO 521
<211> LENGTH: 27
<212> TYPE: DNA
<213> ORGANISM: Artificial Sequence
<220> FEATURE:
<223> OTHER INFORMATION: Synthetic

<400> SEQUENCE: 521
catgatcagc tgggccaaga gtaacac                                           27

<210> SEQ ID NO 522
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 522
aaagtgcatc cttttagagt                                                   20

<210> SEQ ID NO 523
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 523
aaagtgcatc cttttaga                                                     18

<210> SEQ ID NO 524
<211> LENGTH: 30
<212> TYPE: DNA
<213> ORGANISM: Artificial Sequence
<220> FEATURE:
<223> OTHER INFORMATION: Synthetic

<400> SEQUENCE: 524
catgatcagc tgggccaaga aaacctctaa                                        30

<210> SEQ ID NO 525
<211> LENGTH: 29
<212> TYPE: DNA
<213> ORGANISM: Artificial Sequence
```

```
<220> FEATURE:
<223> OTHER INFORMATION: Synthetic

<400> SEQUENCE: 525
catgatcagc tgggccaaga aaacctcta                                            29

<210> SEQ ID NO 526
<211> LENGTH: 28
<212> TYPE: DNA
<213> ORGANISM: Artificial Sequence
<220> FEATURE:
<223> OTHER INFORMATION: Synthetic

<400> SEQUENCE: 526
catgatcagc tgggccaaga aaacctct                                             28

<210> SEQ ID NO 527
<211> LENGTH: 27
<212> TYPE: DNA
<213> ORGANISM: Artificial Sequence
<220> FEATURE:
<223> OTHER INFORMATION: Synthetic

<400> SEQUENCE: 527
catgatcagc tgggccaaga aaacctc                                              27

<210> SEQ ID NO 528
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 528
aaagtgcatc cttttag                                                         17

<210> SEQ ID NO 529
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 529
aaagtgcatc ctttt                                                           15

<210> SEQ ID NO 530
<211> LENGTH: 30
<212> TYPE: DNA
<213> ORGANISM: Artificial Sequence
<220> FEATURE:
<223> OTHER INFORMATION: Synthetic

<400> SEQUENCE: 530
catgatcagc tgggccaaga atcctctaaa                                           30

<210> SEQ ID NO 531
<211> LENGTH: 29
```

```
<212> TYPE: DNA
<213> ORGANISM: Artificial Sequence
<220> FEATURE:
<223> OTHER INFORMATION: Synthetic

<400> SEQUENCE: 531
catgatcagc tgggccaaga atcctctaa                                            29

<210> SEQ ID NO 532
<211> LENGTH: 28
<212> TYPE: DNA
<213> ORGANISM: Artificial Sequence
<220> FEATURE:
<223> OTHER INFORMATION: Synthetic

<400> SEQUENCE: 532
catgatcagc tgggccaaga atcctcta                                             28

<210> SEQ ID NO 533
<211> LENGTH: 27
<212> TYPE: DNA
<213> ORGANISM: Artificial Sequence
<220> FEATURE:
<223> OTHER INFORMATION: Synthetic

<400> SEQUENCE: 533
catgatcagc tgggccaaga atcctct                                              27

<210> SEQ ID NO 534
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 534
aaagtgcatc tttttaga                                                        18

<210> SEQ ID NO 535
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 535
aaagtgcatc tttta                                                           16

<210> SEQ ID NO 536
<211> LENGTH: 30
<212> TYPE: DNA
<213> ORGANISM: Artificial Sequence
<220> FEATURE:
<223> OTHER INFORMATION: Synthetic

<400> SEQUENCE: 536
catgatcagc tgggccaaga acactctaaa                                           30
```

```
<210> SEQ ID NO 537
<211> LENGTH: 29
<212> TYPE: DNA
<213> ORGANISM: Artificial Sequence
<220> FEATURE:
<223> OTHER INFORMATION: Synthetic

<400> SEQUENCE: 537
catgatcagc tgggccaaga acactctaa                                              29

<210> SEQ ID NO 538
<211> LENGTH: 28
<212> TYPE: DNA
<213> ORGANISM: Artificial Sequence
<220> FEATURE:
<223> OTHER INFORMATION: Synthetic

<400> SEQUENCE: 538
catgatcagc tgggccaaga acactcta                                               28

<210> SEQ ID NO 539
<211> LENGTH: 27
<212> TYPE: DNA
<213> ORGANISM: Artificial Sequence
<220> FEATURE:
<223> OTHER INFORMATION: Synthetic

<400> SEQUENCE: 539
catgatcagc tgggccaaga acactct                                                27

<210> SEQ ID NO 540
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 540
caaagtgcct ccctttag                                                          18

<210> SEQ ID NO 541
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 541
caaagtgcct cccttt                                                            16

<210> SEQ ID NO 542
<211> LENGTH: 30
<212> TYPE: DNA
<213> ORGANISM: Artificial Sequence
<220> FEATURE:
<223> OTHER INFORMATION: Synthetic

<400> SEQUENCE: 542
catgatcagc tgggccaaga acagtccaaa                                             30
```

```
<210> SEQ ID NO 543
<211> LENGTH: 29
<212> TYPE: DNA
<213> ORGANISM: Artificial Sequence
<220> FEATURE:
<223> OTHER INFORMATION: Synthetic

<400> SEQUENCE: 543
catgatcagc tgggccaaga acagtccaa                                              29

<210> SEQ ID NO 544
<211> LENGTH: 28
<212> TYPE: DNA
<213> ORGANISM: Artificial Sequence
<220> FEATURE:
<223> OTHER INFORMATION: Synthetic

<400> SEQUENCE: 544
catgatcagc tgggccaaga acagtcca                                               28

<210> SEQ ID NO 545
<211> LENGTH: 27
<212> TYPE: DNA
<213> ORGANISM: Artificial Sequence
<220> FEATURE:
<223> OTHER INFORMATION: Synthetic

<400> SEQUENCE: 545
catgatcagc tgggccaaga acagtcc                                                27

<210> SEQ ID NO 546
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 546
aaagtgcttc cctttgg                                                           17

<210> SEQ ID NO 547
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 5 and/or 6 may
      be modified by 2'-O,4'-C-methylene-beta-D-ribofuranosyl moiety

<400> SEQUENCE: 547
aaagtgcttc ccttt                                                             15

<210> SEQ ID NO 548
<211> LENGTH: 30
<212> TYPE: DNA
<213> ORGANISM: Artificial Sequence
<220> FEATURE:
<223> OTHER INFORMATION: Synthetic

<400> SEQUENCE: 548
```

```
catgatcagc tgggccaaga ccctctaaaa                                          30

<210> SEQ ID NO 549
<211> LENGTH: 29
<212> TYPE: DNA
<213> ORGANISM: Artificial Sequence
<220> FEATURE:
<223> OTHER INFORMATION: Synthetic

<400> SEQUENCE: 549
catgatcagc tgggccaaga ccctctaaa                                           29

<210> SEQ ID NO 550
<211> LENGTH: 28
<212> TYPE: DNA
<213> ORGANISM: Artificial Sequence
<220> FEATURE:
<223> OTHER INFORMATION: Synthetic

<400> SEQUENCE: 550
catgatcagc tgggccaaga ccctctaa                                            28

<210> SEQ ID NO 551
<211> LENGTH: 27
<212> TYPE: DNA
<213> ORGANISM: Artificial Sequence
<220> FEATURE:
<223> OTHER INFORMATION: Synthetic

<400> SEQUENCE: 551
catgatcagc tgggccaaga ccctcta                                             27

<210> SEQ ID NO 552
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 5 and/or 6 may
      be modified by 2'-O,4'-C-methylene-beta-D-ribofuranosyl moiety

<400> SEQUENCE: 552
aaagtgcttc cttttag                                                        17

<210> SEQ ID NO 553
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 553
aaagtgcttc cttttα                                                         16

<210> SEQ ID NO 554
<211> LENGTH: 30
<212> TYPE: DNA
<213> ORGANISM: Artificial Sequence
<220> FEATURE:
<223> OTHER INFORMATION: Synthetic
```

```
<400> SEQUENCE: 554
catgatcagc tgggccaaga aacccaccaa                                    30

<210> SEQ ID NO 555
<211> LENGTH: 29
<212> TYPE: DNA
<213> ORGANISM: Artificial Sequence
<220> FEATURE:
<223> OTHER INFORMATION: Synthetic

<400> SEQUENCE: 555
catgatcagc tgggccaaga aacccacca                                     29

<210> SEQ ID NO 556
<211> LENGTH: 28
<212> TYPE: DNA
<213> ORGANISM: Artificial Sequence
<220> FEATURE:
<223> OTHER INFORMATION: Synthetic

<400> SEQUENCE: 556
catgatcagc tgggccaaga aacccacc                                      28

<210> SEQ ID NO 557
<211> LENGTH: 27
<212> TYPE: DNA
<213> ORGANISM: Artificial Sequence
<220> FEATURE:
<223> OTHER INFORMATION: Synthetic

<400> SEQUENCE: 557
catgatcagc tgggccaaga aacccac                                       27

<210> SEQ ID NO 558
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 558
aaagtgcttc tctttggt                                                 18

<210> SEQ ID NO 559
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 559
aaagtgcttc tctttg                                                   16

<210> SEQ ID NO 560
<211> LENGTH: 30
<212> TYPE: DNA
<213> ORGANISM: Artificial Sequence
```

<220> FEATURE:
<223> OTHER INFORMATION: Synthetic

<400> SEQUENCE: 560
catgatcagc tgggccaaga ccctcaaaaa                               30

<210> SEQ ID NO 561
<211> LENGTH: 29
<212> TYPE: DNA
<213> ORGANISM: Artificial Sequence
<220> FEATURE:
<223> OTHER INFORMATION: Synthetic

<400> SEQUENCE: 561
catgatcagc tgggccaaga ccctcaaaa                                29

<210> SEQ ID NO 562
<211> LENGTH: 28
<212> TYPE: DNA
<213> ORGANISM: Artificial Sequence
<220> FEATURE:
<223> OTHER INFORMATION: Synthetic

<400> SEQUENCE: 562
catgatcagc tgggccaaga ccctcaaa                                 28

<210> SEQ ID NO 563
<211> LENGTH: 27
<212> TYPE: DNA
<213> ORGANISM: Artificial Sequence
<220> FEATURE:
<223> OTHER INFORMATION: Synthetic

<400> SEQUENCE: 563
catgatcagc tgggccaaga ccctcaa                                  27

<210> SEQ ID NO 564
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 564
aaagtgcttc cttttg                                              17

<210> SEQ ID NO 565
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 5 and/or 6 may
      be modified by 2'-O,4'-C-methylene-beta-D-ribofuranosyl moiety

<400> SEQUENCE: 565
aaagtgcttc cttttt                                              16

<210> SEQ ID NO 566
<211> LENGTH: 30

```
<212> TYPE: DNA
<213> ORGANISM: Artificial Sequence
<220> FEATURE:
<223> OTHER INFORMATION: Synthetic

<400> SEQUENCE: 566
catgatcagc tgggccaaga aaccctctaa                                          30

<210> SEQ ID NO 567
<211> LENGTH: 29
<212> TYPE: DNA
<213> ORGANISM: Artificial Sequence
<220> FEATURE:
<223> OTHER INFORMATION: Synthetic

<400> SEQUENCE: 567
catgatcagc tgggccaaga aaccctcta                                           29

<210> SEQ ID NO 568
<211> LENGTH: 28
<212> TYPE: DNA
<213> ORGANISM: Artificial Sequence
<220> FEATURE:
<223> OTHER INFORMATION: Synthetic

<400> SEQUENCE: 568
catgatcagc tgggccaaga aaccctct                                            28

<210> SEQ ID NO 569
<211> LENGTH: 27
<212> TYPE: DNA
<213> ORGANISM: Artificial Sequence
<220> FEATURE:
<223> OTHER INFORMATION: Synthetic

<400> SEQUENCE: 569
catgatcagc tgggccaaga aaccctc                                             27

<210> SEQ ID NO 570
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 570
aagtgcttcc ttttaga                                                        17

<210> SEQ ID NO 571
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 4 and/or 5 may
      be modified by 2'-O,4'-C-methylene-beta-D-ribofuranosyl moiety

<400> SEQUENCE: 571
aagtgcttcc tttta                                                          15
```

```
<210> SEQ ID NO 572
<211> LENGTH: 30
<212> TYPE: DNA
<213> ORGANISM: Artificial Sequence
<220> FEATURE:
<223> OTHER INFORMATION: Synthetic

<400> SEQUENCE: 572
catgatcagc tgggccaaga aaaaaggtta                                        30

<210> SEQ ID NO 573
<211> LENGTH: 29
<212> TYPE: DNA
<213> ORGANISM: Artificial Sequence
<220> FEATURE:
<223> OTHER INFORMATION: Synthetic

<400> SEQUENCE: 573
catgatcagc tgggccaaga aaaaaggtt                                         29

<210> SEQ ID NO 574
<211> LENGTH: 28
<212> TYPE: DNA
<213> ORGANISM: Artificial Sequence
<220> FEATURE:
<223> OTHER INFORMATION: Synthetic

<400> SEQUENCE: 574
catgatcagc tgggccaaga aaaaggt                                           28

<210> SEQ ID NO 575
<211> LENGTH: 27
<212> TYPE: DNA
<213> ORGANISM: Artificial Sequence
<220> FEATURE:
<223> OTHER INFORMATION: Synthetic

<400> SEQUENCE: 575
catgatcagc tgggccaaga aaaagg                                            27

<210> SEQ ID NO 576
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 576
aacacaccca gctaacc                                                      17

<210> SEQ ID NO 577
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 577
aacacaccca gctaa                                                        15
```

<210> SEQ ID NO 578
<211> LENGTH: 30
<212> TYPE: DNA
<213> ORGANISM: Artificial Sequence
<220> FEATURE:
<223> OTHER INFORMATION: Synthetic

<400> SEQUENCE: 578
catgatcagc tgggccaaga aacccaccga                                           30

<210> SEQ ID NO 579
<211> LENGTH: 29
<212> TYPE: DNA
<213> ORGANISM: Artificial Sequence
<220> FEATURE:
<223> OTHER INFORMATION: Synthetic

<400> SEQUENCE: 579
catgatcagc tgggccaaga aacccaccg                                            29

<210> SEQ ID NO 580
<211> LENGTH: 28
<212> TYPE: DNA
<213> ORGANISM: Artificial Sequence
<220> FEATURE:
<223> OTHER INFORMATION: Synthetic

<400> SEQUENCE: 580
catgatcagc tgggccaaga aacccacc                                             28

<210> SEQ ID NO 581
<211> LENGTH: 27
<212> TYPE: DNA
<213> ORGANISM: Artificial Sequence
<220> FEATURE:
<223> OTHER INFORMATION: Synthetic

<400> SEQUENCE: 581
catgatcagc tgggccaaga aacccac                                              27

<210> SEQ ID NO 582
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 7 may be
      modified by 2'-O,4'-C-methylene-beta-D-ribofuranosyl moiety

<400> SEQUENCE: 582
aacattcatt gttgtcggt                                                       19

<210> SEQ ID NO 583
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 583
aacattcatt gttgtcg                                                          17

<210> SEQ ID NO 584
<211> LENGTH: 30
<212> TYPE: DNA
<213> ORGANISM: Artificial Sequence
<220> FEATURE:
<223> OTHER INFORMATION: Synthetic

<400> SEQUENCE: 584
catgatcagc tgggccaaga aaagcgggac                                            30

<210> SEQ ID NO 585
<211> LENGTH: 29
<212> TYPE: DNA
<213> ORGANISM: Artificial Sequence
<220> FEATURE:
<223> OTHER INFORMATION: Synthetic

<400> SEQUENCE: 585
catgatcagc tgggccaaga aaagcggga                                             29

<210> SEQ ID NO 586
<211> LENGTH: 28
<212> TYPE: DNA
<213> ORGANISM: Artificial Sequence
<220> FEATURE:
<223> OTHER INFORMATION: Synthetic

<400> SEQUENCE: 586
catgatcagc tgggccaaga aaagcggg                                              28

<210> SEQ ID NO 587
<211> LENGTH: 27
<212> TYPE: DNA
<213> ORGANISM: Artificial Sequence
<220> FEATURE:
<223> OTHER INFORMATION: Synthetic

<400> SEQUENCE: 587
catgatcagc tgggccaaga aaagcgg                                               27

<210> SEQ ID NO 588
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 588
aactggccct caaagtccc                                                        19

<210> SEQ ID NO 589
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

```
<400> SEQUENCE: 589
aactggccct caaagtc                                                      17

<210> SEQ ID NO 590
<211> LENGTH: 30
<212> TYPE: DNA
<213> ORGANISM: Artificial Sequence
<220> FEATURE:
<223> OTHER INFORMATION: Synthetic

<400> SEQUENCE: 590
catgatcagc tgggccaaga actcacacct                                        30

<210> SEQ ID NO 591
<211> LENGTH: 29
<212> TYPE: DNA
<213> ORGANISM: Artificial Sequence
<220> FEATURE:
<223> OTHER INFORMATION: Synthetic

<400> SEQUENCE: 591
catgatcagc tgggccaaga actcacacc                                         29

<210> SEQ ID NO 592
<211> LENGTH: 28
<212> TYPE: DNA
<213> ORGANISM: Artificial Sequence
<220> FEATURE:
<223> OTHER INFORMATION: Synthetic

<400> SEQUENCE: 592
catgatcagc tgggccaaga actcacac                                          28

<210> SEQ ID NO 593
<211> LENGTH: 27
<212> TYPE: DNA
<213> ORGANISM: Artificial Sequence
<220> FEATURE:
<223> OTHER INFORMATION: Synthetic

<400> SEQUENCE: 593
catgatcagc tgggccaaga actcaca                                           27

<210> SEQ ID NO 594
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Nucleotide at position 4 and/or 8 may be
      modified by 2'-O,4'-C-methylene-beta-D-ribofuranosyl moiety

<400> SEQUENCE: 594
aatccttgga acctaggtg                                                    19

<210> SEQ ID NO 595
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
```

<223> OTHER INFORMATION: Nucleotide at position 3 and/or 5 and/or 8 may
      be modified by 2'-O,4'-C-methylene-beta-D-ribofuranosyl moiety

<400> SEQUENCE: 595
aatccttgga acctagg                                                 17

<210> SEQ ID NO 596
<211> LENGTH: 30
<212> TYPE: DNA
<213> ORGANISM: Artificial Sequence
<220> FEATURE:
<223> OTHER INFORMATION: Synthetic

<400> SEQUENCE: 596
catgatcagc tgggccaaga ttcacaccta                                   30

<210> SEQ ID NO 597
<211> LENGTH: 29
<212> TYPE: DNA
<213> ORGANISM: Artificial Sequence
<220> FEATURE:
<223> OTHER INFORMATION: Synthetic

<400> SEQUENCE: 597
catgatcagc tgggccaaga ttcacacct                                    29

<210> SEQ ID NO 598
<211> LENGTH: 28
<212> TYPE: DNA
<213> ORGANISM: Artificial Sequence
<220> FEATURE:
<223> OTHER INFORMATION: Synthetic

<400> SEQUENCE: 598
catgatcagc tgggccaaga ttcacacc                                     28

<210> SEQ ID NO 599
<211> LENGTH: 27
<212> TYPE: DNA
<213> ORGANISM: Artificial Sequence
<220> FEATURE:
<223> OTHER INFORMATION: Synthetic

<400> SEQUENCE: 599
catgatcagc tgggccaaga ttcacac                                      27

<210> SEQ ID NO 600
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 8 may be
      modified by 2'-O,4'-C-methylene-beta-D-ribofuranosyl moiety

<400> SEQUENCE: 600
aatccttgga acctaggt                                                18

<210> SEQ ID NO 601
<211> LENGTH: 16
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (3)..(8)
<223> OTHER INFORMATION: Nucleotide at position 3 and/or 5 and/or 8 may
      be modified by 2'-O,4'-C-methylene-beta-D-ribofuranosyl moiety

<400> SEQUENCE: 601
aatccttgga acctag                                                   16

<210> SEQ ID NO 602
<211> LENGTH: 30
<212> TYPE: DNA
<213> ORGANISM: Artificial Sequence
<220> FEATURE:
<223> OTHER INFORMATION: Synthetic

<400> SEQUENCE: 602
catgatcagc tgggccaaga cagaatcctt                                    30

<210> SEQ ID NO 603
<211> LENGTH: 29
<212> TYPE: DNA
<213> ORGANISM: Artificial Sequence
<220> FEATURE:
<223> OTHER INFORMATION: Synthetic

<400> SEQUENCE: 603
catgatcagc tgggccaaga cagaatcct                                     29

<210> SEQ ID NO 604
<211> LENGTH: 28
<212> TYPE: DNA
<213> ORGANISM: Artificial Sequence
<220> FEATURE:
<223> OTHER INFORMATION: Synthetic

<400> SEQUENCE: 604
catgatcagc tgggccaaga cagaatcc                                      28

<210> SEQ ID NO 605
<211> LENGTH: 27
<212> TYPE: DNA
<213> ORGANISM: Artificial Sequence
<220> FEATURE:
<223> OTHER INFORMATION: Synthetic

<400> SEQUENCE: 605
catgatcagc tgggccaaga cagaatc                                       27

<210> SEQ ID NO 606
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 606
atgcacctgg gcaagga                                                  17

<210> SEQ ID NO 607
<211> LENGTH: 15
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 607
atgcacctgg gcaag                                                      15

<210> SEQ ID NO 608
<211> LENGTH: 30
<212> TYPE: DNA
<213> ORGANISM: Artificial Sequence
<220> FEATURE:
<223> OTHER INFORMATION: Synthetic

<400> SEQUENCE: 608
catgatcagc tgggccaaga ctgaacccett                                     30

<210> SEQ ID NO 609
<211> LENGTH: 29
<212> TYPE: DNA
<213> ORGANISM: Artificial Sequence
<220> FEATURE:
<223> OTHER INFORMATION: Synthetic

<400> SEQUENCE: 609
catgatcagc tgggccaaga ctgaaccct                                       29

<210> SEQ ID NO 610
<211> LENGTH: 28
<212> TYPE: DNA
<213> ORGANISM: Artificial Sequence
<220> FEATURE:
<223> OTHER INFORMATION: Synthetic

<400> SEQUENCE: 610
catgatcagc tgggccaaga ctgaaccc                                        28

<210> SEQ ID NO 611
<211> LENGTH: 27
<212> TYPE: DNA
<213> ORGANISM: Artificial Sequence
<220> FEATURE:
<223> OTHER INFORMATION: Synthetic

<400> SEQUENCE: 611
catgatcagc tgggccaaga ctgaacc                                         27

<210> SEQ ID NO 612
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 612
atgcacctgg gcaaggg                                                    17

<210> SEQ ID NO 613
<211> LENGTH: 15
<212> TYPE: DNA
```

-continued

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 613
atgcacctgg gcaag                                                    15

<210> SEQ ID NO 614
<211> LENGTH: 30
<212> TYPE: DNA
<213> ORGANISM: Artificial Sequence
<220> FEATURE:
<223> OTHER INFORMATION: Synthetic

<400> SEQUENCE: 614
catgatcagc tgggccaaga tctcacccag                                    30

<210> SEQ ID NO 615
<211> LENGTH: 29
<212> TYPE: DNA
<213> ORGANISM: Artificial Sequence
<220> FEATURE:
<223> OTHER INFORMATION: Synthetic

<400> SEQUENCE: 615
catgatcagc tgggccaaga tctcaccca                                     29

<210> SEQ ID NO 616
<211> LENGTH: 28
<212> TYPE: DNA
<213> ORGANISM: Artificial Sequence
<220> FEATURE:
<223> OTHER INFORMATION: Synthetic

<400> SEQUENCE: 616
catgatcagc tgggccaaga tctcaccc                                      28

<210> SEQ ID NO 617
<211> LENGTH: 27
<212> TYPE: DNA
<213> ORGANISM: Artificial Sequence
<220> FEATURE:
<223> OTHER INFORMATION: Synthetic

<400> SEQUENCE: 617
catgatcagc tgggccaaga tctcacc                                       27

<210> SEQ ID NO 618
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 4 and/or 8 may
      be modified by 2'-O,4'-C-methylene-beta-D-ribofuranosyl moiety

<400> SEQUENCE: 618
aatcctttgt ccctggg                                                  17

<210> SEQ ID NO 619
```

```
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Nucleotide at position 4 and/or 8 may be
      modified by 2'-O,4'-C-methylene-beta-D-ribofuranosyl moiety

<400> SEQUENCE: 619
aatcctttgt ccctgg                                                       16

<210> SEQ ID NO 620
<211> LENGTH: 30
<212> TYPE: DNA
<213> ORGANISM: Artificial Sequence
<220> FEATURE:
<223> OTHER INFORMATION: Synthetic

<400> SEQUENCE: 620
catgatcagc tgggccaaga tttcacccag                                        30

<210> SEQ ID NO 621
<211> LENGTH: 29
<212> TYPE: DNA
<213> ORGANISM: Artificial Sequence
<220> FEATURE:
<223> OTHER INFORMATION: Synthetic

<400> SEQUENCE: 621
catgatcagc tgggccaaga tttcaccca                                         29

<210> SEQ ID NO 622
<211> LENGTH: 28
<212> TYPE: DNA
<213> ORGANISM: Artificial Sequence
<220> FEATURE:
<223> OTHER INFORMATION: Synthetic

<400> SEQUENCE: 622
catgatcagc tgggccaaga tttcaccc                                          28

<210> SEQ ID NO 623
<211> LENGTH: 27
<212> TYPE: DNA
<213> ORGANISM: Artificial Sequence
<220> FEATURE:
<223> OTHER INFORMATION: Synthetic

<400> SEQUENCE: 623
catgatcagc tgggccaaga tttcacc                                           27

<210> SEQ ID NO 624
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 4 and/or 6 may
      be modified by 2'-O,4'-C-methylene-beta-D-ribofuranosyl moiety

<400> SEQUENCE: 624
aatcctttgt ccctggg                                                      17
```

```
<210> SEQ ID NO 625
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 4 and/or 6 may
      be modified by 2'-O,4'-C-methylene-beta-D-ribofuranosyl moiety

<400> SEQUENCE: 625
aatcctttgt ccctg                                                          15

<210> SEQ ID NO 626
<211> LENGTH: 30
<212> TYPE: DNA
<213> ORGANISM: Artificial Sequence
<220> FEATURE:
<223> OTHER INFORMATION: Synthetic

<400> SEQUENCE: 626
catgatcagc tgggccaaga agtggatgac                                          30

<210> SEQ ID NO 627
<211> LENGTH: 29
<212> TYPE: DNA
<213> ORGANISM: Artificial Sequence
<220> FEATURE:
<223> OTHER INFORMATION: Synthetic

<400> SEQUENCE: 627
catgatcagc tgggccaaga agtggatga                                           29

<210> SEQ ID NO 628
<211> LENGTH: 28
<212> TYPE: DNA
<213> ORGANISM: Artificial Sequence
<220> FEATURE:
<223> OTHER INFORMATION: Synthetic

<400> SEQUENCE: 628
catgatcagc tgggccaaga agtggatg                                            28

<210> SEQ ID NO 629
<211> LENGTH: 27
<212> TYPE: DNA
<213> ORGANISM: Artificial Sequence
<220> FEATURE:
<223> OTHER INFORMATION: Synthetic

<400> SEQUENCE: 629
catgatcagc tgggccaaga agtggat                                             27

<210> SEQ ID NO 630
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 630
```
aatcgtacag ggtcat                                                      16

<210> SEQ ID NO 631
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 631
aatcgtacag ggtc                                                        14

<210> SEQ ID NO 632
<211> LENGTH: 30
<212> TYPE: DNA
<213> ORGANISM: Artificial Sequence
<220> FEATURE:
<223> OTHER INFORMATION: Synthetic

<400> SEQUENCE: 632
catgatcagc tgggccaaga gctgccgtat                                       30

<210> SEQ ID NO 633
<211> LENGTH: 29
<212> TYPE: DNA
<213> ORGANISM: Artificial Sequence
<220> FEATURE:
<223> OTHER INFORMATION: Synthetic

<400> SEQUENCE: 633
catgatcagc tgggccaaga gctgccgta                                        29

<210> SEQ ID NO 634
<211> LENGTH: 28
<212> TYPE: DNA
<213> ORGANISM: Artificial Sequence
<220> FEATURE:
<223> OTHER INFORMATION: Synthetic

<400> SEQUENCE: 634
catgatcagc tgggccaaga gctgccgt                                         28

<210> SEQ ID NO 635
<211> LENGTH: 27
<212> TYPE: DNA
<213> ORGANISM: Artificial Sequence
<220> FEATURE:
<223> OTHER INFORMATION: Synthetic

<400> SEQUENCE: 635
catgatcagc tgggccaaga gctgccg                                          27

<210> SEQ ID NO 636
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

```
<400> SEQUENCE: 636
agtgacatca catatacg                                              18

<210> SEQ ID NO 637
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 3 and/or 6 may
      be modified by 2'-O,4'-C-methylene-beta-D-ribofuranosyl moiety

<400> SEQUENCE: 637
agtgacatca catatac                                               17

<210> SEQ ID NO 638
<211> LENGTH: 30
<212> TYPE: DNA
<213> ORGANISM: Artificial Sequence
<220> FEATURE:
<223> OTHER INFORMATION: Synthetic

<400> SEQUENCE: 638
catgatcagc tgggccaaga gctgccatat                                 30

<210> SEQ ID NO 639
<211> LENGTH: 29
<212> TYPE: DNA
<213> ORGANISM: Artificial Sequence
<220> FEATURE:
<223> OTHER INFORMATION: Synthetic

<400> SEQUENCE: 639
catgatcagc tgggccaaga gctgccata                                  29

<210> SEQ ID NO 640
<211> LENGTH: 28
<212> TYPE: DNA
<213> ORGANISM: Artificial Sequence
<220> FEATURE:
<223> OTHER INFORMATION: Synthetic

<400> SEQUENCE: 640
catgatcagc tgggccaaga gctgccat                                   28

<210> SEQ ID NO 641
<211> LENGTH: 27
<212> TYPE: DNA
<213> ORGANISM: Artificial Sequence
<220> FEATURE:
<223> OTHER INFORMATION: Synthetic

<400> SEQUENCE: 641
catgatcagc tgggccaaga gctgcca                                    27

<210> SEQ ID NO 642
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(8)
<223> OTHER INFORMATION: Nucleotide at position 6 and/or 8 may be
``` modified by 2'-O,4'-C-methylene-beta-D-ribofuranosyl moiety

<400> SEQUENCE: 642
aatgacacca catatatg                                                 18

<210> SEQ ID NO 643
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 6 and/or 8 may
      be modified by 2'-O,4'-C-methylene-beta-D-ribofuranosyl moiety

<400> SEQUENCE: 643
aatgacacca catat                                                    15

<210> SEQ ID NO 644
<211> LENGTH: 30
<212> TYPE: DNA
<213> ORGANISM: Artificial Sequence
<220> FEATURE:
<223> OTHER INFORMATION: Synthetic

<400> SEQUENCE: 644
catgatcagc tgggccaaga gctgccatat                                    30

<210> SEQ ID NO 645
<211> LENGTH: 29
<212> TYPE: DNA
<213> ORGANISM: Artificial Sequence
<220> FEATURE:
<223> OTHER INFORMATION: Synthetic

<400> SEQUENCE: 645
catgatcagc tgggccaaga gctgccata                                     29

<210> SEQ ID NO 646
<211> LENGTH: 28
<212> TYPE: DNA
<213> ORGANISM: Artificial Sequence
<220> FEATURE:
<223> OTHER INFORMATION: Synthetic

<400> SEQUENCE: 646
catgatcagc tgggccaaga gctgccat                                      28

<210> SEQ ID NO 647
<211> LENGTH: 27
<212> TYPE: DNA
<213> ORGANISM: Artificial Sequence
<220> FEATURE:
<223> OTHER INFORMATION: Synthetic

<400> SEQUENCE: 647
catgatcagc tgggccaaga gctgcca                                       27

<210> SEQ ID NO 648
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 6 and/or 8 may
      be modified by 2'-O,4'-C-methylene-beta-D-ribofuranosyl moiety

<400> SEQUENCE: 648
aatgacatca catatg                                                     18

<210> SEQ ID NO 649
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Nucleotide at position 4 and/or 6 and/or 8 may
      be modified by 2'-O,4'-C-methylene-beta-D-ribofuranosyl moiety

<400> SEQUENCE: 649
aatgacatca catatat                                                    17

<210> SEQ ID NO 650
<211> LENGTH: 30
<212> TYPE: DNA
<213> ORGANISM: Artificial Sequence
<220> FEATURE:
<223> OTHER INFORMATION: Synthetic

<400> SEQUENCE: 650
catgatcagc tgggccaaga tcaacgggag                                      30

<210> SEQ ID NO 651
<211> LENGTH: 29
<212> TYPE: DNA
<213> ORGANISM: Artificial Sequence
<220> FEATURE:
<223> OTHER INFORMATION: Synthetic

<400> SEQUENCE: 651
catgatcagc tgggccaaga tcaacggga                                       29

<210> SEQ ID NO 652
<211> LENGTH: 28
<212> TYPE: DNA
<213> ORGANISM: Artificial Sequence
<220> FEATURE:
<223> OTHER INFORMATION: Synthetic

<400> SEQUENCE: 652
catgatcagc tgggccaaga tcaacggg                                        28

<210> SEQ ID NO 653
<211> LENGTH: 27
<212> TYPE: DNA
<213> ORGANISM: Artificial Sequence
<220> FEATURE:
<223> OTHER INFORMATION: Synthetic

<400> SEQUENCE: 653
catgatcagc tgggccaaga tcaacgg                                         27

<210> SEQ ID NO 654
<211> LENGTH: 18
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 654
aatgacacga tcactccc                                                   18

<210> SEQ ID NO 655
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 4 and/or 6 may
      be modified by 2'-O,4'-C-methylene-beta-D-ribofuranosyl moiety

<400> SEQUENCE: 655
aatgacacga tcactc                                                     16

<210> SEQ ID NO 656
<211> LENGTH: 30
<212> TYPE: DNA
<213> ORGANISM: Artificial Sequence
<220> FEATURE:
<223> OTHER INFORMATION: Synthetic

<400> SEQUENCE: 656
catgatcagc tgggccaaga tgcacaaccc                                      30

<210> SEQ ID NO 657
<211> LENGTH: 29
<212> TYPE: DNA
<213> ORGANISM: Artificial Sequence
<220> FEATURE:
<223> OTHER INFORMATION: Synthetic

<400> SEQUENCE: 657
catgatcagc tgggccaaga tgcacaacc                                       29

<210> SEQ ID NO 658
<211> LENGTH: 28
<212> TYPE: DNA
<213> ORGANISM: Artificial Sequence
<220> FEATURE:
<223> OTHER INFORMATION: Synthetic

<400> SEQUENCE: 658
catgatcagc tgggccaaga tgcacaac                                        28

<210> SEQ ID NO 659
<211> LENGTH: 27
<212> TYPE: DNA
<213> ORGANISM: Artificial Sequence
<220> FEATURE:
<223> OTHER INFORMATION: Synthetic

<400> SEQUENCE: 659
catgatcagc tgggccaaga tgcacaa                                         27

<210> SEQ ID NO 660
<211> LENGTH: 18
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Nucleotide at position 4 may be modified by
      2'-O,4'-C-methylene-beta-D-ribofuranosyl moiety

<400> SEQUENCE: 660
aatggcgcca ctagggtt                                                    18

<210> SEQ ID NO 661
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 661
aatggcgcca ctaggg                                                      16

<210> SEQ ID NO 662
<211> LENGTH: 30
<212> TYPE: DNA
<213> ORGANISM: Artificial Sequence
<220> FEATURE:
<223> OTHER INFORMATION: Synthetic

<400> SEQUENCE: 662
catgatcagc tgggccaaga gaattcatca                                       30

<210> SEQ ID NO 663
<211> LENGTH: 29
<212> TYPE: DNA
<213> ORGANISM: Artificial Sequence
<220> FEATURE:
<223> OTHER INFORMATION: Synthetic

<400> SEQUENCE: 663
catgatcagc tgggccaaga gaattcatc                                        29

<210> SEQ ID NO 664
<211> LENGTH: 28
<212> TYPE: DNA
<213> ORGANISM: Artificial Sequence
<220> FEATURE:
<223> OTHER INFORMATION: Synthetic

<400> SEQUENCE: 664
catgatcagc tgggccaaga gaattcat                                         28

<210> SEQ ID NO 665
<211> LENGTH: 27
<212> TYPE: DNA
<213> ORGANISM: Artificial Sequence
<220> FEATURE:
<223> OTHER INFORMATION: Synthetic

<400> SEQUENCE: 665
catgatcagc tgggccaaga gaattca                                          27

<210> SEQ ID NO 666
<211> LENGTH: 17
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Nucleotide at position 4 may be modified by
      2'-O,4'-C-methylene-beta-D-ribofuranosyl moiety

<400> SEQUENCE: 666
agaggctggc cgtgatg                                                        17

<210> SEQ ID NO 667
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Nucleotide at position 4 may be modified by
      2'-O,4'-C-methylene-beta-D-ribofuranosyl moiety

<400> SEQUENCE: 667
agaggctggc cgtga                                                          15

<210> SEQ ID NO 668
<211> LENGTH: 30
<212> TYPE: DNA
<213> ORGANISM: Artificial Sequence
<220> FEATURE:
<223> OTHER INFORMATION: Synthetic

<400> SEQUENCE: 668
catgatcagc tgggccaaga agagaggaga                                          30

<210> SEQ ID NO 669
<211> LENGTH: 29
<212> TYPE: DNA
<213> ORGANISM: Artificial Sequence
<220> FEATURE:
<223> OTHER INFORMATION: Synthetic

<400> SEQUENCE: 669
catgatcagc tgggccaaga agagaggag                                           29

<210> SEQ ID NO 670
<211> LENGTH: 28
<212> TYPE: DNA
<213> ORGANISM: Artificial Sequence
<220> FEATURE:
<223> OTHER INFORMATION: Synthetic

<400> SEQUENCE: 670
catgatcagc tgggccaaga agagagga                                            28

<210> SEQ ID NO 671
<211> LENGTH: 27
<212> TYPE: DNA
<213> ORGANISM: Artificial Sequence
<220> FEATURE:
<223> OTHER INFORMATION: Synthetic

<400> SEQUENCE: 671
catgatcagc tgggccaaga agagagg                                             27
```

```
<210> SEQ ID NO 672
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 8 may be
      modified by 2'-O,4'-C-methylene-beta-D-ribofuranosyl moiety

<400> SEQUENCE: 672
agtcatacac ggctctcc                                                 18

<210> SEQ ID NO 673
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 673
agtcatacac ggctct                                                   16

<210> SEQ ID NO 674
<211> LENGTH: 30
<212> TYPE: DNA
<213> ORGANISM: Artificial Sequence
<220> FEATURE:
<223> OTHER INFORMATION: Synthetic

<400> SEQUENCE: 674
catgatcagc tgggccaaga cgaatataac                                    30

<210> SEQ ID NO 675
<211> LENGTH: 29
<212> TYPE: DNA
<213> ORGANISM: Artificial Sequence
<220> FEATURE:
<223> OTHER INFORMATION: Synthetic

<400> SEQUENCE: 675
catgatcagc tgggccaaga cgaatataa                                     29

<210> SEQ ID NO 676
<211> LENGTH: 28
<212> TYPE: DNA
<213> ORGANISM: Artificial Sequence
<220> FEATURE:
<223> OTHER INFORMATION: Synthetic

<400> SEQUENCE: 676
catgatcagc tgggccaaga cgaatata                                      28

<210> SEQ ID NO 677
<211> LENGTH: 27
<212> TYPE: DNA
<213> ORGANISM: Artificial Sequence
<220> FEATURE:
<223> OTHER INFORMATION: Synthetic

<400> SEQUENCE: 677
catgatcagc tgggccaaga cgaatat                                       27
```

<210> SEQ ID NO 678
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 678
agatcgaccg tgttat                                                     16

<210> SEQ ID NO 679
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 679
agatcgaccg tgtt                                                       14

<210> SEQ ID NO 680
<211> LENGTH: 30
<212> TYPE: DNA
<213> ORGANISM: Artificial Sequence
<220> FEATURE:
<223> OTHER INFORMATION: Synthetic

<400> SEQUENCE: 680
catgatcagc tgggccaaga cctccagccc                                      30

<210> SEQ ID NO 681
<211> LENGTH: 29
<212> TYPE: DNA
<213> ORGANISM: Artificial Sequence
<220> FEATURE:
<223> OTHER INFORMATION: Synthetic

<400> SEQUENCE: 681
catgatcagc tgggccaaga cctccagcc                                       29

<210> SEQ ID NO 682
<211> LENGTH: 28
<212> TYPE: DNA
<213> ORGANISM: Artificial Sequence
<220> FEATURE:
<223> OTHER INFORMATION: Synthetic

<400> SEQUENCE: 682
catgatcagc tgggccaaga cctccagc                                        28

<210> SEQ ID NO 683
<211> LENGTH: 27
<212> TYPE: DNA
<213> ORGANISM: Artificial Sequence
<220> FEATURE:
<223> OTHER INFORMATION: Synthetic

<400> SEQUENCE: 683
catgatcagc tgggccaaga cctccag         27

<210> SEQ ID NO 684
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 684
aggaagccct ggaggggct         19

<210> SEQ ID NO 685
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 685
aggaagccct ggagggg         17

<210> SEQ ID NO 686
<211> LENGTH: 30
<212> TYPE: DNA
<213> ORGANISM: Artificial Sequence
<220> FEATURE:
<223> OTHER INFORMATION: Synthetic

<400> SEQUENCE: 686
catgatcagc tgggccaaga gccagctaac         30

<210> SEQ ID NO 687
<211> LENGTH: 29
<212> TYPE: DNA
<213> ORGANISM: Artificial Sequence
<220> FEATURE:
<223> OTHER INFORMATION: Synthetic

<400> SEQUENCE: 687
catgatcagc tgggccaaga gccagctaa         29

<210> SEQ ID NO 688
<211> LENGTH: 28
<212> TYPE: DNA
<213> ORGANISM: Artificial Sequence
<220> FEATURE:
<223> OTHER INFORMATION: Synthetic

<400> SEQUENCE: 688
catgatcagc tgggccaaga gccagcta         28

<210> SEQ ID NO 689
<211> LENGTH: 27
<212> TYPE: DNA
<213> ORGANISM: Artificial Sequence
<220> FEATURE:
<223> OTHER INFORMATION: Synthetic

<400> SEQUENCE: 689
catgatcagc tgggccaaga gccagct                                              27

<210> SEQ ID NO 690
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 690
aggcagtgta ttgttag                                                         17

<210> SEQ ID NO 691
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(7)
<223> OTHER INFORMATION: Nucleotide at position 3 and/or 5 and/or 7 may
      be modified by 2'-O,4'-C-methylene-beta-D-ribofuranosyl moiety

<400> SEQUENCE: 691
aggcagtgta ttgtt                                                           15

<210> SEQ ID NO 692
<211> LENGTH: 30
<212> TYPE: DNA
<213> ORGANISM: Artificial Sequence
<220> FEATURE:
<223> OTHER INFORMATION: Synthetic

<400> SEQUENCE: 692
catgatcagc tgggccaaga ccagctagca                                           30

<210> SEQ ID NO 693
<211> LENGTH: 29
<212> TYPE: DNA
<213> ORGANISM: Artificial Sequence
<220> FEATURE:
<223> OTHER INFORMATION: Synthetic

<400> SEQUENCE: 693
catgatcagc tgggccaaga ccagctagc                                            29

<210> SEQ ID NO 694
<211> LENGTH: 28
<212> TYPE: DNA
<213> ORGANISM: Artificial Sequence
<220> FEATURE:
<223> OTHER INFORMATION: Synthetic

<400> SEQUENCE: 694
catgatcagc tgggccaaga ccagctag                                             28

<210> SEQ ID NO 695
<211> LENGTH: 27
<212> TYPE: DNA
<213> ORGANISM: Artificial Sequence

```
<220> FEATURE:
<223> OTHER INFORMATION: Synthetic

<400> SEQUENCE: 695
catgatcagc tgggccaaga ccagcta                                          27

<210> SEQ ID NO 696
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 696
aggcagtgca ttgcta                                                      16

<210> SEQ ID NO 697
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 697
aggcagtgca ttgc                                                        14

<210> SEQ ID NO 698
<211> LENGTH: 30
<212> TYPE: DNA
<213> ORGANISM: Artificial Sequence
<220> FEATURE:
<223> OTHER INFORMATION: Synthetic

<400> SEQUENCE: 698
catgatcagc tgggccaaga cgagccaggt                                       30

<210> SEQ ID NO 699
<211> LENGTH: 29
<212> TYPE: DNA
<213> ORGANISM: Artificial Sequence
<220> FEATURE:
<223> OTHER INFORMATION: Synthetic

<400> SEQUENCE: 699
catgatcagc tgggccaaga cgagccagg                                        29

<210> SEQ ID NO 700
<211> LENGTH: 28
<212> TYPE: DNA
<213> ORGANISM: Artificial Sequence
<220> FEATURE:
<223> OTHER INFORMATION: Synthetic

<400> SEQUENCE: 700
catgatcagc tgggccaaga cgagccag                                         28

<210> SEQ ID NO 701
<211> LENGTH: 27
```

```
<212> TYPE: DNA
<213> ORGANISM: Artificial Sequence
<220> FEATURE:
<223> OTHER INFORMATION: Synthetic

<400> SEQUENCE: 701
catgatcagc tgggccaaga cgagcca                                          27

<210> SEQ ID NO 702
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 702
aggcagtgcg acctg                                                       15

<210> SEQ ID NO 703
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 703
aggcagtgcg acc                                                         13

<210> SEQ ID NO 704
<211> LENGTH: 30
<212> TYPE: DNA
<213> ORGANISM: Artificial Sequence
<220> FEATURE:
<223> OTHER INFORMATION: Synthetic

<400> SEQUENCE: 704
catgatcagc tgggccaaga caaagttgct                                       30

<210> SEQ ID NO 705
<211> LENGTH: 29
<212> TYPE: DNA
<213> ORGANISM: Artificial Sequence
<220> FEATURE:
<223> OTHER INFORMATION: Synthetic

<400> SEQUENCE: 705
catgatcagc tgggccaaga caaagttgc                                        29

<210> SEQ ID NO 706
<211> LENGTH: 28
<212> TYPE: DNA
<213> ORGANISM: Artificial Sequence
<220> FEATURE:
<223> OTHER INFORMATION: Synthetic

<400> SEQUENCE: 706
catgatcagc tgggccaaga caaagttg                                         28
```

```
<210> SEQ ID NO 707
<211> LENGTH: 27
<212> TYPE: DNA
<213> ORGANISM: Artificial Sequence
<220> FEATURE:
<223> OTHER INFORMATION: Synthetic

<400> SEQUENCE: 707
catgatcagc tgggccaaga caaagtt                                              27

<210> SEQ ID NO 708
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 708
aggttacccg agcaact                                                         17

<210> SEQ ID NO 709
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 709
aggttacccg agcaa                                                           15

<210> SEQ ID NO 710
<211> LENGTH: 30
<212> TYPE: DNA
<213> ORGANISM: Artificial Sequence
<220> FEATURE:
<223> OTHER INFORMATION: Synthetic

<400> SEQUENCE: 710
catgatcagc tgggccaaga aagggttca                                            30

<210> SEQ ID NO 711
<211> LENGTH: 29
<212> TYPE: DNA
<213> ORGANISM: Artificial Sequence
<220> FEATURE:
<223> OTHER INFORMATION: Synthetic

<400> SEQUENCE: 711
catgatcagc tgggccaaga aagggttc                                             29

<210> SEQ ID NO 712
<211> LENGTH: 28
<212> TYPE: DNA
<213> ORGANISM: Artificial Sequence
<220> FEATURE:
<223> OTHER INFORMATION: Synthetic

<400> SEQUENCE: 712
catgatcagc tgggccaaga aagggtt                                              28
```

<210> SEQ ID NO 713
<211> LENGTH: 27
<212> TYPE: DNA
<213> ORGANISM: Artificial Sequence
<220> FEATURE:
<223> OTHER INFORMATION: Synthetic

<400> SEQUENCE: 713
catgatcagc tgggccaaga aaggggt                                        27

<210> SEQ ID NO 714
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 714
gaatgttgct cggtgaac                                                  18

<210> SEQ ID NO 715
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 715
gaatgttgct cggtga                                                    16

<210> SEQ ID NO 716
<211> LENGTH: 30
<212> TYPE: DNA
<213> ORGANISM: Artificial Sequence
<220> FEATURE:
<223> OTHER INFORMATION: Synthetic

<400> SEQUENCE: 716
catgatcagc tgggccaaga cctcatggaa                                     30

<210> SEQ ID NO 717
<211> LENGTH: 29
<212> TYPE: DNA
<213> ORGANISM: Artificial Sequence
<220> FEATURE:
<223> OTHER INFORMATION: Synthetic

<400> SEQUENCE: 717
catgatcagc tgggccaaga cctcatgga                                      29

<210> SEQ ID NO 718
<211> LENGTH: 28
<212> TYPE: DNA
<213> ORGANISM: Artificial Sequence
<220> FEATURE:
<223> OTHER INFORMATION: Synthetic

<400> SEQUENCE: 718

```
catgatcagc tgggccaaga cctcatgg                                    28

<210> SEQ ID NO 719
<211> LENGTH: 27
<212> TYPE: DNA
<213> ORGANISM: Artificial Sequence
<220> FEATURE:
<223> OTHER INFORMATION: Synthetic

<400> SEQUENCE: 719
catgatcagc tgggccaaga cctcatg                                     27

<210> SEQ ID NO 720
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 720
agtggggaac ccttcca                                                17

<210> SEQ ID NO 721
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 721
agtggggaac ccttc                                                  15

<210> SEQ ID NO 722
<211> LENGTH: 30
<212> TYPE: DNA
<213> ORGANISM: Artificial Sequence
<220> FEATURE:
<223> OTHER INFORMATION: Synthetic

<400> SEQUENCE: 722
catgatcagc tgggccaaga tatgaacaat                                  30

<210> SEQ ID NO 723
<211> LENGTH: 29
<212> TYPE: DNA
<213> ORGANISM: Artificial Sequence
<220> FEATURE:
<223> OTHER INFORMATION: Synthetic

<400> SEQUENCE: 723
catgatcagc tgggccaaga tatgaacaa                                   29

<210> SEQ ID NO 724
<211> LENGTH: 28
<212> TYPE: DNA
<213> ORGANISM: Artificial Sequence
<220> FEATURE:
<223> OTHER INFORMATION: Synthetic
```

-continued

<400> SEQUENCE: 724
catgatcagc tgggccaaga tatgaaca                                    28

<210> SEQ ID NO 725
<211> LENGTH: 27
<212> TYPE: DNA
<213> ORGANISM: Artificial Sequence
<220> FEATURE:
<223> OTHER INFORMATION: Synthetic

<400> SEQUENCE: 725
catgatcagc tgggccaaga tatgaac                                     27

<210> SEQ ID NO 726
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Nucleotide at position 2 and/or 4 and/or 7 may
      be modified by 2'-O,4'-C-methylene-beta-D-ribofuranosyl moiety

<400> SEQUENCE: 726
attcctagaa attgttc                                                17

<210> SEQ ID NO 727
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(9)
<223> OTHER INFORMATION: Nucleotide at position 2 and/or 4 and/or 7
      and/or 9 may be modified by 2'-O,4'-C-methylene-beta-D-
      ribofuranosyl moiety

<400> SEQUENCE: 727
attcctagaa attgt                                                  15

<210> SEQ ID NO 728
<211> LENGTH: 30
<212> TYPE: DNA
<213> ORGANISM: Artificial Sequence
<220> FEATURE:
<223> OTHER INFORMATION: Synthetic

<400> SEQUENCE: 728
catgatcagc tgggccaaga tgtgaacaat                                  30

<210> SEQ ID NO 729
<211> LENGTH: 29
<212> TYPE: DNA
<213> ORGANISM: Artificial Sequence
<220> FEATURE:
<223> OTHER INFORMATION: Synthetic

<400> SEQUENCE: 729
catgatcagc tgggccaaga tgtgaacaa                                   29

<210> SEQ ID NO 730
<211> LENGTH: 28
<212> TYPE: DNA

```
<213> ORGANISM: Artificial Sequence
<220> FEATURE:
<223> OTHER INFORMATION: Synthetic

<400> SEQUENCE: 730
catgatcagc tgggccaaga tgtgaaca                                              28

<210> SEQ ID NO 731
<211> LENGTH: 27
<212> TYPE: DNA
<213> ORGANISM: Artificial Sequence
<220> FEATURE:
<223> OTHER INFORMATION: Synthetic

<400> SEQUENCE: 731
catgatcagc tgggccaaga tgtgaac                                               27

<210> SEQ ID NO 732
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Nucleotide at position 2 and/or 4 and/or 7 may
      be modified by 2'-O,4'-C-methylene-beta-D-ribofuranosyl moiety

<400> SEQUENCE: 732
attcctagaa attgtt                                                           16

<210> SEQ ID NO 733
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(9)
<223> OTHER INFORMATION: Nucleotide at position 2 and/or 4 and/or 7
      and/or 9 may be modified by 2'-O,4'-C-methylene-beta-D-
      ribofuranosyl moiety

<400> SEQUENCE: 733
attcctagaa attgtt                                                           16

<210> SEQ ID NO 734
<211> LENGTH: 30
<212> TYPE: DNA
<213> ORGANISM: Artificial Sequence
<220> FEATURE:
<223> OTHER INFORMATION: Synthetic

<400> SEQUENCE: 734
catgatcagc tgggccaaga acctgcacta                                            30

<210> SEQ ID NO 735
<211> LENGTH: 29
<212> TYPE: DNA
<213> ORGANISM: Artificial Sequence
<220> FEATURE:
<223> OTHER INFORMATION: Synthetic

<400> SEQUENCE: 735
catgatcagc tgggccaaga acctgcact                                             29
```

```
<210> SEQ ID NO 736
<211> LENGTH: 28
<212> TYPE: DNA
<213> ORGANISM: Artificial Sequence
<220> FEATURE:
<223> OTHER INFORMATION: Synthetic

<400> SEQUENCE: 736
catgatcagc tgggccaaga acctgcac                                          28

<210> SEQ ID NO 737
<211> LENGTH: 27
<212> TYPE: DNA
<213> ORGANISM: Artificial Sequence
<220> FEATURE:
<223> OTHER INFORMATION: Synthetic

<400> SEQUENCE: 737
catgatcagc tgggccaaga acctgca                                           27

<210> SEQ ID NO 738
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 738
caaagtgctc atagtgca                                                     18

<210> SEQ ID NO 739
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Nucleotide at position 4 and/or 6 and/or 8 may
      be modified by 2'-O,4'-C-methylene-beta-D-ribofuranosyl moiety

<400> SEQUENCE: 739
caaagtgctc atagtg                                                       16

<210> SEQ ID NO 740
<211> LENGTH: 30
<212> TYPE: DNA
<213> ORGANISM: Artificial Sequence
<220> FEATURE:
<223> OTHER INFORMATION: Synthetic

<400> SEQUENCE: 740
catgatcagc tgggccaaga cagcatggag                                        30

<210> SEQ ID NO 741
<211> LENGTH: 29
<212> TYPE: DNA
<213> ORGANISM: Artificial Sequence
<220> FEATURE:
<223> OTHER INFORMATION: Synthetic

<400> SEQUENCE: 741
catgatcagc tgggccaaga cagcatgga                                         29
```

<210> SEQ ID NO 742
<211> LENGTH: 28
<212> TYPE: DNA
<213> ORGANISM: Artificial Sequence
<220> FEATURE:
<223> OTHER INFORMATION: Synthetic

<400> SEQUENCE: 742
catgatcagc tgggccaaga cagcatgg                                          28

<210> SEQ ID NO 743
<211> LENGTH: 27
<212> TYPE: DNA
<213> ORGANISM: Artificial Sequence
<220> FEATURE:
<223> OTHER INFORMATION: Synthetic

<400> SEQUENCE: 743
catgatcagc tgggccaaga cagcatg                                           27

<210> SEQ ID NO 744
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 744
caacctggag gactcca                                                      17

<210> SEQ ID NO 745
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Nucleotide at position 4 and/or 7 may be
      modified by 2'-O,4'-C-methylene-beta-D-ribofuranosyl moiety

<400> SEQUENCE: 745
caacctggag gactc                                                        15

<210> SEQ ID NO 746
<211> LENGTH: 30
<212> TYPE: DNA
<213> ORGANISM: Artificial Sequence
<220> FEATURE:
<223> OTHER INFORMATION: Synthetic

<400> SEQUENCE: 746
catgatcagc tgggccaaga acaaaccaca                                        30

<210> SEQ ID NO 747
<211> LENGTH: 29
<212> TYPE: DNA
<213> ORGANISM: Artificial Sequence
<220> FEATURE:
<223> OTHER INFORMATION: Synthetic

<400> SEQUENCE: 747

```
catgatcagc tgggccaaga acaaaccac                                          29

<210> SEQ ID NO 748
<211> LENGTH: 28
<212> TYPE: DNA
<213> ORGANISM: Artificial Sequence
<220> FEATURE:
<223> OTHER INFORMATION: Synthetic

<400> SEQUENCE: 748
catgatcagc tgggccaaga acaaacca                                           28

<210> SEQ ID NO 749
<211> LENGTH: 27
<212> TYPE: DNA
<213> ORGANISM: Artificial Sequence
<220> FEATURE:
<223> OTHER INFORMATION: Synthetic

<400> SEQUENCE: 749
catgatcagc tgggccaaga acaaacc                                            27

<210> SEQ ID NO 750
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 750
cagcagcaca ctgtgg                                                        16

<210> SEQ ID NO 751
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 751
cagcagcaca ctgtg                                                         15

<210> SEQ ID NO 752
<211> LENGTH: 30
<212> TYPE: DNA
<213> ORGANISM: Artificial Sequence
<220> FEATURE:
<223> OTHER INFORMATION: Synthetic

<400> SEQUENCE: 752
catgatcagc tgggccaaga tgctttgaca                                         30

<210> SEQ ID NO 753
<211> LENGTH: 29
<212> TYPE: DNA
<213> ORGANISM: Artificial Sequence
<220> FEATURE:
<223> OTHER INFORMATION: Synthetic
```

<400> SEQUENCE: 753
catgatcagc tgggccaaga tgctttgac					29

<210> SEQ ID NO 754
<211> LENGTH: 28
<212> TYPE: DNA
<213> ORGANISM: Artificial Sequence
<220> FEATURE:
<223> OTHER INFORMATION: Synthetic

<400> SEQUENCE: 754
catgatcagc tgggccaaga tgctttga					28

<210> SEQ ID NO 755
<211> LENGTH: 27
<212> TYPE: DNA
<213> ORGANISM: Artificial Sequence
<220> FEATURE:
<223> OTHER INFORMATION: Synthetic

<400> SEQUENCE: 755
catgatcagc tgggccaaga tgctttg					27

<210> SEQ ID NO 756
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 756
cagtgcaatg atattgtca					19

<210> SEQ ID NO 757
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 757
cagtgcaatg atattgt					17

<210> SEQ ID NO 758
<211> LENGTH: 30
<212> TYPE: DNA
<213> ORGANISM: Artificial Sequence
<220> FEATURE:
<223> OTHER INFORMATION: Synthetic

<400> SEQUENCE: 758
catgatcagc tgggccaaga tgctttgaca					30

<210> SEQ ID NO 759
<211> LENGTH: 29
<212> TYPE: DNA
<213> ORGANISM: Artificial Sequence

```
<220> FEATURE:
<223> OTHER INFORMATION: Synthetic

<400> SEQUENCE: 759
catgatcagc tgggccaaga tgctttgac                                              29

<210> SEQ ID NO 760
<211> LENGTH: 28
<212> TYPE: DNA
<213> ORGANISM: Artificial Sequence
<220> FEATURE:
<223> OTHER INFORMATION: Synthetic

<400> SEQUENCE: 760
catgatcagc tgggccaaga tgctttga                                               28

<210> SEQ ID NO 761
<211> LENGTH: 27
<212> TYPE: DNA
<213> ORGANISM: Artificial Sequence
<220> FEATURE:
<223> OTHER INFORMATION: Synthetic

<400> SEQUENCE: 761
catgatcagc tgggccaaga tgctttg                                                27

<210> SEQ ID NO 762
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 762
cagtgcaatg gtattgtca                                                         19

<210> SEQ ID NO 763
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 763
cagtgcaatg gtattgt                                                           17

<210> SEQ ID NO 764
<211> LENGTH: 30
<212> TYPE: DNA
<213> ORGANISM: Artificial Sequence
<220> FEATURE:
<223> OTHER INFORMATION: Synthetic

<400> SEQUENCE: 764
catgatcagc tgggccaaga ttcccccttt                                             30

<210> SEQ ID NO 765
<211> LENGTH: 29
```

```
<212> TYPE: DNA
<213> ORGANISM: Artificial Sequence
<220> FEATURE:
<223> OTHER INFORMATION: Synthetic

<400> SEQUENCE: 765
catgatcagc tgggccaaga ttccccctt                                          29

<210> SEQ ID NO 766
<211> LENGTH: 28
<212> TYPE: DNA
<213> ORGANISM: Artificial Sequence
<220> FEATURE:
<223> OTHER INFORMATION: Synthetic

<400> SEQUENCE: 766
catgatcagc tgggccaaga ttcccct                                            28

<210> SEQ ID NO 767
<211> LENGTH: 27
<212> TYPE: DNA
<213> ORGANISM: Artificial Sequence
<220> FEATURE:
<223> OTHER INFORMATION: Synthetic

<400> SEQUENCE: 767
catgatcagc tgggccaaga ttcccc                                             27

<210> SEQ ID NO 768
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 768
cagtgcaatt aaaaggg                                                       17

<210> SEQ ID NO 769
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 769
cagtgcaatt aaaag                                                         15

<210> SEQ ID NO 770
<211> LENGTH: 30
<212> TYPE: DNA
<213> ORGANISM: Artificial Sequence
<220> FEATURE:
<223> OTHER INFORMATION: Synthetic

<400> SEQUENCE: 770
catgatcagc tgggccaaga acggtcctac                                         30
```

```
<210> SEQ ID NO 771
<211> LENGTH: 29
<212> TYPE: DNA
<213> ORGANISM: Artificial Sequence
<220> FEATURE:
<223> OTHER INFORMATION: Synthetic

<400> SEQUENCE: 771
catgatcagc tgggccaaga acggtccta                                    29

<210> SEQ ID NO 772
<211> LENGTH: 28
<212> TYPE: DNA
<213> ORGANISM: Artificial Sequence
<220> FEATURE:
<223> OTHER INFORMATION: Synthetic

<400> SEQUENCE: 772
catgatcagc tgggccaaga acggtcct                                     28

<210> SEQ ID NO 773
<211> LENGTH: 27
<212> TYPE: DNA
<213> ORGANISM: Artificial Sequence
<220> FEATURE:
<223> OTHER INFORMATION: Synthetic

<400> SEQUENCE: 773
catgatcagc tgggccaaga acggtcc                                      27

<210> SEQ ID NO 774
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 774
catgccttga gtgtagg                                                 17

<210> SEQ ID NO 775
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 775
catgccttga gtgta                                                   15

<210> SEQ ID NO 776
<211> LENGTH: 30
<212> TYPE: DNA
<213> ORGANISM: Artificial Sequence
<220> FEATURE:
<223> OTHER INFORMATION: Synthetic

<400> SEQUENCE: 776
catgatcagc tgggccaaga ttgagagtgc                                   30
```

<210> SEQ ID NO 777
<211> LENGTH: 29
<212> TYPE: DNA
<213> ORGANISM: Artificial Sequence
<220> FEATURE:
<223> OTHER INFORMATION: Synthetic

<400> SEQUENCE: 777
catgatcagc tgggccaaga ttgagagtg                                    29

<210> SEQ ID NO 778
<211> LENGTH: 28
<212> TYPE: DNA
<213> ORGANISM: Artificial Sequence
<220> FEATURE:
<223> OTHER INFORMATION: Synthetic

<400> SEQUENCE: 778
catgatcagc tgggccaaga ttgagagt                                     28

<210> SEQ ID NO 779
<211> LENGTH: 27
<212> TYPE: DNA
<213> ORGANISM: Artificial Sequence
<220> FEATURE:
<223> OTHER INFORMATION: Synthetic

<400> SEQUENCE: 779
catgatcagc tgggccaaga ttgagag                                      27

<210> SEQ ID NO 780
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 780
cccagataat ggcact                                                  16

<210> SEQ ID NO 781
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 4 and/or 5 may
      be modified by 2'-O,4'-C-methylene-beta-D-ribofuranosyl moiety

<400> SEQUENCE: 781
cccagataat ggca                                                    14

<210> SEQ ID NO 782
<211> LENGTH: 30
<212> TYPE: DNA
<213> ORGANISM: Artificial Sequence
<220> FEATURE:
<223> OTHER INFORMATION: Synthetic

<400> SEQUENCE: 782

```
<210> SEQ ID NO 783
<211> LENGTH: 29
<212> TYPE: DNA
<213> ORGANISM: Artificial Sequence
<220> FEATURE:
<223> OTHER INFORMATION: Synthetic

<400> SEQUENCE: 783
catgatcagc tgggccaaga ttgagagtg                              29

<210> SEQ ID NO 784
<211> LENGTH: 28
<212> TYPE: DNA
<213> ORGANISM: Artificial Sequence
<220> FEATURE:
<223> OTHER INFORMATION: Synthetic

<400> SEQUENCE: 784
catgatcagc tgggccaaga ttgagagt                               28

<210> SEQ ID NO 785
<211> LENGTH: 27
<212> TYPE: DNA
<213> ORGANISM: Artificial Sequence
<220> FEATURE:
<223> OTHER INFORMATION: Synthetic

<400> SEQUENCE: 785
catgatcagc tgggccaaga ttgagag                                27

<210> SEQ ID NO 786
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 786
cccagataat agcact                                            16

<210> SEQ ID NO 787
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 4 and/or 5 may
      be modified by 2'-O,4'-C-methylene-beta-D-ribofuranosyl moiety

<400> SEQUENCE: 787
cccagataat agca                                              14

<210> SEQ ID NO 788
<211> LENGTH: 30
<212> TYPE: DNA
<213> ORGANISM: Artificial Sequence
<220> FEATURE:
<223> OTHER INFORMATION: Synthetic
```

catgatcagc tgggccaaga ttgagagtgc                             30

```
<400> SEQUENCE: 788
catgatcagc tgggccaaga acacaccaag                                           30

<210> SEQ ID NO 789
<211> LENGTH: 29
<212> TYPE: DNA
<213> ORGANISM: Artificial Sequence
<220> FEATURE:
<223> OTHER INFORMATION: Synthetic

<400> SEQUENCE: 789
catgatcagc tgggccaaga acacaccaa                                            29

<210> SEQ ID NO 790
<211> LENGTH: 28
<212> TYPE: DNA
<213> ORGANISM: Artificial Sequence
<220> FEATURE:
<223> OTHER INFORMATION: Synthetic

<400> SEQUENCE: 790
catgatcagc tgggccaaga acacacca                                             28

<210> SEQ ID NO 791
<211> LENGTH: 27
<212> TYPE: DNA
<213> ORGANISM: Artificial Sequence
<220> FEATURE:
<223> OTHER INFORMATION: Synthetic

<400> SEQUENCE: 791
catgatcagc tgggccaaga acacacc                                              27

<210> SEQ ID NO 792
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 792
ggagaaatta tccttggt                                                        18

<210> SEQ ID NO 793
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 4 and/or 5 may
      be modified by 2'-O,4'-C-methylene-beta-D-ribofuranosyl moiety

<400> SEQUENCE: 793
ggagaaatta tccttgg                                                         17

<210> SEQ ID NO 794
<211> LENGTH: 30
<212> TYPE: DNA
<213> ORGANISM: Artificial Sequence
```

```
<220> FEATURE:
<223> OTHER INFORMATION: Synthetic

<400> SEQUENCE: 794
catgatcagc tgggccaaga gaggaaacca                                            30

<210> SEQ ID NO 795
<211> LENGTH: 29
<212> TYPE: DNA
<213> ORGANISM: Artificial Sequence
<220> FEATURE:
<223> OTHER INFORMATION: Synthetic

<400> SEQUENCE: 795
catgatcagc tgggccaaga gaggaaacc                                             29

<210> SEQ ID NO 796
<211> LENGTH: 28
<212> TYPE: DNA
<213> ORGANISM: Artificial Sequence
<220> FEATURE:
<223> OTHER INFORMATION: Synthetic

<400> SEQUENCE: 796
catgatcagc tgggccaaga gaggaaac                                              28

<210> SEQ ID NO 797
<211> LENGTH: 27
<212> TYPE: DNA
<213> ORGANISM: Artificial Sequence
<220> FEATURE:
<223> OTHER INFORMATION: Synthetic

<400> SEQUENCE: 797
catgatcagc tgggccaaga gaggaaa                                               27

<210> SEQ ID NO 798
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 798
gtcaacactt gctggtt                                                          17

<210> SEQ ID NO 799
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 3 and/or 6 may
      be modified by 2'-O,4'-C-methylene-beta-D-ribofuranosyl moiety

<400> SEQUENCE: 799
gtcaacactt gctgg                                                            15

<210> SEQ ID NO 800
<211> LENGTH: 30
```

```
<212> TYPE: DNA
<213> ORGANISM: Artificial Sequence
<220> FEATURE:
<223> OTHER INFORMATION: Synthetic

<400> SEQUENCE: 800
catgatcagc tgggccaaga ggaaaccagc                                          30

<210> SEQ ID NO 801
<211> LENGTH: 29
<212> TYPE: DNA
<213> ORGANISM: Artificial Sequence
<220> FEATURE:
<223> OTHER INFORMATION: Synthetic

<400> SEQUENCE: 801
catgatcagc tgggccaaga ggaaaccag                                           29

<210> SEQ ID NO 802
<211> LENGTH: 28
<212> TYPE: DNA
<213> ORGANISM: Artificial Sequence
<220> FEATURE:
<223> OTHER INFORMATION: Synthetic

<400> SEQUENCE: 802
catgatcagc tgggccaaga ggaaacca                                            28

<210> SEQ ID NO 803
<211> LENGTH: 27
<212> TYPE: DNA
<213> ORGANISM: Artificial Sequence
<220> FEATURE:
<223> OTHER INFORMATION: Synthetic

<400> SEQUENCE: 803
catgatcagc tgggccaaga ggaaacc                                             27

<210> SEQ ID NO 804
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(9)
<223> OTHER INFORMATION: Nucleotide at position 3, 4, 7 and/or 9 may be
      modified by 2'-O,4'-C-methylene-beta-D-ribofuranosyl moiety
<220> FEATURE:
<221> NAME/KEY: misc_feature
<222> LOCATION: (3)..(9)
<223> OTHER INFORMATION: Nucleotide at position 3 and/or 4 and/or 7
      and/or 9 may be modified by 2'-O,4'-C-methylene-beta-D-
      ribofuranosyl moiety

<400> SEQUENCE: 804
cgtcaacact tgctggt                                                        17

<210> SEQ ID NO 805
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(9)
<223> OTHER INFORMATION: Nucleotide at position 3 and/or 4 and/or 7
      and/or 9 may be modified by 2'-O,4'-C-methylene-beta-D-
``` ribofuranosyl moiety

<400> SEQUENCE: 805
cgtcaacact tgctg                                                        15

<210> SEQ ID NO 806
<211> LENGTH: 30
<212> TYPE: DNA
<213> ORGANISM: Artificial Sequence
<220> FEATURE:
<223> OTHER INFORMATION: Synthetic

<400> SEQUENCE: 806
catgatcagc tgggccaaga taactgcact                                        30

<210> SEQ ID NO 807
<211> LENGTH: 29
<212> TYPE: DNA
<213> ORGANISM: Artificial Sequence
<220> FEATURE:
<223> OTHER INFORMATION: Synthetic

<400> SEQUENCE: 807
catgatcagc tgggccaaga taactgcac                                         29

<210> SEQ ID NO 808
<211> LENGTH: 28
<212> TYPE: DNA
<213> ORGANISM: Artificial Sequence
<220> FEATURE:
<223> OTHER INFORMATION: Synthetic

<400> SEQUENCE: 808
catgatcagc tgggccaaga taactgca                                          28

<210> SEQ ID NO 809
<211> LENGTH: 27
<212> TYPE: DNA
<213> ORGANISM: Artificial Sequence
<220> FEATURE:
<223> OTHER INFORMATION: Synthetic

<400> SEQUENCE: 809
catgatcagc tgggccaaga taactgc                                           27

<210> SEQ ID NO 810
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 810
taaggtgcat ctagtgc                                                      17

<210> SEQ ID NO 811
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 811
taaggtgcat ctagt                                                     15

<210> SEQ ID NO 812
<211> LENGTH: 30
<212> TYPE: DNA
<213> ORGANISM: Artificial Sequence
<220> FEATURE:
<223> OTHER INFORMATION: Synthetic

<400> SEQUENCE: 812
catgatcagc tgggccaaga taacagcact                                     30

<210> SEQ ID NO 813
<211> LENGTH: 29
<212> TYPE: DNA
<213> ORGANISM: Artificial Sequence
<220> FEATURE:
<223> OTHER INFORMATION: Synthetic

<400> SEQUENCE: 813
catgatcagc tgggccaaga taacagcac                                      29

<210> SEQ ID NO 814
<211> LENGTH: 28
<212> TYPE: DNA
<213> ORGANISM: Artificial Sequence
<220> FEATURE:
<223> OTHER INFORMATION: Synthetic

<400> SEQUENCE: 814
catgatcagc tgggccaaga taacagca                                       28

<210> SEQ ID NO 815
<211> LENGTH: 27
<212> TYPE: DNA
<213> ORGANISM: Artificial Sequence
<220> FEATURE:
<223> OTHER INFORMATION: Synthetic

<400> SEQUENCE: 815
catgatcagc tgggccaaga taacagc                                        27

<210> SEQ ID NO 816
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 816
taaggtgcat ctagtgc                                                   17

<210> SEQ ID NO 817
<211> LENGTH: 15
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (4)..(8)
<223> OTHER INFORMATION: Nucleotide at position 4 and/or 6 and/or 8 may
      be modified by 2'-O,4'-C-methylene-beta-D-ribofuranosyl moiety

<400> SEQUENCE: 817
taaggtgcat ctagt                                                          15

<210> SEQ ID NO 818
<211> LENGTH: 30
<212> TYPE: DNA
<213> ORGANISM: Artificial Sequence
<220> FEATURE:
<223> OTHER INFORMATION: Synthetic

<400> SEQUENCE: 818
catgatcagc tgggccaaga cagtactgtt                                          30

<210> SEQ ID NO 819
<211> LENGTH: 29
<212> TYPE: DNA
<213> ORGANISM: Artificial Sequence
<220> FEATURE:
<223> OTHER INFORMATION: Synthetic

<400> SEQUENCE: 819
catgatcagc tgggccaaga cagtactgt                                           29

<210> SEQ ID NO 820
<211> LENGTH: 28
<212> TYPE: DNA
<213> ORGANISM: Artificial Sequence
<220> FEATURE:
<223> OTHER INFORMATION: Synthetic

<400> SEQUENCE: 820
catgatcagc tgggccaaga cagtactg                                            28

<210> SEQ ID NO 821
<211> LENGTH: 27
<212> TYPE: DNA
<213> ORGANISM: Artificial Sequence
<220> FEATURE:
<223> OTHER INFORMATION: Synthetic

<400> SEQUENCE: 821
catgatcagc tgggccaaga cagtact                                             27

<210> SEQ ID NO 822
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 822
tagcagcggg aacagt                                                         16

<210> SEQ ID NO 823
<211> LENGTH: 14
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 823
tagcagcggg aaca                                                        14

<210> SEQ ID NO 824
<211> LENGTH: 30
<212> TYPE: DNA
<213> ORGANISM: Artificial Sequence
<220> FEATURE:
<223> OTHER INFORMATION: Synthetic

<400> SEQUENCE: 824
catgatcagc tgggccaaga cgatgtagtc                                       30

<210> SEQ ID NO 825
<211> LENGTH: 29
<212> TYPE: DNA
<213> ORGANISM: Artificial Sequence
<220> FEATURE:
<223> OTHER INFORMATION: Synthetic

<400> SEQUENCE: 825
catgatcagc tgggccaaga cgatgtagt                                        29

<210> SEQ ID NO 826
<211> LENGTH: 28
<212> TYPE: DNA
<213> ORGANISM: Artificial Sequence
<220> FEATURE:
<223> OTHER INFORMATION: Synthetic

<400> SEQUENCE: 826
catgatcagc tgggccaaga cgatgtag                                         28

<210> SEQ ID NO 827
<211> LENGTH: 27
<212> TYPE: DNA
<213> ORGANISM: Artificial Sequence
<220> FEATURE:
<223> OTHER INFORMATION: Synthetic

<400> SEQUENCE: 827
catgatcagc tgggccaaga cgatgta                                          27

<210> SEQ ID NO 828
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 828
tatgtgcctt tggacta                                                     17

<210> SEQ ID NO 829
<211> LENGTH: 15
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be
      modified by 2'-O,4'-C-methylene-beta-D-ribofuranosyl moiety

<400> SEQUENCE: 829
tatgtgcctt tggac                                                          15

<210> SEQ ID NO 830
<211> LENGTH: 30
<212> TYPE: DNA
<213> ORGANISM: Artificial Sequence
<220> FEATURE:
<223> OTHER INFORMATION: Synthetic

<400> SEQUENCE: 830
catgatcagc tgggccaaga gaggccggga                                          30

<210> SEQ ID NO 831
<211> LENGTH: 29
<212> TYPE: DNA
<213> ORGANISM: Artificial Sequence
<220> FEATURE:
<223> OTHER INFORMATION: Synthetic

<400> SEQUENCE: 831
catgatcagc tgggccaaga gaggccggg                                           29

<210> SEQ ID NO 832
<211> LENGTH: 28
<212> TYPE: DNA
<213> ORGANISM: Artificial Sequence
<220> FEATURE:
<223> OTHER INFORMATION: Synthetic

<400> SEQUENCE: 832
catgatcagc tgggccaaga gaggccgg                                            28

<210> SEQ ID NO 833
<211> LENGTH: 27
<212> TYPE: DNA
<213> ORGANISM: Artificial Sequence
<220> FEATURE:
<223> OTHER INFORMATION: Synthetic

<400> SEQUENCE: 833
catgatcagc tgggccaaga gaggccg                                             27

<210> SEQ ID NO 834
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 834
tattgcactc gtcccg                                                         16
```

```
<210> SEQ ID NO 835
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 835
tattgcactc gtccc                                                          15

<210> SEQ ID NO 836
<211> LENGTH: 30
<212> TYPE: DNA
<213> ORGANISM: Artificial Sequence
<220> FEATURE:
<223> OTHER INFORMATION: Synthetic

<400> SEQUENCE: 836
catgatcagc tgggccaaga agaagacggg                                          30

<210> SEQ ID NO 837
<211> LENGTH: 29
<212> TYPE: DNA
<213> ORGANISM: Artificial Sequence
<220> FEATURE:
<223> OTHER INFORMATION: Synthetic

<400> SEQUENCE: 837
catgatcagc tgggccaaga agaagacgg                                           29

<210> SEQ ID NO 838
<211> LENGTH: 28
<212> TYPE: DNA
<213> ORGANISM: Artificial Sequence
<220> FEATURE:
<223> OTHER INFORMATION: Synthetic

<400> SEQUENCE: 838
catgatcagc tgggccaaga agaagacg                                            28

<210> SEQ ID NO 839
<211> LENGTH: 27
<212> TYPE: DNA
<213> ORGANISM: Artificial Sequence
<220> FEATURE:
<223> OTHER INFORMATION: Synthetic

<400> SEQUENCE: 839
catgatcagc tgggccaaga agaagac                                             27

<210> SEQ ID NO 840
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2, and/or 5 may be
      modified by 2'-O,4'-C-methylene-beta-D-ribofuranosyl moiety

<400> SEQUENCE: 840
tcactcctct cctcccgt                                                       18
```

<210> SEQ ID NO 841
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 841
tcactcctct cctccc                                              16

<210> SEQ ID NO 842
<211> LENGTH: 30
<212> TYPE: DNA
<213> ORGANISM: Artificial Sequence
<220> FEATURE:
<223> OTHER INFORMATION: Synthetic

<400> SEQUENCE: 842
catgatcagc tgggccaaga acaagacggg                               30

<210> SEQ ID NO 843
<211> LENGTH: 29
<212> TYPE: DNA
<213> ORGANISM: Artificial Sequence
<220> FEATURE:
<223> OTHER INFORMATION: Synthetic

<400> SEQUENCE: 843
catgatcagc tgggccaaga acaagacgg                                29

<210> SEQ ID NO 844
<211> LENGTH: 28
<212> TYPE: DNA
<213> ORGANISM: Artificial Sequence
<220> FEATURE:
<223> OTHER INFORMATION: Synthetic

<400> SEQUENCE: 844
catgatcagc tgggccaaga acaagacg                                 28

<210> SEQ ID NO 845
<211> LENGTH: 27
<212> TYPE: DNA
<213> ORGANISM: Artificial Sequence
<220> FEATURE:
<223> OTHER INFORMATION: Synthetic

<400> SEQUENCE: 845
catgatcagc tgggccaaga acaagac                                  27

<210> SEQ ID NO 846
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 846

```
tcactcctcc cctcccgt                                              18
```

<210> SEQ ID NO 847
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 847

```
tcactcctcc cctccc                                                16
```

<210> SEQ ID NO 848
<211> LENGTH: 30
<212> TYPE: DNA
<213> ORGANISM: Artificial Sequence
<220> FEATURE:
<223> OTHER INFORMATION: Synthetic

<400> SEQUENCE: 848

```
catgatcagc tgggccaaga atcgggaggg                                 30
```

<210> SEQ ID NO 849
<211> LENGTH: 29
<212> TYPE: DNA
<213> ORGANISM: Artificial Sequence
<220> FEATURE:
<223> OTHER INFORMATION: Synthetic

<400> SEQUENCE: 849

```
catgatcagc tgggccaaga atcgggagg                                  29
```

<210> SEQ ID NO 850
<211> LENGTH: 28
<212> TYPE: DNA
<213> ORGANISM: Artificial Sequence
<220> FEATURE:
<223> OTHER INFORMATION: Synthetic

<400> SEQUENCE: 850

```
catgatcagc tgggccaaga atcgggag                                   28
```

<210> SEQ ID NO 851
<211> LENGTH: 27
<212> TYPE: DNA
<213> ORGANISM: Artificial Sequence
<220> FEATURE:
<223> OTHER INFORMATION: Synthetic

<400> SEQUENCE: 851

```
catgatcagc tgggccaaga atcggga                                    27
```

<210> SEQ ID NO 852
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Nucleotide at position 4 may be modified by
      2'-O,4'-C-methylene-beta-D-ribofuranosyl moiety

```
<400> SEQUENCE: 852
tcaggctcag tcccctc                                                   17

<210> SEQ ID NO 853
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 853
tcaggctcag tcccc                                                     15

<210> SEQ ID NO 854
<211> LENGTH: 30
<212> TYPE: DNA
<213> ORGANISM: Artificial Sequence
<220> FEATURE:
<223> OTHER INFORMATION: Synthetic

<400> SEQUENCE: 854
catgatcagc tgggccaaga caggctcaaa                                     30

<210> SEQ ID NO 855
<211> LENGTH: 29
<212> TYPE: DNA
<213> ORGANISM: Artificial Sequence
<220> FEATURE:
<223> OTHER INFORMATION: Synthetic

<400> SEQUENCE: 855
catgatcagc tgggccaaga caggctcaa                                      29

<210> SEQ ID NO 856
<211> LENGTH: 28
<212> TYPE: DNA
<213> ORGANISM: Artificial Sequence
<220> FEATURE:
<223> OTHER INFORMATION: Synthetic

<400> SEQUENCE: 856
catgatcagc tgggccaaga caggctca                                       28

<210> SEQ ID NO 857
<211> LENGTH: 27
<212> TYPE: DNA
<213> ORGANISM: Artificial Sequence
<220> FEATURE:
<223> OTHER INFORMATION: Synthetic

<400> SEQUENCE: 857
catgatcagc tgggccaaga caggctc                                        27

<210> SEQ ID NO 858
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
```

-continued

```
<223> OTHER INFORMATION: Nucleotide at position 3 may be modified by
      2'-O,4'-C-methylene-beta-D-ribofuranosyl moiety

<400> SEQUENCE: 858
tccctgagga gccctttga                                                19

<210> SEQ ID NO 859
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 859
tccctgagga gcccttt                                                  17

<210> SEQ ID NO 860
<211> LENGTH: 30
<212> TYPE: DNA
<213> ORGANISM: Artificial Sequence
<220> FEATURE:
<223> OTHER INFORMATION: Synthetic

<400> SEQUENCE: 860
catgatcagc tgggccaaga agagggagac                                    30

<210> SEQ ID NO 861
<211> LENGTH: 29
<212> TYPE: DNA
<213> ORGANISM: Artificial Sequence
<220> FEATURE:
<223> OTHER INFORMATION: Synthetic

<400> SEQUENCE: 861
catgatcagc tgggccaaga agagggaga                                     29

<210> SEQ ID NO 862
<211> LENGTH: 28
<212> TYPE: DNA
<213> ORGANISM: Artificial Sequence
<220> FEATURE:
<223> OTHER INFORMATION: Synthetic

<400> SEQUENCE: 862
catgatcagc tgggccaaga agagggag                                      28

<210> SEQ ID NO 863
<211> LENGTH: 27
<212> TYPE: DNA
<213> ORGANISM: Artificial Sequence
<220> FEATURE:
<223> OTHER INFORMATION: Synthetic

<400> SEQUENCE: 863
catgatcagc tgggccaaga agaggga                                       27

<210> SEQ ID NO 864
<211> LENGTH: 16
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 864
tccgagcctg ggtctc                                                         16

<210> SEQ ID NO 865
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 865
tccgagcctg ggtc                                                           14

<210> SEQ ID NO 866
<211> LENGTH: 30
<212> TYPE: DNA
<213> ORGANISM: Artificial Sequence
<220> FEATURE:
<223> OTHER INFORMATION: Synthetic

<400> SEQUENCE: 866
catgatcagc tgggccaaga ctcggggcag                                          30

<210> SEQ ID NO 867
<211> LENGTH: 29
<212> TYPE: DNA
<213> ORGANISM: Artificial Sequence
<220> FEATURE:
<223> OTHER INFORMATION: Synthetic

<400> SEQUENCE: 867
catgatcagc tgggccaaga ctcggggca                                           29

<210> SEQ ID NO 868
<211> LENGTH: 28
<212> TYPE: DNA
<213> ORGANISM: Artificial Sequence
<220> FEATURE:
<223> OTHER INFORMATION: Synthetic

<400> SEQUENCE: 868
catgatcagc tgggccaaga ctcggggc                                            28

<210> SEQ ID NO 869
<211> LENGTH: 27
<212> TYPE: DNA
<213> ORGANISM: Artificial Sequence
<220> FEATURE:
<223> OTHER INFORMATION: Synthetic

<400> SEQUENCE: 869
catgatcagc tgggccaaga ctcgggg                                             27

<210> SEQ ID NO 870
<211> LENGTH: 17
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 870
tcctgtactg agctgcc                                                    17

<210> SEQ ID NO 871
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 871
tcctgtactg agctg                                                      15

<210> SEQ ID NO 872
<211> LENGTH: 30
<212> TYPE: DNA
<213> ORGANISM: Artificial Sequence
<220> FEATURE:
<223> OTHER INFORMATION: Synthetic

<400> SEQUENCE: 872
catgatcagc tgggccaaga aggtttcccg                                      30

<210> SEQ ID NO 873
<211> LENGTH: 29
<212> TYPE: DNA
<213> ORGANISM: Artificial Sequence
<220> FEATURE:
<223> OTHER INFORMATION: Synthetic

<400> SEQUENCE: 873
catgatcagc tgggccaaga aggtttccc                                       29

<210> SEQ ID NO 874
<211> LENGTH: 28
<212> TYPE: DNA
<213> ORGANISM: Artificial Sequence
<220> FEATURE:
<223> OTHER INFORMATION: Synthetic

<400> SEQUENCE: 874
catgatcagc tgggccaaga aggtttcc                                        28

<210> SEQ ID NO 875
<211> LENGTH: 27
<212> TYPE: DNA
<213> ORGANISM: Artificial Sequence
<220> FEATURE:
<223> OTHER INFORMATION: Synthetic

<400> SEQUENCE: 875
catgatcagc tgggccaaga aggtttc                                         27

<210> SEQ ID NO 876
<211> LENGTH: 16
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 876
tgaaacatac acggga                                                       16

<210> SEQ ID NO 877
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 4 and/or 6 may
      be modified by 2'-O,4'-C-methylene-beta-D-ribofuranosyl moiety

<400> SEQUENCE: 877
tgaaacatac acgg                                                         14

<210> SEQ ID NO 878
<211> LENGTH: 30
<212> TYPE: DNA
<213> ORGANISM: Artificial Sequence
<220> FEATURE:
<223> OTHER INFORMATION: Synthetic

<400> SEQUENCE: 878
catgatcagc tgggccaaga ctggcacaca                                        30

<210> SEQ ID NO 879
<211> LENGTH: 29
<212> TYPE: DNA
<213> ORGANISM: Artificial Sequence
<220> FEATURE:
<223> OTHER INFORMATION: Synthetic

<400> SEQUENCE: 879
catgatcagc tgggccaaga ctggcacac                                         29

<210> SEQ ID NO 880
<211> LENGTH: 28
<212> TYPE: DNA
<213> ORGANISM: Artificial Sequence
<220> FEATURE:
<223> OTHER INFORMATION: Synthetic

<400> SEQUENCE: 880
catgatcagc tgggccaaga ctggcaca                                          28

<210> SEQ ID NO 881
<211> LENGTH: 27
<212> TYPE: DNA
<213> ORGANISM: Artificial Sequence
<220> FEATURE:
<223> OTHER INFORMATION: Synthetic

<400> SEQUENCE: 881
catgatcagc tgggccaaga ctggcac                                           27

<210> SEQ ID NO 882
```

```
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 882
tgaaggtcta ctgtg                                                     15

<210> SEQ ID NO 883
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Nucleotide at position 2 and/or 5 may be
      modified by 2'-O,4'-C-methylene-beta-D-ribofuranosyl moiety

<400> SEQUENCE: 883
tgaaggtcta ctgt                                                      14

<210> SEQ ID NO 884
<211> LENGTH: 30
<212> TYPE: DNA
<213> ORGANISM: Artificial Sequence
<220> FEATURE:
<223> OTHER INFORMATION: Synthetic

<400> SEQUENCE: 884
catgatcagc tgggccaaga agcctatgga                                     30

<210> SEQ ID NO 885
<211> LENGTH: 29
<212> TYPE: DNA
<213> ORGANISM: Artificial Sequence
<220> FEATURE:
<223> OTHER INFORMATION: Synthetic

<400> SEQUENCE: 885
catgatcagc tgggccaaga agcctatgg                                      29

<210> SEQ ID NO 886
<211> LENGTH: 28
<212> TYPE: DNA
<213> ORGANISM: Artificial Sequence
<220> FEATURE:
<223> OTHER INFORMATION: Synthetic

<400> SEQUENCE: 886
catgatcagc tgggccaaga agcctatg                                       28

<210> SEQ ID NO 887
<211> LENGTH: 27
<212> TYPE: DNA
<213> ORGANISM: Artificial Sequence
<220> FEATURE:
<223> OTHER INFORMATION: Synthetic

<400> SEQUENCE: 887
catgatcagc tgggccaaga agcctat                                        27
```

<210> SEQ ID NO 888
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Nucleotide at position 2 and/or 4 and/or 8 may
      be modified by 2'-O,4'-C-methylene-beta-D-ribofuranosyl moiety

<400> SEQUENCE: 888
tgagaactga attccata                                                       18

<210> SEQ ID NO 889
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Nucleotide at position 2 and/or 4 and/or 8 may
      be modified by 2'-O,4'-C-methylene-beta-D-ribofuranosyl moiety

<400> SEQUENCE: 889
tgagaactga attcca                                                         16

<210> SEQ ID NO 890
<211> LENGTH: 30
<212> TYPE: DNA
<213> ORGANISM: Artificial Sequence
<220> FEATURE:
<223> OTHER INFORMATION: Synthetic

<400> SEQUENCE: 890
catgatcagc tgggccaaga tacacacttc                                          30

<210> SEQ ID NO 891
<211> LENGTH: 29
<212> TYPE: DNA
<213> ORGANISM: Artificial Sequence
<220> FEATURE:
<223> OTHER INFORMATION: Synthetic

<400> SEQUENCE: 891
catgatcagc tgggccaaga tacacactt                                           29

<210> SEQ ID NO 892
<211> LENGTH: 28
<212> TYPE: DNA
<213> ORGANISM: Artificial Sequence
<220> FEATURE:
<223> OTHER INFORMATION: Synthetic

<400> SEQUENCE: 892
catgatcagc tgggccaaga tacacact                                            28

<210> SEQ ID NO 893
<211> LENGTH: 27
<212> TYPE: DNA
<213> ORGANISM: Artificial Sequence
<220> FEATURE:
<223> OTHER INFORMATION: Synthetic

<400> SEQUENCE: 893
catgatcagc tgggccaaga tacacac                                27

<210> SEQ ID NO 894
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 3 and/or 6 may
      be modified by 2'-O,4'-C-methylene-beta-D-ribofuranosyl moiety

<400> SEQUENCE: 894
tggaatgtaa agaagtg                                           17

<210> SEQ ID NO 895
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 3 and/or 6 may
      be modified by 2'-O,4'-C-methylene-beta-D-ribofuranosyl moiety

<400> SEQUENCE: 895
tggaatgtaa agaag                                             15

<210> SEQ ID NO 896
<211> LENGTH: 30
<212> TYPE: DNA
<213> ORGANISM: Artificial Sequence
<220> FEATURE:
<223> OTHER INFORMATION: Synthetic

<400> SEQUENCE: 896
catgatcagc tgggccaaga cactgtgggc                             30

<210> SEQ ID NO 897
<211> LENGTH: 29
<212> TYPE: DNA
<213> ORGANISM: Artificial Sequence
<220> FEATURE:
<223> OTHER INFORMATION: Synthetic

<400> SEQUENCE: 897
catgatcagc tgggccaaga cactgtggg                              29

<210> SEQ ID NO 898
<211> LENGTH: 28
<212> TYPE: DNA
<213> ORGANISM: Artificial Sequence
<220> FEATURE:
<223> OTHER INFORMATION: Synthetic

<400> SEQUENCE: 898
catgatcagc tgggccaaga cactgtgg                               28

<210> SEQ ID NO 899
<211> LENGTH: 27
<212> TYPE: DNA
<213> ORGANISM: Artificial Sequence
<220> FEATURE:
<223> OTHER INFORMATION: Synthetic

```
<400> SEQUENCE: 899
catgatcagc tgggccaaga cactgtg                                          27

<210> SEQ ID NO 900
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 900
tggtgcggag agggccca                                                    18

<210> SEQ ID NO 901
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 901
tggtgcggag agggc                                                       15

<210> SEQ ID NO 902
<211> LENGTH: 30
<212> TYPE: DNA
<213> ORGANISM: Artificial Sequence
<220> FEATURE:
<223> OTHER INFORMATION: Synthetic

<400> SEQUENCE: 902
catgatcagc tgggccaaga actgtgggcc                                       30

<210> SEQ ID NO 903
<211> LENGTH: 29
<212> TYPE: DNA
<213> ORGANISM: Artificial Sequence
<220> FEATURE:
<223> OTHER INFORMATION: Synthetic

<400> SEQUENCE: 903
catgatcagc tgggccaaga actgtgggc                                        29

<210> SEQ ID NO 904
<211> LENGTH: 28
<212> TYPE: DNA
<213> ORGANISM: Artificial Sequence
<220> FEATURE:
<223> OTHER INFORMATION: Synthetic

<400> SEQUENCE: 904
catgatcagc tgggccaaga actgtggg                                         28

<210> SEQ ID NO 905
<211> LENGTH: 27
<212> TYPE: DNA
<213> ORGANISM: Artificial Sequence
<220> FEATURE:
```

-continued

```
<223> OTHER INFORMATION: Synthetic

<400> SEQUENCE: 905
catgatcagc tgggccaaga actgtgg                                          27

<210> SEQ ID NO 906
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 906
tggtgcggaa agggcc                                                      16

<210> SEQ ID NO 907
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Nucleotide at position 2 may be modified by
      2'-O,4'-C-methylene-beta-D-ribofuranosyl moiety

<400> SEQUENCE: 907
tggtgcggaa aggg                                                        14

<210> SEQ ID NO 908
<211> LENGTH: 30
<212> TYPE: DNA
<213> ORGANISM: Artificial Sequence
<220> FEATURE:
<223> OTHER INFORMATION: Synthetic

<400> SEQUENCE: 908
catgatcagc tgggccaaga gtagtgggcc                                       30

<210> SEQ ID NO 909
<211> LENGTH: 29
<212> TYPE: DNA
<213> ORGANISM: Artificial Sequence
<220> FEATURE:
<223> OTHER INFORMATION: Synthetic

<400> SEQUENCE: 909
catgatcagc tgggccaaga gtagtgggc                                        29

<210> SEQ ID NO 910
<211> LENGTH: 28
<212> TYPE: DNA
<213> ORGANISM: Artificial Sequence
<220> FEATURE:
<223> OTHER INFORMATION: Synthetic

<400> SEQUENCE: 910
catgatcagc tgggccaaga gtagtggg                                         28

<210> SEQ ID NO 911
<211> LENGTH: 27
<212> TYPE: DNA
```

```
<213> ORGANISM: Artificial Sequence
<220> FEATURE:
<223> OTHER INFORMATION: Synthetic

<400> SEQUENCE: 911
catgatcagc tgggccaaga gtagtgg                                        27

<210> SEQ ID NO 912
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 912
tgtcactcgg ctcggcc                                                   17

<210> SEQ ID NO 913
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Nucleotide at position 3 may be modified by
      2'-O,4'-C-methylene-beta-D-ribofuranosyl moiety

<400> SEQUENCE: 913
tgtcactcgg ctcgg                                                     15

<210> SEQ ID NO 914
<211> LENGTH: 30
<212> TYPE: DNA
<213> ORGANISM: Artificial Sequence
<220> FEATURE:
<223> OTHER INFORMATION: Synthetic

<400> SEQUENCE: 914
catgatcagc tgggccaaga agaggcaggc                                     30

<210> SEQ ID NO 915
<211> LENGTH: 29
<212> TYPE: DNA
<213> ORGANISM: Artificial Sequence
<220> FEATURE:
<223> OTHER INFORMATION: Synthetic

<400> SEQUENCE: 915
catgatcagc tgggccaaga agaggcagg                                      29

<210> SEQ ID NO 916
<211> LENGTH: 28
<212> TYPE: DNA
<213> ORGANISM: Artificial Sequence
<220> FEATURE:
<223> OTHER INFORMATION: Synthetic

<400> SEQUENCE: 916
catgatcagc tgggccaaga agaggcag                                       28

<210> SEQ ID NO 917
```

```
<211> LENGTH: 27
<212> TYPE: DNA
<213> ORGANISM: Artificial Sequence
<220> FEATURE:
<223> OTHER INFORMATION: Synthetic

<400> SEQUENCE: 917
catgatcagc tgggccaaga agaggca                                        27

<210> SEQ ID NO 918
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Nucleotide at position 5 may be modified by
      2'-O,4'-C-methylene-beta-D-ribofuranosyl moiety

<400> SEQUENCE: 918
tgtctgcctg agtgcctg                                                  18

<210> SEQ ID NO 919
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Nucleotide at position 5 may be modified by
      2'-O,4'-C-methylene-beta-D-ribofuranosyl moiety

<400> SEQUENCE: 919
tgtctgcctg agtgcc                                                    16

<210> SEQ ID NO 920
<211> LENGTH: 30
<212> TYPE: DNA
<213> ORGANISM: Artificial Sequence
<220> FEATURE:
<223> OTHER INFORMATION: Synthetic

<400> SEQUENCE: 920
catgatcagc tgggccaaga ttcagttatc                                     30

<210> SEQ ID NO 921
<211> LENGTH: 29
<212> TYPE: DNA
<213> ORGANISM: Artificial Sequence
<220> FEATURE:
<223> OTHER INFORMATION: Synthetic

<400> SEQUENCE: 921
catgatcagc tgggccaaga ttcagttat                                      29

<210> SEQ ID NO 922
<211> LENGTH: 28
<212> TYPE: DNA
<213> ORGANISM: Artificial Sequence
<220> FEATURE:
<223> OTHER INFORMATION: Synthetic

<400> SEQUENCE: 922
catgatcagc tgggccaaga ttcagtta                                       28
```

<210> SEQ ID NO 923
<211> LENGTH: 27
<212> TYPE: DNA
<213> ORGANISM: Artificial Sequence
<220> FEATURE:
<223> OTHER INFORMATION: Synthetic

<400> SEQUENCE: 923
catgatcagc tgggccaaga ttcagtt                                        27

<210> SEQ ID NO 924
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 924
tgtgacagat tgataact                                                  18

<210> SEQ ID NO 925
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 4 and/or 6 may
      be modified by 2'-O,4'-C-methylene-beta-D-ribofuranosyl moiety

<400> SEQUENCE: 925
tgtgacagat tgataa                                                    16

<210> SEQ ID NO 926
<211> LENGTH: 32
<212> TYPE: DNA
<213> ORGANISM: Artificial Sequence
<220> FEATURE:
<223> OTHER INFORMATION: Synthetic

<400> SEQUENCE: 926
catgatcagc tgggccaaga cgtgacatga tg                                  32

<210> SEQ ID NO 927
<211> LENGTH: 29
<212> TYPE: DNA
<213> ORGANISM: Artificial Sequence
<220> FEATURE:
<223> OTHER INFORMATION: Synthetic

<400> SEQUENCE: 927
catgatcagc tgggccaaga cgtgacatg                                      29

<210> SEQ ID NO 928
<211> LENGTH: 28
<212> TYPE: DNA
<213> ORGANISM: Artificial Sequence
<220> FEATURE:
<223> OTHER INFORMATION: Synthetic

<400> SEQUENCE: 928

```
catgatcagc tgggccaaga cgtgacat                                    28
```

<210> SEQ ID NO 929
<211> LENGTH: 27
<212> TYPE: DNA
<213> ORGANISM: Artificial Sequence
<220> FEATURE:
<223> OTHER INFORMATION: Synthetic

<400> SEQUENCE: 929

```
catgatcagc tgggccaaga cgtgaca                                     27
```

<210> SEQ ID NO 930
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Nucleotide at position 4 and/or 6 may be
      modified by 2'-O,4'-C-methylene-beta-D-ribofuranosyl moiety

<400> SEQUENCE: 930

```
ctcggggatc atcatg                                                 16
```

<210> SEQ ID NO 931
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Nucleotide at position 2 and/or 4 may be
      modified by 2'-O,4'-C-methylene-beta-D-ribofuranosyl moiety

<400> SEQUENCE: 931

```
ctcggggatc atcat                                                  15
```

<210> SEQ ID NO 932
<211> LENGTH: 30
<212> TYPE: DNA
<213> ORGANISM: Artificial Sequence
<220> FEATURE:
<223> OTHER INFORMATION: Synthetic

<400> SEQUENCE: 932

```
catgatcagc tgggccaaga aaacatcact                                  30
```

<210> SEQ ID NO 933
<211> LENGTH: 29
<212> TYPE: DNA
<213> ORGANISM: Artificial Sequence
<220> FEATURE:
<223> OTHER INFORMATION: Synthetic

<400> SEQUENCE: 933

```
catgatcagc tgggccaaga aaacatcac                                   29
```

<210> SEQ ID NO 934
<211> LENGTH: 28
<212> TYPE: DNA
<213> ORGANISM: Artificial Sequence
<220> FEATURE:
<223> OTHER INFORMATION: Synthetic

```
<400> SEQUENCE: 934
catgatcagc tgggccaaga aaacatca                                          28

<210> SEQ ID NO 935
<211> LENGTH: 27
<212> TYPE: DNA
<213> ORGANISM: Artificial Sequence
<220> FEATURE:
<223> OTHER INFORMATION: Synthetic

<400> SEQUENCE: 935
catgatcagc tgggccaaga aaacatc                                           27

<210> SEQ ID NO 936
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Nucleotide at position 2 and/or 5 and/or 7 may
      be modified by 2'-O,4'-C-methylene-beta-D-ribofuranosyl moiety

<400> SEQUENCE: 936
ttaagacttg cagtgat                                                      17

<210> SEQ ID NO 937
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Nucleotide at position 2 and/or 5 and/or 7 may
      be modified by 2'-O,4'-C-methylene-beta-D-ribofuranosyl moiety

<400> SEQUENCE: 937
ttaagacttg cagtg                                                        15

<210> SEQ ID NO 938
<211> LENGTH: 30
<212> TYPE: DNA
<213> ORGANISM: Artificial Sequence
<220> FEATURE:
<223> OTHER INFORMATION: Synthetic

<400> SEQUENCE: 938
catgatcagc tgggccaaga gttagtggac                                        30

<210> SEQ ID NO 939
<211> LENGTH: 29
<212> TYPE: DNA
<213> ORGANISM: Artificial Sequence
<220> FEATURE:
<223> OTHER INFORMATION: Synthetic

<400> SEQUENCE: 939
catgatcagc tgggccaaga gttagtgga                                         29

<210> SEQ ID NO 940
<211> LENGTH: 28
<212> TYPE: DNA
<213> ORGANISM: Artificial Sequence
<220> FEATURE:
```

<223> OTHER INFORMATION: Synthetic

<400> SEQUENCE: 940
catgatcagc tgggccaaga gttagtgg  28

<210> SEQ ID NO 941
<211> LENGTH: 27
<212> TYPE: DNA
<213> ORGANISM: Artificial Sequence
<220> FEATURE:
<223> OTHER INFORMATION: Synthetic

<400> SEQUENCE: 941
catgatcagc tgggccaaga gttagtg  27

<210> SEQ ID NO 942
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Nucleotide at position 3 and/or 5 may be modified by 2'-O,4'-C-methylene-beta-D-ribofuranosyl moiety

<400> SEQUENCE: 942
tttgtgacct ggtccac  17

<210> SEQ ID NO 943
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 5 and/or 6 may be modified by 2'-O,4'-C-methylene-beta-D-ribofuranosyl moiety

<400> SEQUENCE: 943
tttgtgacct ggtcc  15

<210> SEQ ID NO 944
<211> LENGTH: 30
<212> TYPE: DNA
<213> ORGANISM: Artificial Sequence
<220> FEATURE:
<223> OTHER INFORMATION: Synthetic

<400> SEQUENCE: 944
catgatcagc tgggccaaga tccacatgga  30

<210> SEQ ID NO 945
<211> LENGTH: 29
<212> TYPE: DNA
<213> ORGANISM: Artificial Sequence
<220> FEATURE:
<223> OTHER INFORMATION: Synthetic

<400> SEQUENCE: 945
catgatcagc tgggccaaga tccacatgg  29

<210> SEQ ID NO 946
<211> LENGTH: 28
<212> TYPE: DNA

<213> ORGANISM: Artificial Sequence
<220> FEATURE:
<223> OTHER INFORMATION: Synthetic

<400> SEQUENCE: 946
catgatcagc tgggccaaga tccacatg    28

<210> SEQ ID NO 947
<211> LENGTH: 27
<212> TYPE: DNA
<213> ORGANISM: Artificial Sequence
<220> FEATURE:
<223> OTHER INFORMATION: Synthetic

<400> SEQUENCE: 947
catgatcagc tgggccaaga tccacat    27

<210> SEQ ID NO 948
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Nucleotide at position 3 and/or 6 may be
      modified by 2'-O,4'-C-methylene-beta-D-ribofuranosyl moiety

<400> SEQUENCE: 948
tgtaacagca actcca    16

<210> SEQ ID NO 949
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 6 and/or 8 may
      be modified by 2'-O,4'-C-methylene-beta-D-ribofuranosyl moiety

<400> SEQUENCE: 949
tgtaacagca actccat    17

<210> SEQ ID NO 950
<211> LENGTH: 30
<212> TYPE: DNA
<213> ORGANISM: Artificial Sequence
<220> FEATURE:
<223> OTHER INFORMATION: Synthetic

<400> SEQUENCE: 950
catgatcagc tgggccaaga ccacacactt    30

<210> SEQ ID NO 951
<211> LENGTH: 29
<212> TYPE: DNA
<213> ORGANISM: Artificial Sequence
<220> FEATURE:
<223> OTHER INFORMATION: Synthetic

<400> SEQUENCE: 951
catgatcagc tgggccaaga ccacacact    29

<210> SEQ ID NO 952

```
<211> LENGTH: 28
<212> TYPE: DNA
<213> ORGANISM: Artificial Sequence
<220> FEATURE:
<223> OTHER INFORMATION: Synthetic

<400> SEQUENCE: 952
catgatcagc tgggccaaga ccacacac                                              28

<210> SEQ ID NO 953
<211> LENGTH: 27
<212> TYPE: DNA
<213> ORGANISM: Artificial Sequence
<220> FEATURE:
<223> OTHER INFORMATION: Synthetic

<400> SEQUENCE: 953
catgatcagc tgggccaaga ccacaca                                               27

<210> SEQ ID NO 954
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 954
tggaatgtaa ggaagt                                                           16

<210> SEQ ID NO 955
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 3 and/or 6 may
      be modified by 2'-O,4'-C-methylene-beta-D-ribofuranosyl moiety

<400> SEQUENCE: 955
tggaatgtaa ggaagtgt                                                         18

<210> SEQ ID NO 956
<211> LENGTH: 29
<212> TYPE: DNA
<213> ORGANISM: Artificial Sequence
<220> FEATURE:
<223> OTHER INFORMATION: Synthetic

<400> SEQUENCE: 956
catgatcagc tgggccaaga tacatactt                                             29

<210> SEQ ID NO 957
<211> LENGTH: 28
<212> TYPE: DNA
<213> ORGANISM: Artificial Sequence
<220> FEATURE:
<223> OTHER INFORMATION: Synthetic

<400> SEQUENCE: 957
catgatcagc tgggccaaga tacatact                                              28
```

<210> SEQ ID NO 958
<211> LENGTH: 27
<212> TYPE: DNA
<213> ORGANISM: Artificial Sequence
<220> FEATURE:
<223> OTHER INFORMATION: Synthetic

<400> SEQUENCE: 958
catgatcagc tgggccaaga tacatac                                    27

<210> SEQ ID NO 959
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Nucleotide at position 3 and/or 6 and/or 8 may
      be modified by 2'-O,4'-C-methylene-beta-D-ribofuranosyl moiety

<400> SEQUENCE: 959
tggaatgtaa agaagta                                               17

<210> SEQ ID NO 960
<211> LENGTH: 30
<212> TYPE: DNA
<213> ORGANISM: Artificial Sequence
<220> FEATURE:
<223> OTHER INFORMATION: Synthetic

<400> SEQUENCE: 960
catgatcagc tgggccaaga tcatacagct                                 30

<210> SEQ ID NO 961
<211> LENGTH: 29
<212> TYPE: DNA
<213> ORGANISM: Artificial Sequence
<220> FEATURE:
<223> OTHER INFORMATION: Synthetic

<400> SEQUENCE: 961
catgatcagc tgggccaaga tcatacagc                                  29

<210> SEQ ID NO 962
<211> LENGTH: 28
<212> TYPE: DNA
<213> ORGANISM: Artificial Sequence
<220> FEATURE:
<223> OTHER INFORMATION: Synthetic

<400> SEQUENCE: 962
catgatcagc tgggccaaga tcatacag                                   28

<210> SEQ ID NO 963
<211> LENGTH: 27
<212> TYPE: DNA
<213> ORGANISM: Artificial Sequence
<220> FEATURE:
<223> OTHER INFORMATION: Synthetic

<400> SEQUENCE: 963
catgatcagc tgggccaaga tcataca                                    27

<210> SEQ ID NO 964
<211> LENGTH: 17

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Nucleotide at position 2 and/or 6 may be
      modified by 2'-O,4'-C-methylene-beta-D-ribofuranosyl moiety

<400> SEQUENCE: 964
tctttggtta tctagct                                                  17

<210> SEQ ID NO 965
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(10)
<223> OTHER INFORMATION: Nucleotide at position 3 and/or 6 and/or 10 may
      be modified by 2'-O,4'-C-methylene-beta-D-ribofuranosyl moiety

<400> SEQUENCE: 965
tctttggtta tctagctgta                                               20

<210> SEQ ID NO 966
<211> LENGTH: 22
<212> TYPE: RNA
<213> ORGANISM: Artificial Sequence
<220> FEATURE:
<223> OTHER INFORMATION: Synthetic

<400> SEQUENCE: 966
aaacaaacau ggugcacuuc uu                                            22

<210> SEQ ID NO 967
<211> LENGTH: 23
<212> TYPE: RNA
<213> ORGANISM: Artificial Sequence
<220> FEATURE:
<223> OTHER INFORMATION: Synthetic

<400> SEQUENCE: 967
aaagugcuuc cacuuugugu gcc                                           23

<210> SEQ ID NO 968
<211> LENGTH: 23
<212> TYPE: RNA
<213> ORGANISM: Artificial Sequence
<220> FEATURE:
<223> OTHER INFORMATION: Synthetic

<400> SEQUENCE: 968
aaagugcauc cauuuuguuu guc                                           23

<210> SEQ ID NO 969
<211> LENGTH: 25
<212> TYPE: RNA
<213> ORGANISM: Artificial Sequence
<220> FEATURE:
<223> OTHER INFORMATION: Synthetic

<400> SEQUENCE: 969
aaagugcauc cuuuuagagu guuac                                         25
```

```
<210> SEQ ID NO 970
<211> LENGTH: 23
<212> TYPE: RNA
<213> ORGANISM: Artificial Sequence
<220> FEATURE:
<223> OTHER INFORMATION: Synthetic

<400> SEQUENCE: 970
aaagugcauc cuuuuagagg uuu                                              23

<210> SEQ ID NO 971
<211> LENGTH: 22
<212> TYPE: RNA
<213> ORGANISM: Artificial Sequence
<220> FEATURE:
<223> OTHER INFORMATION: Synthetic

<400> SEQUENCE: 971
aaagugcauc uuuuuagagg au                                               22

<210> SEQ ID NO 972
<211> LENGTH: 23
<212> TYPE: RNA
<213> ORGANISM: Artificial Sequence
<220> FEATURE:
<223> OTHER INFORMATION: Synthetic

<400> SEQUENCE: 972
caaagugccu cccuuuagag ugu                                              23

<210> SEQ ID NO 973
<211> LENGTH: 22
<212> TYPE: RNA
<213> ORGANISM: Artificial Sequence
<220> FEATURE:
<223> OTHER INFORMATION: Synthetic

<400> SEQUENCE: 973
aaagugcuuc ccuuuggacu gu                                               22

<210> SEQ ID NO 974
<211> LENGTH: 21
<212> TYPE: RNA
<213> ORGANISM: Artificial Sequence
<220> FEATURE:
<223> OTHER INFORMATION: Synthetic

<400> SEQUENCE: 974
aaagugcuuc cuuuuagagg g                                                21

<210> SEQ ID NO 975
<211> LENGTH: 23
<212> TYPE: RNA
<213> ORGANISM: Artificial Sequence
<220> FEATURE:
<223> OTHER INFORMATION: Synthetic

<400> SEQUENCE: 975
aaagugcuuc ucuuuggugg guu                                              23

<210> SEQ ID NO 976
<211> LENGTH: 21
<212> TYPE: RNA
<213> ORGANISM: Artificial Sequence
<220> FEATURE:
<223> OTHER INFORMATION: Synthetic

<400> SEQUENCE: 976
```
aaagugcuuc cuuuuugagg g                                             21

<210> SEQ ID NO 977
<211> LENGTH: 22
<212> TYPE: RNA
<213> ORGANISM: Artificial Sequence
<220> FEATURE:
<223> OTHER INFORMATION: Synthetic

<400> SEQUENCE: 977
aagugcuucc uuuuagaggg uu                                            22

<210> SEQ ID NO 978
<211> LENGTH: 22
<212> TYPE: RNA
<213> ORGANISM: Artificial Sequence
<220> FEATURE:
<223> OTHER INFORMATION: Synthetic

<400> SEQUENCE: 978
aacacaccca gcuaaccuuu uu                                            22

<210> SEQ ID NO 979
<211> LENGTH: 24
<212> TYPE: RNA
<213> ORGANISM: Artificial Sequence
<220> FEATURE:
<223> OTHER INFORMATION: Synthetic

<400> SEQUENCE: 979
aacauucauu guugucggug gguu                                          24

<210> SEQ ID NO 980
<211> LENGTH: 24
<212> TYPE: RNA
<213> ORGANISM: Artificial Sequence
<220> FEATURE:
<223> OTHER INFORMATION: Synthetic

<400> SEQUENCE: 980
aacuggcccu caaagucccg cuuu                                          24

<210> SEQ ID NO 981
<211> LENGTH: 24
<212> TYPE: RNA
<213> ORGANISM: Artificial Sequence
<220> FEATURE:
<223> OTHER INFORMATION: Synthetic

<400> SEQUENCE: 981
aauccuugga accaggugu gagu                                           24

<210> SEQ ID NO 982
<211> LENGTH: 23
<212> TYPE: RNA
<213> ORGANISM: Artificial Sequence
<220> FEATURE:
<223> OTHER INFORMATION: Synthetic

<400> SEQUENCE: 982
aauccuugga accaggugu gaa                                            23

<210> SEQ ID NO 983
<211> LENGTH: 22
<212> TYPE: RNA
<213> ORGANISM: Artificial Sequence

```
<220> FEATURE:
<223> OTHER INFORMATION: Synthetic

<400> SEQUENCE: 983
augcaccugg gcaaggauuc ug                                            22

<210> SEQ ID NO 984
<211> LENGTH: 22
<212> TYPE: RNA
<213> ORGANISM: Artificial Sequence
<220> FEATURE:
<223> OTHER INFORMATION: Synthetic

<400> SEQUENCE: 984
augcaccugg gcaaggguuc ag                                            22

<210> SEQ ID NO 985
<211> LENGTH: 22
<212> TYPE: RNA
<213> ORGANISM: Artificial Sequence
<220> FEATURE:
<223> OTHER INFORMATION: Synthetic

<400> SEQUENCE: 985
aauccuuugu cccuggguga ga                                            22

<210> SEQ ID NO 986
<211> LENGTH: 22
<212> TYPE: RNA
<213> ORGANISM: Artificial Sequence
<220> FEATURE:
<223> OTHER INFORMATION: Synthetic

<400> SEQUENCE: 986
aauccuuugu cccuggguga aa                                            22

<210> SEQ ID NO 987
<211> LENGTH: 21
<212> TYPE: RNA
<213> ORGANISM: Artificial Sequence
<220> FEATURE:
<223> OTHER INFORMATION: Synthetic

<400> SEQUENCE: 987
aaucguacag ggucauccac u                                             21

<210> SEQ ID NO 988
<211> LENGTH: 23
<212> TYPE: RNA
<213> ORGANISM: Artificial Sequence
<220> FEATURE:
<223> OTHER INFORMATION: Synthetic

<400> SEQUENCE: 988
agugacauca cauauacggc agc                                           23

<210> SEQ ID NO 989
<211> LENGTH: 23
<212> TYPE: RNA
<213> ORGANISM: Artificial Sequence
<220> FEATURE:
<223> OTHER INFORMATION: Synthetic

<400> SEQUENCE: 989
aaugacacca cauauauggc agc                                           23
```

-continued

```
<210> SEQ ID NO 990
<211> LENGTH: 23
<212> TYPE: RNA
<213> ORGANISM: Artificial Sequence
<220> FEATURE:
<223> OTHER INFORMATION: Synthetic

<400> SEQUENCE: 990
aaugacauca cauauauggc agc                                               23

<210> SEQ ID NO 991
<211> LENGTH: 23
<212> TYPE: RNA
<213> ORGANISM: Artificial Sequence
<220> FEATURE:
<223> OTHER INFORMATION: Synthetic

<400> SEQUENCE: 991
aaugacacga ucacucccgu uga                                               23

<210> SEQ ID NO 992
<211> LENGTH: 23
<212> TYPE: RNA
<213> ORGANISM: Artificial Sequence
<220> FEATURE:
<223> OTHER INFORMATION: Synthetic

<400> SEQUENCE: 992
aauggcgcca cuagguugu gca                                                23

<210> SEQ ID NO 993
<211> LENGTH: 22
<212> TYPE: RNA
<213> ORGANISM: Artificial Sequence
<220> FEATURE:
<223> OTHER INFORMATION: Synthetic

<400> SEQUENCE: 993
agaggcuggc cgugaugaau uc                                                22

<210> SEQ ID NO 994
<211> LENGTH: 23
<212> TYPE: RNA
<213> ORGANISM: Artificial Sequence
<220> FEATURE:
<223> OTHER INFORMATION: Synthetic

<400> SEQUENCE: 994
agucauacac ggcucuccuc ucu                                               23

<210> SEQ ID NO 995
<211> LENGTH: 21
<212> TYPE: RNA
<213> ORGANISM: Artificial Sequence
<220> FEATURE:
<223> OTHER INFORMATION: Synthetic

<400> SEQUENCE: 995
agaucgaccg uguuauauuc g                                                 21

<210> SEQ ID NO 996
<211> LENGTH: 24
<212> TYPE: RNA
<213> ORGANISM: Artificial Sequence
<220> FEATURE:
<223> OTHER INFORMATION: Synthetic

<400> SEQUENCE: 996
```
aggaagcccu ggaggggcug gagg                                              24

<210> SEQ ID NO 997
<211> LENGTH: 22
<212> TYPE: RNA
<213> ORGANISM: Artificial Sequence
<220> FEATURE:
<223> OTHER INFORMATION: Synthetic

<400> SEQUENCE: 997
aggcagugua uuguuagcug gc                                                22

<210> SEQ ID NO 998
<211> LENGTH: 21
<212> TYPE: RNA
<213> ORGANISM: Artificial Sequence
<220> FEATURE:
<223> OTHER INFORMATION: Synthetic

<400> SEQUENCE: 998
aggcagugca uugcuagcug g                                                 21

<210> SEQ ID NO 999
<211> LENGTH: 20
<212> TYPE: RNA
<213> ORGANISM: Artificial Sequence
<220> FEATURE:
<223> OTHER INFORMATION: Synthetic

<400> SEQUENCE: 999
aggcagugcg accuggcucg                                                   20

<210> SEQ ID NO 1000
<211> LENGTH: 22
<212> TYPE: RNA
<213> ORGANISM: Artificial Sequence
<220> FEATURE:
<223> OTHER INFORMATION: Synthetic

<400> SEQUENCE: 1000
agguuacccg agcaacuuug ca                                                22

<210> SEQ ID NO 1001
<211> LENGTH: 23
<212> TYPE: RNA
<213> ORGANISM: Artificial Sequence
<220> FEATURE:
<223> OTHER INFORMATION: Synthetic

<400> SEQUENCE: 1001
gaauguugcu cggugaaccc cuu                                               23

<210> SEQ ID NO 1002
<211> LENGTH: 22
<212> TYPE: RNA
<213> ORGANISM: Artificial Sequence
<220> FEATURE:
<223> OTHER INFORMATION: Synthetic

<400> SEQUENCE: 1002 agugggaac ccuuccauga gg                                                 22

<210> SEQ ID NO 1003
<211> LENGTH: 20
<212> TYPE: RNA
<213> ORGANISM: Artificial Sequence

```
<220> FEATURE:
<223> OTHER INFORMATION: Synthetic

<400> SEQUENCE: 1003
auuccuagaa auuguucaua                                               20

<210> SEQ ID NO 1004
<211> LENGTH: 20
<212> TYPE: RNA
<213> ORGANISM: Artificial Sequence
<220> FEATURE:
<223> OTHER INFORMATION: Synthetic

<400> SEQUENCE: 1004
auuccuagaa auuguucaca                                               20

<210> SEQ ID NO 1005
<211> LENGTH: 23
<212> TYPE: RNA
<213> ORGANISM: Artificial Sequence
<220> FEATURE:
<223> OTHER INFORMATION: Synthetic

<400> SEQUENCE: 1005
caaagugcuc auagugcagg uag                                           23

<210> SEQ ID NO 1006
<211> LENGTH: 22
<212> TYPE: RNA
<213> ORGANISM: Artificial Sequence
<220> FEATURE:
<223> OTHER INFORMATION: Synthetic

<400> SEQUENCE: 1006
caaccuggag gacuccaugc ug                                            22

<210> SEQ ID NO 1007
<211> LENGTH: 21
<212> TYPE: RNA
<213> ORGANISM: Artificial Sequence
<220> FEATURE:
<223> OTHER INFORMATION: Synthetic

<400> SEQUENCE: 1007
cagcagcaca cugugguuug u                                             21

<210> SEQ ID NO 1008
<211> LENGTH: 24
<212> TYPE: RNA
<213> ORGANISM: Artificial Sequence
<220> FEATURE:
<223> OTHER INFORMATION: Synthetic

<400> SEQUENCE: 1008
cagugcaaug auauugucaa agca                                          24

<210> SEQ ID NO 1009
<211> LENGTH: 24
<212> TYPE: RNA
<213> ORGANISM: Artificial Sequence
<220> FEATURE:
<223> OTHER INFORMATION: Synthetic

<400> SEQUENCE: 1009
cagugcaaug guauugucaa agca                                          24
```

```
<210> SEQ ID NO 1010
<211> LENGTH: 21
<212> TYPE: RNA
<213> ORGANISM: Artificial Sequence
<220> FEATURE:
<223> OTHER INFORMATION: Synthetic

<400> SEQUENCE: 1010
cagugcaauu aaaaggggga a                                               21

<210> SEQ ID NO 1011
<211> LENGTH: 22
<212> TYPE: RNA
<213> ORGANISM: Artificial Sequence
<220> FEATURE:
<223> OTHER INFORMATION: Synthetic

<400> SEQUENCE: 1011
caugccuuga guguaggacc gu                                              22

<210> SEQ ID NO 1012
<211> LENGTH: 21
<212> TYPE: RNA
<213> ORGANISM: Artificial Sequence
<220> FEATURE:
<223> OTHER INFORMATION: Synthetic

<400> SEQUENCE: 1012
cccagauaau ggcacucuca a                                               21

<210> SEQ ID NO 1013
<211> LENGTH: 21
<212> TYPE: RNA
<213> ORGANISM: Artificial Sequence
<220> FEATURE:
<223> OTHER INFORMATION: Synthetic

<400> SEQUENCE: 1013
cccagauaau agcacucuca a                                               21

<210> SEQ ID NO 1014
<211> LENGTH: 22
<212> TYPE: RNA
<213> ORGANISM: Artificial Sequence
<220> FEATURE:
<223> OTHER INFORMATION: Synthetic

<400> SEQUENCE: 1014
ggagaaauua uccuuggugu gu                                              22

<210> SEQ ID NO 1015
<211> LENGTH: 22
<212> TYPE: RNA
<213> ORGANISM: Artificial Sequence
<220> FEATURE:
<223> OTHER INFORMATION: Synthetic

<400> SEQUENCE: 1015
gucaacacuu gcugguuucc uc                                              22

<210> SEQ ID NO 1016
<211> LENGTH: 22
<212> TYPE: RNA
<213> ORGANISM: Artificial Sequence
<220> FEATURE:
<223> OTHER INFORMATION: Synthetic

<400> SEQUENCE: 1016
```
cgucaacacu ugcugguuuu cu                                              22

<210> SEQ ID NO 1017
<211> LENGTH: 22
<212> TYPE: RNA
<213> ORGANISM: Artificial Sequence
<220> FEATURE:
<223> OTHER INFORMATION: Synthetic

<400> SEQUENCE: 1017
uaaggugcau cuagugcagu ua                                              22

<210> SEQ ID NO 1018
<211> LENGTH: 22
<212> TYPE: RNA
<213> ORGANISM: Artificial Sequence
<220> FEATURE:
<223> OTHER INFORMATION: Synthetic

<400> SEQUENCE: 1018
uaaggugcau cuagugcugu ua                                              22

<210> SEQ ID NO 1019
<211> LENGTH: 21
<212> TYPE: RNA
<213> ORGANISM: Artificial Sequence
<220> FEATURE:
<223> OTHER INFORMATION: Synthetic

<400> SEQUENCE: 1019
uagcagcggg aacaguacug c                                               21

<210> SEQ ID NO 1020
<211> LENGTH: 22
<212> TYPE: RNA
<213> ORGANISM: Artificial Sequence
<220> FEATURE:
<223> OTHER INFORMATION: Synthetic

<400> SEQUENCE: 1020
uaugugccuu uggacuacau cg                                              22

<210> SEQ ID NO 1021
<211> LENGTH: 21
<212> TYPE: RNA
<213> ORGANISM: Artificial Sequence
<220> FEATURE:
<223> OTHER INFORMATION: Synthetic

<400> SEQUENCE: 1021
uauugcacuc gucccggccu c                                               21

<210> SEQ ID NO 1022
<211> LENGTH: 23
<212> TYPE: RNA
<213> ORGANISM: Artificial Sequence
<220> FEATURE:
<223> OTHER INFORMATION: Synthetic

<400> SEQUENCE: 1022
ucacuccucu ccucccgucu ucu                                             23

<210> SEQ ID NO 1023
<211> LENGTH: 23
<212> TYPE: RNA
<213> ORGANISM: Artificial Sequence

```
<220> FEATURE:
<223> OTHER INFORMATION: Synthetic

<400> SEQUENCE: 1023
ucacuccucc ccucccgucu ugu                                           23

<210> SEQ ID NO 1024
<211> LENGTH: 22
<212> TYPE: RNA
<213> ORGANISM: Artificial Sequence
<220> FEATURE:
<223> OTHER INFORMATION: Synthetic

<400> SEQUENCE: 1024
ucaggcucag uccccucccg au                                            22

<210> SEQ ID NO 1025
<211> LENGTH: 24
<212> TYPE: RNA
<213> ORGANISM: Artificial Sequence
<220> FEATURE:
<223> OTHER INFORMATION: Synthetic

<400> SEQUENCE: 1025
ucccugagga gcccuuugag ccug                                          24

<210> SEQ ID NO 1026
<211> LENGTH: 21
<212> TYPE: RNA
<213> ORGANISM: Artificial Sequence
<220> FEATURE:
<223> OTHER INFORMATION: Synthetic

<400> SEQUENCE: 1026
uccgagccug ggucucccuc u                                             21

<210> SEQ ID NO 1027
<211> LENGTH: 22
<212> TYPE: RNA
<213> ORGANISM: Artificial Sequence
<220> FEATURE:
<223> OTHER INFORMATION: Synthetic

<400> SEQUENCE: 1027
uccuguacug agcugccccg ag                                            22

<210> SEQ ID NO 1028
<211> LENGTH: 21
<212> TYPE: RNA
<213> ORGANISM: Artificial Sequence
<220> FEATURE:
<223> OTHER INFORMATION: Synthetic

<400> SEQUENCE: 1028
ugaaacauac acgggaaacc u                                             21

<210> SEQ ID NO 1029
<211> LENGTH: 21
<212> TYPE: RNA
<213> ORGANISM: Artificial Sequence
<220> FEATURE:
<223> OTHER INFORMATION: Synthetic

<400> SEQUENCE: 1029
ugaaggucua cugugugcca g                                             21
```

```
<210> SEQ ID NO 1030
<211> LENGTH: 22
<212> TYPE: RNA
<213> ORGANISM: Artificial Sequence
<220> FEATURE:
<223> OTHER INFORMATION: Synthetic

<400> SEQUENCE: 1030
ugagaacuga auuccauagg cu                                                    22

<210> SEQ ID NO 1031
<211> LENGTH: 21
<212> TYPE: RNA
<213> ORGANISM: Artificial Sequence
<220> FEATURE:
<223> OTHER INFORMATION: Synthetic

<400> SEQUENCE: 1031
uggaauguaa agaagugugu a                                                     21

<210> SEQ ID NO 1032
<211> LENGTH: 23
<212> TYPE: RNA
<213> ORGANISM: Artificial Sequence
<220> FEATURE:
<223> OTHER INFORMATION: Synthetic

<400> SEQUENCE: 1032
uggugcggag agggcccaca gug                                                   23

<210> SEQ ID NO 1033
<211> LENGTH: 22
<212> TYPE: RNA
<213> ORGANISM: Artificial Sequence
<220> FEATURE:
<223> OTHER INFORMATION: Synthetic

<400> SEQUENCE: 1033
uggugcggaa agggcccaca gu                                                    22

<210> SEQ ID NO 1034
<211> LENGTH: 23
<212> TYPE: RNA
<213> ORGANISM: Artificial Sequence
<220> FEATURE:
<223> OTHER INFORMATION: Synthetic

<400> SEQUENCE: 1034
ugucacucgg cucggcccac uac                                                   23

<210> SEQ ID NO 1035
<211> LENGTH: 23
<212> TYPE: RNA
<213> ORGANISM: Artificial Sequence
<220> FEATURE:
<223> OTHER INFORMATION: Synthetic

<400> SEQUENCE: 1035
ugucugccug agugccugcc ucu                                                   23

<210> SEQ ID NO 1036
<211> LENGTH: 22
<212> TYPE: RNA
<213> ORGANISM: Artificial Sequence
<220> FEATURE:
<223> OTHER INFORMATION: Synthetic

<400> SEQUENCE: 1036
```
ugugacagau ugauaacuga aa                                      22

<210> SEQ ID NO 1037
<211> LENGTH: 21
<212> TYPE: RNA
<213> ORGANISM: Artificial Sequence
<220> FEATURE:
<223> OTHER INFORMATION: Synthetic

<400> SEQUENCE: 1037
cucggggauc aucaugucac g                                       21

<210> SEQ ID NO 1038
<211> LENGTH: 21
<212> TYPE: RNA
<213> ORGANISM: Artificial Sequence
<220> FEATURE:
<223> OTHER INFORMATION: Synthetic

<400> SEQUENCE: 1038
uuaagacuug cagugauguu u                                       21

<210> SEQ ID NO 1039
<211> LENGTH: 22
<212> TYPE: RNA
<213> ORGANISM: Artificial Sequence
<220> FEATURE:
<223> OTHER INFORMATION: Synthetic

<400> SEQUENCE: 1039
uuugugaccu gguccacuaa cc                                      22

<210> SEQ ID NO 1040
<211> LENGTH: 22
<212> TYPE: RNA
<213> ORGANISM: Artificial Sequence
<220> FEATURE:
<223> OTHER INFORMATION: Synthetic

<400> SEQUENCE: 1040
uguaacagca acuccaugug ga                                      22

<210> SEQ ID NO 1041
<211> LENGTH: 22
<212> TYPE: RNA
<213> ORGANISM: Artificial Sequence
<220> FEATURE:
<223> OTHER INFORMATION: Synthetic

<400> SEQUENCE: 1041
uggaauguaa ggaagugugu gg                                      22

<210> SEQ ID NO 1042
<211> LENGTH: 21
<212> TYPE: RNA
<213> ORGANISM: Artificial Sequence
<220> FEATURE:
<223> OTHER INFORMATION: Synthetic

<400> SEQUENCE: 1042
uggaauguaa agaaguaugu a                                       21

<210> SEQ ID NO 1043
<211> LENGTH: 23
<212> TYPE: RNA
<213> ORGANISM: Artificial Sequence

```
<220> FEATURE:
<223> OTHER INFORMATION: Synthetic

<400> SEQUENCE: 1043
ucuuugguua ucuagcugua uga                                              23
```

METHODS FOR QUANTITATING SMALL RNA MOLECULES

CROSS-REFERENCES TO RELATED APPLICATIONS

This application is a continuation-in-part of U.S. application Ser. No. 10/579,029, which is the National Stage of International Application No. PCT/US2006/002591, filed Jan. 25, 2006, which claims the benefit of U.S. Provisional Application No. 60/647,178, filed Jan. 25, 2005.

FIELD OF THE INVENTION

The present invention relates to methods of amplifying and quantitating small RNA molecules.

BACKGROUND OF THE INVENTION

RNA interference (RNAi) is an evolutionarily conserved process that functions to inhibit gene expression (Bernstein et al. (2001), *Nature* 409:363-6; Dykxhoorn et al. (2003) *Nat. Rev. Mol. Cell. Biol.* 4:457-67). The phenomenon of RNAi was first described in *Caenorhabditis elegans*, where injection of double-stranded RNA (dsRNA) led to efficient sequence-specific gene silencing of the mRNA that was complementary to the dsRNA (Fire et al. (1998) *Nature* 391: 806-11). RNAi has also been described in plants as a phenomenon called post-transcriptional gene silencing (PTGS), which is likely used as a viral defense mechanism (Jorgensen (1990) *Trends Biotechnol.* 8:340-4; Brigneti et al. (1998) *EMBO J.* 17:6739-46; Hamilton & Baulcombe (1999) *Science* 286:950-2).

An early indication that the molecules that regulate PTGS were short RNAs processed from longer dsRNA was the identification of short 21 to 22 nucleotide dsRNA derived from the longer dsRNA in plants (Hamilton & Baulcombe (1999) *Science* 286:950-2). This observation was repeated in *Drosophila* embryo extracts where long dsRNA was found processed into 21-25 nucleotide short RNA by the RNase III type enzyme, Dicer (Elbashir et al. (2001) *Nature* 411:494-8; Elbashir et al. (2001) *EMBO J.* 20:6877-88; Elbashir et al. (2001) *Genes Dev.* 15:188-200). These observations led Elbashir et al. to test if synthetic 21-25 nucleotide synthetic dsRNAs function to specifically inhibit gene expression in *Drosophila* embryo lysates and mammalian cell culture (Elbashir et al. (2001) *Nature* 411:494-8; Elbashir et al. (2001) *EMBO J.* 20:6877-88; Elbashir et al. (2001) *Genes Dev.* 15:188-200). They demonstrated that small interfering RNAs (siRNAs) had the ability to specifically inhibit gene expression in mammalian cell culture without induction of the interferon response.

These observations led to the development of techniques for the reduction, or elimination, of expression of specific genes in mammalian cell culture, such as plasmid-based systems that generate hairpin siRNAs (Brummelkamp et al. (2002) *Science* 296:550-3; Paddison et al. (2002) *Genes Dev.* 16:948-58; Paddison et al. (2002) *Proc. Natl. Acad. Sci. U.S.A.* 99:1443-8; Paul et al. 2002) *Nat. Biotechnol.* 20:404-8). siRNA molecules can also be introduced into cells, in vivo, to inhibit the expression of specific proteins (see, e.g., Soutschek, J., et al., *Nature* 432 (7014):173-178 (2004)).

siRNA molecules have promise both as therapeutic agents for inhibiting the expression of specific proteins, and as targets for drugs that affect the activity of siRNA molecules that function to regulate the expression of proteins involved in a disease state. A first step in developing such therapeutic agents is to measure the amounts of specific siRNA molecules in different cell types within an organism, and thereby construct an "atlas" of siRNA expression within the body. Additionally, it will be useful to measure changes in the amount of specific siRNA molecules in specific cell types in response to a defined stimulus, or in a disease state.

Short RNA molecules are difficult to quantitate. For example, with respect to the use of PCR to amplify and measure the small RNA molecules, most PCR primers are longer than the small RNA molecules, and so it is difficult to design a primer that has significant overlap with a small RNA molecule, and that selectively hybridizes to the small RNA molecule at the temperatures used for primer extension and PCR amplification reactions.

SUMMARY OF THE INVENTION

In one aspect, the present invention provides methods for amplifying a microRNA molecule to produce cDNA molecules. The methods include the steps of: (a) producing a first DNA molecule that is complementary to a target microRNA molecule using primer extension; and (b) amplifying the first DNA molecule to produce amplified DNA molecules using a universal forward primer and a reverse primer. In some embodiments of the method, at least one of the forward primer and the reverse primer comprise at least one locked nucleic acid molecule. It will be understood that, in the practice of the present invention, typically numerous (e.g., millions) of individual microRNA molecules are amplified in a sample (e.g., a solution of RNA molecules isolated from living cells).

In another aspect, the present invention provides methods for measuring the amount of a target microRNA in a sample from a living organism. The methods of this aspect of the invention include the step of measuring the amount of a target microRNA molecule in a multiplicity of different cell types within a living organism, wherein the amount of the target microRNA molecule is measured by a method including the steps of: (1) producing a first DNA molecule complementary to the target microRNA molecule in the sample using primer extension; (2) amplifying the first DNA molecule to produce amplified DNA molecules using a universal forward primer and a reverse primer; and (3) measuring the amount of the amplified DNA molecules. In some embodiments of the method, at least one of the forward primer and the reverse primer comprise at least one locked nucleic acid molecule.

In another aspect, the invention provides nucleic acid primer molecules consisting of sequence SEQ ID NO:1 to SEQ ID NO: 499, as shown in TABLE 1, TABLE 2, TABLE 6, and TABLE 7. The primer molecules of the invention can be used as primers for detecting mammalian microRNA target molecules, using the methods of the invention described herein.

In another aspect, the present invention provides kits for detecting at least one mammalian target microRNA, the kits comprising one or more primer sets specific for the detection of a target microRNA, each primer set comprising (1) an extension primer for producing a cDNA molecule complementary to a target microRNA, (2) a universal forward PCR primer for amplifying the cDNA molecule and (3) a reverse PCR primer for amplifying the cDNA molecule. The extension primer comprises a first portion that hybridizes to the target microRNA molecule and a second portion that includes a hybridization sequence for a universal forward PCR primer. The reverse PCR primer comprises a sequence selected to hybridize to a portion of the cDNA molecule. In some embodiments of the kit, at least one of the universal forward and reverse primers include at least one locked nucleic acid molecule. The kits of the invention may be used to practice various embodiments of the methods of the invention.

The present invention is useful, for example, for quantitating specific microRNA molecules within different types of cells in a living organism, or, for example, for measuring changes in the amount of specific microRNAs in living cells in response to a stimulus (e.g., in response to administration of a drug).

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In accordance with the foregoing, in one aspect, the present invention provides methods for amplifying a microRNA molecule to produce cDNA molecules. The methods include the steps of: (a) using primer extension to make a DNA molecule that is complementary to a target microRNA molecule; and (b) using a universal forward primer and a reverse primer to amplify the DNA molecule to produce amplified DNA molecules. In some embodiments of the method, at least one of the universal forward primer and the reverse primer comprises at least one locked nucleic acid molecule.

As used herein, the term "locked nucleic acid molecule" (abbreviated as LNA molecule) refers to a nucleic acid molecule that includes a 2'-O,4'-C-methylene-β-D-ribofuranosyl moiety. Exemplary 2'-O,4'-C-methylene-β-D-ribofuranosyl moieties, and exemplary LNAs including such moieties, are described, for example, in Petersen, M., and Wengel, J., *Trends in Biotechnology* 21(2):74-81 (2003) which publication is incorporated herein by reference in its entirety.

As used herein, the term "microRNA" refers to an RNA molecule that has a length in the range of from 21 nucleotides to 25 nucleotides. Some microRNA molecules (e.g., siRNA molecules) function in living cells to regulate gene expression.

Figure 1:
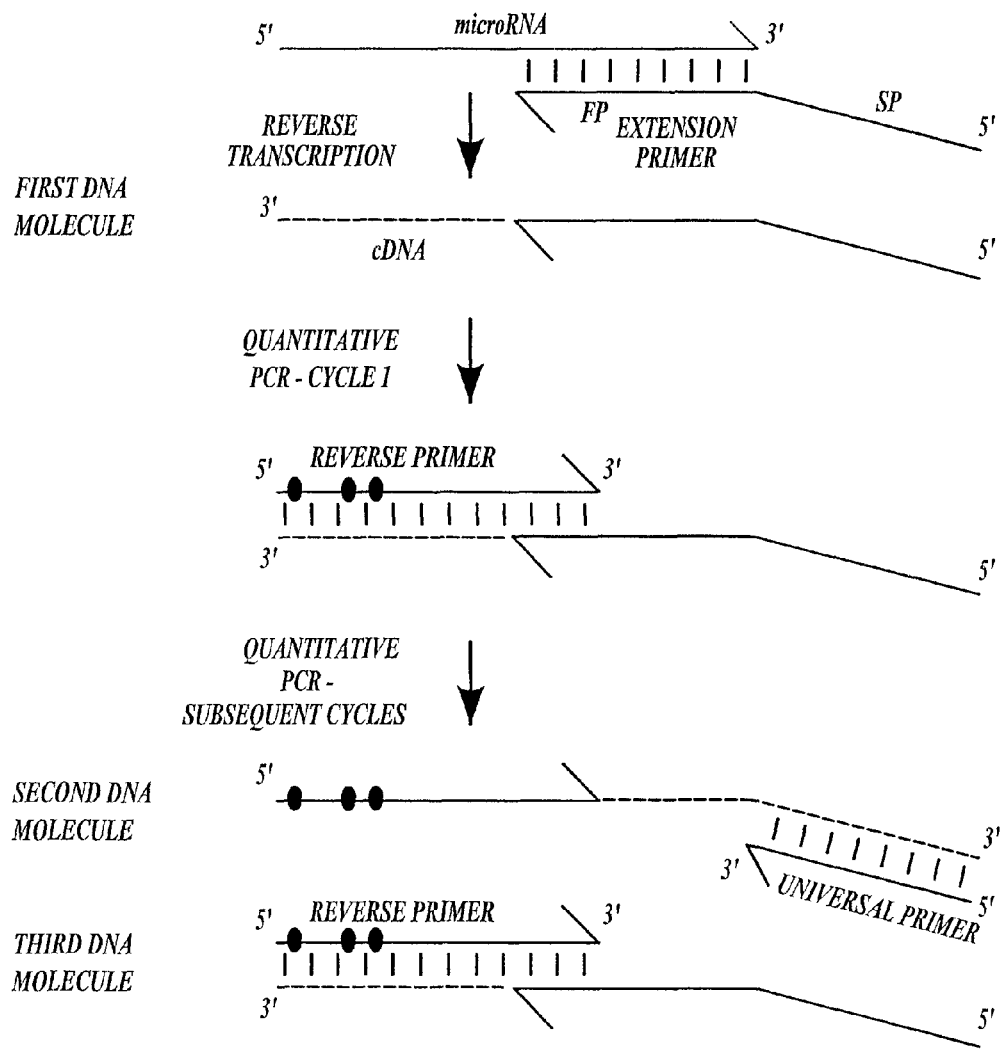
FIG. 1 shows a flow chart of a representative method of the present invention.

Representative Method of the Invention. FIG. 1 shows a flowchart of a representative method of the present invention. In the method represented in FIG. 1, a microRNA is the template for synthesis of a complementary first DNA molecule. The synthesis of the first DNA molecule is primed by an extension primer, and so the first DNA molecule includes the extension primer and newly synthesized DNA (represented by a dotted line in FIG. 1). The synthesis of DNA is catalyzed by reverse transcriptase.

The extension primer includes a first portion (abbreviated as FP in FIG. 1) and a second portion (abbreviated as SP in FIG. 1). The first portion hybridizes to the microRNA target template, and the second portion includes a nucleic acid sequence that hybridizes with a universal forward primer, as described infra.

A quantitative polymerase chain reaction is used to make a second DNA molecule that is complementary to the first DNA molecule. The synthesis of the second DNA molecule is primed by the reverse primer that has a sequence that is selected to specifically hybridize to a portion of the target first DNA molecule. Thus, the reverse primer does not hybridize to nucleic acid molecules other than the first DNA molecule. The reverse primer may optionally include at least one LNA molecule located within the portion of the reverse primer that does not overlap with the extension primer. In FIG. 1, the LNA molecules are represented by shaded ovals.

A universal forward primer hybridizes to the 3' end of the second DNA molecule and primes synthesis of a third DNA molecule. It will be understood that, although a single microRNA molecule, single first DNA molecule, single second DNA molecule, single third DNA molecule and single extension, forward and reverse primers are shown in FIG. 1, typically the practice of the present invention uses reaction mixtures that include numerous copies (e.g., millions of copies) of each of the foregoing nucleic acid molecules.

The steps of the methods of the present invention are now considered in more detail.

Preparation of microRNA Molecules Useful as Templates. microRNA molecules useful as templates in the methods of the invention can be isolated from any organism (e.g., eukaryote, such as a mammal) or part thereof, including organs, tissues, and/or individual cells (including cultured cells). Any suitable RNA preparation that includes microRNAs can be used, such as total cellular RNA.

RNA may be isolated from cells by procedures that involve lysis of the cells and denaturation of the proteins contained therein. Cells of interest include wild-type cells, drug-exposed wild-type cells, modified cells, and drug-exposed modified cells.

Additional steps may be employed to remove some or all of the DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (see, Chirgwin et al., 1979, *Biochemistry* 18:5294-5299). Separation of RNA from DNA can also be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol.

The sample of RNA can comprise a multiplicity of different microRNA molecules, each different microRNA molecule having a different nucleotide sequence. In a specific embodiment, the microRNA molecules in the RNA sample comprise at least 100 different nucleotide sequences. In other embodiments, the microRNA molecules of the RNA sample comprise at least 500, 1,000, 5,000, 10,000, 20,000, 30,000, 40,000, 50,000, 60,000, 70,000, 80,000 90,000, or 100,000 different nucleotide sequences.

The methods of the invention may be used to detect the presence of any microRNA. For example, the methods of the invention can be used to detect one or more of the microRNA targets described in a database such as "the miRBase sequence database" as described in Griffith-Jones et al. (2004), *Nucleic Acids Research* 32:D109-D111, and Griffith-Jones et al. (2006), *Nucleic Acids Research* 34:D140-D144, which is publically accessible on the World Wide Web at the Wellcome Trust Sanger Institute website. A list of exemplary microRNA targets is also described in the following references: Lagos-Quintana et al., *Curr. Biol.* 12(9):735-9 (2002).

Synthesis of DNA Molecules Using microRNA Molecules As Templates. In the practice of the methods of the invention, first DNA molecules are synthesized that are complementary to the microRNA target molecules, and that are composed of an extension primer and newly synthesized DNA (wherein the extension primer primes the synthesis of the newly synthesized DNA). Individual first DNA molecules can be complementary to a whole microRNA target molecule, or to a portion thereof; although typically an individual first DNA molecule is complementary to a whole microRNA target molecule. Thus, in the practice of the methods of the invention, a population of first DNA molecules is synthesized that includes individual DNA molecules that are each complementary to all, or to a portion, of a target microRNA molecule.

The synthesis of the first DNA molecules is catalyzed by reverse transcriptase. Any reverse transcriptase molecule can be used to synthesize the first DNA molecules, such as those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT). A reverse transcriptase lacking RNaseH activity (e.g., SUPERSCRIPT III™ sold by Invitrogen, 1600 Faraday Avenue, P.O. Box 6482, Carlsbad, Calif. 92008) is preferred in order to minimize the amount of double-stranded cDNA synthesized at this stage. The reverse transcriptase molecule should also preferably be thermostable so that the DNA synthesis reaction can be conducted at as high a temperature as possible, while still permitting hybridization of primer to the microRNA target molecules.

Priming the Synthesis of the First DNA Molecules. The synthesis of the first DNA molecules is primed using an extension primer. Typically, the length of the extension primer is in the range of from 10 nucleotides to 100 nucleotides, such as 20 to 35 nucleotides. The nucleic acid sequence of the extension primer is incorporated into the sequence of each, synthesized, DNA molecule. The extension primer includes a first portion that hybridizes to a portion of the microRNA molecule. Typically the first portion of the extension primer includes the 3'-end of the extension primer. The first portion of the extension primer typically has a length in the range of from 6 nucleotides to 20 nucleotides, such as from 10 nucleotides to 12 nucleotides. In some embodiments, the first portion of the extension primer has a length in the range of from 3 nucleotides to 25 nucleotides.

The extension primer also includes a second portion that typically has a length of from 18 to 25 nucleotides. For example, the second portion of the extension primer can be 20 nucleotides long. The second portion of the extension primer is located 5' to the first portion of the extension primer. The second portion of the extension primer includes at least a portion of the hybridization site for the universal forward primer. For example, the second portion of the extension primer can include all of the hybridization site for the universal forward primer, or, for example, can include as little as a single nucleotide of the hybridization site for the universal forward primer (the remaining portion of the hybridization site for the forward primer can, for example, be located in the first portion of the extension primer). An exemplary nucleic acid sequence of a second portion of an extension primer is 5' CATGATCAGCTGGGCCAAGA 3' (SEQ ID NO:1).

Amplification of the DNA Molecules. In the practice of the methods of the invention, the first DNA molecules are enzymatically amplified using the polymerase chain reaction. A universal forward primer and a reverse primer are used to prime the polymerase chain reaction. The reverse primer includes a nucleic acid sequence that is selected to specifically hybridize to a portion of a first DNA molecule.

The reverse primer typically has a length in the range of from 10 nucleotides to 100 nucleotides. In some embodiments, the reverse primer has a length in the range of from 12 nucleotides to 20 nucleotides. The nucleotide sequence of the reverse primer is selected to hybridize to a specific target nucleotide sequence under defined hybridization conditions. The reverse primer and extension primer are both present in the PCR reaction mixture, and so the reverse primer should be sufficiently long so that the melting temperature (Tm) is at least 50° C., but should not be so long that there is extensive overlap with the extension primer which may cause the formation of "primer dimers." "Primer dimers" are formed when the reverse primer hybridizes to the extension primer, and uses the extension primer as a substrate for DNA synthesis, and the extension primer hybridizes to the reverse primer, and uses the reverse primer as a substrate for DNA synthesis. To avoid the formation of "primer dimers," typically the reverse primer and the extension primer are designed so that they do not overlap with each other by more than 6 nucleotides. If it is not possible to make a reverse primer having a Tm of at least 50° C., and wherein the reverse primer and the extension primer do not overlap by more than 6 nucleotides, then it is preferable to lengthen the reverse primer (since Tm usually increases with increasing oligonucleotide length) and decrease the length of the extension primer.

The reverse primer primes the synthesis of a second DNA molecule that is complementary to the first DNA molecule. The universal forward primer hybridizes to the portion of the second DNA molecule that is complementary to the second portion of the extension primer which is incorporated into all of the first DNA molecules. The universal forward primer primes the synthesis of third DNA molecules. The universal forward primer typically has a length in the range of from 16 nucleotides to 100 nucleotides. In some embodiments, the universal forward primer has a length in the range of from 16 nucleotides to 30 nucleotides. The universal forward primer may include at least one locked nucleic acid molecule. In some embodiments, the universal forward primer includes from 1 to 25 locked nucleic acid molecules. The nucleic acid sequence of an exemplary universal forward primer is set forth in SEQ ID NO:13.

In general, the greater the number of amplification cycles during the polymerase chain reaction, the greater the amount of amplified DNA that is obtained. On the other hand, too many amplification cycles (e.g., more than 35 amplification cycles) may result in spurious and unintended amplification of non-target double-stranded DNA. Thus, in some embodiments, a desirable number of amplification cycles is between one and 45 amplification cycles, such as from one to 25 amplification cycles, or such as from five to 15 amplification cycles, or such as ten amplification cycles.

Use of LNA Molecules and Selection of Primer Hybridization Conditions. Hybridization conditions are selected that promote the specific hybridization of a primer molecule to the complementary sequence on a substrate molecule. With respect to the hybridization of a 12 nucleotide first portion of an extension primer to a microRNA, it has been found that specific hybridization occurs at a temperature of 50° C. Similarly, it has been found that hybridization of a 20 nucleotide universal forward primer to a complementary DNA molecule, and hybridization of a reverse primer (having a length in the range of from 12-20 nucleotides, such as from 14-16 nucleotides) to a complementary DNA molecule occurs at a temperature of 50° C. By way of example, it is often desirable to design extension, reverse and universal forward primers that each have a hybridization temperature in the range of from 50° C. to 60° C.

In some embodiments, LNA molecules can be incorporated into at least one of the extension primer, reverse primer, and universal forward primer to raise the Tm of one, or more, of the foregoing primers to at least 50° C. Incorporation of an LNA molecule into the portion of the reverse primer that hybridizes to the target first DNA molecule, but not to the extension primer, may be useful because this portion of the reverse primer is typically no more than 10 nucleotides in length. For example, the portion of the reverse primer that hybridizes to the target first DNA molecule, but not to the extension primer, may include at least one locked nucleic acid molecule (e.g., from 1 to 25 locked nucleic acid molecules). In some embodiments, two or three locked nucleic acid molecules are included within the first 8 nucleotides from the 5' end of the reverse primer.

The number of LNA residues that must be incorporated into a specific primer to raise the Tm to a desired temperature mainly depends on the length of the primer and the nucleotide composition of the primer. A tool for determining the effect on Tm of one or more LNAs in a primer is available on the Internet Web site of Exiqon, Bygstubben 9, DK-2950 Vedbaek, Denmark.

Although one or more LNAs can be included in any of the primers used in the practice of the present invention, it has been found that the efficiency of synthesis of cDNA is low if an LNA is incorporated into the extension primer. While not wishing to be bound by theory, LNAs may inhibit the activity of reverse transcriptase.

Detecting and Measuring the Amount of the Amplified DNA Molecules. The amplified DNA molecules can be detected and quantitated by the presence of detectable marker molecules, such as fluorescent molecules. For example, the amplified DNA molecules can be detected and quantitated by the presence of a dye (e.g., SYBR green) that preferentially or exclusively binds to double stranded DNA during the PCR amplification step of the methods of the present invention. For example, Molecular Probes, Inc. (29851 Willow Creek Road, Eugene, Oreg. 97402) sells quantitative PCR reaction mixtures that include SYBR green dye. By way of further example, another dye (referred to as "BEBO") that can be used to label double stranded DNA produced during real-time PCR is described by Bengtsson, M., et al., *Nucleic Acids Research* 31(8):e45 (Apr. 15, 2003), which publication is incorporated herein by reference. Again by way of example, a forward and/or reverse primer that includes a fluorophore and quencher can be used to prime the PCR amplification step of the methods of the present invention. The physical separation of the fluorophore and quencher that occurs after extension of the labeled primer during PCR permits the fluorophore to fluoresce, and the fluorescence can be used to measure the amount of the PCR amplification products. Examples of commercially available primers that include a fluorophore and quencher include Scorpion primers and Uniprimers, which are both sold by Molecular Probes, Inc.

Representative Uses of the Present Invention. The present invention is useful for producing cDNA molecules from microRNA target molecules. The amount of the DNA molecules can be measured which provides a measurement of the amount of target microRNA molecules in the starting material. For example, the methods of the present invention can be used to measure the amount of specific microRNA molecules (e.g., specific siRNA molecules) in living cells. Again by way of example, the present invention can be used to measure the amount of specific microRNA molecules (e.g., specific siRNA molecules) in different cell types in a living body, thereby producing an "atlas" of the distribution of specific microRNA molecules within the body. Again by way of example, the present invention can be used to measure changes in the amount of specific microRNA molecules (e.g., specific siRNA molecules) in response to a stimulus, such as in response to treatment of a population of living cells with a drug.

Thus, in another aspect, the present invention provides methods for measuring the amount of a target microRNA in a multiplicity of different cell types within a living organism (e.g., to make a microRNA "atlas" of the organism). The methods of this aspect of the invention each include the step of measuring the amount of a target microRNA molecule in a multiplicity of different cell types within a living organism, wherein the amount of the target microRNA molecule is measured by a method comprising the steps of: (1) using primer extension to make a DNA molecule complementary to the target microRNA molecule isolated from a cell type of a living organism; (2) using a universal forward primer and a reverse primer to amplify the DNA molecule to produce amplified DNA molecules, and (3) measuring the amount of the amplified DNA molecules. In some embodiments of the methods, at least one of the forward primer and the reverse primer comprises at least one locked nucleic acid molecule. The measured amounts of amplified DNA molecules can, for example, be stored in an interrogatable database in electronic form, such as on a computer-readable medium (e.g., a floppy disc).

In some embodiments, the methods may be used to discriminate between two or more mammalian target microRNA that have a similar sequence in a sample from a living organism, the method comprising the steps of: (a) producing a first DNA molecule that is complementary to the first microRNA molecule using a first extension primer specific to the first microRNA molecule; (b) amplifying the first DNA molecule to produce a first population of amplified DNA molecules using a universal forward primer and a first reverse primer; (c) producing a second DNA molecule that is complementary to the second microRNA molecule using a second extension primer specific to the second microRNA molecule; (d) amplifying the second DNA molecule to produce a second population of amplified DNA molecules using a universal forward primer and a second reverse primer; (e) measuring the amount of the first and second population of amplified DNA molecules, wherein the first and second extension primers or the first and second reverse primers differ by one or more nucleotides in the portion that is complementary to the target microRNA. This method may be used to discriminate between microRNA targets that differ by one, two, three or more nucleotides, by designing the gene-specific region of the first and second extension primers to hybridize to the region of the microRNA targets that are not identical.

In another aspect, the invention provides nucleic acid primer molecules consisting of sequence SEQ ID NO:1 to SEQ ID NO: 499, as shown in TABLE 1, TABLE 2, TABLE 6, and TABLE 7. The primer molecules of the invention can be used as primers for detecting mammalian microRNA target molecules, using the methods of the invention described herein.

In another aspect, the invention provides sets of nucleic acid primers consisting of SEQ ID NO:500 to SEQ ID NO: 965, as shown in TABLE 8. The sets of primer molecules of the invention can be used for the detection of microRNA target molecules from human, mouse, and rat, using the methods of the invention described herein.

In another aspect, the present invention provides kits for detecting at least one mammalian target microRNA, the kits comprising one or more primer sets specific for the detection of a target microRNA, each primer set comprising (1) an extension primer for producing a cDNA molecule complementary to a target microRNA, (2) a universal forward PCR primer, and (3) a reverse PCR primer for amplifying the cDNA molecule. The extension primer comprises a first portion that hybridizes to the target microRNA molecule and a second portion that includes a hybridization sequence for a universal forward PCR primer. The reverse PCR primer comprises a sequence selected to hybridize to a portion of the cDNA molecule. In some embodiments of the kits, at least one of the universal forward and reverse primers includes at least one locked nucleic acid molecule.

The extension primer, universal forward and reverse primers for inclusion in the kit may be designed to detect any mammalian target microRNA in accordance with the methods described herein. Nonlimiting examples of human target microRNA target molecules and exemplary target-specific extension primers and reverse primers are listed below in TABLE 1, TABLE 2, and TABLE 6. Nonlimiting examples of murine target microRNA target molecules and exemplary target-specific extension primers and reverse primers are listed below in TABLE 7. A nonlimiting example of a universal forward primer is set forth as SEQ ID NO: 13.

In certain embodiments, the kit includes a set of primers comprising an extension primer, reverse and universal forward primers for a selected target microRNA molecule that each have a hybridization temperature in the range of from 50° C. to 60° C.

In certain embodiments, the kit includes a plurality of primer sets that may be used to detect a plurality of mammalian microRNA targets, such as two microRNA targets up to several hundred microRNA targets.

In certain embodiments, the kit comprises one or more primer sets capable of detecting at least one or more of the following human microRNA target templates: of miR-1, miR-7, miR-9*, miR-10a, miR-10b, miR-15a, miR-15b, miR-16, miR-17-3p, miR-17-5p, miR-18, miR-19a, miR-19b, miR-20, miR-21, miR-22, miR-23a, miR-23b, miR-24, miR-25, miR-26a, miR-26b, miR-27a, miR-28, miR-29a, miR-29b, miR-29c, miR-30a-5p, miR-30b, miR-30c, miR-30d, miR-30e-5p, miR-30e-3p, miR-31, miR-32, miR-33, miR-34a, miR-34b, miR-34c, miR-92, miR-93, miR-95, miR-96, miR-98, miR-99a, miR-99b, miR-100, miR-101, miR-103, miR-105, miR-106a, miR-107, miR-122, miR-122a, miR-124, miR-124, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-143, miR-144, miR-145, miR-146, miR-147, miR-148a, miR-148b, miR-149, miR-150, miR-151, miR-152, miR-153, miR-154*, miR-154, miR-155, miR-181a, miR-181b, miR-181c, miR-182*, miR-182, miR-183, miR-184, miR-185, miR-186, miR-187, miR-188, miR-189, miR-190, miR-191, miR-192, miR-193, miR-194, miR-195, miR-196a, miR-196b, miR-197, miR-198, miR-199a*, miR-199a, miR-199b, miR-200a, miR-200b, miR-200c, miR-202, miR-203, miR-204, miR-205, miR-206, miR-208, miR-210, miR-211, miR-212, miR-213, miR-213, miR-214, miR-215, miR-216, miR-217, miR-218, miR-220, miR-221, miR-222, miR-223, miR-224, miR-296, miR-299, miR-301, miR-302a*, miR-302a, miR-302b*, miR-302b, miR-302d, miR-302c*, miR-302c, miR-320, miR-323, miR-324-3p, miR-324-5p, miR-325, miR-326, miR-328, miR-330, miR-331, miR-337, miR-338, miR-339, miR-340, miR-342, miR-345, miR-346, miR-363, miR-367, miR-368, miR-370, miR-371, miR-372, miR-373*, miR-373, miR-374, miR-375, miR-376b, miR-378, miR-379, miR-380-5p, miR-380-3p, miR-381, miR-382, miR-383, miR-410, miR-412, miR-422a, miR-422b, miR-423, miR-424, miR-425, miR-429, miR-431, miR-448, miR-449, miR-450, miR-451, let7a, let7b, let7c, let7d, let7e, let7f, let7g, let7i, miR-376a, and miR-377. The sequences of the above-mentioned microRNA targets are provided in "the miRBase sequence database" as described in Griffith-Jones et al. (2004), *Nucleic Acids Research* 32:D109-D111, and Griffith-Jones et al. (2006), *Nucleic Acids Research* 34:D140-D144, which is publically accessible on the World Wide Web at the Wellcome Trust Sanger Institute website.

Exemplary primers for use in accordance with this embodiment of the kit are provided in TABLE 1, TABLE 2, and TABLE 6 below.

In another embodiment, the kit comprises one or more primer sets capable of detecting at least one or more of the following human microRNA target templates: miR-1, miR-7, miR-10b, miR-26a, miR-26b, miR-29a, miR-30e-3p, miR-95, miR-107, miR-141, miR-143, miR-154*, miR-154, miR-155, miR-181a, miR-181b, miR-181c, miR-190, miR-193, miR-194, miR-195, miR-202, miR-206, miR-208, miR-212, miR-221, miR-222, miR-224, miR-296, miR-299, miR-302c*, miR-302c, miR-320, miR-339, miR363, miR-376b, miR379, miR410, miR412, miR424, miR429, miR431, miR449, miR451, let7a, let7b, let7c, let7d, let7e, let7f, let7g, and let7i. Exemplary primers for use in accordance with this embodiment of the kit are provided in TABLE 1, TABLE 2, and TABLE 6 below.

In another embodiment, the kit comprises one or more primer sets capable of detecting at least one or more of the following human, mouse or rat microRNA target templates: miR-1, miR-9, miR-18b, miR-20b, miR-92b, miR-146b, miR-181d, miR-193b, miR-194, miR-206, miR-291a-3p, miR-291b-3p, miR-301b, miR-329, miR-346, miR-351, miR-362, miR-362-3p, miR-369-5p, miR-384, miR-409-3p, miR-409-5p, miR-425-5p, miR-449b, miR-455, miR-483, miR-484, miR-485-3p, miR-485-5p, miR-486, miR-487b, miR-488, miR-489, miR-490, miR-491, miR-493-3p, miR-494, miR-495, miR-497, miR-499, miR-500, miR-501, miR-503, miR-505, miR-519a, miR-519b, miR-519c, miR-519d, miR-520a, miR-520b, miR-520d, miR-520e, miR-520f, miR-532, miR-539, miR-542-3p, miR-542-5p, miR-615, miR-652, miR-668, miR-671, miR-675-5p, miR-699, miR-721, and miR-758.

Exemplary primers for use in accordance with this embodiment of the kit are provided in TABLE 8.

In another embodiment, the kit comprises at least one oligonucleotide primer selected from the group consisting of SEQ ID NO: 2 to SEQ ID NO: 493, as shown in TABLE 1, TABLE 2, TABLE 6, and TABLE 7.

In another embodiment, the kit comprises at least one oligonucleotide primer selected from the group consisting of SEQ ID NO: 47, 48, 49, 50, 55, 56, 81, 82, 83, 84, 91, 92, 103, 104, 123, 124, 145, 146, 193, 194, 197, 198, 221, 222, 223, 224, 225, 226, 227, 228, 229, 230, 239, 240, 247, 248, 253, 254, 255, 256, 257, 258, 277, 278, 285, 286, 287, 288, 293, 294, 301, 302, 309, 310, 311, 312, 315, 316, 317, 318, 319, 320, 333, 334, 335, 336, 337, 338, 359, 360, 369, 370, 389, 390, 393, 394, 405, 406, 407, 408, 415, 416, 419, 420, 421, 422, 425, 426, 429, 430, 431, 432, 433, 434, 435, 436, 437, 438, 439, 440, 441, 442, 443, 444, 461 and 462, as shown in TABLE 6.

In another embodiment, the kit comprises at least one oligonucleotide primer selected from the group consisting of SEQ ID NO: 500 to SEQ ID NO: 965, as shown in TABLE 8.

A kit of the invention can also provide reagents for primer extension and amplification reactions. For example, in some embodiments, the kit may further include one or more of the following components: a reverse transcriptase enzyme, a DNA polymerase enzyme, a Tris buffer, a potassium salt (e.g., potassium chloride), a magnesium salt (e.g., magnesium chloride), a reducing agent (e.g., dithiothreitol), and deoxynucleoside triphosphates (dNTPs).

In various embodiments, the kit may include a detection reagent such as SYBR green dye or BEBO dye that preferentially or exclusively binds to double stranded DNA during a PCR amplification step. In other embodiments, the kit may include a forward and/or reverse primer that includes a fluorophore and quencher to measure the amount of the PCR amplification products.

The kit optionally includes instructions for using the kit in the detection and quantitation of one or more mammalian microRNA targets. The kit can also be optionally provided in a suitable housing that is preferably useful for robotic handling in a high throughput manner.

The following examples merely illustrate the best mode now contemplated for practicing the invention, but should not be construed to limit the invention.

Example 1

This Example describes a representative method of the invention for producing DNA molecules from microRNA target molecules.

Primer extension was conducted as follows (using InVitrogen SuperScript III® reverse transcriptase and following the guidelines that were provided with the enzyme). The following reaction mixture was prepared on ice:
1 µl of 10 mM dNTPs
1 µl of 2 µM extension primer
1-5 µl of target template
4 µl of "5×cDNA buffer"
1 µl of 0.1 M DTT
1 µl of RNAse OUT
1 µl of SuperScript III® enzyme
water to 20 µl The mixture was incubated at 50° C. for 30 minutes, then 85° C. for 5 minutes, then cooled to room temperature and diluted 10-fold with TE (10 mM Tris, pH 7.6, 0.1 mM EDTA).

Real-time PCR was conducted using an ABI 7900 HTS detection system (Applied Biosystems, Foster City, Calif., U.S.A.) by monitoring SYBR® green fluorescence of double-stranded PCR amplicons as a function of PCR cycle number. A typical 10 µl PCR reaction mixture contained:
5 µl of 2×SYBR® green master mix (ABI)
0.8 µl of 10 µM universal forward primer
0.8 µl of 10 µM reverse primer
1.4 µl of water
2.0 µl of target template (10-fold diluted RT reaction)

The reaction was monitored through 40 cycles of standard "two cycle" PCR (95° C.-15 sec, 60° C.-60 sec) and the fluorescence of the PCR products was measured.

The foregoing method was successfully used in eleven primer extension PCR assays for quantitation of endogenous microRNAs present in a sample of total RNA. The DNA sequences of the extension primers, the universal forward primer sequence, and the LNA substituted reverse primers, used in these 11 assays are shown in TABLE 1.

TABLE 1

| Target microRNA | Primer number | Primer Name | DNA sequence (5' to 3') | SEQ ID NO |
|---|---|---|---|---|
| gene-specific extension primers[1] | | | | |
| humanb let7a | 357 | let7aP4 | CATGATCAGCTGGGCCAAGAAACTATA<u>CAACCT</u> | 2 |
| human miR-1 | 337 | miR1P5 | CATGATCAGCTGGGCCAAGATACA<u>TACTTCT</u> | 3 |
| human miR-15a | 344 | miR15aP3 | CATGATCAGCTGGGCCAAGACACAAA<u>CCATTATG</u> | 4 |
| human miR-16 | 351 | miR16P2 | CATGATCAGCTGGGCCAAGACGCCAATA<u>TTTACGT</u> | 5 |
| human miR-21 | 342 | miR21P6 | CATGATCAGCTGGGCCAAGATCAAC<u>ATCAGT</u> | 6 |
| human miR-24 | 350 | miR24P5 | CATGATCAGCTGGGCCAAGACTGTTCCT<u>GCTG</u> | 7 |
| human miR-122 | 222 | 122-E5F | CATGATCAGCTGGGCCAAGAACAAACACCA<u>TTGTCA</u> | 8 |
| human miR-124 | 226 | 124-E5F | CATGATCAGCTGGGCCAAGATGGCATTCAC<u>CGCGTG</u> | 9 |
| human miR-143 | 362 | miR143P5 | CATGATCAGCTGGGCCAAGATGAGCTA<u>CAGTG</u> | 10 |
| human miR-145 | 305 | miR145P2 | CATGATCAGCTGGGCCAAGAAAGGGATTCC<u>TGGGAA</u> | 11 |
| human miR-155 | 367 | miR155P3 | CATGATCAGCTGGGCCAAGACCCCTAT<u>CACGAT</u> | 12 |
| universal forward primer | | | | |
| | 230 | E5F | CATGATCAGCTGGGCCAAGA | 13 |
| RNA species-specific reverse primers[2] | | | | |
| human let7a | 290 | miRlet7a-1, 2, 3R | TG+AGGT+AGT<u>AGGTTG</u> | 14 |
| human miR-1 | 285 | miR1-1, 2R | TG+GAA+TG+TAA<u>AGAAGTA</u> | 15 |
| human miR-15a | 287 | miR15aR | TAG+CAG+CA<u>CATAATG</u> | 16 |
| human miR-16 | 289 | miR16-1, 2R | T+AGC+AGC<u>ACGTAAA</u> | 17 |
| human miR-21 | 286 | miR21R | T+AG+CT+TATCAG<u>ACTGAT</u> | 18 |
| human miR-24 | 288 | miR24-1, 2R | TGG+CTCAGTT<u>CAGC</u> | 19 |
| human miR-122 | 234 | 122LNAR | T+G+GAG+TG<u>TGACAA</u> | 20 |
| human miR-124 | 235 | 124LNAR | T+TAA+GG<u>CACGCG</u> | 21 |

TABLE 1-continued

| Target microRNA | Primer number | Primer Name | DNA sequence (5' to 3') | SEQ ID NO |
|---|---|---|---|---|
| human miR-143 | 291 | miR143R | TG+AGA+TGAAG<u>CACTG</u> | 22 |
| human miR-145 | 314 | miR145R2 | GT+CCAGT<u>TTTCCCA</u> | 23 |
| human miR-155 | 293 | miR155R | T+TAA+TG+CTA<u>ATCGTGA</u> | 24 |

[1]- Universal forward primer binding sites are shown in italics. The overlap with the RNA-specific reverse primers are underlined.
[2]- LNA molecules are preceded by a "+". Region of overlap of the reverse primers with the corresponding extension primers are underlined.

The assay was capable of detecting microRNA in a concentration range of from 2 nM to 20 fM. The assays were linear at least up to a concentration of 2 nM of synthetic microRNA (>1,000,000 copies/cell).

Example 2

This Example describes the evaluation of the minimum sequence requirements for efficient primer-extension mediated cDNA synthesis using a series of extension primers for microRNA assays having gene specific regions that range in length from 12 to 3 base pairs.

Primer Extension Reactions. Primer extension was conducted using the target molecules miR-195 and miR-215 as follows. The target templates miR-195 and miR-215 were diluted to 1 nM RNA (100,000 copies/cell) in TE zero plus 100 ng/µl total yeast RNA. A no template control (NTC) was prepared with TE zero plus 100 ng/µl total yeast RNA.

The reverse transcriptase reactions were carried out as follows (using InVitrogen SuperScript III® reverse transcriptase and following the guidelines that were provided with the enzyme) using a series of extension primers for miR-195 (SEQ ID NO: 25-34) and a series of extension primers for miR-215 (SEQ ID NO: 35-44) the sequences of which are shown below in TABLE 2.

The following reaction mixtures were prepared on ice:
Set 1: No Template Control
37.5 µl water
12.5 µl of 10 mM dNTPs
12.5 µl 0.1 mM DTT
50 µl of "5×cDNA buffer"
12.5 µl RNAse OUT
12.5 µl Superscript III® reverse transcriptase enzyme
12.5 µl 1 µg/µl Hela cell total RNA (Ambion)
plus 50 µl of 2 µM extension primer
plus 50 µl TEzero+yeast RNA
Set 2: Spike-in Template
37.5 µl water
12.5 µl of 10 mM dNTPs
12.5 µl 0.1 mM DTT
50 µl of "5×cDNA buffer"
12.5 µl RNAse OUT
12.5 µl Superscript III® reverse transcriptase enzyme (InVitrogen)
12.5 µl 1 µg/µl Hela cell total RNA (Ambion)
plus 50 µl of 2 µM extension primer
plus 50 µl 1 nM RNA target template (miR-195 or miR-215)
serially diluted in 10-fold increments The reactions were incubated at 50° C. for 30 minutes, then 85° C. for 5 minutes, and cooled to 4° C. and diluted 10-fold with TE (10 mM Tris, pH 7.6, 0.1 mM EDTA).

Quantitative Real-Time PCR Reactions. Following reverse transcription, quadruplicate measurements of cDNA were made by quantitative real-time (qPCR) using an ABI 7900 HTS detection system (Applied Biosystems, Foster City, Calif., U.S.A.) by monitoring SYBR® green fluorescence of double-stranded PCR amplicons as a function of PCR cycle number. The following reaction mixture was prepared:
5 µl of 2×SYBR green master mix (ABI)
0.8 µl of 10 µM universal forward primer (SEQ ID NO: 13)
0.8 µl of 10 µM reverse primer (miR-195RP:SEQ ID NO: 45 or
miR215RP: SEQ ID NO: 46)
1.4 µl of water
2.0 µl of target template (10-fold diluted miR-195 or miR-215 RT reaction)

Quantitative real-time PCR was performed for each sample in quadruplicate, using the manufacturer's recommended conditions. The reactions were monitored through 40 cycles of standard "two cycle" PCR (95° C.-15 sec, 60° C.-60 sec) and the fluorescence of the PCR products were measured and disassociation curves were generated. The DNA sequences of the extension primers, the universal forward primer sequence, and the LNA substituted reverse primers, used in the miR-195 and miR-215 assays are shown below in TABLE 2. The assay results for miR-195 are shown below in TABLE 3 and the assay results for miR-215 are shown below in TABLE 4.

TABLE 2

| Target microRNA | Primer number | Primer Name | DNA sequence (5' to 3') | SEQ ID NO |
|---|---|---|---|---|
| gene-specific extension primers[1] | | | | |
| miR-195 | 646 | mir195-GS1 | *CATGATCAGCTGGGCCAAGAGC*-CAATATTTCT | 25 |
| miR-195 | 647 | mir195-GS2 | *CATGATCAGCTGGGCCAAGAGC*CAATATTTC | 26 |
| miR-195 | 648 | mir195-GS3 | *CATGATCAGCTGGGCCAAGAGC*CAATATTT | 27 |
| miR-195 | 649 | mir195-GS4 | *CATGATCAGCTGGGCCAAGAGC*CAATATT | 28 |
| miR-195 | 650 | mir195-GS5 | *CATGATCAGCTGGGCCAAGAGC*CAATAT | 29 |
| miR-195 | 651 | mir195-GS6 | *CATGATCAGCTGGGCCAAGAGC*CAATA | 30 |
| miR-195 | 652 | mir195-GS7 | *CATGATCAGCTGGGCCAAGAGC*CAAT | 31 |

TABLE 2-continued

| Target microRNA | Primer number | Primer Name | DNA sequence (5' to 3') | SEQ ID NO |
|---|---|---|---|---|
| miR-195 | 653 | mir195-GS8 | *CATGATCAGCTGGGCCAAGAGCCAA* | 32 |
| miR-195 | 654 | mir195-GS9 | *CATGATCAGCTGGGCCAAGAGCCA* | 33 |
| miR-195 | 655 | mir195-GS10 | *CATGATCAGCTGGGCCAAGAGCC* | 34 |
| miR-215 | 656 | mir215-GS1 | *CATGATCAGCTGGGCCAAGAGTCTGT*-CAATTC | 35 |
| miR-215 | 657 | mir215-GS2 | *CATGATCAGCTGGGCCAAGAGTCTGTCAATT* | 36 |
| miR-215 | 658 | mir215-GS3 | *CATGATCAGCTGGGCCAAGAGTCTGTCAAT* | 37 |
| miR-215 | 659 | mir215-GS4 | *CATGATCAGCTGGGCCAAGAGTCTGTCAA* | 38 |
| miR-215 | 660 | mir215-GS5 | *CATGATCAGCTGGGCCAAGAGTCTGTCA* | 39 |
| miR-215 | 661 | mir215-GS6 | *CATGATCAGCTGGGCCAAGAGTCTGTC* | 40 |
| miR-215 | 662 | mir215-GS7 | *CATGATCAGCTGGGCCAAGAGTCTGT* | 41 |
| miR-215 | 663 | mir215-GS8 | *CATGATCAGCTGGGCCAAGAGTCTG* | 42 |
| miR-215 | 664 | mir215-GS9 | *CATGATCAGCTGGGCCAAGAGTCT* | 43 |
| miR-215 | 665 | mir215-GS10 | *CATGATCAGCTGGGCCAAGAGTC* | 44 |

RNA species-specific reverse primers[2]

| miR-195 | 442 | mir195RP | T+AGC+AGCACAGAAAT | 45 |
| miR-215 | 446 | mir215RP | A+T+GA+CCTATGAATTG | 146 |

[1] - Universal forward primer binding sites are shown in italics.
[2] - The "+" symbol precedes the LNA molecules.

Results:

The sensitivity of each assay was measured by the cycle threshold (Ct) value which is defined as the cycle count at which fluorescence was detected in an assay containing microRNA target template. The lower this Ct value (e.g. the fewer number of cycles), the more sensitive was the assay. For microRNA samples, it was generally observed that while samples that contain template and no template controls both eventually cross the detection threshold, the samples with template do so at a much lower cycle number. The ΔCt value is the difference between the number of cycles (Ct) between template containing samples and no template controls, and serves as a measure of the dynamic range of the assay. Assays with a high dynamic range allow measurements of very low microRNA copy numbers. Accordingly, desirable characteristics of a microRNA detection assay include high sensitivity (low Ct value) and broad dynamic range (ΔCt≧12) between the signal of a sample containing target template and a no template background control sample.

The results of the miR195 and miR215 assays using extension primers having a gene specific portion ranging in size from 12 nucleotides to 3 nucleotides are shown below in TABLE 3 and TABLE 4, respectively. The results of these experiments unexpectedly demonstrate that gene-specific priming sequences as short as 3 nucleotides exhibit template specific priming. For both the miR-195 assay sets (shown in TABLE 3) and the miR-215 assay sets (shown in TABLE 4), the results demonstrate that the dynamic range (ΔCt) for both sets of assays are fairly consistent for extension primers having gene specific regions that are greater or equal to 8 nucleotides in length. The dynamic range of the assay (ΔCt) begins to decrease for extension primers having gene specific regions below 8 nucleotides, with a reduction in assay specificity below 7 nucleotides in the miR-195 assays, and below 6 nucleotides in the miR-215 assays. A melting point analysis of the miR-215 samples demonstrated that even at 3 nucleotides, there is specific PCR product present in the plus template samples (data not shown). Taken together, these data demonstrate that the gene specific region of extension primers is ideally ≧8 nucleotides, but can be as short as 3 nucleotides in length.

TABLE 3

MIR195 ASSAY RESULTS

| GS Primer Length | Ct: No Template Control | Ct: Plus Template | Δ Ct |
|---|---|---|---|
| 12 | 34.83 | 20.00 | 14.82 |
| 12 | 34.19 | 19.9 | 14.3 |
| 11 | 40.0 | 19.8 | 20.2 |
| 10 | 36.45 | 21.2 | 15.2 |
| 9 | 36.40 | 22.2 | 14.2 |
| 8 | 40.0 | 23.73 | 16.27 |
| 7 | 36.70 | 25.96 | 10.73 |
| 6 | 30.95 | 26.58 | 4.37 |
| 5 | 30.98 | 31.71 | −0.732 |
| 4 | 32.92 | 33.28 | −0.364 |
| 3 | 35.98 | 35.38 | −0.605 |

Ct = the cycle count where the fluorescence exceeds the threshold of detection.
ΔCt = the difference between the Ct value with template and no template.

TABLE 4

MIR215 ASSAY RESULTS

| GS Primer Length | Ct: No Template Control | Ct: Plus Template | Δ Ct |
|---|---|---|---|
| 12 | 33.4 | 13.57 | 19.83 |
| 12 | 33.93 | 14.15 | 19.77 |
| 11 | 35.51 | 15.76 | 19.75 |
| 10 | 35.33 | 15.49 | 19.84 |
| 9 | 36.02 | 16.84 | 19.18 |
| 8 | 35.79 | 17.07 | 18.72 |
| 7 | 32.29 | 17.58 | 14.71 |
| 6 | 34.38 | 20.62 | 13.75 |
| 5 | 34.41 | 28.65 | 5.75 |
| 4 | 36.36 | 33.92 | 2.44 |
| 3 | 35.09 | 33.38 | 1.70 |

Ct = the cycle count where the fluorescence exceeds the threshold of detection.
ΔCt = the difference between the Ct value with template and no template.

Example 3

This Example describes assays and primer sets designed for quantitative analysis of human microRNA expression patterns.

Primer Design:

microRNA target templates: the sequence of the target templates as described herein are publically available accessible on the World Wide Web at the Wellcome Trust Sanger Institute Web site in the "miRBase sequence database" as described in Griffith-Jones et al. (2004), *Nucleic Acids Research* 32:D109-D111, and Griffith-Jones et al. (2006), *Nucleic Acids Research* 34:D140-D144.

Extension primers: gene specific primers for primer extension of a microRNA to form a cDNA followed by quantitative PCR (qPCR) amplification were designed to (1) convert the RNA template into cDNA; (2) to introduce a "universal" PCR binding site (SEQ ID NO:1) to one end of the cDNA molecule; and (3) to extend the length of the cDNA to facilitate subsequent monitoring by qPCR.

Reverse primers: unmodified reverse primers and locked nucleic acid (LNA) containing reverse primers (RP) were designed to quantify the primer-extended, full length cDNA in combination with a generic universal forward primer (SEQ ID NO:13). For the locked nucleic acid containing reverse primers, two or three LNA modified bases were substituted within the first 8 nucleotides from the 5' end of the reverse primer oligonucleotide, as shown below in the exemplary reverse primer sequences provided in TABLE 6. The LNA base substitutions were selected to raise the predicted Tm of the primer by the highest amount, and the final predicted Tm of the selected primers were specified to be preferably less than or equal to 55° C.

An example describing an assay utilizing an exemplary set of primers the detection of miR-95 and miR-424 is described below.

Primer Extension Reactions: primer extension was conducted using DNA templates corresponding to miR-95 and miR-424 as follows. The DNA templates were diluted to 0 nM, 1 nM, 100 pM, 10 pM, and 1 pM dilutions in TE zero (10 mM Tris pH 7.6, 0.1 mM EDTA) plus 100 ng/µl yeast total RNA (Ambion, Austin, Tex.).

The reverse transcriptase reactions were carried out using the following primers:

```
Extension primers: (diluted to 500 nM)
miR-95GSP
(SEQ ID NO: 123)
CATGATCAGCTGGGCCAAGATGCTCAATAA miR-424GSP
(SEQ ID NO: 415)
CATGATCAGCTGGGCCAAGATTCAAAACAT Reverse primers: (diluted to 10 mM)
  miR-95_RP4
  (SEQ ID NO: 124)
  TT+CAAC+GGGTATTTATTGA miR-424RP2
  (SEQ ID NO: 416)
  C+AG+CAGCAATTCATGTTTT
```

Reverse Transcription (Per Reaction):

2 µl water

2 µl of "5×cDNA buffer" (InVitrogen, Carlsbad, Calif.)

0.5 µl of 0.1 mM DTT (InVitrogen, Carlsbad, Calif.)

0.5 µl of 10 mM dNTPs (InVitrogen, Carlsbad, Calif.)

0.5 µl RNAse OUT (InVitrogen, Carlsbad, Calif.)

0.5 µl Superscript III® reverse transcriptase enzyme (InVitrogen, Carlsbad, Calif.)

2 µl of extension primer plus 2 µl of template dilution

The reactions were mixed and incubated at 50° C. for 30 minutes, then 85° C. for 5 minutes, and cooled to 4° C. and diluted 10-fold with TE zero.

Quantitative Real-Time PCR Reactions (Per Reaction):

5 µl 2×SYBR mix (Applied Biosystems, Foster City, Calif.)

1.4 µl water 0.8 µl universal primer (CATGATCAGCTGGGCCAAGA (SEQ ID NO: 13))

2.0 µl of diluted reverse transcription (RT) product from above.

Quantitative real-time PCR was performed for each sample in quadruplicate, using the manufacturer's recommended conditions. The reactions were monitored through 40 cycles of standard "two cycle" PCR (95° C.-15 sec, 60° C.-60 sec) and the fluorescence of the PCR products were measured and disassociation curves were generated. The DNA sequences of the extension primers, the universal forward primer sequence, and the LNA substituted reverse primers, used in the representative miR-95 and miR-424 assays as well as primer sets for 212 different human microRNA templates are shown below in TABLE 6. Primer sets for assays requiring extensive testing and design modification to achieve a sensitive assay with a high dynamic range are indicated in TABLE 6 with the symbol # following the primer name.

Figure 2:
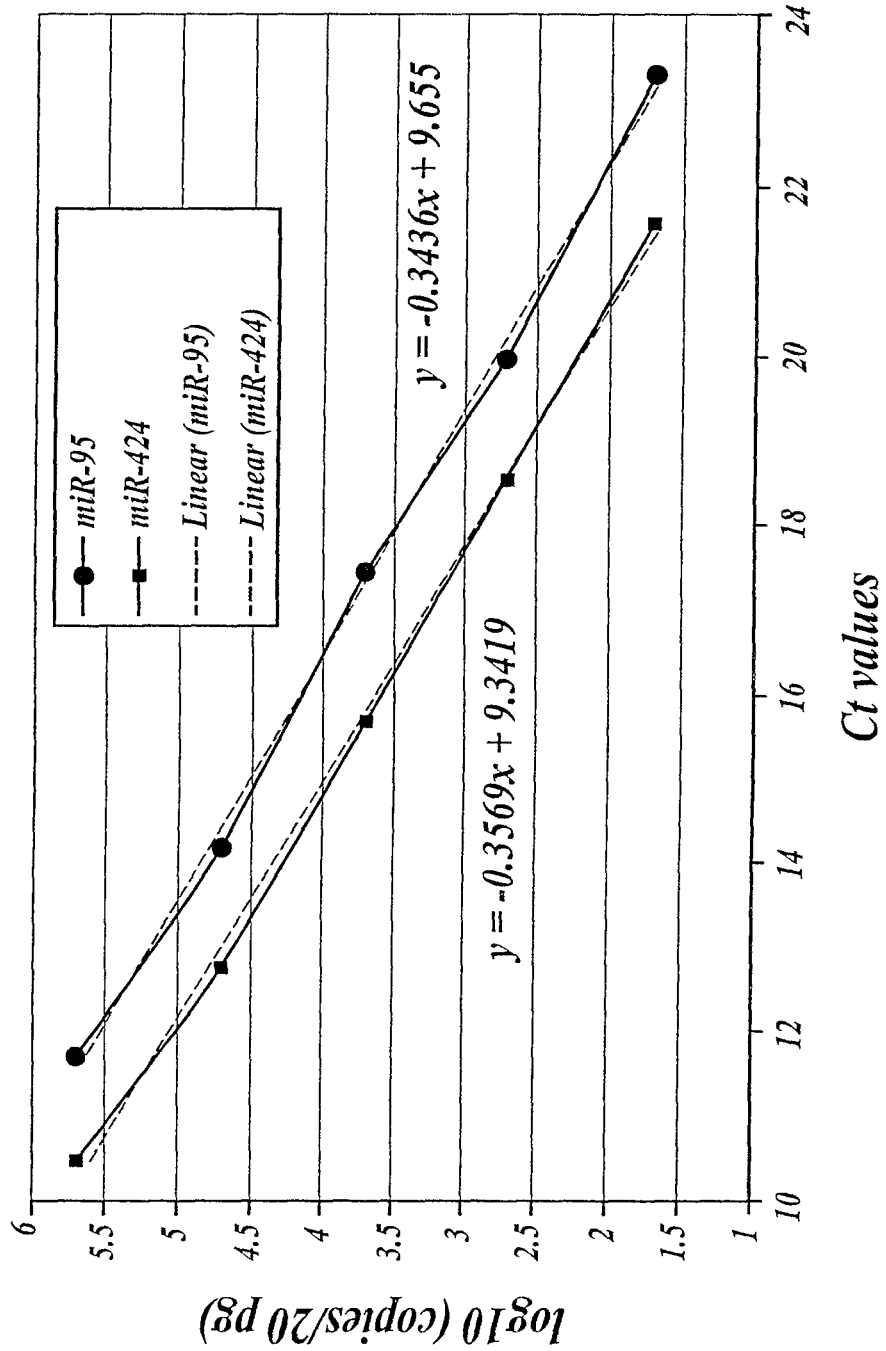
FIG. 2 graphically illustrates the standard curves for assays specific for the detection of microRNA targets miR-95 and miR-424 as described in EXAMPLE 3.

Results:

TABLE 5 shows the Ct values (averaged from four samples) from the miR-95 and miR-424 assays, which are plotted in the graph shown in FIG. 2. The results of these assays are provided as representative examples in order to explain the significance of the assay parameters shown in TABLE 6 designated as slope (column 6), intercept (column 7) and background (column 8).

As shown in TABLE 5, the Ct value for each template at various concentrations is provided. The Ct values (x-axis) are plotted as a function of template concentration (y-axis) to generate a standard curve for each assay, as shown in FIG. 2. The slope and intercept define the assay measurement characteristics that permit an estimation of number of copies/cell for each microRNA. For example, when the Ct values for 50 µg total RNA input for the miR-95 assay are plotted, a standard curve is generated with a slope and intercept of −0.03569 and 9.655, respectively. When these standard curve parameters are applied to the Ct of an unknown sample (x), they yield log 10 (copies/20 pg total RNA) (y). Because the average cell yields 20 pg of total RNA, these measurements equate to copies of microRNA/cell. The background provides an estimate of the minimum copy number that can be measured in a sample and is computed by inserting the no template control (NTC) value into this equation. In this example, as shown in TABLE 6, miR-95 yields a background of 1.68 copies/20 pg at 50 µg of RNA input.

As further shown in TABLE 6, reverse primers that do not contain LNA may also be used in accordance with the methods of the invention. See, e.g., SEQ ID NO:494-499. The sensitivity and dynamic range of the assays using non-LNA containing reverse primers SEQ ID NO:494-499, yielded similar results to the corresponding assays using LNA-containing reverse primers.

TABLE 5

| | Ct Values (averaged from four samples) | | | | | |
|---|---|---|---|---|---|---|
| | Template concentration | | | | | |
| | 10 nM | 1 nM | 0.1 nM | 0.01 nM | 0.001 nM | NTC |
| copies/20 pg RNA (50 μg input) | 500,000 | 50,000 | 5000 | 500 | 50 | |
| copies/20 pg RNA (5 μg input) | 5,000,000 | 500,000 | 50,000 | 5000 | 500 | |
| miR-95 | 11.71572163 | 14.17978 | 17.46353 | 19.97259 | 23.33171 | 27.44383 |
| miR-424 | 10.47708975 | 12.76806 | 15.69251 | 18.53729 | 21.56897 | 23.2813 |
| log 10 (copies for 50 μg input) | 5.698970004 | 4.69897 | 3.69897 | 2.69897 | 1.69897 | |

TABLE 6

PRIMERS TO DETECT HUMAN MICRORNA TARGET TEMPLATES

| Human Target microRNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-1 | miR1GSP10# | CATGATCAGCTGGGCCAAGATACATACTTC SEQ ID NO: 47 | miR-1RP# | T+G+GAA+TG+TAAAGAAGT SEQ ID NO: 48 | -0.2758 | 8.3225 | 2.44 | 24.36 |
| miR-7 | miR-7GSP10# | CATGATCAGCTGGGCCAAGACACAAAATC SEQ ID NO: 49 | miR-7_RP6# | T+GGAA+GACTAGTGATTTT SEQ ID NO: 50 | -0.2982 | 10.435 | 11.70 | 116.99 |
| miR-9* | miR-9*GSP | CATGATCAGCTGGGCCAAGAACTTTCGGTT SEQ ID NO: 51 | miR-9*RP | TAAA+GCT+AGATAACCG SEQ ID NO: 52 | -0.2405 | 8.9145 | 3.71 | 37.15 |
| miR-10a | miR-10aGSP | CATGATCAGCTGGGCCAAGACACAAATTCG SEQ ID NO: 53 | miR-10aRP | T+AC+CCTGTAGATCCG SEQ ID NO: 54 | -0.2755 | 8.6976 | 0.09 | 0.94 |
| miR-10b | miR-10b_GSP11# | CATGATCAGCTGGGCCAAGAACAAATTCGGT SEQ ID NO: 55 | miR-10b_RP2# | TA+CCC+TGT+AGAACCGA SEQ ID NO: 56 | -0.3505 | 8.7109 | 0.55 | 5.52 |
| miR-15a | miR-15aGSP | CATGATCAGCTGGGCCAAGACACAAACCAT SEQ ID NO: 57 | miR-15aRP | T+AG+CAGCACATAATG SEQ ID NO: 58 | -0.2831 | 8.4519 | 4.40 | 44.01 |
| miR-15b | miR-15bGSP2 | CATGATCAGCTGGGCCAAGACATGTAAACCA SEQ ID NO: 59 | miR-15bRP | T+AG+CAGCACATCAT SEQ ID NO: 60 | -0.2903 | 8.4206 | 0.18 | 1.84 |
| miR-16 | miR-16GSP2 | CATGATCAGCTGGGCCAAGACGCCAATAT SEQ ID NO: 61 | miR-16RP | T+AG+CAGCACGTAAA SEQ ID NO: 62 | -0.2542 | 9.3689 | 1.64 | 16.42 |
| miR-17-3p | miR-17-3pGSP | CATGATCAGCTGGGCCAAGAACAAGTGCCT SEQ ID NO: 63 | miR-17-3pRP | A+CT+GCAGTGAAGGC SEQ ID NO: 64 | -0.2972 | 8.2625 | 1.08 | 10.78 |
| miR-17-5p | miR-17-5pGSP2 | CATGATCAGCTGGGCCAAGAACTACCTGC SEQ ID NO: 65 | miR-17-5pRP | C+AA+AGTGCTTACAGTG SEQ ID NO: 66 | -0.2956 | 7.9101 | 0.13 | 1.32 |
| miR-19a | miR-19aGSP2 | CATGATCAGCTGGGCCAAGATACAGTTTTG SEQ ID NO: 67 | miR-19aRP | TG+TG+CAAATCTATGC SEQ ID NO: 68 | -0.2984 | 9.461 | 0.02 | 0.23 |
| miR-19b | miR-19bGSP | CATGATCAGCTGGGCCAAGATCAGTTTTGC SEQ ID NO: 69 | miR-19bRP | TG+TG+CAAATCCATG SEQ ID NO: 70 | -0.294 | 8.1434 | 2.26 | 22.55 |
| miR-20 | miR-20GSP3 | CATGATCAGCTGGGCCAAGACTACCTGC SEQ ID NO: 71 | miR-20RP | T+AA+AGTGCTTATAGTGCA SEQ ID NO: 72 | -0.2979 | 7.9929 | 0.16 | 1.60 |
| miR-21 | miR-21GSP2 | CATGATCAGCTGGGCCAAGATCAACATCA SEQ ID NO: 73 | miR-21RP | T+AG+CTTATCAGACTGATG SEQ ID NO: 74 | -0.2849 | 8.1624 | 1.80 | 17.99 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-23a | miR-23aGSP | CATGATCAGCTGGGCCAAGAGAGAAATCCCT SEQ ID NO: 75 | miR-23aRP | A+TC+ACATTGCCAGG SEQ ID NO: 76 | -0.3172 | 9.4253 | 2.41 | 24.08 |
| miR-23b | miR-23bGSP | CATGATCAGCTGGGCCAAGAGGTAAATCCCT SEQ ID NO: 77 | miR-23bRP | A+TC+ACATTGCCAGG SEQ ID NO: 78 | -0.2944 | 9.0985 | 5.39 | 53.85 |
| miR-25 | miR-25GSP | CATGATCAGCTGGGCCAAGATCAGACCCAG SEQ ID NO: 79 | miR-25RP | C+AT+TGCACTTGTCTC SEQ ID NO: 80 | -0.3009 | 8.2482 | 1.52 | 15.19 |
| miR-26a | miR-26aGSP9# | CATGATCAGCTGGGCCAAGAGCCTATCCT SEQ ID NO: 81 | miR-26aRP2# | TT+CA+AGTAATCCAGGAT SEQ ID NO: 82 | -0.2807 | 8.558 | 0.26 | 2.56 |
| miR-26b | miR-26bGSP9# | CATGATCAGCTGGGCCAAGAAACCTATCC SEQ ID NO: 83 | miR-26bRP2# | TT+CA+AGT+AATTCAGGAT SEQ ID NO: 84 | -0.2831 | 8.7885 | 0.37 | 3.67 |
| miR-27a | miR-27aGSP | CATGATCAGCTGGGCCAAGAGCGGAACTTA SEQ ID NO: 85 | miR-27aRP | TT+CA+CAGTGGCTAA SEQ ID NO: 86 | -0.2765 | 9.5239 | 5.15 | 51.51 |
| miR-27b | miR-27bGSP | CATGATCAGCTGGGCCAAGAGCAGAACTTA SEQ ID NO: 87 | miR-27bRP | TT+CA+CAGTGGCTAA SEQ ID NO: 88 | -0.28 | 9.5483 | 5.97 | 59.71 |
| miR-28 | miR-28GSP | CATGATCAGCTGGGCCAAGACTCAATAGAC SEQ ID NO: 89 | miR-28RP | A+AG+GAGCTCACAGT SEQ ID NO: 90 | -0.3226 | 10.071 | 7.19 | 71.87 |
| miR-29a | miR-29aGSP8# | CATGATCAGCTGGGCCAAGAAACCGATT SEQ ID NO: 91 | miR-29aRP2# | T+AG+CACCATCTGAAAT SEQ ID NO: 92 | -0.29 | 8.8731 | 0.04 | 0.38 |
| miR-29b | miR-29bGSP2 | CATGATCAGCTGGGCCAAGAAACACTGAT SEQ ID NO: 93 | miR-29bRP2 | T+AG+CACCATTTGAAATCAG SEQ ID NO: 94 | -0.3162 | 9.6276 | 3.56 | 35.57 |
| miR-30a-5p | miR-30a-5pGSP | CATGATCAGCTGGGCCAAGACTTCCAGTCG SEQ ID NO: 95 | miR-30a-5pRP | T+GT+AAACATCCTCGAC SEQ ID NO: 96 | -0.2772 | 9.0694 | 1.92 | 19.16 |
| miR-30b | miR-30bGSP | CATGATCAGCTGGGCCAAGAAGCTGAGTGT SEQ ID NO: 97 | miR-30bRP | T+AAA+CATCCTACACT SEQ ID NO: 98 | -0.2621 | 8.5974 | 0.11 | 1.13 |
| miR-30c | miR-30cGSP | CATGATCAGCTGGGCCAAGAGCTGAGAGTG SEQ ID NO: 99 | miR-30cRP | TGT+AAA+CATCCTACACT SEQ ID NO: 100 | -0.2703 | 8.699 | 0.15 | 1.48 |
| miR-30d | miR-30dGSP | CATGATCAGCTGGGCCAAGAGCTTCCAGTCG SEQ ID NO: 101 | miR-30dRP | T+GTAAA+CATCCCCG SEQ ID NO: 102 | -0.2506 | 9.3875 | 0.23 | 2.31 |
| miR-30e-3p | miR-30e-GSP9# | CATGATCAGCTGGGCCAAGAGCTGTAAAC SEQ ID NO: 103 | miR-30e-3pRP5# | CTTT+CAGT+CGATGTTT SEQ ID NO: 104 | -0.325 | 11.144 | 6.37 | 63.70 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-30e-5p | miR-30e-5pGSP | CATGATCAGCTGGGCCAAGATCCAGTCAAG SEQ ID NO: 105 | miR-30e-5pRP | TG+TAAA+CATCCTTGAC SEQ ID NO: 106 | −0.2732 | 8.1604 | 8.50 | 85.03 |
| miR-31 | miR-31GSP | CATGATCAGCTGGGCCAAGACAGCTATGCC SEQ ID NO: 107 | miR-31RP | G+GC+AAGATGCTGGC SEQ ID NO: 108 | −0.3068 | 8.2605 | 3.74 | 37.43 |
| miR-32 | miR-32GSP | CATGATCAGCTGGGCCAAGAGCAACTTAGT SEQ ID NO: 109 | miR-32RP | TATTG+CA+CATTACTAAG SEQ ID NO: 110 | −0.2785 | 8.9581 | 0.39 | 3.93 |
| miR-33 | miR-33GSP2 | CATGATCAGCTGGGCCAAGACAATGCAAC SEQ ID NO: 111 | miR-33RP | G+TG+CATTGTAGTTGC SEQ ID NO: 112 | −0.3031 | 8.42 | 2.81 | 28.14 |
| miR-34a | miR-34aGSP | CATGATCAGCTGGGCCAAGAAACAACCAGC SEQ ID NO: 113 | miR-34aRP | T+GG+CAGTGTCTTAG SEQ ID NO: 114 | −0.3062 | 9.1522 | 2.40 | 23.99 |
| miR-34b | miR-34bGSP | CATGATCAGCTGGGCCAAGACAATCAGCTA SEQ ID NO: 115 | miR-34bRP | TA+GG+CAGTGTCATT SEQ ID NO: 116 | −0.3208 | 9.054 | 0.04 | 0.37 |
| miR-34c | miR-34cGSP | CATGATCAGCTGGGCCAAGAGCAATCAGCT SEQ ID NO: 117 | miR-34cRP | A+GG+CAGTGTAGTTA SEQ ID NO: 118 | −0.2995 | 10.14 | 1.08 | 10.83 |
| miR-92 | miR-92GSP | CATGATCAGCTGGGCCAAGACAGGCCGGGA SEQ ID NO: 119 | miR-92RP | T+AT+TGCACTTGTCCC SEQ ID NO: 120 | −0.3012 | 8.6908 | 8.92 | 89.17 |
| miR-93 | miR-93GSP | CATGATCAGCTGGGCCAAGACTACCTGCAC SEQ ID NO: 121 | miR-93RP | AA+AG+TGCTGTTCGT SEQ ID NO: 122 | −0.3025 | 7.9933 | 4.63 | 46.30 |
| miR-95 | miR_95GSP# | CATGATCAGCTGGGCCAAGATGCTCAATAA SEQ ID NO: 123 | miR-95_RP4# | TT+CAAC+GGGTATTTATTGA SEQ ID NO: 124 | −0.3436 | 9.655 | 1.68 | 16.80 |
| miR-96 | miR-96GSP | CATGATCAGCTGGGCCAAGAGCAAAAATGT SEQ ID NO: 125 | miR-96RP | T+TT+GGCACTAGCAC SEQ ID NO: 126 | −0.2968 | 9.2611 | 0.00 | 0.05 |
| miR-98 | miR-98GSP | CATGATCAGCTGGGCCAAGAAACAATACAA SEQ ID NO: 127 | miR-98RP | TGA+GGT+AGTAAGTTG SEQ ID NO: 128 | −0.2797 | 9.5654 | 1.05 | 10.48 |
| miR-99a | miR-99aGSP | CATGATCAGCTGGGCCAAGACACAAGATCG SEQ ID NO: 129 | miR-99aRP | A+AC+CCGTAGATCCG SEQ ID NO: 130 | −0.2768 | 8.781 | 0.21 | 2.08 |
| miR-99b | miR-99bGSP | CATGATCAGCTGGGCCAAGACGCAAGGTCG SEQ ID NO: 131 | miR-99bRP | C+AC+CCGTAGAACCG SEQ ID NO: 132 | −0.2747 | 7.9855 | 0.25 | 2.53 |
| miR-100 | miR-100GSP | CATGATCAGCTGGGCCAAGACACAAGTTCG SEQ ID NO: 133 | miR-100RP | A+AC+CCGTAGATCCG SEQ ID NO: 134 | −0.2902 | 8.669 | 0.04 | 0.35 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-101 | miR-101GSP | CATGATCAGCTGGGCCAAGACTTCAGTTAT SEQ ID NO: 135 | miR-101RP | TA+CAG+TACTGTGATAACT SEQ ID NO: 136 | −0.3023 | 8.2976 | 0.46 | 4.63 |
| miR-103 | miR-103GSP | CATGATCAGCTGGGCCAAGATCATAGCCCT SEQ ID NO: 137 | miR-103RP | A+GC+AGCATTGTACA SEQ ID NO: 138 | −0.3107 | 8.5776 | 0.02 | 0.21 |
| miR-105 | miR-105GSP | CATGATCAGCTGGGCCAAGAACAGGAGTCT SEQ ID NO: 139 | miR-105RP | T+CAAA+TGCTCAGACT SEQ ID NO: 140 | −0.2667 | 8.9832 | 0.93 | 9.28 |
| miR-106a | miR-106aGSP | CATGATCAGCTGGGCCAAGAGCTACCTGCA SEQ ID NO: 141 | miR-106aRP | AAA+AG+TGCTTACAGTG SEQ ID NO: 142 | −0.3107 | 8.358 | 0.03 | 0.31 |
| miR-106b | miR-106bGSP | CATGATCAGCTGGGCCAAGAATCTGCACTG SEQ ID NO: 143 | miR-106bRP | T+AAAAG+TGCTGACAGT SEQ ID NO: 144 | −0.2978 | 8.7838 | 0.10 | 1.04 |
| miR-107 | miR-107GSP8# | CATGATCAGCTGGGCCAAGATGATAGCC SEQ ID NO: 145 | miR-107RP2# | A+GC+AGCATTGTACAG SEQ ID NO: 146 | −0.304 | 9.1666 | 0.34 | 3.41 |
| miR-122a | miR-122aGSP | CATGATCAGCTGGGCCAAGAACAAACACA SEQ ID NO: 147 | miR-122aRP | T+GG+AGTGTGACAAT SEQ ID NO: 148 | −0.3016 | 8.1479 | 0.06 | 0.58 |
| miR-124a | miR-124aGSP | CATGATCAGCTGGGCCAAGATGGCATTCAC SEQ ID NO: 149 | miR-124aRP | T+TA+AGGCACGCGGT SEQ ID NO: 150 | −0.3013 | 8.6906 | 0.56 | 5.63 |
| miR-125a | miR-125aGSP | CATGATCAGCTGGGCCAAGACACAGGTTAA SEQ ID NO: 151 | miR-125aRP | T+CC+CTGAGACCCTT SEQ ID NO: 152 | −0.2938 | 8.6754 | 0.09 | 0.91 |
| miR-125b | miR-125bGSP | CATGATCAGCTGGGCCAAGATCACAAGTTA SEQ ID NO: 153 | miR-125bRP | T+CC+CTGAGACCCTA SEQ ID NO: 154 | −0.283 | 8.1251 | 0.20 | 1.99 |
| miR-126 | miR-126GSP | CATGATCAGCTGGGCCAAGAGCATTATTAC SEQ ID NO: 155 | miR-126RP | T+CG+TACCGTGAGTA SEQ ID NO: 156 | −0.26 | 8.937 | 0.18 | 1.80 |
| miR-126* | miR-126*GSP3 | CATGATCAGCTGGGCCAAGACGCGTACC SEQ ID NO: 157 | miR-126*RP | C+ATT+ATTA+CTTTTGGTACG SEQ ID NO: 158 | −0.2969 | 8.184 | 3.58 | 35.78 |
| miR-127 | miR-127GSP | CATGATCAGCTGGGCCAAGAAGCCAAGCTC SEQ ID NO: 159 | miR-127RP | T+CG+GATCCGTCTGA SEQ ID NO: 160 | −0.2432 | 9.1013 | 1.11 | 11.13 |
| miR-128a | miR-128aGSP | CATGATCAGCTGGGCCAAGAAAAAGAGACC SEQ ID NO: 161 | miR-128aRP | T+CA+CAGTGAACCGG SEQ ID NO: 162 | −0.2866 | 8.0867 | 0.16 | 1.60 |
| miR-128b | miR-128bGSP | CATGATCAGCTGGGCCAAGAGAGAAGAGACC SEQ ID NO: 163 | miR-128bRP | T+CA+CAGTGAACCGG SEQ ID NO: 164 | −0.2923 | 8.0608 | 0.07 | 0.74 |

TABLE 6-continued

PRIMERS TO DETECT HUMAN MICRORNA TARGET TEMPLATES

| Human Target microRNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-129 | miR-129GSP | CATGATCAGCTGGGCCAAGAGAGCCCAG SEQ ID NO: 165 | miR-129RP | CTTTT+TG+CGGTCTG SEQ ID NO: 166 | −0.2942 | 9.7731 | 0.88 | 8.85 |
| miR-130a | miR-130aGSP | CATGATCAGCTGGGCCAAGAATGCCCTTTT SEQ ID NO: 167 | miR-130aRP | C+AG+TGCAATGTTAAAAG SEQ ID NO: 168 | −0.2943 | 8.7465 | 1.28 | 12.78 |
| miR-130b | miR-130bGSP | CATGATCAGCTGGGCCAAGAATGCCCTTTC SEQ ID NO: 169 | miR-130bRP | C+AG+TGCAATGATGA SEQ ID NO: 170 | −0.2377 | 9.1403 | 3.14 | 31.44 |
| miR-132 | miR-132GSP | CATGATCAGCTGGGCCAAGACGACCATGGC SEQ ID NO: 171 | miR-132RP | T+AA+CAGTCTACAGCC SEQ ID NO: 172 | −0.2948 | 8.1167 | 0.11 | 1.13 |
| miR-133a | miR-133aGSP | CATGATCAGCTGGGCCAAGAACAGCTGGTT SEQ ID NO: 173 | miR-133aRP | T+TG+GTCCCCTTCAA SEQ ID NO: 174 | −0.295 | 9.3679 | 0.10 | 1.04 |
| miR-133b | miR-133bGSP | CATGATCAGCTGGGCCAAGATAGCTGGTTG SEQ ID NO: 175 | miR-133bRP | T+TG+GTCCCCTTCAA SEQ ID NO: 176 | −0.3062 | 8.3649 | 0.02 | 0.18 |
| miR-134 | miR-134GSP | CATGATCAGCTGGGCCAAGACCCTCTGGTC SEQ ID NO: 177 | miR-134RP | T+GT+GACTGGTTGAC SEQ ID NO: 178 | −0.2965 | 9.0483 | 0.14 | 1.39 |
| miR-135a | miR-135aGSP | CATGATCAGCTGGGCCAAGATCACATAGGA SEQ ID NO: 179 | miR-135aRP | T+AT+GGCTTTTTATTCCT SEQ ID NO: 180 | −0.2914 | 8.092 | 1.75 | 17.50 |
| miR-135b | miR-135bGSP | CATGATCAGCTGGGCCAAGACACATAGAA SEQ ID NO: 181 | miR-135bRP | T+AT+GGCTTTTCATTCC SEQ ID NO: 182 | −0.2962 | 7.8986 | 0.05 | 0.49 |
| miR-136 | miR-136GSP | CATGATCAGCTGGGCCAAGATCCATCATCA SEQ ID NO: 183 | miR-136RP | A+CT+CCATTGTTTTGATG SEQ ID NO: 184 | −0.3616 | 10.229 | 0.68 | 6.77 |
| miR-137 | miR-137GSP | CATGATCAGCTGGGCCAAGACTACGCGTAT SEQ ID NO: 185 | miR-137RP | T+AT+TGCTTAAGAATACGC SEQ ID NO: 186 | −0.2876 | 8.234 | 8.57 | 85.71 |
| miR-138 | miR-138GSP2 | CATGATCAGCTGGGCCAAGACGGCCTGAT SEQ ID NO: 187 | miR-138RP | A+GC+TGGTGTTGTGA SEQ ID NO: 188 | −0.3023 | 9.0814 | 0.22 | 2.19 |
| miR-139 | miR-139GSP | CATGATCAGCTGGGCCAAGAAGACACGTGC SEQ ID NO: 189 | miR-139RP | T+CT+ACAGTGCACGT SEQ ID NO: 190 | −0.2983 | 8.1141 | 6.92 | 69.21 |
| miR-140 | miR-140GSP | CATGATCAGCTGGGCCAAGACTACCATAGG SEQ ID NO: 191 | miR-140RP | A+GT+GGTTTTACCCT SEQ ID NO: 192 | −0.2312 | 8.3231 | 0.13 | 1.34 |
| miR-141 | miR-141GSP9# | CATGATCAGCTGGGCCAAGACCATCTTTA SEQ ID NO: 193 | miR-141RP2# | TAA+CAC+TGTCTGGTAA SEQ ID NO: 194 | −0.2805 | 9.6671 | 0.13 | 1.26 |

TABLE 6-continued

PRIMERS TO DETECT HUMAN MICRORNA TARGET TEMPLATES

| Human Target microRNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-142-3p | miR-142-3pGSP3 | CATGATCAGCTGGGCCAAGATCCATAAA SEQ ID NO: 195 | miR-142-3pRP | TGT+AG+TGTTTCCTACT SEQ ID NO: 196 | -0.2976 | 8.4046 | 0.03 | 0.27 |
| miR-143 | miR-143GSP8# | CATGATCAGCTGGGCCAAGATGAGCTAC SEQ ID NO: 197 | miR-143RP2# | T+GA+GATGAAGCACTG SEQ ID NO: 198 | -0.3008 | 9.2675 | 0.37 | 3.71 |
| miR-144 | miR-144GSP2 | CATGATCAGCTGGGCCAAGACTAGTACAT SEQ ID NO: 199 | miR-144RP | TA+CA+GTAT+AGATGATG SEQ ID NO: 200 | -0.2407 | 9.4441 | 0.95 | 9.52 |
| miR-145 | miR-145GSP2 | CATGATCAGCTGGGCCAAGAAAGGGATTC SEQ ID NO: 201 | miR-145RP | G+TC+CAGTTTTCCCA SEQ ID NO: 202 | -0.2937 | 8.0791 | 0.39 | 3.86 |
| miR-146 | miR-146GSP3 | CATGATCAGCTGGGCCAAGAGAAACCCATG SEQ ID NO: 203 | miR-146RP | T+GA+GAACTGAATTCCA SEQ ID NO: 204 | -0.2861 | 8.8246 | 0.08 | 0.75 |
| miR-147 | miR-147GSP | CATGATCAGCTGGGCCAAGAGAGCAGAAGCAT SEQ ID NO: 205 | miR-147RP | G+TG+TGTGGAAATGC SEQ ID NO: 206 | -0.2989 | 8.8866 | 1.65 | 16.47 |
| miR-148a | miR-148aGSP2 | CATGATCAGCTGGGCCAAGAAACAAAGTTC SEQ ID NO: 207 | miR-148aRP2 | T+CA+GTGCACTACAGAACT SEQ ID NO: 208 | -0.2928 | 9.4654 | 1.27 | 12.65 |
| miR-148b | miR-148bGSP2 | CATGATCAGCTGGGCCAAGAAACAAAGTTC SEQ ID NO: 209 | miR-148bRP | T+CA+GTGCATCACAG SEQ ID NO: 210 | -0.2982 | 10.417 | 0.24 | 2.44 |
| miR-149 | miR-149GSP2 | CATGATCAGCTGGGCCAAGAGAGAGTGAAG SEQ ID NO: 211 | miR-149RP | T+CT+GGCTCCGTGTC SEQ ID NO: 212 | -0.2996 | 8.3392 | 2.15 | 21.50 |
| miR-150 | miR-150GSP3 | CATGATCAGCTGGGCCAAGACACTGGTA SEQ ID NO: 213 | miR-150RP | T+CT+CCCAACCCTTG SEQ ID NO: 214 | -0.2943 | 8.3945 | 0.06 | 0.56 |
| miR-151 | miR-151GSP2 | CATGATCAGCTGGGCCAAGACCTCAAGGA SEQ ID NO: 215 | miR-151RP | A+CT+AGACTGAAGCTC SEQ ID NO: 216 | -0.2975 | 8.651 | 0.16 | 1.60 |
| miR-152 | miR-152GSP2 | CATGATCAGCTGGGCCAAGACCCAAGTTC SEQ ID NO: 217 | miR-152RP | T+CA+GTGCATGACAG SEQ ID NO: 218 | -0.2741 | 8.7404 | 0.33 | 3.25 |
| miR-153 | miR-153GSP2 | CATGATCAGCTGGGCCAAGATCACTTTTG SEQ ID NO: 219 | miR-153RP | TTG+CAT+AGTCACAAAA SEQ ID NO: 220 | -0.2723 | 9.5732 | 3.32 | 33.19 |
| miR-154* | miR-154*GSP9# | CATGATCAGCTGGGCCAAGAAATAGGTCA SEQ ID NO: 221 | miR-154*RP2# | AATCA+TA+CACGGTTGAC SEQ ID NO: 222 | -0.3056 | 8.8502 | 0.07 | 0.74 |
| miR-154 | miR-154GSP9# | CATGATCAGCTGGGCCAAGACGAAGGCAA SEQ ID NO: 223 | miR-154RP3# | TA+GGTTA+TCCGTGTT SEQ ID NO: 224 | -0.3062 | 9.3947 | 0.10 | 0.96 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-155 | miR-155GSP8# | CATGATCAGCTGGGCCAAGACCCCTATC SEQ ID NO: 225 | miR-155RP2# | TT+AA+TGCTAATCGTGATAGG SEQ ID NO: 226 | -0.3201 | 8.474 | 5.49 | 54.91 |
| miR-181a | miR-181aGSP9# | CATGATCAGCTGGGCCAAGAACTCACCGA SEQ ID NO: 227 | miR-181aRP2# | AA+CATT+CAACGCTGTC SEQ ID NO: 228 | -0.2919 | 7.968 | 1.70 | 17.05 |
| miR-181c | miR-181cGSP9# | CATGATCAGCTGGGCCAAGAACTCACCGA SEQ ID NO: 229 | miR-181cRP2# | AA+CATT+CAACCTGTCG SEQ ID NO: 230 | -0.3102 | 7.9029 | 1.08 | 10.78 |
| miR-182* | miR-182*GSP | CATGATCAGCTGGGCCAAGATAGTTGGCAA SEQ ID NO: 231 | miR-182*RP | T+GG+TTCTAGACTTGC SEQ ID NO: 232 | -0.2978 | 8.5876 | 4.25 | 42.47 |
| miR-182 | miR-182GSP2 | CATGATCAGCTGGGCCAAGATGTGAGTTC SEQ ID NO: 233 | miR-182RP | TTT+GG+CAATGGTAG SEQ ID NO: 234 | -0.2863 | 9.0854 | 1.52 | 15.20 |
| miR-183 | miR-183GSP2 | CATGATCAGCTGGGCCAAGACAGTGAATT SEQ ID NO: 235 | miR-183RP | T+AT+GGCACTGGTAG SEQ ID NO: 236 | -0.2774 | 9.9254 | 1.95 | 19.51 |
| miR-184 | miR-184GSP2 | CATGATCAGCTGGGCCAAGAACCCTTATC SEQ ID NO: 237 | miR-184RP | T+GG+ACGGAGAACTG SEQ ID NO: 238 | -0.2906 | 7.9585 | 0.05 | 0.49 |
| miR-186 | miR-186GSP9# | CATGATCAGCTGGGCCAAGAAAGCCCAAA SEQ ID NO: 239 | miR-186RP3# | CA+AA+GAATT+CTCCTTTGG SEQ ID NO: 240 | -0.2861 | 8.6152 | 0.32 | 3.18 |
| miR-187 | miR-187GSP | CATGATCAGCTGGGCCAAGACGGCTGCAAC SEQ ID NO: 241 | miR-187RP | T+CG+TGTCTTGTGTT SEQ ID NO: 242 | -0.2953 | 7.9329 | 1.23 | 12.31 |
| miR-188 | miR-188GSP | CATGATCAGCTGGGCCAAGAACCCTCCACC SEQ ID NO: 243 | miR-188RP | C+AT+CCCTTGCATGG SEQ ID NO: 244 | -0.2925 | 8.0782 | 8.49 | 84.92 |
| miR-189 | miR-189GSP2 | CATGATCAGCTGGGCCAAGAACTGATATC SEQ ID NO: 245 | miR-189RP | G+TG+CCTACTGAGCT SEQ ID NO: 246 | -0.2981 | 8.8964 | 0.21 | 2.08 |
| miR-190 | miR-190GSP9# | CATGATCAGCTGGGCCAAGAACCTAATAT SEQ ID NO: 247 | miR-190RP4# | T+GA+TA+TGTTTGATATATTAG SEQ ID NO: 248 | -0.3317 | 9.8766 | 0.43 | 4.34 |
| miR-191 | miR-191GSP2 | CATGATCAGCTGGGCCAAGAAGTGCTTT SEQ ID NO: 249 | miR-191RP2 | C+AA+CGGAATCCCAAAG SEQ ID NO: 250 | -0.299 | 9.0317 | 0.41 | 4.07 |
| miR-192 | miR-192GSP2 | CATGATCAGCTGGGCCAAGAGGCTGTCAA SEQ ID NO: 251 | miR-192RP | C+TGA+CCTATGAATTGAC SEQ ID NO: 252 | -0.2924 | 9.5012 | 1.10 | 10.98 |
| miR-193 | miR-193GSP9# | CATGATCAGCTGGGCCAAGACTGGGACTT SEQ ID NO: 253 | miR-193RP2# | AA+CT+GGCCTACAAAG SEQ ID NO: 254 | -0.3183 | 8.9942 | 0.17 | 1.72 |

TABLE 6-continued

PRIMERS TO DETECT HUMAN MICRORNA TARGET TEMPLATES

| Human Target microRNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-194 | mir194GSP8# | CATGATCAGCTGGGCCAAGATCCACATG SEQ ID NO: 255 | mir194RP# | TG+TAA+CAGCAACTCCA SEQ ID NO: 256 | -0.3078 | 8.8045 | 0.37 | 3.69 |
| miR-195 | miR-195GSP9# | CATGATCAGCTGGGCCAAGAGCCAAATATT SEQ ID NO: 257 | miR-195RP3# | T+AG+CAG+CACAGAAATA SEQ ID NO: 258 | -0.2955 | 10.213 | 0.76 | 7.58 |
| miR-196b | miR-196bGSP | CATGATCAGCTGGGCCAAGACCAACAACAG SEQ ID NO: 259 | miR-196bRP | TA+GGT+AGTTTCCTGT SEQ ID NO: 260 | -0.301 | 8.1641 | 1.47 | 14.66 |
| miR-196a | miR-196aGSP | CATGATCAGCTGGGCCAAGACCAACAACAT SEQ ID NO: 261 | miR-196aRP | TA+GG+TAGTTTCATGTTG SEQ ID NO: 262 | -0.2932 | 8.0448 | 8.04 | 80.37 |
| miR-197 | miR-197GSP2 | CATGATCAGCTGGGCCAAGAGTGGGTGG SEQ ID NO: 263 | miR-197RP | TT+CA+CCACTTCTC SEQ ID NO: 264 | -0.289 | 8.2822 | 0.71 | 7.10 |
| miR-198 | miR-198GSP3 | CATGATCAGCTGGGCCAAGACCTATCTC SEQ ID NO: 265 | miR-198RP | G+GT+CCAGAGGGAG SEQ ID NO: 266 | -0.2986 | 8.1359 | 0.31 | 3.15 |
| miR-199a* | miR-199a*GSP2 | CATGATCAGCTGGGCCAAGAAAACCAATGT SEQ ID NO: 267 | miR-199a*RP | T+AC+AGTAGTCTGCAC SEQ ID NO: 268 | -0.3029 | 9.0509 | 0.25 | 2.52 |
| miR-199a | miR-199aGSP2 | CATGATCAGCTGGGCCAAGAGAGAACAGGTA SEQ ID NO: 269 | miR-199aRP | C+CC+AGTGTTCAGAC SEQ ID NO: 270 | -0.3187 | 9.2268 | 0.12 | 1.16 |
| miR-199b | miR-199bGSP | CATGATCAGCTGGGCCAAGAGAACAGATAG SEQ ID NO: 271 | miR-199bRP | C+CC+AGTGTTTAGAC SEQ ID NO: 272 | -0.3165 | 9.3935 | 2.00 | 20.04 |
| miR-200a | miR-200aGSP2 | CATGATCAGCTGGGCCAAGAACATCGTTA SEQ ID NO: 273 | miR-200aRP | TAA+CAC+TGTCTGGT SEQ ID NO: 274 | -0.2754 | 9.1227 | 0.08 | 0.78 |
| miR-200b | miR-200bGSP2 | CATGATCAGCTGGGCCAAGAGTCATCATT SEQ ID NO: 275 | miR-200bRP | TAATA+CTG+CCTGGTAAT SEQ ID NO: 276 | -0.2935 | 8.5461 | 0.08 | 0.85 |
| miR-202 | miR-202GSP10# | CATGATCAGCTGGGCCAAGATTTTCCCATG SEQ ID NO: 277 | miR-202RP# | A+GA+GGTATA+GGGCAT SEQ ID NO: 278 | -0.2684 | 9.056 | 0.25 | 2.48 |
| miR-203 | miR-203GSP2 | CATGATCAGCTGGGCCAAGACTAGTGGTC SEQ ID NO: 279 | miR-203RP | G+TG+AAATGTTTAGGACC SEQ ID NO: 280 | -0.2852 | 8.1279 | 1.60 | 16.03 |
| miR-204 | miR-204GSP2 | CATGATCAGCTGGGCCAAGAAGGCATAGG SEQ ID NO: 281 | miR-204RP | T+TC+CCTTTGTCATCC SEQ ID NO: 282 | -0.2925 | 8.7648 | 0.16 | 1.59 |
| miR-205 | miR-205GSP | CATGATCAGCTGGGCCAAGACAGACTCCGG SEQ ID NO: 283 | miR-205RP | T+CCTT+CATTCCACC SEQ ID NO: 284 | -0.304 | 8.2407 | 9.21 | 92.15 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-206 | mir206GSP7# | CATGATCAGCTGGGCCAAGACCACACA SEQ ID NO: 285 | miR-206RP# | T+G+GAA+TGTAAGGAAGTGT SEQ ID NO: 286 | −0.2815 | 8.2206 | 0.29 | 2.86 |
| miR-208 | miR-208_GSP13# | CATGATCAGCTGGGCCAAGAACAAGCTTTTTGC SEQ ID NO: 287 | miR-208_RP4# | ATAA+GA+CG+AGCAAAAAG SEQ ID NO: 288 | −0.2072 | 7.9097 | 57.75 | 577.52 |
| miR-210 | miR-210GSP | CATGATCAGCTGGGCCAAGATCAGCCGCTG SEQ ID NO: 289 | miR-210RP | C+TG+TGCGTGTGACA SEQ ID NO: 290 | −0.2717 | 8.249 | 0.18 | 1.77 |
| miR-211 | miR-211GSP2 | CATGATCAGCTGGGCCAAGAAGGCGAAGG SEQ ID NO: 291 | miR-211RP | T+TC+CCTTTGTCATCC SEQ ID NO: 292 | −0.2926 | 8.3106 | 0.10 | 1.00 |
| miR-212 | miR-212GSP9# | CATGATCAGCTGGGCCAAGAGAGGCCGTGAC SEQ ID NO: 293 | miR-212RP2# | T+AA+CAGTCTCCAGTCA SEQ ID NO: 294 | −0.2916 | 8.0745 | 0.59 | 5.86 |
| miR-213 | miR-213GSP | CATGATCAGCTGGGCCAAGAGTACAATCA SEQ ID NO: 295 | miR-213RP | A+CC+ATCGACCGTTG SEQ ID NO: 296 | −0.2934 | 8.1848 | 2.96 | 29.59 |
| miR-214 | miR-214GSP | CATGATCAGCTGGGCCAAGACTGCCTGTCT SEQ ID NO: 297 | miR-214RP | A+CA+GCAGGCACAGA SEQ ID NO: 298 | −0.2947 | 7.82 | 0.84 | 8.44 |
| miR-215 | miR-215GSP2 | CATGATCAGCTGGGCCAAGAGTCTGTCAA SEQ ID NO: 299 | miR-215RP | A+TGA+CCTATGAATTGAC SEQ ID NO: 300 | −0.2932 | 8.9273 | 1.51 | 15.05 |
| miR-216 | miR-216GSP9# | CATGATCAGCTGGGCCAAGACACAGTTGC SEQ ID NO: 301 | mir216RP# | TAA+TCT+CAGTGGCA SEQ ID NO: 302 | −0.273 | 8.5829 | 0.95 | 9.50 |
| miR-217 | miR-217GSP2 | CATGATCAGCTGGGCCAAGAATCCAATCA SEQ ID NO: 303 | miR-217RP2 | T+AC+TGCATCAGGAACTGA SEQ ID NO: 304 | −0.3089 | 9.6502 | 0.07 | 0.71 |
| miR-218 | miR-218GSP2 | CATGATCAGCTGGGCCAAGAACATGGTTA SEQ ID NO: 305 | miR-218RP | TTG+TGCTT+GATCTAAC SEQ ID NO: 306 | −0.2778 | 8.4363 | 1.00 | 10.05 |
| miR-220 | miR-220GSP | CATGATCAGCTGGGCCAAGAAAAAGTGTCAG SEQ ID NO: 307 | miR-220RP | C+CA+CACCGTATCTG SEQ ID NO: 308 | −0.2755 | 9.0728 | 8.88 | 88.75 |
| miR-221 | miR-221GSP9# | CATGATCAGCTGGGCCAAGAGAAACCCAG SEQ ID NO: 309 | miR-221RP# | A+GC+TACATTGTCTGC SEQ ID NO: 310 | −0.2886 | 8.5743 | 0.12 | 1.17 |
| miR-222 | miR-222GSP8# | CATGATCAGCTGGGCCAAGAGAGACCCA SEQ ID NO: 311 | miR-222RP# | A+GC+TACATCTGGCT SEQ ID NO: 312 | −0.283 | 8.91 | 1.64 | 16.41 |
| miR-223 | miR-223GSP | CATGATCAGCTGGGCCAAGAGAGGGTATTTG SEQ ID NO: 313 | miR-223RP | TG+TC+AGTTTGTCAAA SEQ ID NO: 314 | −0.2998 | 8.6669 | 0.94 | 9.44 |

TABLE 6-continued

PRIMERS TO DETECT HUMAN MICRORNA TARGET TEMPLATES

| Human Target microRNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-224 | miR-224GSP8# | CATGATCAGCTGGGCCAAGATAAACGGA SEQ ID NO: 315 | miR-224RP2# | C+AAG+TCACTAGTGGTT SEQ ID NO: 316 | −0.2802 | 7.5575 | 0.56 | 5.63 |
| miR-296 | miR-296GSP9# | CATGATCAGCTGGGCCAAGAACAGGATTG SEQ ID NO: 317 | miR-296RP2# | A+GG+GCCCCCCTCAA SEQ ID NO: 318 | −0.3178 | 8.3856 | 0.10 | 0.96 |
| miR-299 | miR-299GSP9# | CATGATCAGCTGGGCCAAGAATGTATGTG SEQ ID NO: 319 | miR-299RP# | T+GG+TTTACCGTCCC SEQ ID NO: 320 | −0.3155 | 7.9383 | 1.30 | 12.96 |
| miR-301 | miR-301GSP | CATGATCAGCTGGGCCAAGAGAGCTTTGACAA SEQ ID NO: 321 | miR-301RP | C+AG+TGCAATAGTATTGT SEQ ID NO: 322 | −0.2839 | 8.314 | 2.55 | 25.52 |
| miR-302a* | miR-302a*GSP | CATGATCAGCTGGGCCAAGAAAAGCAAGTA SEQ ID NO: 323 | miR-302a*RP | TAAA+CG+TGGATGTAC SEQ ID NO: 324 | −0.2608 | 8.3921 | 0.04 | 0.41 |
| miR-302a | miR-302aGSP | CATGATCAGCTGGGCCAAGATCACCAAAAC SEQ ID NO: 325 | miR-302aRP | T+AAG+TGCTTCCATGT SEQ ID NO: 326 | −0.2577 | 9.6657 | 2.17 | 21.67 |
| miR-302b* | miR-302b*GSP | CATGATCAGCTGGGCCAAGAAGAAAGCACT SEQ ID NO: 327 | miR-302b*RP | A+CTTTAA+CATGGAAGTG SEQ ID NO: 328 | −0.2702 | 8.5153 | 0.02 | 0.24 |
| miR-302b | miR-302bGSP | CATGATCAGCTGGGCCAAGAGACTACTAAAAC SEQ ID NO: 329 | miR-302bRP | T+AAG+TGCTTCCATGT SEQ ID NO: 330 | −0.2398 | 9.1459 | 5.11 | 51.11 |
| miR-302d | miR-302dGSP | CATGATCAGCTGGGCCAAGAACACTCAAAC SEQ ID NO: 331 | miR-302dRP | T+AAG+TGCTTCCATGT SEQ ID NO: 332 | −0.2368 | 8.5602 | 5.98 | 59.78 |
| miR-302c* | miR-302c*_GSP9# | CATGATCAGCTGGGCCAAGACACAGCAGTA SEQ ID NO: 333 | miR-302c*_RP2# | TT+TAA+CAT+GGGGGTACC SEQ ID NO: 334 | −0.312 | 8.2904 | 0.33 | 3.28 |
| miR-302c | miR-302cGSP9# | CATGATCAGCTGGGCCAAGACCACTGAAA SEQ ID NO: 335 | miR-302cRP5# | T+AAG+TGCTTCCATGTTTCA SEQ ID NO: 336 | −0.2945 | 8.381 | 14.28 | 142.76 |
| miR-320 | miR-320_GSP8# | CATGATCAGCTGGGCCAAGATTCGCCCT SEQ ID NO: 337 | miR-320_RP3# | AAAA+GCT+GGGTTGAGAGG SEQ ID NO: 338 | −0.2677 | 7.8956 | 6.73 | 67.29 |
| miR-323 | miR-323GSP | CATGATCAGCTGGGCCAAGAAGAGGTCGAC SEQ ID NO: 339 | miR-323RP | G+CA+CATTACACGGT SEQ ID NO: 340 | −0.2878 | 8.2546 | 0.19 | 1.92 |
| miR-324-3p | miR-324-3pGSP | CATGATCAGCTGGGCCAAGACCAGCAGCAC SEQ ID NO: 341 | miR-324-3pRP | C+CA+CTGCCCCAGGT SEQ ID NO: 342 | −0.2698 | 8.5223 | 2.54 | 25.41 |
| miR-324-5p | miR-324-5pGSP | CATGATCAGCTGGGCCAAGAACACCAATGC SEQ ID NO: 343 | miR-324-5pRP | C+GC+ATCCCCTAGGG SEQ ID NO: 344 | −0.2861 | 7.6865 | 0.06 | 0.62 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-325 | miR-325GSP | CATGATCAGCTGGGCCAAGAACACTTACTG SEQ ID NO: 345 | miR-325RP | C+CT+AGTAGGTGTCC SEQ ID NO: 346 | -0.2976 | 8.1925 | 0.01 | 0.14 |
| miR-326 | miR-326GSP | CATGATCAGCTGGGCCAAGACTGGAGGAAG SEQ ID NO: 347 | miR-326RP | C+CT+CTGGGCCTTC SEQ ID NO: 348 | -0.2806 | 7.897 | 0.59 | 5.87 |
| miR-328 | miR-328GSP | CATGATCAGCTGGGCCAAGAACGGAAGGGC SEQ ID NO: 349 | miR-328RP | C+TG+GCCCTCTCTGC SEQ ID NO: 350 | -0.293 | 7.929 | 3.17 | 31.69 |
| miR-330 | miR-330GSP | CATGATCAGCTGGGCCAAGATCTCTGCAGG SEQ ID NO: 351 | miR-330RP | G+CA+AAGCACACGGC SEQ ID NO: 352 | -0.3009 | 7.7999 | 0.13 | 1.30 |
| miR-331 | miR-331GSP | CATGATCAGCTGGGCCAAGATTCTTAGGATA SEQ ID NO: 353 | miR-331RP | G+CC+CCTGGGCTAT SEQ ID NO: 354 | -0.2816 | 8.1643 | 0.45 | 4.54 |
| miR-337 | miR-337GSP | CATGATCAGCTGGGCCAAGAAAAGGCATCA SEQ ID NO: 355 | miR-337RP | T+CC+AGTCTCTATATG SEQ ID NO: 356 | -0.2968 | 8.7313 | 0.10 | 1.02 |
| miR-338 | miR-338GSP | CATGATCAGCTGGGCCAAGATCAACAAAAT SEQ ID NO: 357 | miR-338RP2 | T+CC+AGCATCAGTGATTT SEQ ID NO: 358 | -0.2768 | 8.5618 | 0.52 | 5.17 |
| miR-339 | miR-339GSP9# | CATGATCAGCTGGGCCAAGATGAGAGCTCCT SEQ ID NO: 359 | miR-339RP2# | T+CC+CTGTCCTCCAGG SEQ ID NO: 360 | -0.303 | 8.4873 | 0.27 | 2.72 |
| miR-340 | miR-340GSP | CATGATCAGCTGGGCCAAGAGGCTATAAAG SEQ ID NO: 361 | miR-340RP | TG+CG+TCTCAGTTAC SEQ ID NO: 362 | -0.2846 | 9.6673 | 0.15 | 1.45 |
| miR-342 | miR-342GSP3 | CATGATCAGCTGGGCCAAGAGAGACGGGTG SEQ ID NO: 363 | miR-342RP | T+CT+CACACAGAAATCG SEQ ID NO: 364 | -0.293 | 8.1553 | 4.69 | 46.85 |
| miR-345 | miR-345GSP | CATGATCAGCTGGGCCAAGAGCCCTGGACT SEQ ID NO: 365 | miR-345RP | T+GC+TGACTCCTAGT SEQ ID NO: 366 | -0.2909 | 8.468 | 0.04 | 0.40 |
| miR-346 | miR-346GSP | CATGATCAGCTGGGCCAAGAGAGGCAGGC SEQ ID NO: 367 | miR-346RP | T+GT+CTGCCCCCATG SEQ ID NO: 368 | -0.2959 | 8.1958 | 0.25 | 2.54 |
| miR-363 | miR-363GSP10# | CATGATCAGCTGGGCCAAGATACAGATGGA SEQ ID NO: 369 | miR-363RP# | AAT+TG+CAC+GGTATCC SEQ ID NO: 370 | -0.2362 | 8.9762 | 0.44 | 4.36 |
| miR-367 | miR-367GSP | CATGATCAGCTGGGCCAAGATCACCATTGC SEQ ID NO: 371 | miR-367RP | AAT+TG+CACTTTAGCAAT SEQ ID NO: 372 | -0.2819 | 8.6711 | 0.00 | 0.03 |
| miR-368 | miR-368GSP | CATGATCAGCTGGGCCAAGAAAACGTGAA SEQ ID NO: 373 | miR-368RP2 | A+CATAGA+GGAAATTCCAC SEQ ID NO: 374 | -0.2953 | 8.0067 | 6.01 | 60.11 |

TABLE 6-continued

PRIMERS TO DETECT HUMAN MICRORNA TARGET TEMPLATES

| Human Target microRNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-370 | miR-370GSP | CATGATCAGCTGGGCCAAGACCAGGTTCCA SEQ ID NO: 375 | miR-370RP | G+CC+TGCTGGGGTGG SEQ ID NO: 376 | −0.2825 | 8.3162 | 1.45 | 14.55 |
| miR-371 | miR-371GSP | CATGATCAGCTGGGCCAAGAACACTCAAAA SEQ ID NO: 377 | miR-371RP | G+TG+CCGCCATCTTT SEQ ID NO: 378 | −0.295 | 7.8812 | 2.51 | 25.12 |
| miR-372 | miR-372GSP | CATGATCAGCTGGGCCAAGAACGCTCAAAT SEQ ID NO: 379 | miR-372RP | A+AA+GTTGCTGCCACA SEQ ID NO: 380 | −0.2984 | 8.9183 | 0.05 | 0.53 |
| miR-373* | miR-373*GSP | CATGATCAGCTGGGCCAAGAGGAAAGCGCC SEQ ID NO: 381 | miR-373*RP | A+CT+CAAAATGGGGG SEQ ID NO: 382 | −0.2705 | 8.4513 | 0.20 | 1.99 |
| miR-373 | miR-373GSP | CATGATCAGCTGGGCCAAGAACACCCCCAAA SEQ ID NO: 383 | miR-373RP2 | GA+AG+TGCTTCGATTTTGG SEQ ID NO: 384 | −0.307 | 7.9056 | 9.13 | 91.32 |
| miR-374 | miR-374GSP | CATGATCAGCTGGGCCAAGACACTTATCA SEQ ID NO: 385 | miR-374RP | TT+AT+AATA+CAACCTGATAAG SEQ ID NO: 386 | −0.2655 | 9.3795 | 9.16 | 91.60 |
| miR-375 | miR-375GSP | CATGATCAGCTGGGCCAAGATCACGCGAGC SEQ ID NO: 387 | miR-375RP | TT+TG+TTCGTTCGGC SEQ ID NO: 388 | −0.3041 | 8.1181 | 0.09 | 0.90 |
| miR-376b | miR-376bGSP8# | CATGATCAGCTGGGCCAAGAAACATGGA SEQ ID NO: 389 | miR-376bRP# | AT+CAT+AGA+GGAAAATCCA SEQ ID NO: 390 | −0.2934 | 9.0188 | 1.07 | 10.74 |
| miR-378 | miR-378GSP | CATGATCAGCTGGGCCAAGAACACAGGACC SEQ ID NO: 391 | miR-378RP | C+TC+CTGACTCCAGG SEQ ID NO: 392 | −0.2899 | 8.1467 | 0.07 | 0.73 |
| miR-379 | miR-379_GSP7# | CATGATCAGCTGGGCCAAGATACGTTC SEQ ID NO: 393 | miR-379RP2# | T+GGT+AGACTATGGAACG SEQ ID NO: 394 | −0.2902 | 8.2149 | 10.89 | 108.86 |
| miR-380-5p | miR-380-5pGSP | CATGATCAGCTGGGCCAAGAGAGCGCATGTTC SEQ ID NO: 395 | miR-380-5pRP | T+GGT+TGACCATAGA SEQ ID NO: 396 | −0.2462 | 9.4324 | 1.30 | 13.04 |
| miR-380-3p | miR-380-3pGSP | CATGATCAGCTGGGCCAAGAAAGATGTGGA SEQ ID NO: 397 | miR-380-3pRP | TA+TG+TAATATGGTCCACA SEQ ID NO: 398 | −0.3037 | 8.0356 | 3.69 | 36.89 |
| miR-381 | miR-381GSP2 | CATGATCAGCTGGGCCAAGAACAGAGAGC SEQ ID NO: 399 | miR-381RP2 | TATA+CAA+GGGCAAGCT SEQ ID NO: 400 | −0.3064 | 8.8704 | 1.72 | 17.16 |
| miR-382 | miR-382GSP | CATGATCAGCTGGGCCAAGACGAATCCACC SEQ ID NO: 401 | miR-382RP | G+AA+GTTGTTCGTGT SEQ ID NO: 402 | −0.2803 | 7.6738 | 0.66 | 6.57 |
| miR-383 | miR-383GSP | CATGATCAGCTGGGCCAAGAAGCCACAATC SEQ ID NO: 403 | miR-383RP2 | A+GATC+AGAAGGTGATTGT SEQ ID NO: 404 | −0.2866 | 8.1463 | 0.54 | 5.45 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| miR-410 | miR-410GSP9# | CATGATCAGCTGGGCCAAGAACAGGCCAT SEQ ID NO: 405 | miR-410RP# | AA+TA+TAA+CA+CAGATGGC SEQ ID NO: 406 | -0.2297 | 8.5166 | 4.27 | 42.71 |
| miR-412 | miR-412GSP10# | CATGATCAGCTGGGCCAAGAACGGCTAGTG SEQ ID NO: 407 | miR-412RP# | A+CTT+CACCTGGTCCACTA SEQ ID NO: 408 | -0.3001 | 7.9099 | 4.24 | 42.37 |
| miR-422a | miR-422aGSP | CATGATCAGCTGGGCCAAGAGGCCTTCTGA SEQ ID NO: 409 | miR-422aRP | C+TG+GACTTAGGGTC SEQ ID NO: 410 | -0.3079 | 9.3108 | 5.95 | 59.54 |
| miR-422b | miR-422bGSP | CATGATCAGCTGGGCCAAGAGGCCTTTCTGA SEQ ID NO: 411 | miR-422bRP | C+TG+GACTTGGAGTC SEQ ID NO: 412 | -0.2993 | 8.9437 | 4.86 | 48.56 |
| miR-423 | miR-423GSP | CATGATCAGCTGGGCCAAGACTGAGGGGCC SEQ ID NO: 413 | miR-423RP | A+GC+TCGGTCTGAGG SEQ ID NO: 414 | -0.3408 | 9.2274 | 6.06 | 60.62 |
| miR-424 | miR-424GSP# | CATGATCAGCTGGGCCAAGATTCAAAACAT SEQ ID NO: 415 | miR-424RP2# | C+AG+CAGCAATTCATGTTTT SEQ ID NO: 416 | -0.3569 | 9.3419 | 10.78 | 107.85 |
| miR-425 | miR-425GSP | CATGATCAGCTGGGCCAAGAGGCGGACACG SEQ ID NO: 417 | miR-425RP | A+TC+GGGAATGTCGT SEQ ID NO: 418 | -0.2932 | 7.9786 | 0.39 | 3.93 |
| miR-429 | miR-429_GSP11# | CATGATCAGCTGGGCCAAGAACGTTTTACC SEQ ID NO: 419 | miR-429RP5# | T+AATAC+TG+TCTGGTAAAA SEQ ID NO: 420 | -0.2458 | 8.2805 | 16.21 | 162.12 |
| miR-431 | miR-431GSP10# | CATGATCAGCTGGGCCAAGATGCATGACGG SEQ ID NO: 421 | miR-431RP# | T+GT+CTTGCAGGCCG SEQ ID NO: 422 | -0.3107 | 7.7127 | 7.00 | 70.05 |
| miR-448 | miR-448GSP | CATGATCAGCTGGGCCAAGAATGGGACATC SEQ ID NO: 423 | miR-448RP | TTG+CATA+TGTAGGATG SEQ ID NO: 424 | -0.3001 | 8.4969 | 0.12 | 1.16 |
| miR-449 | miR-449GSP10# | CATGATCAGCTGGGCCAAGAACCAGCTAAC SEQ ID NO: 425 | miR-449RP2# | T+GG+CAGTGTATTGTTAGC SEQ ID NO: 426 | -0.3225 | 8.4953 | 2.57 | 25.70 |
| miR-450 | miR-450GSP | CATGATCAGCTGGGCCAAGATATTAGGAAC SEQ ID NO: 427 | miR-450RP | TTTT+TG+CGATGTGTT SEQ ID NO: 428 | -0.2906 | 8.1404 | 0.48 | 4.82 |
| miR-451 | miR-451GSP10# | CATGATCAGCTGGGCCAAGAAAACTCAGTA SEQ ID NO: 429 | miR-451RP# | AAA+CCG+TTA+CCATTACTGA SEQ ID NO: 430 | -0.2544 | 8.0291 | 1.73 | 17.35 |
| let7a | let7a-GSP2# | CATGATCAGCTGGGCCAAGAAACTATAC SEQ ID NO: 431 | let7a-RP# | T+GA+GGTAGTAGGTTG SEQ ID NO: 432 | -0.3089 | 9.458 | 0.04 | 0.38 |
| let7b | let7b-GSP2# | CATGATCAGCTGGGCCAAGAACCACAC SEQ ID NO: 433 | let7b-RP# | T+GA+GGTAGTAGGTTG SEQ ID NO: 432 | -0.2978 | 7.9144 | 0.05 | 0.54 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | Background RNA input 5 ug |
|---|---|---|---|---|---|---|---|---|
| let7c | let7c-GSP2# | CATGATCAGCTGGGCCAAGAAACCATAC SEQ ID NO: 434 | let7c-RP# | T+GA+GGTAGTAGGTTG SEQ ID NO: 432 | -0.308 | 7.9854 | 0.01 | 0.14 |
| let7d | let7d-GSP2# | CATGATCAGCTGGGCCAAGAACTATGCA SEQ ID NO: 435 | let7d-RP# | A+GA+GGTAGTAGGTTG SEQ ID NO: 436 | -0.3238 | 8.3359 | 0.06 | 0.57 |
| let7e | let7e-GSP2# | CATGATCAGCTGGGCCAAGAACTATACA SEQ ID NO: 437 | let7e-RP# | T+GA+GGTAGGAGGTTG SEQ ID NO: 438 | -0.3284 | 9.7594 | 0.22 | 2.20 |
| let7f | let7f-GSP2# | CATGATCAGCTGGGCCAAGAAACTATAC SEQ ID NO: 439 | let7f-RP# | T+GA+GGTAGTAGATTG SEQ ID NO: 440 | -0.2901 | 11.107 | 0.32 | 3.18 |
| let7g | let7gGSp2# | CATGATCAGCTGGGCCAAGAACTGTACA SEQ ID NO: 441 | let7g-RP# | T+GA+GGTAGTAGTTTG SEQ ID NO: 442 | -0.3469 | 9.8235 | 0.16 | 1.64 |
| let7i | let7i-GSP2# | CATGATCAGCTGGGCCAAGAACAGCACA SEQ ID NO: 443 | let7i-RP# | T+GA+GGTAGTAGTTTG SEQ ID NO: 444 | -0.321 | 10.82 | 0.20 | 1.99 |
| miR-377 | miR-377GSP | CATGATCAGCTGGGCCAAGAACAAAGTTG SEQ ID NO: 445 | miR-377RP2 | AT+CA+CACAAAGGCAAC SEQ ID NO: 446 | -0.2979 | 10.612 | 13.45 | 134.48 |
| miR-376a | miR-376a_GSP7 | CATGATCAGCTGGGCCAAGAACTGGA SEQ ID NO: 447 | miR-376a_RP5 | AT+CAT+AGA+GGAAAATCC SEQ ID NO: 448 | -0.2938 | 10.045 | 63.00 | 630.00 |
| miR-22 | miR-22GSP | CATGATCAGCTGGGCCAAGAACAGTTCTTC SEQ ID NO: 449 | miR-22RP | A+AG+CTGCCAGTTGA SEQ ID NO: 450 | -0.2862 | 8.883 | 20.46 | 204.58 |
| miR-200c | miR-200cGSP2 | CATGATCAGCTGGGCCAAGAACCATCATTA SEQ ID NO: 451 | miR-200cRP | T+AA+TACTGCCGGGT SEQ ID NO: 452 | -0.3094 | 11.5 | 15.99 | 159.91 |
| miR-24 | miR-24GSP | CATGATCAGCTGGGCCAAGAACTGTTCCTGC SEQ ID NO: 453 | miR-24RP | T+GG+CTCAGTTCAGC SEQ ID NO: 454 | -0.3123 | 8.6824 | 24.34 | 243.38 |
| miR-29cDNA | miR-29cGSP10 | CATGATCAGCTGGGCCAAGAACCGATTTCA SEQ ID NO: 455 | miR-29cRP | T+AG+CACCATTTGAAAT SEQ ID NO: 456 | -0.2975 | 8.8441 | 23.22 | 232.17 |
| miR-18 | miR-18GSP | CATGATCAGCTGGGCCAAGATATCTGCACT SEQ ID NO: 457 | miR-18RP | T+AA+GGTGCATCTAGT SEQ ID NO: 458 | -0.3209 | 9.0999 | 14.90 | 149.01 |
| miR-185 | miR-185GSP | CATGATCAGCTGGGCCAAGAGAACTGCCTT SEQ ID NO: 459 | miR-185RP | T+GG+AGAGAAGGCA SEQ ID NO: 460 | -0.3081 | 8.9289 | 15.73 | 157.32 |

TABLE 6-continued

PRIMERS TO DETECT HUMAN MICRORNA TARGET TEMPLATES

| Human Target micro RNA | Extension Primer Name | Extension Primer Sequence | Reverse Primer Name | Reverse Primer Sequence | Slope | Intercept | Background RNA input 50 ug | 5 ug |
|---|---|---|---|---|---|---|---|---|
| miR-181b | miR-181bGSP8# | CATGATCAGCTGGGCCAAGACCCACCGA SEQ ID NO: 461 | miR-181bRP2# | AA+CATT+CATTGCTGTC SEQ ID NO: 462 | -0.3115 | 10.846 | 15.87 | 158.67 |
| miR-128a | miR-128aGSP | CATGATCAGCTGGGCCAAGAAAAAGAGACC SEQ ID NO: 161 | miR-128anLRP | TCACAGTGAACCGGT SEQ ID NO: 494 | approx. -0.2866 | approx. 8.0867 | approx. 0.16 | approx. 1.60 |
| miR-138 | miR-138GSP2 | CATGATCAGCTGGGCCAAGACGGCCTGAT SEQ ID NO: 187 | miR-138nLRP | AGCTGGTGTTGTGAA SEQ ID NO: 495 | approx. -0.3023 | approx. 9.0814 | approx. 0.22 | approx. 2.19 |
| miR-143 | miR-143GSP8# | CATGATCAGCTGGGCCAAGATGAGCTAC SEQ ID NO: 197 | miR-143LRP | TGAGATGAAGCACTGT SEQ ID NO: 496 | approx. -0.3008 | approx. 9.2675 | approx. 0.37 | approx. 3.71 |
| miR-150 | miR-150GSP3 | CATGATCAGCTGGGCCAAGACACTGGTA SEQ ID NO: 213 | miR-150nLRP | TCTCCCAACCCTTGTA SEQ ID NO: 497 | approx. -0.2943 | approx. 8.3945 | approx. 0.06 | approx. 0.56 |
| miR-181a | miR-181aGSP9# | CATGATCAGCTGGGCCAAGAACTCACCGA SEQ ID NO: 227 | miR-181anLRP | AACATTCAACGCTGT SEQ ID NO: 498 | approx. -0.2919 | approx. 7.968 | approx. 1.70 | approx. 17.05 |
| miR-194 | mir194GSP8# | CATGATCAGCTGGGCCAAGATCCACATG SEQ ID NO: 255 | miR-194nLRP | TGTAACAGCAACTCCA SEQ ID NO: 499 | approx. -0.3078 | approx. 8.8045 | approx. 0.37 | approx. 3.69 | denotes primers for assays that required extensive testing and primer design modification to achieve optimal assay results including high sensitivity and high dynamic range.

Example 4

This Example describes assays and primers designed for quantitative analysis of murine miRNA expression patterns.

Methods: The representative murine microRNA target templates described in TABLE 7 are publically available accessible on the World Wide Web at the Wellcome Trust Sanger Institute website in the "miRBase sequence database" as described in Griffith-Jones et al. (2004), *Nucleic Acids Research* 32:D109-D111 and Griffith-Jones et al. (2006), *Nucleic Acids Research* 34: D140-D144. As indicated below in TABLE 7, the murine microRNA templates are either totally identical to the corresponding human microRNA templates, identical in the overlapping sequence with differing ends, or contain one or more base pair changes as compared to the human microRNA sequence. The murine microRNA templates that are identical or that have identical overlapping sequence to the corresponding human templates can be assayed using the same primer sets designed for the human microRNA templates, as indicated in TABLE 7. For the murine microRNA templates with one or more base pair changes in comparison to the corresponding human templates, primer sets have been designed specifically for detection of the murine microRNA, and these primers are provided in TABLE 7. The extension primer reaction and quantitative PCR reactions for detection of the murine microRNA templates may be carried out as described in EXAMPLE 3.

TABLE 7

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-1 | miR 1GSP10 | CATGATCAGCTGGGCCAAGATACATACTTC SEQ ID NO: 47 | miR-1RP | T+G+GAA+TG+TAAAGAAGT SEQ ID NO: 48 | Identical |
| miR-7 | miR-7GSP10 | CATGATCAGCTGGGCCAAGAAACAAAATC SEQ ID NO: 486 | miR-7_RP6 | T+GGAA+GACTTGTGATTTT SEQ ID NO: 487 | one or more base pairs differ |
| miR-9* | miR-9*GSP | CATGATCAGCTGGGCCAAGAACTTTCGGTT SEQ ID NO: 51 | miR-9*RP | TAAA+GCT+AGATAACCG SEQ ID NO: 52 | Identical over-lapping sequence, ends differ |
| miR-10a | miR-10aGSP | CATGATCAGCTGGGCCAAGACACAAATTCG SEQ ID NO: 53 | miR-10aRP | T+AC+CCTGTAGATCCG SEQ ID NO: 54 | Identical |
| miR-10b | miR-10b_GSP11 | CATGATCAGCTGGGCCAAGAACACAAATTCG SEQ ID NO: 492 | miR-10b_RP2 | C+CC+TGT+AGAACCGAAT SEQ ID NO: 493 | one or more base pairs differ |
| miR-15a | miR-15aGSP | CATGATCAGCTGGGCCAAGACACAAACCAT SEQ ID NO: 57 | miR-15aRP | T+AG+CAGCACATAATG SEQ ID NO: 58 | Identical |
| miR-15b | miR-15bGSP2 | CATGATCAGCTGGGCCAAGATGTAAACCA SEQ ID NO: 59 | miR-15bRP | T+AG+CAGCACATCAT SEQ ID NO: 60 | Identical |
| miR-16 | miR-16GSP2 | CATGATCAGCTGGGCCAAGACGCCAATAT SEQ ID NO: 61 | miR-16RP | T+AG+CAGCACGTAAA SEQ ID NO: 62 | Identical |
| miR-17-3p | miR-17-3pGSP | CATGATCAGCTGGGCCAAGAACAAGTGCCC SEQ ID NO: 463 | miR-17-3pRP | A+CT+GCAGTGAGGGC SEQ ID NO: 464 | one or more base pairs differ |
| miR-17-5p | miR-17-5pGSP2 | CATGATCAGCTGGGCCAAGAACTACCTGC SEQ ID NO: 65 | miR-17-5pRP | C+AA+AGTGCTTACAGTG SEQ ID NO: 66 | Identical |
| miR-19a | miR-19aGSP2 | CATGATCAGCTGGGCCAAGATCAGTTTTG SEQ ID NO: 67 | miR-19aRP | TG+TG+CAAATCTATGC SEQ ID NO: 68 | Identical |
| miR-19b | miR-19bGSP | CATGATCAGCTGGGCCAAGATCAGTTTTGC SEQ ID NO: 69 | miR-19bRP | TG+TG+CAAATCCATG SEQ ID NO: 70 | Identical |
| miR-20 | miR-20GSP3 | CATGATCAGCTGGGCCAAGACTACCTGC SEQ ID NO: 71 | miR-20RP | T+AA+AGTGCTTATAGTGCA SEQ ID NO: 72 | Identical |
| miR-21 | miR-21GSP2 | CATGATCAGCTGGGCCAAGATCAACATCA SEQ ID NO: 73 | miR-21RP | T+AG+CTTATCAGACTGATG SEQ ID NO: 74 | Identical |
| miR-23a | miR-23aGSP | CATGATCAGCTGGGCCAAGAGGAAATCCCT SEQ ID NO: 75 | miR-23aRP | A+TC+ACATTGCCAGG SEQ ID NO: 76 | Identical |
| miR-23b | miR-23bGSP | CATGATCAGCTGGGCCAAGAGGTAATCCCT SEQ ID NO: 77 | miR-23bRP | A+TC+ACATTGCCAGG SEQ ID NO: 78 | Identical |
| miR-24 | miR-24P5 | CATGATCAGCTGGGCCAAGACTGTTCCTGCTG SEQ ID NO: 7 | miR24-1, 2R | TGG+CTCAGTTCAGC SEQ ID NO: 19 | Identical |
| miR-25 | miR-25GSP | CATGATCAGCTGGGCCAAGATCAGACCGAG SEQ ID NO: 79 | miR-25RP | C+AT+TGCACTTGTCTC SEQ ID NO: 80 | Identical |

TABLE 7-continued

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-26a | miR-26aGSP9 | CATGATCAGCTGGGCCAAGAGCCTATCCT SEQ ID NO: 81 | miR-26aRP2 | TT+CA+AGTAATCCAGGAT SEQ ID NO: 82 | Identical |
| miR-26b | miR-26bGSP9 | CATGATCAGCTGGGCCAAGAAACCTATCC SEQ ID NO: 83 | miR-26bRP2 | TT+CA+AGT+AATTCAGGAT SEQ ID NO: 84 | Identical |
| miR-27a | miR-27aGSP | CATGATCAGCTGGGCCAAGAGCGGAACTTA SEQ ID NO: 85 | miR-27aRP | TT+CA+CAGTGGCTAA SEQ ID NO: 86 | Identical |
| miR-27b | miR-27bGSP | CATGATCAGCTGGGCCAAGAGCAGAACTTA SEQ ID NO: 87 | miR-27bRP | TT+CA+CAGTGGCTAA SEQ ID NO: 88 | Identical |
| miR-28 | miR-28GSP | CATGATCAGCTGGGCCAAGACTCAATAGAC SEQ ID NO: 89 | miR-28RP | A+AG+GAGCTCACAGT SEQ ID NO: 90 | Identical |
| miR-29a | miR-29aGSP8 | CATGATCAGCTGGGCCAAGAAACCGATT SEQ ID NO: 91 | miR-29aRP2 | T+AG+CACCATCTGAAAT SEQ ID NO: 92 | Identical |
| miR-29b | miR-29bGSP2 | CATGATCAGCTGGGCCAAGAAACACTGAT SEQ ID NO: 93 | miR-29bRP2 | T+AG+CACCATTTGAAATCAG SEQ ID NO: 94 | Identical |
| miR-30a-5p | miR-30a-5pGSP | CATGATCAGCTGGGCCAAGACTTCCAGTCG SEQ ID NO: 95 | miR-30a-5pRP | T+GT+AAACATCCTCGAC SEQ ID NO: 96 | Identical |
| miR-30b | miR-30bGSP | CATGATCAGCTGGGCCAAGAAGCTGAGTGT SEQ ID NO: 97 | miR-30bRP | TGT+AAA+CATCCTACACT SEQ ID NO: 98 | Identical |
| miR-30c | miR-30cGSP | CATGATCAGCTGGGCCAAGAGCTGAGAGTG SEQ ID NO: 99 | miR-30cRP | TGT+AAA+CATCCTACACT SEQ ID NO: 100 | Identical |
| miR-30d | miR-30dGSP | CATGATCAGCTGGGCCAAGACTTCCAGTCG SEQ ID NO: 101 | miR-30dRP | T+GTAAA+CATCCCCG SEQ ID NO: 102 | Identical |
| miR-30e-3p | miR-30e-3pGSP9 | CATGATCAGCTGGGCCAAGAGCTGTAAAC SEQ ID NO: 103 | miR-30e-3pRP5 | CTTT+CAGT+CGGATGTTT SEQ ID NO: 104 | Identical |
| miR-31 | miR-31GSP | CATGATCAGCTGGGCCAAGACAGCTATGCC SEQ ID NO: 107 | miR-31RP | G+GC+AAGATGCTGGC SEQ ID NO: 108 | Identical overlapping sequence, ends differ |
| miR-32 | miR-32GSP | CATGATCAGCTGGGCCAAGAGCAACTTAGT SEQ ID NO: 109 | miR-32RP | TATTG+CA+CATTACTAAG SEQ ID NO: 110 | Identical |
| miR-33 | miR-33GSP2 | CATGATCAGCTGGGCCAAGACAATGCAAC SEQ ID NO: 111 | miR-33RP | G+TG+CATTGTAGTTGC SEQ ID NO: 112 | Identical |
| miR-34a | miR-34aGSP | CATGATCAGCTGGGCCAAGAAACAACCAGC SEQ ID NO: 113 | miR-34aRP | T+GG+CAGTGTCTTAG SEQ ID NO: 114 | Identical |
| miR-34b | miR-34bGSP | CATGATCAGCTGGGCCAAGACAATCAGCTA SEQ ID NO: 115 | miR-34bRP | TA+GG+CAGTGTAATT SEQ ID NO: 482 | one or more base pairs differ |
| miR-34c | miR-34cGSP | CATGATCAGCTGGGCCAAGAGCAATCAGCT SEQ ID NO: 117 | miR-34cRP | A+GG+CAGTGTAGTTA SEQ ID NO: 118 | Identical |
| miR-92 | miR-92GSP | CATGATCAGCTGGGCCAAGACAGGCCGGGA SEQ ID NO: 119 | miR-92RP | T+AT+TGCACTTGTCCC SEQ ID NO: 120 | Identical |
| miR-93 | miR-93GSP | CATGATCAGCTGGGCCAAGACTACCTGCAC SEQ ID NO: 121 | miR-93RP | AA+AG+TGCTGTTCGT SEQ ID NO: 122 | Identical overlapping sequence, ends differ |
| miR-96 | miR-96GSP | CATGATCAGCTGGGCCAAGAGCAAAAATGT SEQ ID NO: 125 | miR-96RP | T+TT+GGCACTAGCAC SEQ ID NO: 126 | Identical overlapping sequence, ends differ |
| miR-98 | miR-98GSP | CATGATCAGCTGGGCCAAGAAACAATACAA SEQ ID NO: 127 | miR-98RP | TGA+GGT+AGTAAGTTG SEQ ID NO: 128 | Identical |
| miR-99a | miR-99aGSP | CATGATCAGCTGGGCCAAGACACAAGATCG SEQ ID NO: 129 | miR-99aRP | A+AC+CCGTAGATCCG SEQ ID NO: 130 | Identical overlapping sequence, ends differ |

TABLE 7-continued

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-99b | miR-99bGSP | CATGATCAGCTGGGCCAAGACGCAAGGTCG SEQ ID NO: 131 | miR-99bRP | C+AC+CCGTAGAACCG SEQ ID NO: 132 | Identical |
| miR-100 | miR-100GSP | CATGATCAGCTGGGCCAAGACACAAGTTCG SEQ ID NO: 133 | miR-100RP | A+AC+CCGTAGATCCG SEQ ID NO: 134 | Identical |
| miR-101 | miR-101GSP | CATGATCAGCTGGGCCAAGACTTCAGTTAT SEQ ID NO: 135 | miR-101RP | TA+CAG+TACTGTGATAACT SEQ ID NO: 136 | Identical |
| miR-103 | miR-103GSP | CATGATCAGCTGGGCCAAGATCATAGCCCT SEQ ID NO: 137 | miR-103RP | A+GC+AGCATTGTACA SEQ ID NO: 138 | Identical |
| miR-106a | miR-106aGSP | CATGATCAGCTGGGCCAAGATACCTGCAC SEQ ID NO: 472 | miR-106aRP | CAA+AG+TGCTAACAGTG SEQ ID NO: 473 | one or more base pairs differ |
| miR-106b | miR-106bGSP | CATGATCAGCTGGGCCAAGAATCTGCACTG SEQ ID NO: 143 | miR-106bRP | T+AAAG+TGCTGACAGT SEQ ID NO: 144 | Identical |
| miR-107 | miR-107GSP8 | CATGATCAGCTGGGCCAAGATGATAGCC SEQ ID NO: 145 | miR-107RP2 | A+GC+AGCATTGTACAG SEQ ID NO: 146 | Identical |
| miR-122a | miR-122aGSP | CATGATCAGCTGGGCCAAGAACAAACACCA SEQ ID NO: 147 | miR-122aRP | T+GG+AGTGTGACAAT SEQ ID NO: 148 | Identical |
| miR-124a | miR-124aGSP | CATGATCAGCTGGGCCAAGATGGCATTCAC SEQ ID NO: 149 | miR-124aRP | T+TA+AGGCACGCGGT SEQ ID NO: 150 | Identical over-lapping sequence, ends differ |
| miR-125a | miR-125aGSP | CATGATCAGCTGGGCCAAGACACAGGTTAA SEQ ID NO: 151 | miR-125aRP | T+CC+CTGAGACCCTT SEQ ID NO: 152 | Identical |
| miR-125b | miR-125bGSP | CATGATCAGCTGGGCCAAGATCACAAGTTA SEQ ID NO: 153 | miR-125bRP | T+CC+CTGAGACCCTA SEQ ID NO: 154 | Identical |
| miR-126 | miR-126GSP | CATGATCAGCTGGGCCAAGAGCATTATTAC SEQ ID NO: 155 | miR-126RP | T+CG+TACCGTGAGTA SEQ ID NO: 156 | Identical |
| miR-126* | miR-126*GSP3 | CATGATCAGCTGGGCCAAGACGCGTACC SEQ ID NO: 157 | miR-126*RP | C+ATT+ATTA+CTTTTGGTACG SEQ ID NO: 158 | Identical |
| miR-127 | miR-127GSP | CATGATCAGCTGGGCCAAGAAGCCAAGCTC SEQ ID NO: 159 | miR-127RP | T+CG+GATCCGTCTGA SEQ ID NO: 160 | Identical over-lapping sequence, ends differ |
| miR-128a | miR-128aGSP | CATGATCAGCTGGGCCAAGAAAAAGAGACC SEQ ID NO: 161 | miR-128aRP | T+CA+CAGTGAACCGG SEQ ID NO: 162 | Identical |
| miR-128b | miR-128bGSP | CATGATCAGCTGGGCCAAGAGAAAGAGACC SEQ ID NO: 163 | miR-128bRP | T+CA+CAGTGAACCGG SEQ ID NO: 164 | Identical |
| miR-130a | miR-130aGSP | CATGATCAGCTGGGCCAAGAATGCCCTTTT SEQ ID NO: 167 | miR-130aRP | C+AG+TGCAATGTTAAAG SEQ ID NO: 168 | Identical |
| miR-130b | miR-130bGSP | CATGATCAGCTGGGCCAAGAATGCCCTTTC SEQ ID NO: 169 | miR-130bRP | C+AG+TGCAATGATGA SEQ ID NO: 170 | Identical |
| miR-132 | miR-132GSP | CATGATCAGCTGGGCCAAGACGACCATGGC SEQ ID NO: 171 | miR-132RP | T+AA+CAGTCTACAGCC SEQ ID NO: 172 | Identical |
| miR-133a | miR-133aGSP | CATGATCAGCTGGGCCAAGAACAGCTGGTT SEQ ID NO: 173 | miR-133aRP | T+TG+GTCCCCTTCAA SEQ ID NO: 174 | Identical |
| miR-133b | miR-133bGSP | CATGATCAGCTGGGCCAAGATAGCTGGTTG SEQ ID NO: 175 | miR-133bRP | T+TG+GTCCCCTTCAA SEQ ID NO: 176 | Identical |
| miR-134 | miR-134GSP | CATGATCAGCTGGGCCAAGACCCTCTGGTC SEQ ID NO: 177 | miR-134RP | T+GT+GACTGGTTGAC SEQ ID NO: 178 | Identical over-lapping sequence, ends differ |
| miR-135a | miR-135aGSP | CATGATCAGCTGGGCCAAGATCACATAGGA SEQ ID NO: 179 | miR-135aRP | T+AT+GGCTTTTTATTCCT SEQ ID NO: 180 | Identical |

TABLE 7-continued

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-135b | miR-135bGSP | CATGATCAGCTGGGCCAAGACACATAGGAA SEQ ID NO: 181 | miR-135bRP | T+AT+GGCTTTTCATTCC SEQ ID NO: 182 | Identical |
| miR-136 | miR-136GSP | CATGATCAGCTGGGCCAAGATCCATCATCA SEQ ID NO: 183 | miR-136RP | A+CT+CCATTTGTTTTGATG SEQ ID NO: 184 | Identical |
| miR-137 | miR-137GSP | CATGATCAGCTGGGCCAAGACTACGCGTAT SEQ ID NO: 185 | miR-137RP | T+AT+TGCTTAAGAATACGC SEQ ID NO: 186 | Identical overlapping sequence, ends differ |
| miR-138 | miR-138GSP2 | CATGATCAGCTGGGCCAAGACGGCCTGAT SEQ ID NO: 187 | miR-138RP | A+GC+TGGTGTTGTGA SEQ ID NO: 188 | Identical |
| miR-139 | miR-139GSP | CATGATCAGCTGGGCCAAGAAGACACGTGC SEQ ID NO: 189 | miR-139RP | T+CT+ACAGTGCACGT SEQ ID NO: 190 | Identical |
| miR-140 | miR-140GSP | CATGATCAGCTGGGCCAAGACTACCATAGG SEQ ID NO: 191 | miR-140RP | A+GT+GGTTTTACCCT SEQ ID NO: 192 | Identical overlapping sequence, ends differ |
| miR-141 | miR-141GSP9 | CATGATCAGCTGGGCCAAGACCATCTTTA SEQ ID NO: 193 | miR-141RP2 | TAA+CAC+TGTCTGGTAA SEQ ID NO: 194 | Identical |
| miR-142-3p | miR-142-3pGSP3 | CATGATCAGCTGGGCCAAGATCCATAAA SEQ ID NO: 195 | miR-142-3pRP | TGT+AG+TGTTTCCTACT SEQ ID NO: 196 | Identical overlapping sequence, ends differ |
| miR-143 | miR-143GSP8 | CATGATCAGCTGGGCCAAGATGAGCTAC SEQ ID NO: 197 | miR-143RP2 | T+GA+GATGAAGCACTG SEQ ID NO: 198 | Identical |
| miR-144 | miR-144GSP2 | CATGATCAGCTGGGCCAAGACTAGTACAT SEQ ID NO: 199 | miR-144RP | TA+CA+GTAT+AGATGATG SEQ ID NO: 200 | Identical |
| miR-145 | miR-145GSP2 | CATGATCAGCTGGGCCAAGAAAGGGATTC SEQ ID NO: 201 | miR-145RP | G+TC+CAGTTTTCCCA SEQ ID NO: 202 | Identical |
| miR-146 | miR-146GSP3 | CATGATCAGCTGGGCCAAGAAACCCATG SEQ ID NO: 203 | miR-146RP | T+GA+GAACTGAATTCCA SEQ ID NO: 204 | Identical |
| miR-148a | miR-148aGSP2 | CATGATCAGCTGGGCCAAGAACAAAGTTC SEQ ID NO: 207 | miR-148aRP2 | T+CA+GTGCACTACAGAACT SEQ ID NO: 208 | Identical |
| miR-148b | miR-148bGSP2 | CATGATCAGCTGGGCCAAGAACAAAGTTC SEQ ID NO: 209 | miR-148bRP | T+CA+GTGCATCACAG SEQ ID NO: 210 | Identical |
| miR-149 | miR-149GSP2 | CATGATCAGCTGGGCCAAGAGGAGTGAAG SEQ ID NO: 211 | miR-149RP | T+CT+GGCTCCGTGTC SEQ ID NO: 212 | Identical |
| miR-150 | miR-150GSP3 | CATGATCAGCTGGGCCAAGACACTGGTA SEQ ID NO: 213 | miR-150RP | T+CT+CCCAACCCTTG SEQ ID NO: 214 | Identical |
| miR-151 | miR-151GSP2 | CATGATCAGCTGGGCCAAGACCTCAAGGA SEQ ID NO: 215 | miR-151RP | A+CT+AGACTGAGGCTC SEQ ID NO: 477 | one or more base pairs differ |
| miR-152 | miR-152GSP2 | CATGATCAGCTGGGCCAAGACCCAAGTTC SEQ ID NO: 217 | miR-152RP | T+CA+GTGCATGACAG SEQ ID NO: 218 | Identical |
| miR-153 | miR-153GSP2 | CATGATCAGCTGGGCCAAGATCACTTTTG SEQ ID NO: 219 | miR-153RP | TTG+CAT+AGTCACAAAA SEQ ID NO: 220 | Identical overlapping sequence, ends differ |
| miR-154 | miR-154GSP9 | CATGATCAGCTGGGCCAAGACGAAGGCAA SEQ ID NO: 223 | miR-154RP3 | TA+GGTTA+TCCGTGTT SEQ ID NO: 224 | Identical |
| miR-155 | miR-155GSP8 | CATGATCAGCTGGGCCAAGACCCCTATC SEQ ID NO: 225 | miR-155RP2 | TT+AA+TGCTAATTGTGATAGG SEQ ID NO: 489 | one or more base pairs differ |
| miR-181a | miR-181aGSP9 | CATGATCAGCTGGGCCAAGAACTCACCGA SEQ ID NO: 227 | miR-181aRP2 | AA+CATT+CAACGCTGTC SEQ ID NO: 228 | Identical |
| miR-181c | miR-181cGSP9 | CATGATCAGCTGGGCCAAGAACTCACCGA SEQ ID NO: 229 | miR-181cRP2 | AA+CATT+CAACCTGTCG SEQ ID NO: 230 | Identical |

TABLE 7-continued

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-182 | miR-182*GSP | CATGATCAGCTGGGCCAAGATAGTTGGCAA SEQ ID NO: 231 | miR-182*RP | T+GG+TTCTAGACTTGC SEQ ID NO: 232 | Identical |
| miR-183 | miR-183GSP2 | CATGATCAGCTGGGCCAAGACAGTGAATT SEQ ID NO: 235 | miR-183RP | T+AT+GGCACTGGTAG SEQ ID NO: 236 | Identical |
| miR-184 | miR-184GSP2 | CATGATCAGCTGGGCCAAGAACCCTTATC SEQ ID NO: 237 | miR-184RP | T+GG+ACGGAGAACTG SEQ ID NO: 238 | Identical |
| miR-186 | miR-186GSP9 | CATGATCAGCTGGGCCAAGAAAGCCCAAA SEQ ID NO: 239 | miR-186RP3 | CA+AA+GAATT+CTCCTTTTGG SEQ ID NO: 240 | Identical |
| miR-187 | miR-187GSP | CATGATCAGCTGGGCCAAGACGGCTGCAAC SEQ ID NO: 241 | miR-187RP | T+CG+TGTCTTGTGTT SEQ ID NO: 242 | Identical overlapping sequence, ends differ |
| miR-188 | miR-188GSP | CATGATCAGCTGGGCCAAGAACCCTCCACC SEQ ID NO: 243 | miR-188RP | C+AT+CCCTTGCATGG SEQ ID NO: 244 | Identical |
| miR-189 | miR-189GSP2 | CATGATCAGCTGGGCCAAGAACTGATATC SEQ ID NO: 245 | miR-189RP | G+TG+CCTACTGAGCT SEQ ID NO: 246 | Identical |
| miR-190 | miR-190GSP9 | CATGATCAGCTGGGCCAAGAACCTAATAT SEQ ID NO: 247 | miR-190RP4 | T+GA+TA+TGTTTGATATATTAG SEQ ID NO: 248 | Identical |
| miR-191 | miR-191GSP2 | CATGATCAGCTGGGCCAAGAAGCTGCTTT SEQ ID NO: 249 | miR-191RP2 | C+AA+CGGAATCCCAAAAG SEQ ID NO: 250 | Identical |
| miR-192 | miR-192GSP2 | CATGATCAGCTGGGCCAAGAGGCTGTCAA SEQ ID NO: 251 | miR-192RP | C+TGA+CCTATGAATTGAC SEQ ID NO: 252 | Identical overlapping sequence, ends differ |
| miR-193 | miR-193GSP9 | CATGATCAGCTGGGCCAAGACTGGGACTT SEQ ID NO: 253 | miR-193RP2 | AA+CT+GGCCTACAAAG SEQ ID NO: 254 | Identical |
| miR-194 | mir194GSP8 | CATGATCAGCTGGGCCAAGATCCACATG SEQ ID NO: 255 | mir194RP | TG+TAA+CAGCAACTCCA SEQ ID NO: 256 | Identical |
| miR-195 | miR-195GSP9 | CATGATCAGCTGGGCCAAGAGCCAATATT SEQ ID NO: 257 | miR-195RP3 | T+AG+CAG+CACAGAAATA SEQ ID NO: 258 | Identical |
| miR-196a | miR-196aGSP | CATGATCAGCTGGGCCAAGACCAACAACAT SEQ ID NO: 261 | miR-196aRP | TA+GG+TAGTTTCATGTTG SEQ ID NO: 262 | Identical |
| miR-196b | miR-196bGSP | CATGATCAGCTGGGCCAAGACCAACAACAG SEQ ID NO: 259 | miR-196bRP | TA+GGT+AGTTTCCTGT SEQ ID NO: 260 | Identical |
| miR-199a* | miR-199a*GSP2 | CATGATCAGCTGGGCCAAGAAACCAATGT SEQ ID NO: 267 | miR-199a*RP | T+AC+AGTAGTCTGCAC SEQ ID NO: 268 | Identical |
| miR-199a | miR-199aGSP2 | CATGATCAGCTGGGCCAAGAGAACAGGTA SEQ ID NO: 269 | miR-199aRP | C+CC+AGTGTTCAGAC SEQ ID NO: 270 | Identical |
| miR-199b | miR-199bGSP | CATGATCAGCTGGGCCAAGAGAACAGGTAG SEQ ID NO: 475 | miR-199bRP | C+CC+AGTGTTTAGAC SEQ ID NO: 272 | one or more base pairs differ |
| miR-200a | miR-200aGSP2 | CATGATCAGCTGGGCCAAGAACATCGTTA SEQ ID NO: 273 | miR-200aRP | TAA+CAC+TGTCTGGT SEQ ID NO: 274 | Identical |
| miR-200b | miR-200bGSP2 | CATGATCAGCTGGGCCAAGAGTCATCATT SEQ ID NO: 275 | miR-200bRP | TAATA+CTG+CCTGGTAAT SEQ ID NO: 276 | Identical |
| miR-203 | miR-203GSP2 | CATGATCAGCTGGGCCAAGACTAGTGGTC SEQ ID NO: 279 | miR-203RP | G+TG+AAATGTTTAGGACC SEQ ID NO: 280 | Identical overlapping sequence, ends differ |
| miR-204 | miR-204GSP2 | CATGATCAGCTGGGCCAAGAAGGCATAGG SEQ ID NO: 281 | miR-204RP | T+TC+CCTTTGTCATCC SEQ ID NO: 282 | Identical overlapping sequence, ends differ |
| miR-205 | miR-205GSP | CATGATCAGCTGGGCCAAGACAGACTCCGG SEQ ID NO: 283 | miR-205RP | T+CCTT+CATTCCACC SEQ ID NO: 284 | Identical |

TABLE 7-continued

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-206 | mir 206GSP7 | CATGATCAGCTGGGCCAAGACCACACA SEQ ID NO: 285 | miR-206RP | T+G+GAA+TGTAAGGAAGTGT SEQ ID NO: 286 | Identical |
| miR-208 | miR-208_GSP13 | CATGATCAGCTGGGCCAAGAACAAGCTTTTTGC SEQ ID NO: 287 | miR-208_RP4 | ATAA+GA+CG+AGCAAAAAG SEQ ID NO: 288 | Identical |
| miR-210 | miR-210GSP | CATGATCAGCTGGGCCAAGATCAGCCGCTG SEQ ID NO: 289 | miR-210RP | C+TG+TGCGTGTGACA SEQ ID NO: 290 | Identical |
| miR-211 | miR-211GSP2 | CATGATCAGCTGGGCCAAGAAGGCAAAGG SEQ ID NO: 491 | miR-211RP | T+TC+CCTTTGTCATCC SEQ ID NO: 292 | one or more base pairs differ |
| miR-212 | miR-212GSP9 | CATGATCAGCTGGGCCAAGAGGCCGTGAC SEQ ID NO: 293 | miR-212RP2 | T+AA+CAGTCTCCAGTCA SEQ ID NO: 294 | Identical |
| miR-213 | miR-213GSP | CATGATCAGCTGGGCCAAGAGGTACAATCA SEQ ID NO: 295 | miR-213RP | A+CC+ATCGACCGTTG SEQ ID NO: 296 | Identical |
| miR-214 | miR-214GSP | CATGATCAGCTGGGCCAAGACTGCCTGTCT SEQ ID NO: 297 | miR-214RP | A+CA+GCAGGCACAGA SEQ ID NO: 298 | Identical |
| miR-215 | miR-215GSP2 | CATGATCAGCTGGGCCAAGAGTCTGTCAA SEQ ID NO: 299 | miR-215RP | A+TGA+CCTATGATTTGAC SEQ ID NO: 469 | one or more base pairs differ |
| miR-216 | miR-216GSP9 | CATGATCAGCTGGGCCAAGACACAGTTGC SEQ ID NO: 301 | mir216RP | TAA+TCT+CAGCTGGCA SEQ ID NO: 302 | Identical |
| miR-217 | miR-217GSP2 | CATGATCAGCTGGGCCAAGAATCCAGTCA SEQ ID NO: 481 | miR-217RP2 | T+AC+TGCATCAGGAACTGA SEQ ID NO: 304 | one or more base pairs differ |
| miR-218 | miR-218GSP2 | CATGATCAGCTGGGCCAAGAACATGGTTA SEQ ID NO: 305 | miR-218RP | TTG+TGCTT+GATCTAAC SEQ ID NO: 306 | Identical |
| miR-221 | miR-221GSP9 | CATGATCAGCTGGGCCAAGAGAAACCCAG SEQ ID NO: 309 | miR-221RP | A+GC+TACATTGTCTGC SEQ ID NO: 310 | Identical overlapping sequence, ends differ |
| miR-222 | miR-222GSP8 | CATGATCAGCTGGGCCAAGAGAGACCCA SEQ ID NO: 311 | miR-222RP | A+GC+TACATCTGGCT SEQ ID NO: 312 | Identical |
| miR-223 | miR-223GSP | CATGATCAGCTGGGCCAAGAGGGGTATTTG SEQ ID NO: 313 | miR-223RP | TG+TC+AGTTTGTCAAA SEQ ID NO: 314 | Identical |
| miR-224 | miR-224GSP8 | CATGATCAGCTGGGCCAAGATAAACGGA SEQ ID NO: 315 | miR-224RP2 | C+AAG+TCACTAGTGGTT SEQ ID NO: 316 | Identical overlapping sequence, ends differ |
| miR-296 | miR-296GSP9 | CATGATCAGCTGGGCCAAGAACAGGATTG SEQ ID NO: 317 | miR-296RP2 | A+GG+GCCCCCCTCAA SEQ ID NO: 318 | Identical |
| miR-299 | miR-299GSP9 | CATGATCAGCTGGGCCAAGAATGTATGTG SEQ ID NO: 319 | miR-299RP | T+GG+TTTACCGTCCC SEQ ID NO: 320 | Identical |
| miR-301 | miR-301GSP | CATGATCAGCTGGGCCAAGAGCTTTGACAA SEQ ID NO: 321 | miR-301RP | C+AG+TGCAATAGTATTGT SEQ ID NO: 322 | Identical |
| miR-302a | miR-302aGSP | CATGATCAGCTGGGCCAAGATCACCAAAAC SEQ ID NO: 325 | miR-302aRP | T+AAG+TGCTTCCATGT SEQ ID NO: 326 | Identical |
| miR-320 | miR-320_GSP8 | CATGATCAGCTGGGCCAAGATTCGCCCT SEQ ID NO: 337 | miR-320_RP3 | AAAA+GCT+GGGTTGAGAGG SEQ ID NO: 338 | Identical |
| miR-323 | miR-323GSP | CATGATCAGCTGGGCCAAGAAGAGGTCGAC SEQ ID NO: 339 | miR-323RP | G+CA+CATTACACGGT SEQ ID NO: 340 | Identical |
| miR-324-3p | miR-324-3pGSP | CATGATCAGCTGGGCCAAGACCAGCAGCAC SEQ ID NO: 341 | miR-324-3pRP | C+CA+CTGCCCCAGGT SEQ ID NO: 342 | Identical |
| miR-324-5p | miR-324-5pGSP | CATGATCAGCTGGGCCAAGAACACCAATGC SEQ ID NO: 343 | miR-324-5pRP | C+GC+ATCCCCTAGGG SEQ ID NO: 344 | Identical overlapping sequence, ends differ |

TABLE 7-continued

PRIMERS TO DETECT MURINE MICRORNA TARGET TEMPLATES

| Mouse Target micro-RNA: | Extension Primer Name | Extension Primer Sequence | Reverse Primer Name | Reverse Prime Sequence | Mouse microRNA as compared to Human microRNA |
|---|---|---|---|---|---|
| miR-325 | miR-325GSP | CATGATCAGCTGGGCCAAGAACACTTACTG SEQ ID NO: 345 | miR-325RP | C+CT+AGTAGGTGCTC SEQ ID NO: 476 | one or more base pairs differ |
| miR-326 | miR-326GSP | CATGATCAGCTGGGCCAAGACTGGAGGAAG SEQ ID NO: 347 | miR-326RP | C+CT+CTGGGCCCTTC SEQ ID NO: 348 | Identical overlapping sequence, ends differ |
| miR-328 | miR-328GSP | CATGATCAGCTGGGCCAAGAACGGAAGGGC SEQ ID NO: 349 | miR-328RP | C+TG+GCCCTCTCTGC SEQ ID NO: 350 | Identical |
| miR-330 | miR-330GSP | CATGATCAGCTGGGCCAAGATCTCTGCAGG SEQ ID NO: 351 | miR-330RP | G+CA+AAGCACAGGGC SEQ ID NO: 478 | one or more base pairs differ |
| miR-331 | miR-331GSP | CATGATCAGCTGGGCCAAGATTCTAGGATA SEQ ID NO: 353 | miR-331RP | G+CC+CCTGGGCCTAT SEQ ID NO: 354 | Identical |
| miR-337 | miR-337GSP | CATGATCAGCTGGGCCAAGAAAAGGCATCA SEQ ID NO: 355 | miR-337RP | T+TC+AGCTCCTATATG SEQ ID NO: 490 | one or more base pairs differ |
| miR-338 | miR-338GSP | CATGATCAGCTGGGCCAAGATCAACAAAAT SEQ ID NO: 357 | miR-338RP2 | T+CC+AGCATCAGTGATTT SEQ ID NO: 358 | Identical |
| miR-339 | miR-339GSP9 | CATGATCAGCTGGGCCAAGATGAGCTCCT SEQ ID NO: 359 | miR-339RP2 | T+CC+CTGTCCTCCAGG SEQ ID NO: 360 | Identical |
| miR-340 | miR-340GSP | CATGATCAGCTGGGCCAAGAGGCTATAAAG SEQ ID NO: 361 | miR-340RP | TC+CG+TCTCAGTTAC SEQ ID NO: 362 | Identical |
| miR-342 | miR-342GSP3 | CATGATCAGCTGGGCCAAGAGACGGGTG SEQ ID NO: 363 | miR-342RP | T+CT+CACACAGAAATCG SEQ ID NO: 364 | Identical |
| miR-345 | miR-345GSP | CATGATCAGCTGGGCCAAGAGCACTGGACT SEQ ID NO: 484 | miR-345RP | T+GC+TGACCCCTAGT SEQ ID NO: 485 | one or more base pairs differ |
| miR-346 | miR-346GSP | CATGATCAGCTGGGCCAAGAAGAGGCAGGC SEQ ID NO: 367 | miR-346RP | T+GT+CTGCCCGAGTG SEQ ID NO: 488 | one or more base pairs differ |
| miR-363 | miR-363GSP10 | CATGATCAGCTGGGCCAAGATACAGATGGA SEQ ID NO: 369 | miR-363RP | AAT+TG+CAC+GGTATCC SEQ ID NO: 370 | Identical |
| miR-370 | miR-370GSP | CATGATCAGCTGGGCCAAGACCAGGTTCCA SEQ ID NO: 375 | miR-370RP | G+CC+TGCTGGGGTGG SEQ ID NO: 376 | Identical overlapping sequence, ends differ |
| miR-375 | miR-375GSP | CATGATCAGCTGGGCCAAGATCACGCGAGC SEQ ID NO: 387 | miR-375RP | TT+TG+TTCGTTCGGC SEQ ID NO: 388 | Identical |
| miR-376a | miR-376aGSP3 | CATGATCAGCTGGGCCAAGAACGTGGAT SEQ ID NO: 467 | miR-376aRP2 | A+TCGTAGA+GGAAAATCCAC SEQ ID NO: 468 | one or more base pairs differ |
| miR-378 | miR-378GSP | CATGATCAGCTGGGCCAAGAACACAGGACC SEQ ID NO: 391 | miR-378RP | C+TC+CTGACTCCAGG SEQ ID NO: 392 | Identical |
| miR-379 | miR-379_GSP7 | CATGATCAGCTGGGCCAAGATACGTTC SEQ ID NO: 393 | miR-379RP2 | T+GGT+AGACTATGGAACG SEQ ID NO: 394 | Identical overlapping sequence, ends differ |
| miR-380-5p | miR-380-5pGSP | CATGATCAGCTGGGCCAAGAGCGCATGTTC SEQ ID NO: 395 | miR-380-5pRP | T+GGT+TGACCATAGA SEQ ID NO: 396 | Identical |
| miR-380-3p | miR-380-3pGSP | CATGATCAGCTGGGCCAAGAAAGATGTGGA SEQ ID NO: 395 | miR-380-3pRP | TA+TG+TAGTATGGTCCACA SEQ ID NO: 483 | one or more base pairs differ |
| miR-381 | miR-381GSP2 | CATGATCAGCTGGGCCAAGAACAGAGAGC SEQ ID NO: 399 | miR-381RP2 | TATA+CAA+GGGCAAGCT SEQ ID NO: 400 | Identical |
| miR-382 | miR-382GSP | CATGATCAGCTGGGCCAAGACGAATCCACC SEQ ID NO: 401 | miR-382RP | G+AA+GTTGTTCGTGGT SEQ ID NO: 402 | Identical |
| miR-383 | miR-383GSP | CATGATCAGCTGGGCCAAGAAGCCACAGTC SEQ ID NO: 465 | miR-383RP2 | A+GATC+AGAAGGTGACTGT SEQ ID NO: 466 | one or more base pairs differ |

TABLE 7-continued

PRIMERS TO DETECT MURINE MICRORNA TARGET TEMPLATES

| Mouse Target microRNA: | Extension Primer Name | Extension Primer Sequence | Reverse Primer Name | Reverse Prime Sequence | Mouse microRNA as compared to Human microRNA |
|---|---|---|---|---|---|
| miR-384 | miR-384_GSP9 | CATGATCAGCTGGGCCAAGATGTGAACAA SEQ ID NO: 470 | miR-384_RP5 | ATT+CCT+AG+AAATTGTTC SEQ ID NO: 471 | one or more base pairs differ |
| miR-410 | miR-410 GSP9 | CATGATCAGCTGGGCCAAGAACAGGCCAT SEQ ID NO: 405 | miR-410RP | AA+TA+TAA+CA+CAGATGGC SEQ ID NO: 406 | Identical |
| miR-412 | miR-412 GSP10 | CATGATCAGCTGGGCCAAGAACGGCTAGTG SEQ ID NO: 407 | miR-412RP | A+CTT+CACCTGGTCCACTA SEQ ID NO: 408 | Identical |
| miR-424 | miR-424GSP | CATGATCAGCTGGGCCAAGATCCAAAACAT SEQ ID NO: 474 | miR-424RP2 | C+AG+CAGCAATTCATGTTTT SEQ ID NO: 414 | one or more base pairs differ |
| miR-425 | miR-425GSP | CATGATCAGCTGGGCCAAGAGGCGGACACG SEQ ID NO: 417 | miR-425RP | A+TC+GGGAATGTCGT SEQ ID NO: 418 | Identical |
| miR-429 | miR-429_GSP11 | CATGATCAGCTGGGCCAAGAACGGCATTACC SEQ ID NO: 479 | miR-429RP5 | T+AATAC+TG+TCTGGTAATG SEQ ID NO: 480 | one or more base pairs differ |
| miR-431 | miR-431 GSP10 | CATGATCAGCTGGGCCAAGATGCATGACGG SEQ ID NO: 421 | miR-431RP | T+GT+CTTGCAGGCCG SEQ ID NO: 422 | Identical overlapping sequence, ends differ |
| miR-448 | miR-448GSP | CATGATCAGCTGGGCCAAGAATGGGACATC SEQ ID NO: 423 | miR-448RP | TTG+CATA+TGTAGGATG SEQ ID NO: 424 | Identical |
| miR-449 | miR-449GSP10 | CATGATCAGCTGGGCCAAGAACCAGCTAAC SEQ ID NO: 425 | miR-449RP2 | T+GG+CAGTGTATTGTTAGC SEQ ID NO: 426 | Identical |
| miR-450 | miR-450GSP | CATGATCAGCTGGGCCAAGATATTAGGAAC SEQ ID NO: 427 | miR-450RP | TTTT+TG+CGATGTGTT SEQ ID NO: 428 | Identical |
| miR-451 | miR-451 GSP10 | CATGATCAGCTGGGCCAAGAAACTCAGTA SEQ ID NO: 429 | miR-451RP | AAA+CCG+TTA+CCATTACTGA SEQ ID NO: 430 | Identical overlapping sequence, ends differ |
| let7a | let7a-GSP2 | CATGATCAGCTGGGCCAAGAAACTATAC SEQ ID NO: 431 | let7a-RP | T+GA+GGTAGTAGGTTG SEQ ID NO: 432 | Identical overlapping sequence, ends differ |
| let7b | let7b-GSP2 | CATGATCAGCTGGGCCAAGAAACCACAC SEQ ID NO: 433 | let7b-RP | T+GA+GGTAGTAGGTTG SEQ ID NO: 432 | Identical |
| let7c | let7c-GSP2 | CATGATCAGCTGGGCCAAGAAACCATAC SEQ ID NO: 434 | let7c-RP | T+GA+GGTAGTAGGTTG SEQ ID NO: 432 | Identical |
| let7d | let7d-GSP2 | CATGATCAGCTGGGCCAAGAACTATGCA SEQ ID NO: 435 | let7d-RP | A+GA+GGTAGTAGGTTG SEQ ID NO: 436 | Identical |
| let7e | let7e-GSP2 | CATGATCAGCTGGGCCAAGAACTATACA SEQ ID NO: 437 | let7e-RP | T+GA+GGTAGGAGGTTG SEQ ID NO: 438 | Identical |
| let7f | let7f-GSP2 | CATGATCAGCTGGGCCAAGAAACTATAC SEQ ID NO: 439 | let7f-RP | T+GA+GGTAGTAGATTG SEQ ID NO: 440 | Identical overlapping sequence, ends differ |
| let7g | let7g-GSP2 | CATGATCAGCTGGGCCAAGAACTGTACA SEQ ID NO: 441 | let7g-RP | T+GA+GGTAGTAGTTTG SEQ ID NO: 442 | Identical |
| let7i | let7i-GSP2 | CATGATCAGCTGGGCCAAGAACAGCACA SEQ ID NO: 443 | let7i-RP | T+GA+GGTAGTAGTTTG SEQ ID NO: 444 | Identical |

Example 5

This Example describes the detection and analysis of expression profiles for three microRNAs in total RNA isolated from twelve different tissues using methods in accordance with an embodiment of the present invention.

Methods: Quantitative analysis of miR-1, miR-124 and miR-150 microRNA templates was determined using 0.5 μg of First Choice total RNA (Ambion, Inc.) per 10 μl primer extension reaction isolated from the following tissues: brain, heart, intestine, kidney, liver, lung, lymph, ovary, skeletal muscle, spleen, thymus and uterus. The primer extension enzyme and quantitative PCR reactions were carried out as described above in EXAMPLE 3, using the following PCR primers:

miR-1 Template:

```
extension primer:
CATGATCAGCTGGGCCAAGATACATACTTC    (SEQ ID NO: 47)

reverse primer:
T+G+GAA+TG+TAAAGAAGT              (SEQ ID NO: 48)

forward primer:
CATGATCAGCTGGGCCAAGA              (SEQ ID NO: 13)
``` miR-124 Template:

```
extension primer:
CATGATCAGCTGGGCCAAGATGGCATTCAC    (SEQ ID NO: 149)

reverse primer:
T+TA+AGGCACGCGGT                  (SEQ ID NO: 150)

forward primer:
CATGATCAGCTGGGCCAAGA              (SEQ ID NO: 13)
``` miR-150 Template:

```
extension primer:
CATGATCAGCTGGGCCAAGACACTGGTA      (SEQ ID NO: 213)

reverse primer:
T+CT+CCCAACCCTTG                  (SEQ ID NO: 214)

forward primer:
CATGATCAGCTGGGCCAAGA              (SEQ ID NO: 13)
```

Figure 3A:
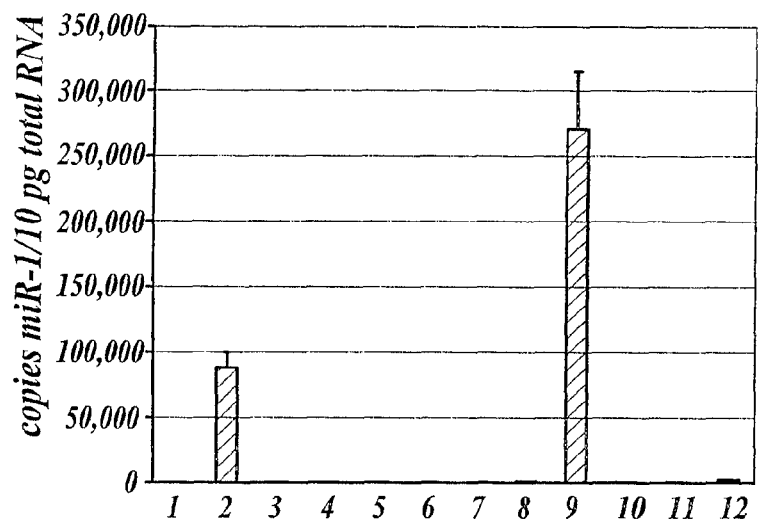
FIG. 3A is a histogram plot showing the expression profile of miR-1 across a panel of total RNA isolated from twelve tissues as described in EXAMPLE 5.
Figure 3B:
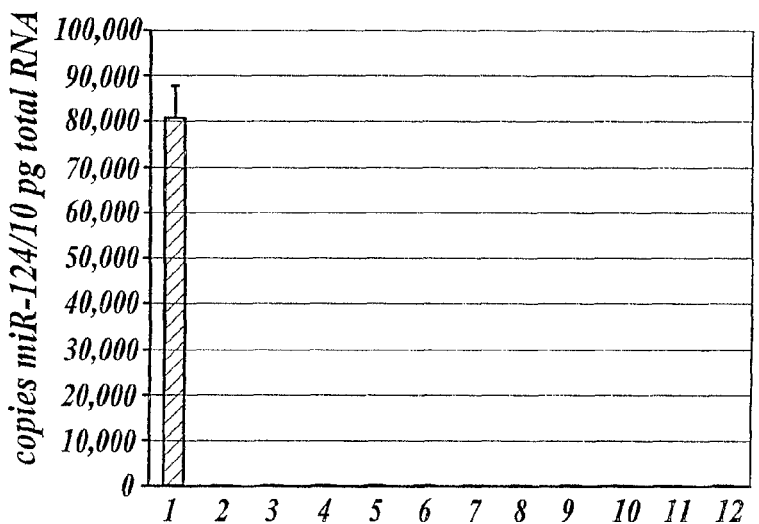
FIG. 3B is a histogram plot showing the expression profile of miR-124 across a panel of total RNA isolated from twelve tissues as described in EXAMPLE 5.
Figure 3C:
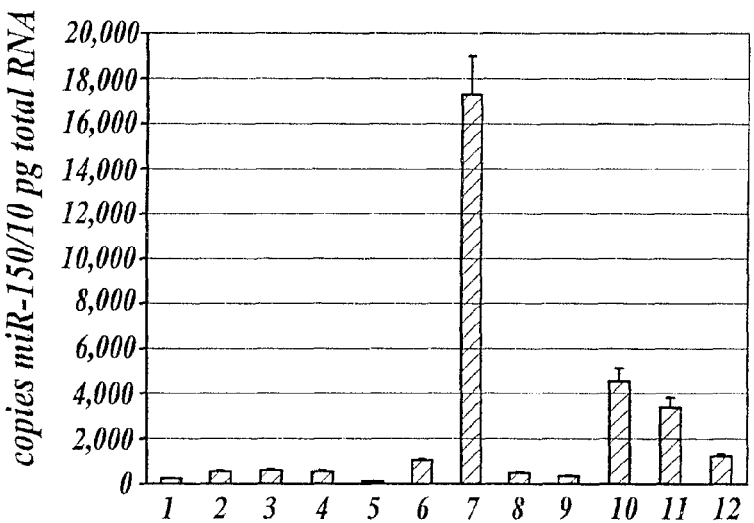
FIG. 3C is a histogram plot showing the expression profile of miR-150 across a panel of total RNA isolated from twelve tissues as described in EXAMPLE 5.

Results. The expression profiles for miR-1, miR-124 and miR-150 are shown in FIGS. 3A, 3B, and 3C, respectively. The data in FIGS. 3A-3C are presented in units of microRNA copies per 10 pg of total RNA (y-axis). These units were chosen since human cell lines typically yield ≦10 pg of total RNA per cell. Hence the data shown are estimates of microRNA copies per cell. The numbers on the x-axis correspond to the following tissues: (1) brain, (2) heart, (3) intestine, (4) kidney, (5) liver, (6) lung, (7) lymph, (8) ovary, (9) skeletal muscle, (10) spleen, (11) thymus and (12) uterus.

Consistent with previous reports, very high levels of striated muscle-specific expression were found for miR-1 (as shown in FIG. 3A), and high levels of brain expression were found for miR-124 (as shown in FIG. 3B) (see Lagos-Quintana et al., *RNA* 9:175-179, 2003). Quantitative analysis reveals that these microRNAs are present at tens to hundreds of thousands of copies per cell. These data are in agreement with quantitative Northern blot estimates of miR-1 and miR-124 levels (see Lim et al., *Nature* 433:769-773, 2005). As shown in FIG. 3C, miR-150 was found to be highly expressed in the immune-related lymph node, thymus and spleen samples which is also consistent with previous findings (see Baskerville et al., *RNA* 11:241-247, 2005).

Example 6

This Example describes the selection and validation of primers for detecting mammalian microRNAs of interest.

Rationale: In order to perform multiple assays to detect a plurality of microRNA targets in a single sample (i.e., multiplex PCR), it is important that the assays work under uniform reverse transcriptase and PCR cycling conditions in a common buffer system with a single universal primer. The following primer design principles and high throughput assays were utilized to identify useful primer sets for desired microRNA targets that work well under the designated reaction conditions.

Primer Design:

As described in Example 2, the sensitivity of an assay to detect mammalian microRNA targets using the methods of the invention may be measured by the cycle threshold (Ct) value. The lower the Ct value (e.g., the fewer number of cycles), the more sensitive is the assay. The Δ Ct value is the difference between the number of cycles (Ct) between template containing samples and no template controls, and serves as a measure of the dynamic range of the assay. Assays with a high dynamic range allow measurements of very low microRNA copy numbers. Accordingly, desirable characteristics of a microRNA detection assay include high sensitivity (low Ct value) (preferably in the range of from about 5 to about 25, such as from about 10 to about 20), broad dynamic range (preferably in the range of from about 10 and 35, such as Δ Ct≧12) between the signal of a sample containing target template and a no template background control sample.

microRNA Target Templates: Representative mammalian microRNA target templates (h=human, r=rat, m=mouse) are provided in Table 9 (SEQ ID NO:966 to SEQ ID NO:1043) which are publically available and accessible on the World Wide Web at the Wellcome Trust Sanger Institute website in the "miRBase sequence database" as described in Griffith-Jones et al. (2004), *Nucleic Acids Research* 32:D109-D111 and Griffith-Jones et al. (2006), *Nucleic Acids Research* 34:D140-D144.

Extension Primers:

Empirical data generated as described in Examples 1-5 suggests that gene specific (GS) extension primers are primarily responsible for the dynamic range of the assays for detecting mammalian microRNA targets using the methods described herein. As described in Example 2, it was determined that the dynamic range (Δ Ct) and specificity of the assays tested decreased for extension primers having gene specific regions below 6 to 7 nucleotides. Therefore, in order to optimize microRNA detection assays, extension primers were designed that have 7 to 10 nucleotide overlap with the microRNA target of interest. Exemplary extension primers for the microRNA targets listed in TABLE 9 are provided in TABLE 8 (SEQ ID NO:500 to SEQ ID NO:965). These exemplary extension primers have a gene specific (GS) region from 7 to 10 nucleotide overlap with the microRNA target of interest.

Reverse Primers:

Unmodified and locked nucleic acid (LNA)-containing reverse primers were designed to quantify the primer-extended, full length cDNA in combination with a generic universal forward primer (SEQ ID NO:13). Based on the data generated as described in Examples 1-5, it was determined that the design of the reverse primers contributes to the efficiency of the PCR reactions, with the observation that the longer the reverse primer, the better the PCR performance. However, it was also observed that the longer the overlap with the extension primer, the higher the background. Therefore, the reverse primers were designed to be as long as possible while minimizing the overlap with the gene specific portion of the extension primer, in order to reduce the non-specific background signal.

In addition, as described in Example 3, LNA base substitutions may be selected to raise the predicted Tm of the primer, with two or three LNA base substitutions typically substituted within the first 8 nucleotides from the 5' end of the reverse primer oligonucleotide. Exemplary reverse primers for the microRNA targets listed in TABLE 9 are provided in TABLE 8. While these exemplary reverse primers contain LNA base substitutions (the "+" symbol preceding a nucleotide designates an LNA substitution), this feature is optional and not required.

Selection and Validation of Primers for a Desired Target:

Assay Oligonucleotide Selection is Made in Two Steps as Follows:

1) Primer designs were determined using the principles described above. Typically, 4 extension primer candidates and 2 reverse primer candidates were designed for each microRNA target of interest. The extension primers in each set overlap the gene specific region by 7, 8, 9 and 10 nucleotides, respectively, at the 3' end. Exemplary primers designed according to these design principles are provided in TABLE 8 for the microRNA targets listed in TABLE 9.

Assay Design to Validate the Candidate Primer Sets (Assay #1)

microRNA Target:

Exemplary target microRNA miR-495 has an RNA target sequence (SEQ ID NO:966) that is conserved across human (h), mouse (m) and rat (r), as indicated by the designation "hmr"-miR-495 in TABLE 9. Therefore, the primer designed for this target sequence would be expected to be useful to detect miR-495 in samples obtained from human, mouse, and rat.

microRNA miR-495 Target RNA Sequence:

```
AAACAAACAUGGUGCACUUCUU 3'    (SEQ ID NO: 966)
```

Extension Primers (4 Candidates)

```
hmr-miR-495GS10:
                                  (SEQ ID NO: 500)
5' CATGATCAGCTGGGCCAAGAAAGAAGTGCA 3' hmr-miR-495GS9:
                                  (SEQ ID NO: 501)
5' CATGATCAGCTGGGCCAAGAAAGAAGTGC 3' hmr-miR-495GS8:
                                  (SEQ ID NO: 502)
5' CATGATCAGCTGGGCCAAGAAAGAAGTG 3' hmr-miR-495GS7:
                                  (SEQ ID NO: 503)
5' CATGATCAGCTGGGCCAAGAAAGAAGT 3'
```

Reverse Primers (2 Candidates)

```
hmr-miR-495RP1:
5' AAA+CAAA+CA+TGGTGCAC 3'    (SEQ ID NO: 504)

hmr-miR-495RP2:
5' AAA+C+AAA+CATGGTGC 3'      (SEQ ID NO: 505)
```

2) The primers designed as described above were tested to find pairs that showed both high sensitivity and high dynamic range in quantitative PCR assays, using the assay methods described in Example 2. The optimal combination of extension primer and reverse primer was determined for the target microRNA by testing all combinations of primers in the presence or absence of DNA template. It is preferable to use DNA rather than RNA template to test the oligo pairs because it is less likely to degrade than RNA. Degraded templates result in misleading assay data. Therefore, HPLC purified DNA template molecules are preferred.

TABLE 8 shows exemplary primer sets for use in detection assays for 78 microRNA targets (shown in TABLE 9). The candidate primers for use in these assays were designed to specifically detect human (h), mouse (m) and rat (r) microRNAs, or microRNAs from one or more species. For example, assays with the "hmr" prefix are designed to detect a perfectly conserved microRNA in all three species, whereas a "mr" prefix means the assay is designed to detect a microRNA conserved between mouse and rat, but not human. Nucleotides preceded by a plus (+) sign may be optionally locked (LNA). TABLE 9 shows the microRNA target sequence for each assay.

TABLE 8

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 1 | hmr-miR-495 | Hmr-miR-495GS10 | CATGATCAGCTGGGCCAA GAAAGAAGTGCA SEQ ID NO: 500 | Hmr-miR-495RP1 | AAA+CAAA+CA+GGTGCAC SEQ ID NO: 504 | Conserved across all three species |
|  |  | Hmr-miR-495GS9 | CATGATCAGCTGGGCCAA GAAAGAAGTGC SEQ ID NO: 501 | Hmr-miR-495RP2 | AAA+C+AAA+CATGGTGC SEQ ID NO: 505 |  |
|  |  | Hmr-miR-495GS8 | CATGATCAGCTGGGCCAA GAAAGAAGTG SEQ ID NO: 502 |  |  |  |
|  |  | Hmr-miR-495GS7 | CATGATCAGCTGGGCCAA GAAAGAAGT SEQ ID NO: 503 |  |  |  |
| 2 | mr-miR-291a-3p | mr-mIR-291a-3pGS10 | CATGATCAGCTGGGCCAA GAGGCACACAAA SEQ ID NO: 506 | mr-mIR-291a-3pRP1 | AA+AG+TGCTTCCACTTTGT SEQ ID NO: 510 | Mouse/rat specific; seed region ortholog to human miR-371/2 |
|  |  | mr-mIR-291a-3pGS9 | CATGATCAGCTGGGCCAA GAGGCACACAA SEQ ID NO: 507 | mr-mIR-291a-3pRP2 | AA+AG+TG+CTTCCACTTT SEQ ID NO: 511 |  |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | mr-mIR-291a-3pGS8 | CATGATCAGCTGGGCCAA GAGGCACACA SEQ ID NO: 508 | | | |
| | | mr-mIR-291a-3pGS7 | CATGATCAGCTGGGCCAA GAGGCACAC SEQ ID NO: 509 | | | |
| 3 | m-miR-291b-3p | m-mIR-291b-3pGS10 | CATGATCAGCTGGGCCAA GAGACAAACAAA SEQ ID NO: 512 | m-mIR-291b-3pRP1 | AA+AG+TG+CAT+CCATTTTGT SEQ ID NO: 516 | Mouse specific; seed region ortholog to human miR-371/2 |
| | | m-mIR-291b-3pGS9 | CATGATCAGCTGGGCCAA GAGACAAACAA SEQ ID NO: 513 | m-mIR-291b-3pRP2 | AA+AG+TG+CATCCATTTT SEQ ID NO: 517 | |
| | | m-mIR-291b-3pGS8 | CATGATCAGCTGGGCCAA GAGACAAACA SEQ ID NO: 514 | | | |
| | | m-mIR-291b-3pGS7 | CATGATCAGCTGGGCCAA GAGACAAAC SEQ ID NO: 515 | | | |
| 4 | h-miR-519a | h-miR-519aGS10 | CATGATCAGCTGGGCCAA GAGTAACACTCT SEQ ID NO: 518 | h-miR-519aRP1 | AA+AG+TG+CATCCTTTTAGAGT SEQ ID NO: 522 | Human specific; implicated in oncogenesis |
| | | h-miR-519aGS9 | CATGATCAGCTGGGCCAA GAGTAACACTC SEQ ID NO: 519 | h-miR-519aRP2 | AA+AG+TG+CATCCTTTTAGA SEQ ID NO: 523 | |
| | | h-miR-519aGS8 | CATGATCAGCTGGGCCAA GAGTAACACT SEQ ID NO: 520 | | | |
| | | h-miR-519aGS7 | CATGATCAGCTGGGCCAA GAGTAACAC SEQ ID NO: 521 | | | |
| 5 | h-miR-519b | h-miR-519bGS10 | CATGATCAGCTGGGCCAA GAAAACCTCTAA SEQ ID NO: 524 | h-miR-519bRP1 | AA+AG+TG+CATCCTTTTAG SEQ ID NO: 528 | Human specific; implicated in oncogenesis |
| | | h-miR-519bGS9 | CATGATCAGCTGGGCCAA GAAAACCTCTA SEQ ID NO: 525 | h-miR-519bRP2 | AA+AG+TG+CATCCTTTT SEQ ID NO: 529 | |
| | | h-miR-519bGS8 | CATGATCAGCTGGGCCAA GAAAACCTCT SEQ ID NO: 526 | | | |
| | | h-miR-519bGS7 | CATGATCAGCTGGGCCAA GAAAACCTC SEQ ID NO: 527 | | | |
| 6 | h-miR-519c | h-miR-519cGS10 | CATGATCAGCTGGGCCAA GAATCCTCTAAA SEQ ID NO: 530 | h-miR-519cRP1 | AA+AG+TG+CATCTTTTAGA SEQ ID NO: 534 | Human specific; implicated in oncogenesis |
| | | h-miR-519cGS9 | CATGATCAGCTGGGCCAA GAATCCTCTAA SEQ ID NO: 531 | h-miR-519cRP2 | AA+AG+TG+CATCTTTTTA SEQ ID NO: 535 | |
| | | h-miR-519cGS8 | CATGATCAGCTGGGCCAA GAATCCTCTA SEQ ID NO: 532 | | | |
| | | h-miR-519cGS7 | CATGATCAGCTGGGCCAA GAATCCTCT SEQ ID NO: 533 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 7 | h-miR-519d | h-miR-519dGS10 | CATGATCAGCTGGGCCAAGAACACTCTAAA SEQ ID NO: 536 | h-miR-519dRP1 | C+AAAG+TGCCTCCCTTTAG SEQ ID NO: 540 | Human specific; implicated in oncogenesis |
| | | h-miR-519dGS9 | CATGATCAGCTGGGCCAAGAACACTCTAA SEQ ID NO: 537 | h-miR-519dRP2 | C+AA+AG+TGCCTCCCTTT SEQ ID NO: 541 | |
| | | h-miR-519dGS8 | CATGATCAGCTGGGCCAAGAACACTCTA SEQ ID NO: 538 | | | |
| | | h-miR-519dGS7 | CATGATCAGCTGGGCCAAGAACACTCT SEQ ID NO: 539 | | | |
| 8 | h-miR-520a | h-miR-520aGS10 | CATGATCAGCTGGGCCAAGAACAGTCCAAA SEQ ID NO: 542 | h-miR-520aRP1 | AA+AG+TGCTTCCCTTTGG SEQ ID NO: 546 | Human specific; implicated in oncogenesis |
| | | h-miR-520aGS9 | CATGATCAGCTGGGCCAAGAACAGTCCAA SEQ ID NO: 543 | h-miR-520aRP2 | AA+AG+T+GCTTCCCTTT SEQ ID NO: 547 | |
| | | h-miR-520aGS8 | CATGATCAGCTGGGCCAAGAACAGTCCA SEQ ID NO: 544 | | | |
| | | h-miR-520aGS7 | CATGATCAGCTGGGCCAAGAACAGTCC SEQ ID NO: 545 | | | |
| 9 | h-miR-520b | h-miR-520bGS10 | CATGATCAGCTGGGCCAAGACCCTCTAAAA SEQ ID NO: 548 | h-miR-520bRP1 | AA+AG+T+GCTTCCTTTTAG SEQ ID NO: 552 | Human specific; implicated in oncogenesis |
| | | h-miR-520bGS9 | CATGATCAGCTGGGCCAAGACCCTCTAAA SEQ ID NO: 549 | h-miR-520bRP2 | AA+AG+TG+CTTCCTTTTA SEQ ID NO: 553 | |
| | | h-miR-520bGS8 | CATGATCAGCTGGGCCAAGACCCTCTAA SEQ ID NO: 550 | | | |
| | | h-miR-520bGS7 | CATGATCAGCTGGGCCAAGACCCTCTA SEQ ID NO: 551 | | | |
| 10 | h-miR-520d | h-miR-520dGS10 | CATGATCAGCTGGGCCAAGAAACCCACCAA SEQ ID NO: 554 | h-miR-520dRP1 | AA+AG+TGCTTCTCTTTGGT SEQ ID NO: 558 | Human specific; implicated in oncogenesis |
| | | h-miR-520dGS9 | CATGATCAGCTGGGCCAAGAAACCCACCA SEQ ID NO: 555 | h-miR-520dRP2 | AA+AG+TG+CTTCTCTTTG SEQ ID NO: 559 | |
| | | h-miR-520dGS8 | CATGATCAGCTGGGCCAAGAAACCCACC SEQ ID NO: 556 | | | |
| | | h-miR-520dGS7 | CATGATCAGCTGGGCCAAGAAACCCAC SEQ ID NO: 557 | | | |
| 11 | h-miR-520e | h-miR-520eGS10 | CATGATCAGCTGGGCCAAGACCCTCAAAAA SEQ ID NO: 560 | h-miR-520eRP1 | AA+AG+TGCTTCCTTTTTG SEQ ID NO: 564 | Human specific; implicated in oncogenesis |
| | | h-miR-520eGS9 | CATGATCAGCTGGGCCAAGACCCTCAAAA SEQ ID NO: 561 | h-miR-520eRP2 | AA+AG+T+GCTTCCTTTTT SEQ ID NO: 565 | |
| | | h-miR- | CATGATCAGCTGGGCCAA | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | 520eGS8 | GACCCTCAAA SEQ ID NO: 562 | | | |
| | | h-miR-520eGS7 | CATGATCAGCTGGGCCAA GACCCTCAA SEQ ID NO: 563 | | | |
| 12 | h-miR-520f | h-miR-520fGS10 | CATGATCAGCTGGGCCAA GAAACCCTCTAA SEQ ID NO: 566 | h-miR-520fRP1 | A+AG+TGCTTCCTTTTAGA SEQ ID NO: 570 | Human specific; implicated in oncogenesis |
| | | h-miR-520fGS9 | CATGATCAGCTGGGCCAA GAAACCCTCTA SEQ ID NO: 567 | h-miR-520fRP2 | A+AG+T+GCTTCCTTTTA SEQ ID NO: 571 | |
| | | h-miR-520fGS8 | CATGATCAGCTGGGCCAA GAAACCCTCT SEQ ID NO: 568 | | | |
| | | h-miR-520fGS7 | CATGATCAGCTGGGCCAA GAAACCCTC SEQ ID NO: 569 | | | |
| 13 | mr-miR-329 | mr-miR-329GS10 | CATGATCAGCTGGGCCAA GAAAAAGGTTA SEQ ID NO: 572 | mr-miR-329RP1 | AA+CA+CACCCAGCTAACC SEQ ID NO: 576 | Specific for mouse/rat ortholog |
| | | mr-miR-329GS9 | CATGATCAGCTGGGCCAA GAAAAAGGTT SEQ ID NO: 573 | mr-miR-329RP2 | AA+CA+CACCCAGCTAA SEQ ID NO: 577 | |
| | | mr-miR-329GS8 | CATGATCAGCTGGGCCAA GAAAAAGGT SEQ ID NO: 574 | | | |
| | | mr-miR-329GS7 | CATGATCAGCTGGGCCAA GAAAAAGG SEQ ID NO: 575 | | | |
| 14 | hmr-miR-181d | hmr-miR-181dGS10 | CATGATCAGCTGGGCCAA GAAACCCACCGA SEQ ID NO: 578 | hmr-miR-181dRP1 | AA+CATT+CATTGTTGTCGGT SEQ ID NO: 582 | Conserved across all three species |
| | | hmr-miR-181dGS9 | CATGATCAGCTGGGCCAA GAAACCCACCG SEQ ID NO: 579 | hmr-miR-181dRP2 | AA+CA+TT+CATTGTTGTCG SEQ ID NO: 583 | |
| | | hmr-miR-181dGS8 | CATGATCAGCTGGGCCAA GAAACCCACC SEQ ID NO: 580 | | | |
| | | hmr-miR-181dGS7 | CATGATCAGCTGGGCCAA GAAACCCAC SEQ ID NO: 581 | | | |
| 15 | has-miR-193b | hmr-miR-193bGS10 | CATGATCAGCTGGGCCAA GAAAAGCGGGAC SEQ ID NO: 584 | hmr-miR-193bRP1 | AA+CT+GGCCCTCAAAGTCCC SEQ ID NO: 588 | Conserved across all three species |
| | | hmr-miR-193bGS9 | CATGATCAGCTGGGCCAA GAAAAGCGGGA SEQ ID NO: 585 | hmr-miR-193bRP2 | AA+CT+GGCCCTCAAAGTC SEQ ID NO: 589 | |
| | | hmr-miR-193bGS8 | CATGATCAGCTGGGCCAA GAAAAGCGGG SEQ ID NO: 586 | | | |
| | | hmr-miR-193bGS7 | CATGATCAGCTGGGCCAA GAAAAGCGG SEQ ID NO: 587 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 16 | h-miR-362 | h-miR-362GS10 | CATGATCAGCTGGGCCAAGAACTCACACCT SEQ ID NO: 590 | h-miR-362RP1 | AAT+CCTT+GGAACCTAGGTG SEQ ID NO: 594 | Assay specific for human ortholog |
| | | h-miR-362GS9 | CATGATCAGCTGGGCCAAGAACTCACACC SEQ ID NO: 591 | h-miR-362RP2 | AA+TC+CTT+GGAACCTAGG SEQ ID NO: 595 | |
| | | h-miR-362GS8 | CATGATCAGCTGGGCCAAGAACTCACAC SEQ ID NO: 592 | | | |
| | | h-miR-362GS7 | CATGATCAGCTGGGCCAAGAACTCACA SEQ ID NO: 593 | | | |
| 17 | mr-miR-362 | mr-mIR-362-3pGS10 | CATGATCAGCTGGGCCAAGATTCACACCTA SEQ ID NO: 596 | mr-mIR-362-3pRP1 | AA+TCCTT+GGAACCTAGGT SEQ ID NO: 600 | Assay specific for rodent ortholog |
| | | mr-miR-362-3pGS9 | CATGATCAGCTGGGCCAAGATTCACACCT SEQ ID NO: 597 | mr-mIR-362-3pRP2 | AA+TC+CTT+GGAACCTAG SEQ ID NO: 601 | |
| | | mr-miR-362-3pGS8 | CATGATCAGCTGGGCCAAGATTCACACC SEQ ID NO: 598 | | | |
| | | mr-miR-362-3pGS7 | CATGATCAGCTGGGCCAAGATTCACAC SEQ ID NO: 599 | | | |
| 18 | h-miR-500 | h-miR-500GS10 | CATGATCAGCTGGGCCAAGACAGAATCCTT SEQ ID NO: 602 | h-miR-500RP1 | A+TG+CACCTGGGCAAGGA SEQ ID NO: 606 | Assay specific for human ortholog |
| | | h-miR-500GS9 | CATGATCAGCTGGGCCAAGACAGAATCCT SEQ ID NO: 603 | h-miR-500RP2 | A+TG+CACCTGGGCAAG SEQ ID NO: 607 | |
| | | h-miR-500GS8 | CATGATCAGCTGGGCCAAGACAGAATCC SEQ ID NO: 604 | | | |
| | | h-miR-500GS7 | CATGATCAGCTGGGCCAAGACAGAATC SEQ ID NO: 605 | | | |
| 19 | mmu-miR-500 | mr-miR-500GS10 | CATGATCAGCTGGGCCAAGACTGAACCCTT SEQ ID NO: 608 | mr-miR-500RP1 | A+TGCA+CCTGGGCAAGGG SEQ ID NO: 612 | Assay specific for rodent ortholog |
| | | mr-miR-500GS9 | CATGATCAGCTGGGCCAAGACTGAACCCT SEQ ID NO: 609 | mr-miR-500RP2 | A+TGCA+CCTGGGCAAG SEQ ID NO: 613 | |
| | | mr-miR-500GS8 | CATGATCAGCTGGGCCAAGACTGAACCC SEQ ID NO: 610 | | | |
| | | mr-miR-500GS7 | CATGATCAGCTGGGCCAAGACTGAACC SEQ ID NO: 611 | | | |
| 20 | h-miR-501 | h-miR-501GS10 | CATGATCAGCTGGGCCAAGATCTCACCCAG SEQ ID NO: 614 | h-miR-501RP1 | AA+T+CCTT+TGTCCCTGGG SEQ ID NO: 618 | Assay specific for human ortholog |
| | | h-miR-501GS9 | CATGATCAGCTGGGCCAAGATCTCACCCA SEQ ID NO: 615 | h-miR-501RP2 | AAT+CCTT+TGTCCCTGG SEQ ID NO: 619 | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | h-miR-501GS8 | CATGATCAGCTGGGCCAA GATCTCACCC SEQ ID NO: 616 | | | |
| | | h-miR-501GS7 | CATGATCAGCTGGGCCAA GATCTCACC SEQ ID NO: 617 | | | |
| 21 | mr-miR-501 | mr-miR-501GS10 | CATGATCAGCTGGGCCAA GATTTCACCCAG SEQ ID NO: 620 | mr-miR-501RP1 | AA+T+CC+TTTGTCCCTGGG SEQ ID NO: 624 | Assay specific for rodent ortholog |
| | | mr-miR-501GS9 | CATGATCAGCTGGGCCAA GATTTCACCCA SEQ ID NO: 621 | mr-miR-501RP2 | AA+T+CC+TTTGTCCCTG SEQ ID NO: 625 | |
| | | mr-miR-501GS8 | CATGATCAGCTGGGCCAA GATTTCACCC SEQ ID NO: 622 | | | |
| | | mr-miR-501GS7 | CATGATCAGCTGGGCCAA GATTTCACC SEQ ID NO: 623 | | | |
| 22 | hmr-miR-487b | hmr-miR-487bGS10 | CATGATCAGCTGGGCCAA GAAGTGGATGAC SEQ ID NO: 626 | hmr-miR-487bRP1 | AAT+CG+TACAGGGTCAT SEQ ID NO: 630 | Conserved across all three species |
| | | hmr-miR-487bGS9 | CATGATCAGCTGGGCCAA GAAGTGGATGA SEQ ID NO: 627 | hmr-miR-487bRP2 | A+AT+CG+TACAGGGTC SEQ ID NO: 631 | |
| | | hmr-miR-487bGS8 | CATGATCAGCTGGGCCAA GAAGTGGATG SEQ ID NO: 628 | | | |
| | | hmr-miR-487bGS7 | CATGATCAGCTGGGCCAA GAAGTGGAT SEQ ID NO: 629 | | | |
| 23 | h-miR-489 | h-miR-489GS10 | CATGATCAGCTGGGCCAA GAGCTGCCGTAT SEQ ID NO: 632 | h-miR-489RP1 | AG+TGA+CATCACATATACG SEQ ID NO: 636 | Assay specific for human ortholog |
| | | h-miR-489GS9 | CATGATCAGCTGGGCCAA GAGCTGCCGTA SEQ ID NO: 633 | h-miR-489RP2 | A+G+TGA+CATCACATATAC SEQ ID NO: 637 | |
| | | h-miR-489GS8 | CATGATCAGCTGGGCCAA GAGCTGCCGT SEQ ID NO: 634 | | | |
| | | h-miR-489GS7 | CATGATCAGCTGGGCCAA GAGCTGCCG SEQ ID NO: 635 | | | |
| 24 | m-miR-489 | m-miR-489GS10 | CATGATCAGCTGGGCCAA GAGCTGCCATAT SEQ ID NO: 638 | m-miR-489RP1 | AATGA+CA+CCACATATATG SEQ ID NO: 642 | Assay specific for mouse ortholog |
| | | m-miR-489GS9 | CATGATCAGCTGGGCCAA GAGCTGCCATA SEQ ID NO: 639 | m-miR-489RP2 | AA+TGA+CA+CCACATAT SEQ ID NO: 643 | |
| | | m-miR-489GS8 | CATGATCAGCTGGGCCAA GAGCTGCCAT SEQ ID NO: 640 | | | |
| | | m-miR-489GS7 | CATGATCAGCTGGGCCAA GAGCTGCCA SEQ ID NO: 641 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 25 | r-miR-489 | r-miR-489GS10 | CATGATCAGCTGGGCCAAGAGCTGCCATAT SEQ ID NO: 644 | r-miR-489RP1 | AA+TGA+CA+TCACATATATG SEQ ID NO: 648 | Assay specific for rat ortholog |
|  |  | r-miR-489GS9 | CATGATCAGCTGGGCCAAGAGCTGCCATA SEQ ID NO: 645 | r-miR-489RP2 | AAT+GA+CA+TCACATATAT SEQ ID NO: 649 |  |
|  |  | r-miR-489GS8 | CATGATCAGCTGGGCCAAGAGCTGCCAT SEQ ID NO: 646 |  |  |  |
|  |  | r-miR-489GS7 | CATGATCAGCTGGGCCAAGAGCTGCCA SEQ ID NO: 647 |  |  |  |
| 26 | hmr-miR-425-5p | hmr-miR-425-5pGS10 | CATGATCAGCTGGGCCAAGATCAACGGGAG SEQ ID NO: 650 | hmr-miR-425-5pRP1 | AA+TGA+CACGATCACTCCC SEQ ID NO: 654 | Conserved across all three species |
|  |  | hmr-miR-425-5pGS9 | CATGATCAGCTGGGCCAAGATCAACGGGA SEQ ID NO: 651 | hmr-miR-425-5pRP2 | AA+T+GA+CACGATCACTC SEQ ID NO: 655 |  |
|  |  | hmr-miR-425-5pGS8 | CATGATCAGCTGGGCCAAGATCAACGGG SEQ ID NO: 652 |  |  |  |
|  |  | hmr-miR-425-5pGS7 | CATGATCAGCTGGGCCAAGATCAACGG SEQ ID NO: 653 |  |  |  |
| 27 | hmr-miR-652 | hmr-miR-652GS10 | CATGATCAGCTGGGCCAAGATGCACAACCC SEQ ID NO: 656 | hmr-miR-652RP1 | AAT+GGCGCCACTAGGGTT SEQ ID NO: 660 | Conserved across all three species |
|  |  | hmr-miR-652GS9 | CATGATCAGCTGGGCCAAGATGCACAACC SEQ ID NO: 657 | hmr-miR-652RP2 | AAT+GG+CGCCACTAGGG SEQ ID NO: 661 |  |
|  |  | hmr-miR-652GS8 | CATGATCAGCTGGGCCAAGATGCACAAC SEQ ID NO: 658 |  |  |  |
|  |  | hmr-miR-652GS7 | CATGATCAGCTGGGCCAAGATGCACAA SEQ ID NO: 659 |  |  |  |
| 28 | hmr-miR-485-5p | hmr-miR-485-5pGS10 | CATGATCAGCTGGGCCAAGAGAATTCATCA SEQ ID NO: 662 | hmr-miR-485-5pRP1 | AGA+GGCTGGCCGTGATG SEQ ID NO: 666 | Conserved across all three species |
|  |  | hmr-miR-485-5pGS9 | CATGATCAGCTGGGCCAAGAGAATTCATC SEQ ID NO: 663 | hmr-miR-485-5pRP2 | AGA+GGCTGGCCGTGA SEQ ID NO: 667 |  |
|  |  | hmr-miR-485-5pGS8 | CATGATCAGCTGGGCCAAGAGAATTCAT SEQ ID NO: 664 |  |  |  |
|  |  | hmr-miR-485-5pGS7 | CATGATCAGCTGGGCCAAGAGAATTCA SEQ ID NO: 665 |  |  |  |
| 29 | has-miR-485-3p | hmr-miR-485-3pGS10 | CATGATCAGCTGGGCCAAGAAGAGAGGAGA SEQ ID NO: 668 | hmr-miR-485-3pRP1 | AG+TCATA+CACGGCTCTCC SEQ ID NO: 672 | Conserved across all three species |
|  |  | hmr-miR-485-3pGS9 | CATGATCAGCTGGGCCAAGAAGAGAGGAG SEQ ID NO: 669 | hmr-miR-485-3pRP2 | AG+TC+ATACACGGCTCT SEQ ID NO: 673 |  |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | hmr-miR-485-3pGS8 | CATGATCAGCTGGGCCAA GAAGAGAGGA SEQ ID NO: 670 | | | |
| | | hmr-miR-485-3pGS7 | CATGATCAGCTGGGCCAA GAAGAGAGG SEQ ID NO: 671 | | | |
| 30 | hmr-miR-369-5p | hmr-miR-369-5pGS10 | CATGATCAGCTGGGCCAA GACGAATATAAC SEQ ID NO: 674 | hmr-miR-369-5pRP1 | A+GA+TC+GACCGTGTTAT SEQ ID NO: 678 | Conserved across all three species |
| | | hmr-miR-369-5pGS9 | CATGATCAGCTGGGCCAA GACGAATATAA SEQ ID NO: 675 | hmr-miR-369-5pRP2 | A+GA+TCGACCGTGTT SEQ ID NO: 679 | |
| | | hmr-miR-369-5pGS8 | CATGATCAGCTGGGCCAA GACGAATATA SEQ ID NO: 676 | | | |
| | | hmr-miR-369-5pGS7 | CATGATCAGCTGGGCCAA GACGAATAT SEQ ID NO: 677 | | | |
| 31 | hmr-miR-671 | hmr-miR-671GS10 | CATGATCAGCTGGGCCAA GACCTCCAGCCC SEQ ID NO: 680 | hmr-miR-671RP1 | A+GGAAGCCCTGGAGGGGCT SEQ ID NO: 684 | Conserved across all three species |
| | | hmr-miR-671GS9 | CATGATCAGCTGGGCCAA GACCTCCAGCC SEQ ID NO: 681 | hmr-miR-671RP2 | A+GGAAGCCCTGGAGGGG SEQ ID NO: 685 | |
| | | hmr-miR-671GS8 | CATGATCAGCTGGGCCAA GACCTCCAGC SEQ ID NO: 682 | | | |
| | | hmr-miR-671GS7 | CATGATCAGCTGGGCCAA GACCTCCAG SEQ ID NO: 683 | | | |
| 32 | h-miR-449b | h-miR-449bGS10 | CATGATCAGCTGGGCCAA GAGCCAGCTAAC SEQ ID NO: 686 | h-miR-449bRP1 | A+GGC+AGTGTATTGTTAG SEQ ID NO: 690 | Assay specific for human ortholog |
| | | h-miR-449bGS9 | CATGATCAGCTGGGCCAA GAGCCAGCTAA SEQ ID NO: 687 | h-miR-449bRP2 | AG+GC+AG+TGTATTGTT SEQ ID NO: 691 | |
| | | h-miR-449bGS8 | CATGATCAGCTGGGCCAA GAGCCAGCTA SEQ ID NO: 688 | | | |
| | | h-miR-449bGS7 | CATGATCAGCTGGGCCAA GAGCCAGCT SEQ ID NO: 689 | | | |
| 33 | mr-miR-449b | mr-miR-449bGS10 | CATGATCAGCTGGGCCAA GACCAGCTAGCA SEQ ID NO: 692 | mr-miR-449bRP1 | A+GGC+AGTGCATTGCTA SEQ ID NO: 696 | Assay specific for rodent ortholog |
| | | mr-miR-449bGS9 | CATGATCAGCTGGGCCAA GACCAGCTAGC SEQ ID NO: 693 | mr-miR-449bRP2 | A+GG+CAGTGCATTGC SEQ ID NO: 697 | |
| | | mr-miR-449bGS8 | CATGATCAGCTGGGCCAA GACCAGCTAG SEQ ID NO: 694 | | | |
| | | mr-miR-449bGS7 | CATGATCAGCTGGGCCAA GACCAGCTA SEQ ID NO: 695 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 34 | m-miR-699 | m-miR-699GS10 | CATGATCAGCTGGGCCAAGACGAGCCAGGT SEQ ID NO: 698 | m-miR-699RP1 | A+GGCAGTGCGACCTG SEQ ID NO: 702 | Mouse specific; ortholog to miR-34c |
| | | m-miR-699GS9 | CATGATCAGCTGGGCCAAGACGAGCCAGG SEQ ID NO: 699 | m-miR-699RP2 | A+GG+CAGTGCGACC SEQ ID NO: 703 | |
| | | m-miR-699GS8 | CATGATCAGCTGGGCCAAGACGAGCCAG SEQ ID NO: 700 | | | |
| | | m-miR-699GS7 | CATGATCAGCTGGGCCAAGACGAGCCA SEQ ID NO: 701 | | | |
| 35 | hmr-miR-409-5p | hmr-miR-409-5pGS10 | CATGATCAGCTGGGCCAAGACAAAGTTGCT SEQ ID NO: 704 | hmr-miR-409-5pRP1 | A+GGT+TACCCGAGCAACT SEQ ID NO: 708 | Conserved across all three species |
| | | hmr-miR-409-5pGS9 | CATGATCAGCTGGGCCAAGACAAAGTTGC SEQ ID NO: 705 | hmr-miR-409-5pRP2 | A+GG+TTACCCGAGCAA SEQ ID NO: 709 | |
| | | hmr-miR-409-5pGS8 | CATGATCAGCTGGGCCAAGACAAAGTTG SEQ ID NO: 706 | | | |
| | | hmr-miR-409-5pGS7 | CATGATCAGCTGGGCCAAGACAAAGTT SEQ ID NO: 707 | | | |
| 36 | hmr-miR-409-3p | hmr-miR-409-3pGS10 | CATGATCAGCTGGGCCAAGAAAGGGGTTCA SEQ ID NO: 710 | hmr-miR-409-3pRP1 | G+AA+TGTTGCTCGGTGAAC SEQ ID NO: 714 | Conserved across all three species |
| | | hmr-miR-409-3pGS9 | CATGATCAGCTGGGCCAAGAAAGGGGTTC SEQ ID NO: 711 | hmr-miR-409-3pRP2 | G+AA+TGTTGCTCGGTGA SEQ ID NO: 715 | |
| | | hmr-miR-409-3pGS8 | CATGATCAGCTGGGCCAAGAAAGGGGTT SEQ ID NO: 712 | | | |
| | | hmr-miR-409-3pGS7 | CATGATCAGCTGGGCCAAGAAAGGGGT SEQ ID NO: 713 | | | |
| 37 | hmr-miR-491 | hmr-miR-491GS10 | CATGATCAGCTGGGCCAAGACCTCATGGAA SEQ ID NO: 716 | hmr-miR-491RP1 | AG+TGG+GGAACCCTTCCA SEQ ID NO: 720 | Conserved across alll three species |
| | | hmr-miR-491GS9 | CATGATCAGCTGGGCCAAGACCTCATGGA SEQ ID NO: 717 | hmr-miR-491RP2 | AG+TG+GGGAACCCTTC SEQ ID NO: 721 | |
| | | hmr-miR-491GS8 | CATGATCAGCTGGGCCAAGACCTCATGG SEQ ID NO: 718 | | | |
| | | hmr-miR-491GS7 | CATGATCAGCTGGGCCAAGACCTCATG SEQ ID NO: 719 | | | |
| 38 | h-miR-384 | h-miR-384GS10 | CATGATCAGCTGGGCCAAGATATGAACAAT SEQ ID NO: 722 | h-miR-384RP1 | A+TT+CCT+AGAAATTGTTC SEQ ID NO: 726 | Assay specific for human ortholog |
| | | h-miR-384GS9 | CATGATCAGCTGGGCCAAGATATGAACAA SEQ ID NO: 723 | h-miR-384RP2 | A+TT+CCT+AG+AAATTGT SEQ ID NO: 727 | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | h-miR-384GS8 | CATGATCAGCTGGGCCAA GATATGAACA SEQ ID NO: 724 | | | |
| | | h-miR-384GS7 | CATGATCAGCTGGGCCAA GATATGAAC SEQ ID NO: 725 | | | |
| 39 | mr-miR-384 | mr-miR-384GS10 | CATGATCAGCTGGGCCAA GATGTGAACAAT SEQ ID NO: 728 | mr-miR-384RP1 | A+TT+CCT+AGAAATTGTT SEQ ID NO: 732 | Assay specific for rodent ortholog |
| | | mr-miR-384GS9 | CATGATCAGCTGGGCCAA GATGTGAACAA SEQ ID NO: 729 | mr-miR-384RP2 | A+TT+CCT+AG+AAATTGTT SEQ ID NO: 733 | |
| | | mr-miR-384GS8 | CATGATCAGCTGGGCCAA GATGTGAACA SEQ ID NO: 730 | | | |
| | | mr-miR-384GS7 | CATGATCAGCTGGGCCAA GATGTGAAC SEQ ID NO: 731 | | | |
| 40 | hmr-miR-20b | hmr-miR-20bGS10 | CATGATCAGCTGGGCCAA GAACCTGCACTA SEQ ID NO: 734 | hmr-miR-20bRP1 | C+AA+AG+TGCTCATAGTGCA SEQ ID NO: 738 | Conserved across all three species |
| | | hmr-miR-20bGS9 | CATGATCAGCTGGGCCAA GAACCTGCACT SEQ ID NO: 735 | hmr-miR-20bRP2 | CAA+AG+TG+CTCATAGTG SEQ ID NO: 739 | |
| | | hmr-miR-20bGS8 | CATGATCAGCTGGGCCAA GAACCTGCAC SEQ ID NO: 736 | | | |
| | | hmr-miR-20bGS7 | CATGATCAGCTGGGCCAA GAACCTGCA SEQ ID NO: 737 | | | |
| 41 | hmr-miR-490 | hmr-miR-490GS10 | CATGATCAGCTGGGCCAA GACAGCATGGAG SEQ ID NO: 740 | hmr-miR-490RP1 | C+AA+CCTGGAGGACTCCA SEQ ID NO: 744 | Conserved across all three species |
| | | hmr-miR-490GS9 | CATGATCAGCTGGGCCAA GACAGCATGGA SEQ ID NO: 741 | hmr-miR-490RP2 | CAA+CCT+GGAGGACTC SEQ ID NO: 745 | |
| | | hmr-miR-490GS8 | CATGATCAGCTGGGCCAA GACAGCATGG SEQ ID NO: 742 | | | |
| | | hmr-miR-490GS7 | CATGATCAGCTGGGCCAA GACAGCATG SEQ ID NO: 743 | | | |
| 42 | hmr-miR-497 | hmr-miR-497GS10 | CATGATCAGCTGGGCCAA GAACAAACCACA SEQ ID NO: 746 | hmr-miR-497RP1 | C+AG+CAGCACACTGTGG SEQ ID NO: 750 | Conserved across all three species |
| | | hmr-miR-497GS9 | CATGATCAGCTGGGCCAA GAACAAACCAC SEQ ID NO: 747 | hmr-miR-497RP2 | C+AG+CAGCACACTGTG SEQ ID NO: 751 | |
| | | hmr-miR-497GS8 | CATGATCAGCTGGGCCAA GAACAAACCA SEQ ID NO: 748 | | | |
| | | hmr-miR-497GS7 | CATGATCAGCTGGGCCAA GAACAAACC SEQ ID NO: 749 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 43 | h-miR-301b | h-miR-301bGS10 | CATGATCAGCTGGGCCAAGATGCTTTGACA SEQ ID NO: 752 | h-miR-301bRP1 | C+AG+TG+CAATGATATTGTCA SEQ ID NO: 756 | Assay specific for human ortholog |
| | | h-miR-301bGS9 | CATGATCAGCTGGGCCAAGATGCTTTGAC SEQ ID NO: 753 | h-miR-301bRP2 | C+AG+TG+CAATGATATTGT SEQ ID NO: 757 | |
| | | h-miR-301bGS8 | CATGATCAGCTGGGCCAAGATGCTTTGA SEQ ID NO: 754 | | | |
| | | h-miR-301bGS7 | CATGATCAGCTGGGCCAAGATGCTTTG SEQ ID NO: 755 | | | |
| 44 | mr-miR-301b | mr-miR-301bGS10 | CATGATCAGCTGGGCCAAGATGCTTTGACA SEQ ID NO: 758 | mr-miR-301bRP1 | C+AG+TG+CAATGGTATTGTCA SEQ ID NO: 762 | Assay specific for rodent ortholog |
| | | mr-miR-301bGS9 | CATGATCAGCTGGGCCAAGATGCTTTGAC SEQ ID NO: 759 | mr-miR-301bRP2 | C+AG+TG+CAATGGTATTGT SEQ ID NO: 763 | |
| | | mr-miR-301bGS8 | CATGATCAGCTGGGCCAAGATGCTTTGA SEQ ID NO: 760 | | | |
| | | mr-miR-301bGS7 | CATGATCAGCTGGGCCAAGATGCTTTG SEQ ID NO: 761 | | | |
| 45 | hmr-miR-721 | hmr-miR-721GS10 | CATGATCAGCTGGGCCAAGATTCCCCCTTT SEQ ID NO: 764 | hmr-miR-721RP1 | C+AG+TG+CAATTAAAAGGG SEQ ID NO: 768 | Conserved across all three species |
| | | hmr-miR-721GS9 | CATGATCAGCTGGGCCAAGATTCCCCCTT SEQ ID NO: 765 | hmr-miR-721RP2 | C+AG+TG+CAATTAAAAG SEQ ID NO: 769 | |
| | | hmr-miR-721GS8 | CATGATCAGCTGGGCCAAGATTCCCCCT SEQ ID NO: 766 | | | |
| | | hmr-miR-721GS7 | CATGATCAGCTGGGCCAAGATTCCCCC SEQ ID NO: 767 | | | |
| 46 | hmr-miR-532 | hmr-miR-532GS10 | CATGATCAGCTGGGCCAAGAACGGTCCTAC SEQ ID NO: 770 | hmr-miR-532RP1 | CA+TG+CCTTGAGTGTAGG SEQ ID NO: 774 | Conserved across all three species |
| | | hmr-miR-532GS9 | CATGATCAGCTGGGCCAAGAACGGTCCTA SEQ ID NO: 771 | hmr-miR-532RP2 | CA+TG+CCTTGAGTGTA SEQ ID NO: 775 | |
| | | hmr-miR-532GS8 | CATGATCAGCTGGGCCAAGAACGGTCCT SEQ ID NO: 772 | | | |
| | | hmr-miR-532GS7 | CATGATCAGCTGGGCCAAGAACGGTCC SEQ ID NO: 773 | | | |
| 47 | h-miR-488 | h-miR-488GS10 | CATGATCAGCTGGGCCAAGATTGAGAGTGC SEQ ID NO: 776 | h-miR-488RP1 | C+CCA+GATAATGGCACT SEQ ID NO: 780 | Assay specific for human ortholog |
| | | h-miR-488GS9 | CATGATCAGCTGGGCCAAGATTGAGAGTG SEQ ID NO: 777 | h-miR-488RP2 | C+CC+A+GATAATGGCA SEQ ID NO: 781 | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | h-miR-488GS8 | CATGATCAGCTGGGCCAA GATTGAGAGT SEQ ID NO: 778 | | | |
| | | h-miR-488GS7 | CATGATCAGCTGGGCCAA GATTGAGAG SEQ ID NO: 779 | | | |
| 48 | mr-miR-488 | mr-miR-488GS10 | CATGATCAGCTGGGCCAA GATTGAGAGTGC SEQ ID NO: 782 | mr-miR-488RP1 | C+CCA+GATAATAGCACT SEQ ID NO: 786 | Assay specific for rodent ortholog |
| | | mr-miR-488GS9 | CATGATCAGCTGGGCCAA GATTGAGAGTG SEQ ID NO: 783 | mr-miR-488RP2 | C+CC+A+GATAATAGCA SEQ ID NO: 787 | |
| | | mr-miR-488GS8 | CATGATCAGCTGGGCCAA GATTGAGAGT SEQ ID NO: 784 | | | |
| | | mr-miR-488GS7 | CATGATCAGCTGGGCCAA GATTGAGAG SEQ ID NO: 785 | | | |
| 49 | hmr-miR-539 | hmr-miR-539GS10 | CATGATCAGCTGGGCCAA GAACACACCAAG SEQ ID NO: 788 | hmr-miR-539RP1 | GG+AG+AAATTATCCTTGGT SEQ ID NO: 792 | Conserved across all three species |
| | | hmr-miR-539GS9 | CATGATCAGCTGGGCCAA GAACACACCAA SEQ ID NO: 789 | hmr-miR-539RP2 | G+GA+G+AAATTATCCTTGG SEQ ID NO: 793 | |
| | | hmr-miR-539GS8 | CATGATCAGCTGGGCCAA GAACACACCA SEQ ID NO: 790 | | | |
| | | hmr-miR-539GS7 | CATGATCAGCTGGGCCAA GAACACACC SEQ ID NO: 791 | | | |
| 50 | h-miR-505 | h-miR-505GS10 | CATGATCAGCTGGGCCAA GAGAGGAAACCA SEQ ID NO: 794 | h-miR-505RP1 | GT+CAA+CACTTGCTGGTT SEQ ID NO: 798 | Assay specific for human ortholog |
| | | h-miR-505GS9 | CATGATCAGCTGGGCCAA GAGAGGAAACC SEQ ID NO: 795 | h-miR-505RP2 | G+T+CAA+CACTTGCTGG SEQ ID NO: 799 | |
| | | h-miR-505GS8 | CATGATCAGCTGGGCCAA GAGAGGAAAC SEQ ID NO: 796 | | | |
| | | h-miR-505GS7 | CATGATCAGCTGGGCCAA GAGAGGAAA SEQ ID NO: 797 | | | |
| 51 | mr-miR-505 | mr-miR-505GS10 | CATGATCAGCTGGGCCAA GAGGAAACCAGC SEQ ID NO: 800 | mr-miR-505RP1 | CG+T+CAA+CA+CTTGCTGGT SEQ ID NO: 804 | Assay specific for rodent ortholog |
| | | mr-miR-505GS9 | CATGATCAGCTGGGCCAA GAGGAAACCAG SEQ ID NO: 801 | mr-miR-505RP2 | CG+T+CAA+CA+CTTGCTG SEQ ID NO: 805 | |
| | | mr-miR-505GS8 | CATGATCAGCTGGGCCAA GAGGAAACCA SEQ ID NO: 802 | | | |
| | | mr-miR-505GS7 | CATGATCAGCTGGGCCAA GAGGAAACC SEQ ID NO: 803 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 52 | h-miR-18b | h-miR-18bGS10 | CATGATCAGCTGGGCCAAGATAACTGCACT SEQ ID NO: 806 | h-miR-18bRP1 | TAA+GG+TGCATCTAGTGC SEQ ID NO: 810 | Assay specific for human ortholog |
|  |  | h-miR-18bGS9 | CATGATCAGCTGGGCCAAGATAACTGCAC SEQ ID NO: 807 | h-miR-18bRP2 | T+AA+GG+TGCATCTAGT SEQ ID NO: 811 |  |
|  |  | h-miR-18bGS8 | CATGATCAGCTGGGCCAAGATAACTGCA SEQ ID NO: 808 |  |  |  |
|  |  | h-miR-18bGS7 | CATGATCAGCTGGGCCAAGATAACTGC SEQ ID NO: 809 |  |  |  |
| 53 | mr-miR-18b | mr-miR-18bGS10 | CATGATCAGCTGGGCCAAGATAACAGCACT SEQ ID NO: 812 | mr-miR-18bRP1 | T+AA+GG+TGCATCTAGTGC SEQ ID NO: 816 | Assay specific for rodent ortholog |
|  |  | mr-miR-18bGS9 | CATGATCAGCTGGGCCAAGATAACAGCAC SEQ ID NO: 813 | mr-miR-18bRP2 | TAA+GG+TG+CATCTAGT SEQ ID NO: 817 |  |
|  |  | mr-miR-18bGS8 | CATGATCAGCTGGGCCAAGATAACAGCA SEQ ID NO: 814 |  |  |  |
|  |  | mr-miR-18bGS7 | CATGATCAGCTGGGCCAAGATAACAGC SEQ ID NO: 815 |  |  |  |
| 54 | hmr-miR-503 | hmr-miR-503GS10 | CATGATCAGCTGGGCCAAGACAGTACTGTT SEQ ID NO: 818 | hmr-miR-503RP1 | T+AGC+AGCGGGAACAGT SEQ ID NO: 822 | Conserved across all three species |
|  |  | hmr-miR-503GS9 | CATGATCAGCTGGGCCAAGACAGTACTGT SEQ ID NO: 819 | hmr-miR-503RP2 | T+AGC+AGCGGGAACA SEQ ID NO: 823 |  |
|  |  | hmr-miR-503GS8 | CATGATCAGCTGGGCCAAGACAGTACTG SEQ ID NO: 820 |  |  |  |
|  |  | hmr-miR-503GS7 | CATGATCAGCTGGGCCAAGACAGTACT SEQ ID NO: 821 |  |  |  |
| 55 | hmr-miR-455 | hmr-miR-455GS10 | CATGATCAGCTGGGCCAAGACGATGTAGTC SEQ ID NO: 824 | hmr-miR-455RP1 | TA+TG+TGCCTTTGGACTA SEQ ID NO: 828 | Conserved across all three species |
|  |  | hmr-miR-455GS9 | CATGATCAGCTGGGCCAAGACGATGTAGT SEQ ID NO: 825 | hmr-miR-455RP2 | TA+TG+TGCCTTTGGAC SEQ ID NO: 829 |  |
|  |  | hmr-miR-455GS8 | CATGATCAGCTGGGCCAAGACGATGTAG SEQ ID NO: 826 |  |  |  |
|  |  | hmr-miR-455GS7 | CATGATCAGCTGGGCCAAGACGATGTA SEQ ID NO: 827 |  |  |  |
| 56 | hmr-miR-92b | hmr-miR-92bGS10 | CATGATCAGCTGGGCCAAGAGAGGCCGGGA SEQ ID NO: 830 | hmr-miR-92bRP1 | TAT+TG+CACTCGTCCCG SEQ ID NO: 834 | Conserved across all three species |
|  |  | hmr-miR-92bGS9 | CATGATCAGCTGGGCCAAGAGAGGCCGGG SEQ ID NO: 831 | hmr-miR-92bRP2 | TAT+TG+CACTCGTCCC SEQ ID NO: 835 |  |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | hmr-miR-92bGS8 | CATGATCAGCTGGGCCAA GAGAGGCCGG SEQ ID NO: 832 | | | |
| | | hmr-miR-92bGS7 | CATGATCAGCTGGGCCAA GAGAGGCCG SEQ ID NO: 833 | | | |
| 57 | h-miR-483 | h-miR-483GS10 | CATGATCAGCTGGGCCAA GAAGAAGACGGG SEQ ID NO: 836 | h-miR-483RP1 | T+CAC+TCCTCTCCTCCCGT SEQ ID NO: 840 | Assay specific for human ortholog |
| | | h-miR-483GS9 | CATGATCAGCTGGGCCAA GAAGAAGACGG SEQ ID NO: 837 | h-miR-483RP2 | T+CAC+TCCTCTCCTCCC SEQ ID NO: 841 | |
| | | h-miR-483GS8 | CATGATCAGCTGGGCCAA GAAGAAGACG SEQ ID NO: 838 | | | |
| | | h-miR-483GS7 | CATGATCAGCTGGGCCAA GAAGAAGAC SEQ ID NO: 839 | | | |
| 58 | mr-miR-483 | mr-miR-483GS10 | CATGATCAGCTGGGCCAA GAACAAGACGGG SEQ ID NO: 842 | mr-miR-483RP1 | TC+ACTCCTCCCCTCCCGT SEQ ID NO: 846 | Assay specific for rodent ortholog |
| | | mr-miR-483GS9 | CATGATCAGCTGGGCCAA GAACAAGACGG SEQ ID NO: 843 | mr-miR-483RP2 | TC+ACTCCTCCCCTCCC SEQ ID NO: 847 | |
| | | mr-miR-483GS8 | CATGATCAGCTGGGCCAA GAACAAGACG SEQ ID NO: 844 | | | |
| | | mr-miR-483GS7 | CATGATCAGCTGGGCCAA GAACAAGAC SEQ ID NO: 845 | | | |
| 59 | hmr-miR-484 | hmr-miR-484GS10 | CATGATCAGCTGGGCCAA GAATCGGGAGGG SEQ ID NO: 848 | hmr-miR-484RP1 | TCA+GGCTCAGTCCCCTC SEQ ID NO: 852 | Conserved across all three species |
| | | hmr-miR-484GS9 | CATGATCAGCTGGGCCAA GAATCGGGAGG SEQ ID NO: 849 | hmr-miR-484RP2 | TC+AGGCTCAGTCCCC SEQ ID NO: 853 | |
| | | hmr-miR-484GS8 | CATGATCAGCTGGGCCAA GAATCGGGAG SEQ ID NO: 850 | | | |
| | | hmr-miR-484GS7 | CATGATCAGCTGGGCCAA GAATCGGGA SEQ ID NO: 851 | | | |
| 60 | mmu-miR-351 | hmr-miR-351GS10 | CATGATCAGCTGGGCCAA GACAGGCTCAAA SEQ ID NO: 854 | hmr-miR-351RP1 | TC+CCTGAGGAGCCCTTTGA SEQ ID NO: 858 | Rodent specific; ortholog to human miR-125 |
| | | hmr-miR-351GS9 | CATGATCAGCTGGGCCAA GACAGGCTCAA SEQ ID NO: 855 | hmr-miR-351RP2 | TC+CCTGAGGAGCCCTTT SEQ ID NO: 859 | |
| | | hmr-miR-351GS8 | CATGATCAGCTGGGCCAA GACAGGCTCA SEQ ID NO: 856 | | | |
| | | hmr-miR-351GS7 | CATGATCAGCTGGGCCAA GACAGGCTC SEQ ID NO: 857 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 61 | hmr-miR-615 | hmr-miR-615GS10 | CATGATCAGCTGGGCCAAGAAGAGGGAGAC SEQ ID NO: 860 | hmr-miR-615RP1 | TC+CGAGCCTGGGTCTC SEQ ID NO: 864 | Conserved across all three species |
| | | hmr-miR-615GS9 | CATGATCAGCTGGGCCAAGAAGAGGGAGA SEQ ID NO: 861 | hmr-miR-615RP2 | TC+CGAGCCTGGGTC SEQ ID NO: 865 | |
| | | hmr-miR-615GS8 | CATGATCAGCTGGGCCAAGAAGAGGGAG SEQ ID NO: 862 | | | |
| | | hmr-miR-615GS7 | CATGATCAGCTGGGCCAAGAAGAGGGA SEQ ID NO: 863 | | | |
| 62 | hmr-miR-486 | hmr-miR-486GS10 | CATGATCAGCTGGGCCAAGACTCGGGGCAG SEQ ID NO: 866 | hmr-miR-486RP1 | T+CC+TGTACTGAGCTGCC SEQ ID NO: 870 | Conserved across all three species |
| | | hmr-miR-486GS9 | CATGATCAGCTGGGCCAAGACTCGGGGCA SEQ ID NO: 867 | hmr-miR-486RP2 | T+CC+TGTACTGAGCTG SEQ ID NO: 871 | |
| | | hmr-miR-486GS8 | CATGATCAGCTGGGCCAAGACTCGGGGC SEQ ID NO: 868 | | | |
| | | hmr-miR-486GS7 | CATGATCAGCTGGGCCAAGACTCGGGG SEQ ID NO: 869 | | | |
| 63 | hmr-miR-494 | hmr-miR-494GS10 | CATGATCAGCTGGGCCAAGAAGGTTTCCCG SEQ ID NO: 872 | hmr-miR-494RP1 | T+GA+AA+CATACACGGGA SEQ ID NO: 876 | Conserved across all three species |
| | | hmr-miR-494GS9 | CATGATCAGCTGGGCCAAGAAGGTTTCCC SEQ ID NO: 873 | hmr-miR-494RP2 | T+GA+AA+CATACACGG SEQ ID NO: 877 | |
| | | hmr-miR-494GS8 | CATGATCAGCTGGGCCAAGAAGGTTTCC SEQ ID NO: 874 | | | |
| | | hmr-miR-494GS7 | CATGATCAGCTGGGCCAAGAAGGTTTC SEQ ID NO: 875 | | | |
| 64 | hmr-miR-493-3p | hmr-miR-493-3pGS10 | CATGATCAGCTGGGCCAAGACTGGCACACA SEQ ID NO: 878 | hmr-miR-493-3pRP1 | T+GAA+GGTCTACTGTG SEQ ID NO: 882 | Conserved across all three species |
| | | hmr-miR-493-3pGS9 | CATGATCAGCTGGGCCAAGACTGGCACAC SEQ ID NO: 879 | hmr-miR-493-3pRP2 | T+GAA+GGTCTACTGT SEQ ID NO: 883 | |
| | | hmr-miR-493-3pGS8 | CATGATCAGCTGGGCCAAGACTGGCACA SEQ ID NO: 880 | | | |
| | | hmr-miR-493-3pGS7 | CATGATCAGCTGGGCCAAGACTGGCAC SEQ ID NO: 881 | | | |
| 65 | hmr-miR-146b | hmr-miR-146bGS10 | CATGATCAGCTGGGCCAAGAAGCCTATGGA SEQ ID NO: 884 | hmr-miR-146bRP1 | T+GA+GAAC+TGAATTCCATA SEQ ID NO: 888 | Conserved across all three species |
| | | hmr-miR-146bGS9 | CATGATCAGCTGGGCCAAGAAGCCTATGG SEQ ID NO: 885 | hmr-miR-146bRP2 | T+GA+GAAC+TGAATTCCA SEQ ID NO: 889 | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| | | hmr-miR-146bGS8 | CATGATCAGCTGGGCCAA GAAGCCTATG SEQ ID NO: 886 | | | |
| | | hmr-miR-146bGS7 | CATGATCAGCTGGGCCAA GAAGCCTAT SEQ ID NO: 887 | | | |
| 66 | r-miR-1 | r-miR-1GS10 | CATGATCAGCTGGGCCAA GATACACACTTC SEQ ID NO: 890 | r-miR-1RP1 | T+G+GAA+TGTAAAGAAGTG SEQ ID NO: 894 | Assay specific for rat ortholog |
| | | r-miR-1GS9 | CATGATCAGCTGGGCCAA GATACACACTT SEQ ID NO: 891 | r-miR-1RP2 | T+G+GAA+TGTAAAGAAG SEQ ID NO: 895 | |
| | | r-miR-1GS8 | CATGATCAGCTGGGCCAA GATACACACT SEQ ID NO: 892 | | | |
| | | r-miR-1GS7 | CATGATCAGCTGGGCCAA GATACACAC SEQ ID NO: 893 | | | |
| 67 | h-miR-675-5p | h-miR-675-5pGS10 | CATGATCAGCTGGGCCAA GACACTGTGGGC SEQ ID NO: 896 | h-miR-675-5pRP1 | T+GGTGCGGAGAGGGCCCA SEQ ID NO: 900 | Assay specific for human ortholog |
| | | h-miR-675-5pGS9 | CATGATCAGCTGGGCCAA GACACTGTGGG SEQ ID NO: 897 | h-miR-675-5pRP2 | T+GGTGCGGAGAGGGC SEQ ID NO: 901 | |
| | | h-miR-675-5pGS8 | CATGATCAGCTGGGCCAA GACACTGTGG SEQ ID NO: 898 | | | |
| | | h-miR-675-5pGS7 | CATGATCAGCTGGGCCAA GACACTGTG SEQ ID NO: 899 | | | |
| 68 | mr-miR-675-5p | mr-miR-675-5pGS10 | CATGATCAGCTGGGCCAA GAACTGTGGGCC SEQ ID NO: 902 | mr-miR-675-5pRP1 | T+GGTGCGGAAAGGGCC SEQ ID NO: 906 | Assay specific for rodent ortholog |
| | | mr-miR-675-5pGS9 | CATGATCAGCTGGGCCAA GAACTGTGGGC SEQ ID NO: 903 | mr-miR-675-5pRP2 | T+GGTGCGGAAAGGG SEQ ID NO: 907 | |
| | | mr-miR-675-5pGS8 | CATGATCAGCTGGGCCAA GAACTGTGGG SEQ ID NO: 904 | | | |
| | | mr-miR-675-5pGS7 | CATGATCAGCTGGGCCAA GAACTGTGG SEQ ID NO: 905 | | | |
| 69 | hmr-miR-668 | hmr-miR-668GS10 | CATGATCAGCTGGGCCAA GAGTAGTGGGCC SEQ ID NO: 908 | hmr-miR-668RP1 | TG+TCACTCGGCTCGGCC SEQ ID NO: 912 | Conserved across all three species |
| | | hmr-miR-668GS9 | CATGATCAGCTGGGCCAA GAGTAGTGGGC SEQ ID NO: 909 | hmr-miR-668RP2 | TG+TCACTCGGCTCGG SEQ ID NO: 913 | |
| | | hmr-miR-668GS8 | CATGATCAGCTGGGCCAA GAGTAGTGGG SEQ ID NO: 910 | | | |
| | | hmr-miR-668GS7 | CATGATCAGCTGGGCCAA GAGTAGTGG SEQ ID NO: 911 | | | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
| 70 | r-miR-346 | r-miR-346GS10 | CATGATCAGCTGGGCCAAGAAGAGGCAGGC SEQ ID NO: 914 | r-miR-346RP1 | TGTC+TGCCTGAGTGCCTG SEQ ID NO: 918 | Assay specific for rat ortholog |
| | | r-miR-346GS9 | CATGATCAGCTGGGCCAAGAAGAGGCAGG SEQ ID NO: 915 | r-miR-346RP2 | TGTC+TGCCTGAGTGCC SEQ ID NO: 919 | |
| | | r-miR-346GS8 | CATGATCAGCTGGGCCAAGAAGAGGCAG SEQ ID NO: 916 | | | |
| | | r-miR-346GS7 | CATGATCAGCTGGGCCAAGAAGAGGCA SEQ ID NO: 917 | | | |
| 71 | hmr-miR-542-3p | hmr-miR-542-3pGS10 | CATGATCAGCTGGGCCAAGATTCAGTTATC SEQ ID NO: 920 | hmr-miR-542-3pRP1 | TG+TGA+CAGATTGATAACT SEQ ID NO: 924 | Conserved across all three species |
| | | hmr-miR-542-3pGS9 | CATGATCAGCTGGGCCAAGATTCAGTTAT SEQ ID NO: 921 | hmr-miR-542-3pRP2 | TG+T+GA+CAGATTGATAA SEQ ID NO: 925 | |
| | | hmr-miR-542-3pGS8 | CATGATCAGCTGGGCCAAGATTCAGTTA SEQ ID NO: 922 | | | |
| | | hmr-miR-542-3pGS7 | CATGATCAGCTGGGCCAAGATTCAGTT SEQ ID NO: 923 | | | |
| 72 | hmr-miR-542-5p | hmr-miR-542-5pGS10 | CATGATCAGCTGGGCCAAGACGTGACATGATG SEQ ID NO: 926 | hmr-miR-542-5pRP1 | CTC+GG+GGATCATCATG SEQ ID NO: 930 | Conserved across all three species |
| | | hmr-miR-542-5pGS9 | CATGATCAGCTGGGCCAAGACGTGACATG SEQ ID NO: 927 | hmr-miR-542-5pRP2 | C+TC+GGGGATCATCAT SEQ ID NO: 931 | |
| | | hmr-miR-542-5pGS8 | CATGATCAGCTGGGCCAAGACGTGACAT SEQ ID NO: 928 | | | |
| | | hmr-miR-542-5pGS7 | CATGATCAGCTGGGCCAAGACGTGACA SEQ ID NO: 929 | | | |
| 73 | hmr-miR-499 | hmr-miR-499GS10 | CATGATCAGCTGGGCCAAGAAAACATCACT SEQ ID NO: 932 | hmr-miR-499RP1 | T+TAA+GA+CTTGCAGTGAT SEQ ID NO: 936 | Conserved across all three species |
| | | hmr-miR-499GS9 | CATGATCAGCTGGGCCAAGAAAACATCAC SEQ ID NO: 933 | hmr-miR-499RP2 | T+TAA+GA+CTTGCAGTG SEQ ID NO: 937 | |
| | | hmr-miR-499GS8 | CATGATCAGCTGGGCCAAGAAAACATCA SEQ ID NO: 934 | | | |
| | | hmr-miR-499GS7 | CATGATCAGCTGGGCCAAGAAAACATC SEQ ID NO: 935 | | | |
| 74 | hmr-miR-758 | hmr-miR-758GS10 | CATGATCAGCTGGGCCAAGAGTTAGTGGAC SEQ ID NO: 938 | hmr-miR-758RP1 | TT+TG+TGACCTGGTCCAC SEQ ID NO: 942 | Conserved across all three species |
| | | hmr-miR-758GS9 | CATGATCAGCTGGGCCAAGAGTTAGTGGA SEQ ID NO: 939 | hmr-miR-758RP2 | TT+TG+T+GACCTGGTCC SEQ ID NO: 943 | |

TABLE 8-continued

EXEMPLARY PRIMER SETS FOR DETECTING MAMMALIAN MICRORNA TARGETS

| Assay Number | Target microRNA | Extension Primer Name | Extension Primer Sequence | Reverse Primer Name | Reverse Primer Sequence | Comments |
|---|---|---|---|---|---|---|
|  |  | hmr-miR-758GS8 | CATGATCAGCTGGGCCAA GAGTTAGTGG SEQ ID NO: 940 |  |  |  |
|  |  | hmr-miR-758GS7 | CATGATCAGCTGGGCCAA GAGTTAGTG SEQ ID NO: 941 |  |  |  |
| 75 | hmr-miR-194 | miR-194GSP10 | CATGATCAGCTGGGCCAA GATCCACATGGA SEQ ID NO: 944 | miR-194RP1 | TG+TAA+CAGCAACTCCA SEQ ID NO: 948 | Conserved across all three species |
|  |  | miR-194GSP9 | CATGATCAGCTGGGCCAA GATCCACATGG SEQ ID NO: 945 | miR-RP2 | TG+TAA+CA+GCAACTCCAT SEQ ID NO: 949 |  |
|  |  | miR-194GSP8 | CATGATCAGCTGGGCCAA GATCCACATG SEQ ID NO: 946 |  |  |  |
|  |  | miR-194GSP7 | CATGATCAGCTGGGCCAA GATCCACAT SEQ ID NO: 947 |  |  |  |
| 76 | hmr-miR-206 | mir-206GSP10 | CATGATCAGCTGGGCCAA GACCACACACTT SEQ ID NO: 950 | mir-206RP1 | T+GGAA+TGTAAGGAAGT SEQ ID NO: 954 | Conserved across all three species |
|  |  | mir-206GSP9 | CATGATCAGCTGGGCCAA GACCACACACT SEQ ID NO: 951 | miR-206RP2 | T+G+AA+TGTAAGGAAGTGT SEQ ID NO: 955 |  |
|  |  | mir-206GSP8 | CATGATCAGCTGGGCCAA GACCACACAC SEQ ID NO: 952 |  |  |  |
|  |  | mir-206GSP7 | CATGATCAGCTGGGCCAA GACCACACA SEQ ID NO: 953 |  |  |  |
| 77 | hmr-miR-1 | miR-1GS10 | CATGATCAGCTGGGCCAA miR-1RP1 GATACATACTTC (SEQ ID NO: 47) | miR-1RP1 | TG+GAA+TG+TAAAGAAGTA (SEQ ID NO: 959) | Conserved across all three species |
|  |  | miR-1GS9 | CATGATCAGCTGGGCCAA miR-1RP2 GATACATACTT (SEQ ID NO: 956) | miR-1RP2 | T+G+GAA+TG+TAAAGAAGT (SEQ ID NO: 48) |  |
|  |  | miR-1GS8 | CATGATCAGCTGGGCCAA GATACATACT (SEQ ID NO: 957) |  |  |  |
|  |  | miR-1GS7 | CATGATCAGCTGGGCCAA GATACATAC (SEQ ID NO: 958) |  |  |  |
| 78 | hmr-miR-9 | miR-9GS10 | CATGATCAGCTGGGCCAA miR-9RP1 GATCATACAGCT (SEQ ID NO: 960) | miR-9RP1 | T+CTTT+GGTTATCTAGCT (SEQ ID NO: 964) | Conserved across all three species |
|  |  | miR-9GS9 | CATGATCAGCTGGGCCAA miR-9RP2 GATCATACAGC (SEQ ID NO: 961) | miR-9RP2 | TC+TTT+GGTT+ATCTAGCTGT A (SEQ ID NO: 965) |  |
|  |  | miR-9GS8 | CATGATCAGCTGGGCCAA GATCATACAG (SEQ ID NO: 962) |  |  |  |
|  |  | miR-9GS7 | CATGATCAGCTGGGCCAA GATCATACA (SEQ ID NO 963) |  |  |  |

TABLE 9

| Assay Number | Target MicroRNA Name | RNA target sequence | SEQ ID NO: |
|---|---|---|---|
| 1. | hmr-miR-495 | AAACAAACAUGGUGCACUUCUU | 966 |
| 2. | mr-miR-291a-3p | AAAGUGCUUCCACUUUGUGUGCC | 967 |
| 3. | m-mIR-291b-3p | AAAGUGCAUCCAUUUUGUUUGUC | 968 |
| 4. | h-miR-519a | AAAGUGCAUCCUUUUAGAGUGUUAC | 969 |
| 5. | h-miR-519b | AAAGUGCAUCCUUUUAGAGGUUU | 970 |
| 6. | h-miR-519c | AAAGUGCAUCUUUUUAGAGGAU | 971 |
| 7. | h-miR-519d | CAAAGUGCCUCCCUUUAGAGUGU | 972 |
| 8. | h-miR-520a | AAAGUGCUUCCCUUUGGACUGU | 973 |
| 9. | h-miR-520b | AAAGUGCUUCCUUUUAGAGGG | 974 |
| 10. | h-miR-520d | AAAGUGCUUCUCUUUGGUGGGUU | 975 |
| 11. | h-miR-520e | AAAGUGCUUCCUUUUUGAGGG | 976 |
| 12. | h-miR-520f | AAGUGCUUCCUUUUAGAGGGUU | 977 |
| 13. | mr-miR-329 | AACACACCCAGCUAACCUUUUU | 978 |
| 14. | hmr-miR-181d | AACAUUCAUUGUUGUCGGUGGGUU | 979 |
| 15. | hmr-miR-193b | AACUGGCCCUCAAAGUCCCGCUUU | 980 |
| 16. | h-miR-362 | AAUCCUUGGAACCUAGGUGUGAGU | 981 |
| 17. | mr-mIR-362-3p | AAUCCUUGGAACCUAGGUGUGAA | 982 |
| 18. | h-miR-500 | AUGCACCUGGGCAAGGAUUCUG | 983 |
| 19. | mr-miR-500 | AUGCACCUGGGCAAGGGUUCAG | 984 |
| 20. | h-miR-501 | AAUCCUUUGUCCCUGGGUGAGA | 985 |
| 21. | mr-miR-501 | AAUCCUUUGUCCCUGGGUGAAA | 986 |
| 22. | hmr-miR-487b | AAUCGUACAGGGUCAUCCACU | 987 |
| 23. | h-miR-489 | AGUGACAUCACAUAUACGGCAGC | 988 |
| 24. | m-miR-489 | AAUGACACCACAUAUAUGGCAGC | 989 |
| 25. | r-miR-489 | AAUGACAUCACAUAUAUGGCAGC | 990 |
| 26. | hmr-miR-425-5p | AAUGACACGAUCACUCCCGUUGA | 991 |
| 27. | hmr-miR-652 | AAUGGCGCCACUAGGGUUGUGCA | 992 |
| 28. | hmr-miR-485-5p | AGAGGCUGGCCGUGAUGAAUUC | 993 |
| 29. | hmr-miR-485-3p | AGUCAUACACGGCUCUCCUCUCU | 994 |
| 30. | hmr-miR-369-5p | AGAUCGACCGUGUUAUAUUCG | 995 |
| 31. | hmr-miR-671 | AGGAAGCCCUGGAGGGGCUGGAGG | 996 |
| 32. | h-miR-449b | AGGCAGUGUAUUGUUAGCUGGC | 997 |
| 33. | mr-miR-449b | AGGCAGUGCAUUGCUAGCUGG | 998 |
| 34. | m-miR-699 | AGGCAGUGCGACCUGGCUCG | 999 |
| 35. | hmr-miR-409-5p | AGGUUACCCGAGCAACUUUGCA | 1000 |
| 36. | hmr-miR-409-3p | GAAUGUUGCUCGGUGAACCCCUU | 1001 |
| 37. | hmr-miR-491 | AGUGGGGAACCCUUCCAUGAGG | 1002 |
| 38. | h-miR-384 | AUUCCUAGAAAUUGUUCAUA | 1003 |
| 39. | mr-miR-384 | AUUCCUAGAAAUUGUUCACA | 1004 |
| 40. | hmr-miR-20b | CAAAGUGCUCAUAGUGCAGGUAG | 1005 |
| 41. | hmr-miR-490 | CAACCUGGAGGACUCCAUGCUG | 1006 |
| 42. | hmr-miR-497 | CAGCAGCACACUGUGGUUUGU | 1007 |
| 43. | h-miR-301b | CAGUGCAAUGAUAUUGUCAAAGCA | 1008 |
| 44. | mr-miR-301b | CAGUGCAAUGGUAUUGUCAAAGCA | 1009 |
| 45. | hmr-miR-721 | CAGUGCAAUUAAAAGGGGGAA | 1010 |
| 46. | hmr-miR-532 | CAUGCCUUGAGUGUAGGACCGU | 1011 |
| 47. | h-miR-488 | CCCAGAUAAUGGCACUCUCAA | 1012 |
| 48. | mr-miR-488 | CCCAGAUAAUAGCACUCUCAA | 1013 |
| 49. | hmr-miR-539 | GGAGAAAUUAUCCUUGGUGUGU | 1014 |
| 50. | h-miR-505 | GUCAACACUUGCUGGUUUCCUC | 1015 |
| 51. | mr-miR-505 | CGUCAACACUUGCUGGUUUUCU | 1016 |
| 52. | h-miR-18b | UAAGGUGCAUCUAGUGCAGUUA | 1017 |
| 53. | mr-miR-18b | UAAGGUGCAUCUAGUGCUGUUA | 1018 |
| 54. | hmr-miR-503 | UAGCAGCGGGAACAGUACUGC | 1019 |
| 55. | hmr-miR-455 | UAUGUGCCUUUGGACUACAUCG | 1020 |
| 56. | hmr-miR-92b | UAUUGCACUCGUCCCGGCCUC | 1021 |
| 57. | h-miR-483 | UCACUCCUCUCCUCCCGUCUUCU | 1022 |
| 58. | mr-miR-483 | UCACUCCUCCCCUCCCGUCUUGU | 1023 |
| 59. | hmr-miR-484 | UCAGGCUCAGUCCCCUCCCGAU | 1024 |
| 60. | hmr-miR-351 | UCCCUGAGGAGCCCUUUGAGCCUG | 1025 |
| 61. | hmr-miR-615 | UCCGAGCCUGGGUCUCCCUCU | 1026 |
| 62. | hmr-miR-486 | UCCUGUACUGAGCUGCCCCGAG | 1027 |
| 63. | hmr-miR-494 | UGAAACAUACACGGGAAACCU | 1028 |
| 64. | hmr-miR-493-3p | UGAAGGUCUACUGUGUGCCAG | 1029 |
| 65. | hmr-miR-146b | UGAGAACUGAAUUCCAUAGGCU | 1030 |
| 66. | r-miR-1 | UGGAAUGUAAAGAAGUGUGUA | 1031 |
| 67. | h-miR-675-5p | UGGUGCGGAGAGGGCCCACAGUG | 1032 |
| 68. | mr-miR-675-5p | UGGUGCGGAAAGGGCCCACAGU | 1033 |
| 69. | hmr-miR-668 | UGUCACUCGGCUCGGCCCACUAC | 1034 |
| 70. | r-miR-346 | UGUCUGCCUGAGUGCCUGCCUCU | 1035 |

TABLE 9-continued

| Assay Number | Target MicroRNA Name | RNA target sequence | SEQ ID NO: |
|---|---|---|---|
| 71. | hmr-miR-542-3p | UGUGACAGAUUGAUAACUGAAA | 1036 |
| 72. | hmr-miR-542-5p | CUCGGGGAUCAUCAUGUCACG | 1037 |
| 73. | hmr-miR-499 | UUAAGACUUGCAGUGAUGUUU | 1038 |
| 74. | hmr-miR-758 | UUUGUGACCUGGUCCACUAACC | 1039 |
| 75. | hmiR-194 | UGUAACAGCAACUCCAUGUGGA | 1040 |
| 76. | hmiR-206 | UGGAAUGUAAGGAAGUGUGUGG | 1041 |
| 77. | hmiR-1 | UGGAAUGUAAAGAAGUAUGUA | 1042 |
| 78. | hmiR-9 | UCUUUGGUUAUCUAGCUGUAUGA | 1043 |

Assay Format:

Several candidate primer sets shown above in TABLE 8 were tested in a high-throughput assay testing format as follows:

Each test assay (e.g., assay #75, #76, #77 and #78 listed in TABLE 8) was run in 4×4 wells of a 96 well plate, with 6 assays per 96 well plate, thereby allowing for rapid determination of the optimal primer pair for each target.

For each assay, each of the 4 candidate extension (GS) primers were tested in a separate row of the 96 well plate.

Each of the 2 reverse primers were tested plus (1 nM DNA) or minus template (10 mM Tris pH 7.6, 0.1 mM EDTA, 100 ng/ul yeast total RNA). Following reverse transcription, one set of duplicate non-template control and template samples was tested against reverse primer 1 (RP1) and the other against reverse primer 2 (RP2).

Reverse Transcriptase Assay Conditions:

6 µl of RT master mix was added to all 96 wells

2 µl of 0.5 µM GS primers was added to four successive wells yeast RNA in TE (10 mM Tris pH 7.6, 0.1 mM EDTA) was added to all odd-numbered wells and pre-diluted DNA templates was added to even-numbered wells Samples were mixed well and the reverse transcriptase step was carried out, followed by dilution with 80 µl TE (10 mM Tris pH 7.6, 0.1 mM EDTA).

2 µl of the reverse transcription mixture was transferred into quadruplicate wells of a 384 well PCR plate preloaded with 8 µl PCR mix per well containing universal primer plus the appropriate reverse primers.

The quantitative PCR reaction results were evaluated on a real-time PCR instrument compatible with 384 well plates.

Ct values for the PCR reactions were determined based on a baseline threshold of 0.01. The sensitivity (Ct value of 1 nM template) and dynamic range (Ct of no-template control minus the Ct of the 1 nM template) were determined for each primer pair in each assay. The results of exemplary assays #75, #76, #77 and #78, listed in TABLE 8, are shown in TABLE 10 below.

TABLE 10

ASSAY RESULTS USING CANDIDATE PRIMER SETS FOR DETECTING MIR-1, MIR-9; MIR-194 AND MIR-206

| microRNA target | Extension primer | Reverse primer | Sensitivity | Dynamic Range | Selected for use in profiling |
|---|---|---|---|---|---|
| miR-9 (SEQ ID NO: 1043) | miR-9GS10 (SEQ ID NO: 960) | miR-9 RP1 (SEQ ID NO: 964) | 13 | 9 | − |
| | miR-9GS9 (SEQ ID NO: 961) | miR-9 RP1 (SEQ ID NO: 964) | 13 | 4 | − |
| | miR-9GS8 (SEQ ID NO: 962) | miR-9 RP1 (SEQ ID NO: 964) | 10 | 0 | − |
| | miR-9GS7 (SEQ ID NO: 963) | miR-9 RP1 (SEQ ID NO: 964) | 16 | 8 | − |
| | miR-9GS10 (SEQ ID NO: 960) | miR-9 RP2 (SEQ ID NO: 965) | 13 | 5 | − |
| | miR-9GS9 (SEQ ID NO: 961) | miR-9 RP2 (SEQ ID NO: 965) | 14 | 4 | − |
| | miR-9GS8 (SEQ ID NO: 962) | miR-9 RP2 (SEQ ID NO: 965) | 10 | 0 | − |
| | miR-9GS7 (SEQ ID NO: 963) | miR-9 RP2 (SEQ ID NO: 965) | 17 | 8 | − |
| miR-194 (SEQ ID NO: 1040) | miR-194GS10 (SEQ ID NO: 944) | miR-194RP1 (SEQ ID NO: 948) | 9 | 6 | − |
| | miR-194GS9 (SEQ ID NO: 945) | miR-194RP1 (SEQ ID NO: 948) | 11 | 5 | − |
| | miR-194GS8 (SEQ ID NO: 946) | miR-194RP1 (SEQ ID NO: 948) | 13 | 17 | + |
| | miR-194GS7 (SEQ ID NO: 947) | miR-194RP1 (SEQ ID NO: 948) | 15 | 17 | − |
| | miR-194GS10 (SEQ ID NO: 944) | miR-194RP2 (SEQ ID NO: 949) | 10 | 6 | − |
| | miR-194GS9 (SEQ ID NO: 945) | miR-194RP2 (SEQ ID NO: 949) | 11 | 6 | − |
| | miR-194GS8 (SEQ ID NO: 946) | miR-194RP2 (SEQ ID NO: 949) | 13 | 16 | − |
| | miR-194GS7 (SEQ ID NO: 947) | miR-194RP2 (SEQ ID NO: 949) | 17 | 16 | − |

TABLE 10-continued

ASSAY RESULTS USING CANDIDATE PRIMER SETS FOR
DETECTING MIR-1, MIR-9; MIR-194 AND MIR-206

| microRNA target | Extension primer | Reverse primer | Sensitivity | Dynamic Range | Selected for use in profiling |
|---|---|---|---|---|---|
| miR-1 (SEQ ID NO: 1042) | miR-1 GS10 (SEQ ID NO: 47) | miR-1 RP1 (SEQ ID NO: 959) | 15 | 15 | − |
| | miR-1 GS9 (SEQ ID NO: 956) | miR-1 RP1 (SEQ ID NO: 959) | 17 | 8 | − |
| | miR-1 GS8 (SEQ ID NO: 957) | miR-1 RP1 (SEQ ID NO: 959) | 19 | 11 | − |
| | miR-1 GS7 (SEQ ID NO: 958) | miR-1 RP1 (SEQ ID NO: 959) | 22 | 11 | − |
| | miR-1 GS10 (SEQ ID NO: 47) | miR-1 RP2 (SEQ ID NO: 48) | 13 | 15 | + |
| | miR-1 GS9 (SEQ ID NO: 956) | miR-1 RP2 (SEQ ID NO: 48) | 15 | 8 | − |
| | miR-1 GS8 (SEQ ID NO: 957) | miR-1 RP2 (SEQ ID NO: 48) | 17 | 11 | − |
| | miR-1 GS7 (SEQ ID NO: 958) | miR-1 RP2 (SEQ ID NO: 48) | 19 | 10 | − |
| miR-206 (SEQ ID NO: 1041) | miR-206 GS10 (SEQ ID NO: 950) | miR-206RP1 (SEQ ID NO: 954) | 15 | 10 | − |
| | miR-206 GS9 (SEQ ID NO: 951) | miR-206RP1 (SEQ ID NO: 954) | 16 | 10 | − |
| | miR-206 GS8 (SEQ ID NO: 952) | miR-206RP1 (SEQ ID NO: 954) | 17 | 14 | − |
| | miR-206 GS7 (SEQ ID NO: 953) | miR-206RP1 (SEQ ID NO: 954) | 20 | 20 | − |
| | miR-206 GS10 (SEQ ID NO: 950) | miR-206RP2 (SEQ ID NO: 955) | 10 | 8 | − |
| | miR-206 GS9 (SEQ ID NO: 951) | miR-206RP2 (SEQ ID NO: 955) | 11 | 9 | − |
| | miR-206 GS8 (SEQ ID NO: 952) | miR-206RP2 (SEQ ID NO: 955) | 11 | 11 | − |
| | miR-206 GS7 (SEQ ID NO: 953) | miR-206RP2 (SEQ ID NO: 955) | 13 | 20 | + |

Optimal primer pairs were identified based on superior sensitivity (e.g., a preferred range between 5 and 25) and dynamic range (e.g., a preferred range between 10 and 35) characteristics. As shown above in TABLE 10, an optimal primer pair was identified for miR-194: GS8 (SEQ ID NO:946) and RP1 (SEQ ID NO:948) with a sensitivity of 13 and a dynamic range of 17. An optimal primer pair was identified for miR-1: GS10 (SEQ ID NO:47) and RP2 (SEQ ID NO:48) with a sensitivity of 13 and a dynamic range of 15. An optimal primer pair was identified for miR-206: GS7 (SEQ ID NO:953) and RP2 (SEQ ID NO:955) with a sensitivity of 13 and a dynamic range of 20. As also shown in TABLE 10, the GS primers control specificity, as shown by the significant increase in dynamic range (driven by a decrease in background) in going from GS9 to GS8 (see, e.g., miR-194).

Candidate primers designed based on the principles described above, such as the additional exemplary primers listed in TABLE 8, or other candidate primers designed using the design principles described herein, may be tested using the screening methods described above. The assays may be further optimized by using HPLC purified templates to avoid problems associated with degraded templates.

It has also been determined that microRNAs that differ from each other in sequence by only 1, 2 or 3 nucleotide changes can be readily distinguished from one another through the use of the primers designed according to the design principles and methods described herein.

While the preferred embodiment of the invention has been illustrated and described, it will be appreciated that various changes can be made therein without departing from the spirit and scope of the invention.

The invention claimed is:

1. A kit for detecting at least one mammalian microRNA, comprising at least one oligonucleotide primer selected from the group consisting of SEQ ID NO:2.

2. The kit according to claim 1, comprising at least one or more oligonucleotide primers selected from the group consisting of SEQ ID NOS:47.

3. An oligonucleotide primer for detecting a human microRNA selected from the group consisting of SEQ ID NO:2.

4. An oligonucleotide primer according to claim 3, wherein the primer is selected from the group consisting of SEQ ID NO:47.

5. A kit for detecting at least one mammalian microRNA comprising at least one oligonucleotide primer selected from the group consisting of SEQ ID NO:500.

6. An oligonucleotide primer for detecting a mammalian microRNA selected from the group consisting of SEQ ID NO:500.

* * * * *